US009364466B2

(12) United States Patent
Verma et al.

(10) Patent No.: US 9,364,466 B2
(45) Date of Patent: Jun. 14, 2016

(54) HETEROCYCLIC COMPOUNDS AS PROTEIN KINASE INHIBITORS

(71) Applicant: Daiichi Sankyo Company, Limited, Chuo-ku, Tokyo (JP)

(72) Inventors: Ashwani Kumar Verma, New Dehli (IN); Kumaragurubaran Nagaswamy, Hyderabad (IN); Lalima Sharma, Chandigarh (IN); Soma Ghosh, Ganguly Bagan (IN); Balkrishna Ramchandra Kale, Nasik (IN); Aniruddha Mondal, Falta (IN); Punit Kumar Srivastava, Gurgaon (IN); Sunanda Ghosh Dastidar, New Delhi (IN); Rijwan Jaffer Momin, Kedgaon (IN); Pradip Balu Wagh, Nashik (IN); Sonali Nanasaheb Pansare, Darewadi (IN); Pramod Raosaheb Markad, Kedgaon (IN); Yogesh Balasaheb Khairnar, Nashik (IN); Rie Miyauchi, Funabashi (JP); Takeshi Murata, Edogawa-ku (JP); Masayuki Ishizaki, Edogawa-ku (JP); Masatoshi Nagamochi, Koto-ku (JP); Shin Iimura, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 14/622,560

(22) Filed: Feb. 13, 2015

(65) Prior Publication Data

US 2015/0157613 A1 Jun. 11, 2015

Related U.S. Application Data

(60) Division of application No. 14/088,093, filed on Nov. 22, 2013, now Pat. No. 8,980,911, which is a continuation of application No. PCT/IB2012/052214, filed on May 3, 2012.

(30) Foreign Application Priority Data

May 26, 2011 (IN) ............................ 1510/DEL/2011

(51) Int. Cl.
| | |
|---|---|
| *A61K 31/437* | (2006.01) |
| *A61K 31/4353* | (2006.01) |
| *C07D 471/04* | (2006.01) |
| *A61K 31/506* | (2006.01) |
| *A61K 31/5377* | (2006.01) |

(52) U.S. Cl.
CPC ............. *A61K 31/437* (2013.01); *A61K 31/506* (2013.01); *A61K 31/5377* (2013.01); *C07D 471/04* (2013.01)

(58) Field of Classification Search
CPC .......................... A61K 31/437; A61K 31/4353

USPC .......................................................... 514/300
See application file for complete search history.

(56) References Cited

U.S. PATENT DOCUMENTS

| | | |
|---|---|---|
| 6,800,640 B2 | 10/2004 | Bernotas |
| 7,297,705 B2 | 11/2007 | Bernotas |
| 7,354,924 B2 | 4/2008 | Wang |
| 7,501,420 B2 | 3/2009 | Wang |
| 7,585,876 B2 | 9/2009 | Bernotas |
| 7,622,480 B2 | 11/2009 | Fonquerna Pou |
| 7,662,823 B2 | 2/2010 | Wang |
| 8,741,897 B2 | 6/2014 | Bekkali |
| 2005/0228000 A1 | 10/2005 | Smallheer |
| 2010/0063047 A1 | 3/2010 | Borchardt |
| 2010/0093752 A1 | 4/2010 | Wang |
| 2010/0256365 A1 | 10/2010 | Ibrahim |
| 2010/0311743 A1 | 12/2010 | Farmer |
| 2010/0317643 A1 | 12/2010 | Goodacre |

FOREIGN PATENT DOCUMENTS

| | | |
|---|---|---|
| DE | 10 2009 001 438 A1 | 9/2010 |
| DE | 10 2009 015 070 A1 | 10/2010 |
| EP | 0 778 277 A1 | 6/1997 |
| EP | 1 837 329 A1 | 9/2007 |
| WO | 02/098876 A1 | 12/2002 |
| WO | 2005/028434 A2 | 3/2005 |
| WO | 2005/082367 A1 | 9/2005 |
| WO | 2005/097129 A2 | 10/2005 |

(Continued)

OTHER PUBLICATIONS

Darnell, J.E., Jr., et al., "Jak-STAT Pathways and Transcriptional Activation in Response to IFNs and Other Extracellular Signaling Proteins," Science 264(5164):1415-1421, Jun. 1994.
Firmbach-Kraft, I., et al., "Tyk2, Prototype of a Novel Class of Non-Receptor Tyrosine Kinase Genes," Oncogene 5(9):1329-1336, Sep. 1990.
Fischer, E.H., and E.G. Krebs, "Relationship of Structure to Function of Muscle Phosphorylase," Federation Proceedings 25(5):1511-1520, Sep.-Oct. 1966.
Hunter, T., "A Thousand and One Protein Kinases," Cell 50(6):823-829, Sep. 1987.
Ihle, J.N., et al., "Signaling Through the Hematopoietic Cytokine Receptors," Annual Review of Immunology 13:369-398, Apr. 1995.
Karaghiosoff, M., et al., "Partial Impairment of Cytokine Responses in Tyk2-Deficient Mice," Immunity 13(4):549-560, Oct. 2000.

(Continued)

*Primary Examiner* — Niloofar Rahmani
(74) *Attorney, Agent, or Firm* — Christensen O'Connor Johnson Kindness PLLC

(57) ABSTRACT

The present invention provides a heterocyclic compound of formula (I), a pharmaceutically acceptable salt thereof, a prodrug thereof or a hydrate thereof, wherein A, A' B, D, $R^1$, $R^2$ and $R^3$ are as defined herein, a pharmaceutical composition comprising a compound of formula (I) as an active ingredient, methods of production, and methods of use thereof. Particularly, the present invention provides a compound of formula (I) useful for treating or preventing a disease, condition or disorder associated with protein kinases, preferably Janus Kinase family.

7 Claims, No Drawings

(56) References Cited

FOREIGN PATENT DOCUMENTS

| | | | |
|---|---|---|---|
| WO | 2009/075830 | A1 | 6/2009 |
| WO | 2009/129335 | A2 | 10/2009 |
| WO | 2010/142752 | A1 | 12/2010 |
| WO | 2011/113802 | A2 | 9/2011 |

OTHER PUBLICATIONS

Kawamura, M., et al., "Molecular Cloning of L-JAK, a Janus Family Protein-Tyrosine Kinase Expressed in Natural Killer Cells and Activated Leukocytes," Proceedings of the National Academy of Sciences USA (PNAS) 91(14):6374-6378, Jul. 1994.
Krueger, G.G., et al., "A Human Interleukin-12/23 Monoclonal Antibody for the Treatment of Psoriasis," New England Journal of Medicine 356(6):580-592, Feb. 2007.
Leonard, W.J., and J.J. O'Shea, "JAKs and STATs: Biological Implications," Annual Review of Immunology 16:293-322, Apr. 1998.
Levy, D.E., and J.E. Darnell Jr., "STATs: Transcriptional Control and Biological Impact," Nature Reviews: Molecular Cell Biology 3(9):651-662, Sep. 2002.
Liu, K.D., et al., "JAK/STAT Signaling by Cytokine Receptors," Current Opinion in Immunology 10(3):271-278, Jun. 1998.
Mannon, P.J., et al., "Anti-Interleukin-12 Antibody for Active Crohn's Disease," New England Journal of Medicine 351(20):2069-2079, Nov. 2004.
Musso, T., et al., "Regulation of JAK3 Expression in Human Monocytes: Phosphorylation in Response to Interleukins 2,4, and 7," Journal of Experimental Medicine 181(4):1425-1431, Apr. 1995.
Reich, K, et al., "Ustekinumab," Nature Reviews: Drug Discovery 8(5):355-356, May 2009.
Schindler, T., et al., "Structural Mechanism for STI-571 Inhibition of Abelson Tyrosine Kinase," Science 289(5486):1938-1942, Sep. 2000.
Shimoda, K., et al., "Tyk2 Plays a Restricted Role in IFNα Signaling, Although it is Required for IL-12-Mediated T Cell Function," Immunity 13(4):561-571, Oct. 2000.
Wilks, A. F., "Two Putative Protein-Tyrosine Kinases Identified by Application of the Polymerase Chain Reaction," Proceedings of the National Academy of Sciences USA (PNAS) 86(5):1603-1607, Mar. 1989.
Feener, E.P., et al., "Tyrosine Phosphorylation of Jak2 in the JH2 Domain Inhibits Cytokine Signaling," Molecular and Cellular Biology 24(11):4968-4978, Jun. 2004.
International Search Report mailed Aug. 1,2012, issued in corresponding International Application No. PCT/IB2012/052214, filed May 3,2012, 5 pages.
Kiselyov, A.S., et al., "2-((1H-Azol-1-yl)methyl)-N-arylbenzamides: Novel Dual Inhibitors of VEGFR-1/2 Kinases," Bioorganic & Medicinal Chemistry Letters 16(6):1726-1730, Mar. 2006.
Manning, G., et al., "The Protein Kinase Complement of the Human Genome," Science 298(5600):1912-1916, 1933-1934, Dec. 2002.
"Methanone (1-ethyl-1H-pyrrolo[2,3-c]pyridin-3-yl)(4-methoxyphenyl)," Database Accession No. 947013-96-9, Database Registry [Online], Chemical Abstracts Service, Columbus, Ohio, Sep. 13, 2007, 1 page.
"Methanone (7-chloro-1H-pyrrolo[2,3-c]pyridin-3-yl)(4-fluorophenyl)," Database Accession No. 1214520-65-6, Database Registry [Online], Chemical Abstracts Service, Columbus, Ohio, Mar. 25, 2010, 1 page.
O'Neil, M.J., et al., "Indole," Entry 4985, "The Merck Index: An Encyclopedia of Chemicals, Drugs, and Biologicals," 13th ed., Merck Research Laboratory, Whitehouse Station, N.J., 2001, p. 891.
Zhang, Z., et al., "An Effective Procedure for the Acylation of Azaindoles at C-3," Journal of Organic Chemistry 67(17):6226-6227, Aug. 2002.
Frydman, B., and M.E. Despuy, "Pyrroles From Azaindoles: A Synthesis of Porphobilinogen," Journal of the American Chemical Society 87(15):3530-3531, Aug. 1965.
Kelly, A.H., and J. Parrick, "Diazaindenes (Azaindoles). Part II: Thermal Indolisation of 3- and 4-Pyridylhydrazones," Journal of the Chemical Society C: Organic 2:303-307, 1970.

HETEROCYCLIC COMPOUNDS AS PROTEIN KINASE INHIBITORS

CROSS-REFERENCES TO RELATED APPLICATIONS

This application is a division of U.S. patent application Ser. No. 14/088,093, filed Nov. 22, 2013, which is the national stage of International Application No. PCT/IB2012/052214, filed May 3, 2012, which claims the benefit of Indian Application No. 1510/DEL/2011, filed May 26, 2011. Each application is incorporated herein by reference in its entirety.

FIELD OF THE INVENTION

The present invention provides a heterocyclic compound of formula (I), a pharmaceutically acceptable salt thereof, a prodrug thereof or a hydrate thereof, wherein A, B, R', R'', $R^1$, $R^2$ and $R^3$ are as defined herein, a pharmaceutical composition comprising a compound of formula (I) as an active ingredient, methods of production, and methods of use thereof. Particularly, the present invention provides a compound of formula (I) useful for treating or preventing a disease, condition or disorder associated with protein kinases, preferably Janus Kinase family.

BACKGROUND OF THE INVENTION

The importance of protein phosphorylation as a fundamental mechanism that controls cell physiology was established by the pioneering work of Krebs and Fisher (*Fed. Proc.*, 1996, 25, 1511-1520). Protein kinases modify protein function by transferring phosphate groups from ATP or GTP to free hydroxyl groups of amino acids. Most protein kinases phosphorylate serine and threonine residues, but a subset of protein kinases selectively phosphorylate tyrosine residues. There are 90 protein tyrosine kinases (PTKs) which play specific roles (Hunter, *Cell*, 1987, 50, 823-829). PTKs can be further divided into the two main subgroups, receptor tyrosine kinase (RTKs) and non-receptor, cytosolic tyrosine kinases. RTKs contain an extracellular ligand binding domain, transmembrane region and intracellular cytoplasmic kinase domain. PTKs have a conserved kinase domain structure that consists of an N-terminal lobe (N-lobe) composed of a five-stranded β-sheet and a single α-helix, connected to a larger C-terminal lobe (C-lobe) by a hinge region. The protein substrate binds to a surface groove formed by the α-helical C-lobe, and an ATP binding pocket is formed by the hinge region and N- and C-lobes. The C-lobe contains the activation loop (A-loop), which becomes phosphorylated. Phosphorylation leads to the conformational stabilization and activation, allowing the transfer of the γ-phosphate from bound ATP to the bound substrate protein. All protein kinases share structural similarities but show greater structural distinction in their inactive state (Schinlder et. al., *Science*, 2000, 289, 1938-1942).

Janus Kinases (JAKs) are non-receptor tyrosine kinases and were discovered in searches for novel protein tyrosine using PCR based strategies (Firmbach-Kraft et al., *Oncogene*, 1990, 5, 1329-1336 and Wils A F, *Proc. Natl. Acad. Sci. USA*, 1989, 86, 1603-1607). In mammalians, JAKs have four members JAK1, JAK2, JAK3 and TYK2 enzymes. Since the sequencing of other vertebrate genomes has been completed, we know that there are four JAK family members in mammals, birds and fishes. In humans, the JAK1 gene is located on chromosome) p31.3 and JAK2 is on 9p24; JAK3 and TYK2 genes are clustered together on chromosome19p13.1 and 19p13.2, respectively. The three-dimensional structure of the JAKs is at present unknown but seven JAK homology (JH) domains have been identified, numbered from carboxyl to the amino terminal. The JH1 domain at the carboxyl terminal has all the features of a typical eukaryotic tyrosine kinase domain. Interestingly, this domain is most closely related to the kinase domains of the epidermal growth factor family of receptor tyrosine kinases, suggesting that JAK family may have arisen from the larger family of protein kinases (Manning et al., *Science*, 2002, 298, 1912-1934).

In mammals, JAK1, JAK2 and TYK2 are ubiquitously expressed. In contrast the expression of JAK3 is more restricted; it is predominantly expressed in hematopoietic cells and is highly regulated the cell development and activation. At the cellular level, JAKs can be found in the cytosol when they are experimentally expressed in the absence of cytokine receptors, but, because of their intimate association with cytokine receptors, they ordinarily localize to endosome and the plasma membrane, along with their cognate receptors (Kawamura et al., *Proc. Natl. Acad. Sci USA*, 1994, 91, 6374-6378 and Musso et al., *J. Exp. Med.*, 1995, 181, 1425-1431). A large number of cytokines are dependent upon JAK1, including a family that use a shared receptor subunit called common γ chain (γc), which includes interleukin (IL)-2, IL-4, IL-7, IL-9, IL-15 and IL-21. These cytokines are also dependent on JAK3, because JAK3 binds γc. JAK1 is also essential for another family that uses the shared receptor subunit gp130 (IL-6, IL-11, oncostatin M, leukemia inhibitory factor (LIF), ciliary neutrophilic factor (CNF) as well as granulocyte colony-stimulating factor (G-CSF) and IFNs. JAK2 is essential for the hormone-like cytokines such as growth hormone (GH), prolactin (PRL), erythropoietin (EPO), thrombopoietin (TPO) and the family of cytokines that signal through the IL-3 receptor (IL-3, IL-5 and GM-CSF). JAK2 is also important for cytokines that use the gp130 receptor and for some IFNs.

JAK3 probably has the most discrete function, as is associated with only one cytokine receptor—the common gamma chain or γc. This is a shared receptor subunit that pairs with other ligand-specific subunits to form the receptors for IL-2, IL-4, IL-7, II-9, IL-15 and IL-21. The immune abnormalities associated with JAK3 deficiency were confirmed with the generation of JAK3 knockout mice; similar to humans, these mice have SCID that resembles γδ deficiency with small thymuses, absence of lymph nodes and reduced numbers of α/β and γ/δ T-cells. JAK3 mice also have a profound reduction in thymic progenitor cells and reduced ability to reconstitute T cell development. No effect on myeloid or erthyroid cells was noted in JAK3 deficient mice consistent with observations in humans and indicative of a specific effect on lymphoid precursors. However, murine JAK3 deficiency is associated with a T-cell dependent autoimmune disease characterized by infiltration of tissues by mononuclear cells, splenomegaly, and expansion of neutrophils and monocytic cells. These auto-immune diseases are T-cell dependent.

TYK2 was the first JAK to be implicated in IFN signaling, but subsequent studies indicate that TYK2 is essential for IL-12, IL-6, and IL-10 signaling, but not for cytokines that use gp130. IL-12 induced IFN-γ production by NK cells and activated T-cells was highly dependent on TYK2. Infact, TYK2 was shown to be involved in IL-23 induced STAT3 phosphorylation of activated T-cells and in IFN-γ production. Furthermore, TYK2 plays a crucial role in IL-23 induced IL-17a production by γδ T cells. The importance of TYK2 in the in vivo differentiation of Antigen-specific Th1 cells has also not been defined. TYK2 mice also have defective responses to lipopolysaccharide (LPS, a component of the outer membrane of gram-positive bacteria), but whether this is a direct or indirect effect has not been defined. In particular, a role of TYK2 in signaling through the Toll receptor, which mediates the response to LPS, has not been established (Shimoda et al., *Immunity*, 2000, 13, 561-571; Karaghiosoff et al., *Immunity*, 2000, 13, 549-560).

JAKs are continuously associated with the membrane-proximal regions of cytokine receptors, although in some cases interaction between the JAK and the receptor is increased upon ligand binding. It has been proposed that ligand binding brings a conformational change in the receptor, which promotes JAK activation through reciprocal interaction of two juxtapositioned JAK kinases and auto- and/or trans-phosphorylation of tyrosine residues on the activation loop of the JAK kinase domain. Like other tyrosine kinases, JAKs undergo autophosphorylation, but the importance of this modification in JAK-dependent signaling is not very well understood. Autophosphorylation within the activation loop positively regulates kinase activity; in JAK3, however, phosphorylation in this region can enhance or inhibit catalytic activity, depending upon the site of phosphorylation. Other sites of phosphorylation have recently been identified, e.g., a conserved residue in the hinge region between JH1 and JH2 is a prominent site of auto-phosphorylation (Tyr813 in JAK2 and Tyr785 in JAK3). This site serves to recruit the adapter protein Sh2-Bb, which positively regulates JAK2 activity (Feener et al., *Mol. Cell Biol.*, 1994, 24, 4968-4978).

Tyrosine phosphorylation of cytokine receptors provides binding sites for signaling molecules. The main family of DNA-binding signaling proteins with transcriptional activity responsible for mediating signals from cytokine receptors is the STAT family. The seven members of the mammalian signal transducer and activator of transcription (STAT) family participates in a wide range of biological processes with impact both on the generation and the functional regulation of the cells involved in immunity. STATs bind phosphorylated receptors and in turn are substrates for the JAKs. Phosphorylated STAT can interact, dimerize, traffic into the nucleus, and regulate gene expression. The mechanisms by which cytokine activation of a restricted number of JAKs results in such different and specific downstream signaling events are still not understood. A large number of cytokines uses only four PTKs and seven STAT proteins for their specific signaling transmission. Activation of STATs by JAKs is a hallmark of both innate and adaptive immune responses. Hence, lymphocyte development, survival, and proliferation resulting in the outcome of an immune response by T-helper (Th) cell lineage-defining cytokines all depend on JAK activation as a primary step. Genetic analysis of JAKs in human with certain immune diseases and the generation of JAK-specific knockout (KO) mice helped in understanding the exact role of JAKs in immune cell signaling (Darnell et al., *Science*, 1994, 264, 1451-1421; Ihle et al., *Annu. Rev. Immunol.*, 1995, 13, 369-398; Leonard et al., *Ann. Rev. Immunol.*, 1998, 16, 293-322; Liu et al., *Curr. Opin. Immunol.*, 1998, 10, 271-278 and Levy et al., *Nat. Rev. Mol. Cell Biol.*, 2002, 3, 651-662).

Cytokines are crucial for development, survival, proliferation and differentiation of hematopoietic cells. Type I and type II cytokine receptors lack receptor-intrinsic tyrosine kinase activity and instead transmit their signals through receptor associated JAKs. In principle, all four JAKs might be considered as useful therapeutic targets.

Due to T-cell dependencies and their Th1 and Th17 modulation activities TYK2 enzyme inhibitors may have roles in auto-immune disorders such as rheumatoid arthritis, multiple sclerosis, psoriasis, intestinal bowel disease, and also in a few inflammatory disorders such as chronic obstructive pulmonary disease or allergy. A fully human monoclonal antibody targeting the shared p40 subunit of the IL-12 and IL-23 cytokines was recently approved by the European Commission for the treatment of moderate to severe plaque psoriasis (Krueger et al., *N. Engl. J. Med.*, 2007, 356, 380-92 and Reich et al., *Nat. Rev. Drug Discov.*, 2009, 8, 355-356). In addition, an antibody targeting the IL-12 and IL-23 pathways underwent clinical trials for treating Crohn's disease (Mannon et al., *N. Engl. J. Med.*, 2004, 351, 2069-79).

Many pharmaceutical companies have established JAK targeted drug development programs, including Pfizer, Vertex, Rigel and Incyte. Pfizer has progressed CP-690550, which is a potent JAK3 inhibitor. This compound was reported to show efficacy in an animal model of organ transplantation and clinical trials, however the molecule is not selective for JAK3 and also inhibits JAK2 kinase with almost equipotency.

WO2010/142752 and US2010/0317643 disclose compounds having TYK2 inhibitory activity. DE102009001438 and DE102009015070 disclose carbonylamino substituted anilino pyrimidine derivatives as TYK2 inhibiters. WO2011/113802 discloses imidazopyridine compounds useful for treating diseases mediated by TYK2 kinase. US2010/0311743 discloses the compounds which are inhibitors of protein kinases, particularly JAK family kinases. US2010/0256365 discloses compounds which are active on protein kinases. WO2005/082367 discloses compounds having kinase inhibitory activity.

WO2005/097129 discloses 6-azaindole compounds having superior Iκβ kinase inhibitory activity. US2005/0228000 discloses bicyclic heterocycles useful as serine protease inhibitors. US2010/063047 discloses inhibitors of histamine receptor. WO2009/129335 discloses Inhibitors of histone deacetylase. WO2005/028434 discloses compounds which are inhibitors of HSP90. WO2002/098876 discloses CAK inhibitors. EP778277 discloses CRF antagonists.

While progress has been made in this field, there is a great need to develop a novel compound that inhibits protein kinase. In particular, it would be desirable to develop compounds that inhibit JAK family kinases such as JAK1, JAK2, JAK3 and TYK2. Accordingly, the present invention provides novel compounds which modulate the JAK pathway and are useful for the prevention and/or treatment of auto-immune and/or inflammatory diseases.

SUMMARY OF THE INVENTION

Accordingly, the present invention provides heterocyclic compound of formula (I), a pharmaceutically acceptable salt thereof, a prodrug thereof or a hydrate thereof, a pharmaceutical composition comprising a compound of formula (I) as an active ingredient, methods of production, and methods of use thereof. Particularly, the present invention provides a compound of formula (I) useful for treating or preventing autoimmune and inflammatory disease, condition or disorder associated with dysregulation of protein kinases, preferably with Janus Kinase family such as JAK1, JAK2, JAK3, TYK2 or combination thereof.

It is evident from the literature that there is no potent compound in the preclinical or clinical trial having selectivity for TYK2 over other kinases such as JAK1, JAK2 and JAK3. A TYK2 selective inhibitor would not interfere with the signaling pathways mediated/controlled by other members of kinases such as JAK1, JAK2, and JAK3. One drawback of some of the current JAK3 inhibitors is that they also have activities towards other kinases, which also play critical roles to the signaling of many hematopoietic cytokine and growth factor receptors.

The availability of compounds that selectively inhibit one kinase compared to other kinases would therefore be desirable. The inventors of the present invention have studied heterocyclic compounds (e.g., azaindole compounds) having excellent Janus kinase inhibitory activity, and are thus useful agents for the treatment or prevention of disease, condition or disorder mediated by Janus kinase. In particular, the compounds of the present invention have excellent TYK2 inhibitory activity over other kinases, and are useful in preventing and/or treating autoimmune and/or inflammatory disease, condition or disorder selected from, but are not limited to, rheumatoid arthritis (RA), psoriasis, organ transplant rejection, multiple sclerosis (MS), inflammatory bowel disease (IBD), chronic obstructive pulmonary disease (COPD), asthma or cancer.

Thus, one aspect of the present invention provides a compound having the structure of formula (I),

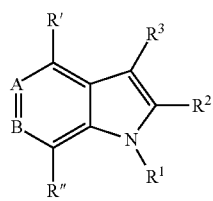

formula (I)

a pharmaceutically acceptable salt thereof, a prodrug thereof or a hydrate thereof, wherein:
A and B independently represent N or CR, with the proviso that both A and B are not N;
R, R' and R" independently represent H, $(C_1-C_6)$ alkyl, halogen, —CN, —$NR^aR^b$, —$NR^aCOR^b$ or —$CONR^aR^b$, with the proviso that R' represents H, halogen or —$NR^aCOR^b$ when A is N and R" represents H, halogen or —$NR^aCOR^b$ when B is N;
$R^1$ represents H, $(C_1-C_3)$ alkyl or —$COR^4$;
$R^2$ represents H, $(C_1-C_3)$ alkyl, halo or —CN;
$R^3$ represents H, $(C_1-C_3)$ alkyl, halo, —CN or —$COR^4$;
$R^4$ represents optionally substituted phenyl, with the proviso that $R^1$ represents —$COR^4$ when A is N and $R^3$ represents —$COR^4$ when B is N;
$R^a$ and $R^b$ independently represent H, $(C_1-C_8)$ alkyl, $(C_3-C_8)$ cycloalkyl or $OR'''$;
$R^a$ and $R^b$ are taken together with the N atom to which they are attached to form 3-8 membered heterocyclyl, optionally containing additional heteroatom(s) selected from N, O or S, wherein heterocyclyl is optionally substituted; and $R'''$ is H or $(C_1-C_3)$ alkyl.

The present invention may involve one or more of the following embodiments associated with the compound of formula (I). For example, in one embodiment, there is provided a compound of formula (I), a pharmaceutically acceptable salt thereof, a prodrug thereof, or a hydrate thereof, wherein A represents N.

In another embodiment, there is provided a compound of formula (I), a pharmaceutically acceptable salt thereof, a prodrug thereof or a hydrate thereof, wherein B represents N.

In another embodiment, there is provided a compound of formula (I), a pharmaceutically acceptable salt thereof, a prodrug thereof or a hydrate thereof, wherein A represents N, R' represents H or —$NR^aCOR^b$ and $R^1$ represents —$COR^4$.

In another embodiment, there is provided a compound of formula (I), a pharmaceutically acceptable salt thereof, a prodrug thereof or a hydrate thereof, wherein A represents N, R' represents —$NR^aCOR^b$ and $R^1$ represents —$COR^4$.

In another embodiment, there is provided a compound of formula (I), a pharmaceutically acceptable salt thereof, a prodrug thereof or a hydrate thereof, wherein B represents N, R" represents H or —$NR^aCOR^b$ and $R^3$ represents —$COR^4$.

In another embodiment, there is provided a compound of formula (I), a pharmaceutically acceptable salt thereof, a prodrug thereof or a hydrate thereof, wherein B represents N, R" represents —$NR^aCOR^b$ and $R^3$ represents —$COR^4$.

In another embodiment, there is provided a compound of formula (I), a pharmaceutically acceptable salt thereof, a prodrug thereof or a hydrate thereof, wherein $R^1$ represents H or $(C_1-C_3)$ alkyl and $R^3$ represents —$COR^4$.

In another embodiment, there is provided a compound of formula (I), a pharmaceutically acceptable salt thereof, a prodrug thereof or a hydrate thereof, wherein $R^1$ represents —$COR^4$ and $R^3$ represents H, $(C_1-C_3)$ alkyl, halo or —CN.

In another embodiment, there is provided a compound of formula (I), a pharmaceutically acceptable salt thereof, a prodrug thereof or a hydrate thereof, wherein $R^1$ represents —$COR^4$ and $R^3$ represents H.

In another embodiment, there is provided a compound of formula (I), a pharmaceutically acceptable salt thereof, a prodrug thereof or a hydrate thereof, wherein $R^1$ represents H and $R^3$ represents —$COR^4$.

In yet another embodiment of the present invention, there is provided a compound of formula (I), a pharmaceutically acceptable salt thereof, a prodrug thereof or a hydrate thereof, wherein $R^4$ represents a group selected from

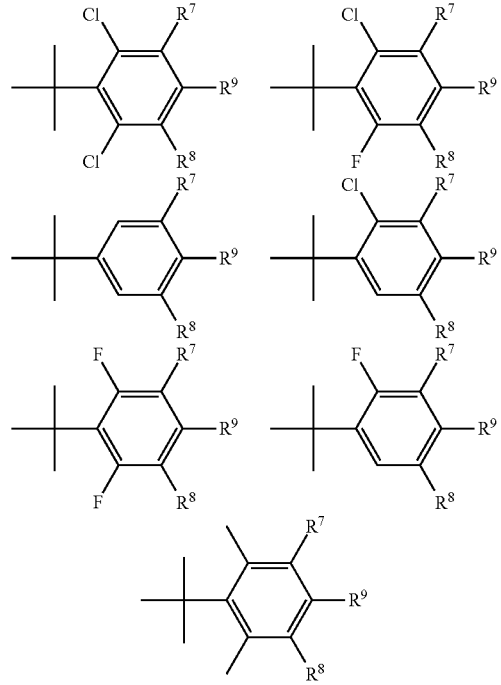

wherein:
$R^7$, $R^8$ and $R^9$ independently represent H, alkyl, alkenyl, alkynyl, cycloalkyl, aryl, aralkyl, heteroaryl, heteroarylalkyl, heterocyclyl, heterocyclylalkyl, alkoxy, halo, —$NO_2$, —$(CH_2)_qC(O)NR^cR^d$, —$(CH_2)_qNR^cCOR^d$, —$(CH_2)_qNR^c$-

CONR$^c$R$^d$, —(CH$_2$)$_q$NR$^c$C(O)OR$^d$, —(CH$_2$)$_q$NR$^c$R$^d$, —(CH=CH)—(CH$_2$)$_s$C(O)OR$^e$, —(CH=CH)—(CH$_2$)$_s$CONR$^c$R$^d$, —(CH=CH)—(CH$_2$)$_s$CN, —(CH=CH)—(CH$_2$)$_s$R$^e$, —(CH$_2$)$_s$C(O)OR$^e$, —(CH)$_r$CN, —(CH$_2$)$_r$OR$^e$, —(CH$_2$)$_r$R$^e$, —(CH$_2$)$_r$C(O)OR$^e$, —(CH)$_r$halo, —S(O)$_p$R$^e$, —S(O)$_p$NR$^c$R$^d$, —NR$^c$S(O)$_p$R$^d$, and wherein alkyl, alkenyl, alkynyl, cycloalkyl, aryl, heteroaryl heterocyclyl are optionally substituted;

R$^c$ and R$^d$ independently represent H, (C$_1$-C$_8$) alkyl, (C$_3$-C$_8$) cycloalkyl, aryl, aralkyl, heteroaryl, heteroarylalkyl, —(CH$_2$)$_r$OR$^e$, —(CH$_2$)$_r$SR$^e$, —(CH$_2$)$_r$CN, —(CH$_2$)$_r$halo, —(CH$_2$)$_r$C(O)OR$^e$, —(CH$_2$)$_r$NR$^c$R$^d$, —COR$^e$, —S(O)$_p$R$^e$ or —(CH$_2$)$_r$R$^e$, wherein alkyl, cycloalkyl, aryl and heteroaryl are optionally substituted;

R$^c$ and R$^d$ are taken together with the N atom to which they are attached to form 3-8 membered heterocyclyl, optionally containing additional heteroatom(s) selected from N, O or S, wherein heterocyclyl is optionally substituted;

R$^e$ represents H, (C$_1$-C$_6$) alkyl, —CF$_3$, (C$_3$-C$_8$) cycloalkyl, heterocyclyl, aryl or heteroaryl; wherein alkyl, cycloalkyl, heterocyclyl, aryl and heteroaryl are optionally substituted;

p represents an integer of 1 or 2;
q represents an integer of 0, 1, 2 or 3;
r represents an integer of 0, 1, 2, 3 or 4; and
s represents an integer of 0, 1 or 2.

In yet another embodiment, the present invention provides a compound of formula (I), a pharmaceutically acceptable salt thereof, a prodrug thereof or a hydrate thereof, wherein R$^a$ represents H or (C$_1$-C$_3$) alkyl and R$^b$ represents H, (C$_1$-C$_3$) alkyl, (C$_1$-C$_3$) alkoxy or (C$_3$-C$_5$) cycloalkyl.

One embodiment of the present invention provides a compound of formula (I) selected from:

(2-Chloro-6-fluorophenyl)(1H-pyrrolo[2,3-c]pyridine-3-yl)methanone (Compound No. 1), 3,5-Dichloro-N-ethyl-4-(1H-pyrrolo[2,3-c]pyridin-3-ylcarbonyl)benzamide (Compound No. 2), (4-Amino-2,6-dichlorophenyl)(1H-pyrrolo[2,3-c]pyridin-3-yl)methanone (Compound No. 3),

[2,6-Dichloro-4-(2-methoxypyrimidin-5-yl)phenyl](1H-pyrrolo[2,3-c]pyridin-3-yl)methanone (Compound No. 4), N-[3-(2,6-Dichlorobenzoyl)-1H-pyrrolo[2,3-c]pyridin-7-yl]cyclopropanecarboxamide (Compound No. 5), 3,5-Dichloro-4-(1H-pyrrolo[2,3-c]pyridin-3-ylcarbonyl)benzonitrile (Compound No. 6), 4-{[7-(Acetylamino)-1H-pyrrolo[2,3-c]pyridin-3-yl]carbonyl}-3,5-dichloro-N-methylbenzamide (Compound No. 7), N-[3-(2-Chloro-6-fluorobenzoyl)-1H-pyrrolo[2,3-c]pyridin-7-yl]acetamide (Compound No. 8), 4-{[7-(Acetylamino)-1H-pyrrolo[2,3-c]pyridin-3-yl]carbonyl}-3,5-dichloro-N-ethylbenzamide (Compound No. 9), (4-Bromo-2,6-dichlorophenyl)(1H-pyrrolo[2,3-c]pyridin-3-yl)methanone (Compound No. 10), N-[3-(2-Chloro-6-fluorobenzoyl)-1H-pyrrolo[2,3-c]pyridin-7-yl]cyclopropanecarboxamide (Compound No. 11), 3,5-Dichloro-4-({7-[(cyclopropylcarbonyl)amino]-1H-pyrrolo[2,3-c]pyridin-3-yl}carbonyl)-N-methylbenzamide (Compound No. 12), 3,5-Dichloro-4-({7-[(cyclopropylcarbonyl)amino]-1H-pyrrolo[2,3-c]pyridin-3-yl}carbonyl)-N-ethylbenzamide (Compound No. 13), 3,5-Dichloro-N-(2-methoxyethyl)-4-(1H-pyrrolo[2,3-c]pyridin-3-ylcarbonyl)benzamide (Compound No. 14), 4-{[7-(Acetylamino)-1H-pyrrolo[2,3-c]pyridin-3-yl]carbonyl}-3,5-dichloro-N-propylbenzamide (Compound No. 15), 3,5-Dichloro-4-({7-[(cyclopropylcarbonyl)amino]-1H-pyrrolo[2,3-c]pyridin-3-yl}carbonyl)-N-(2-methoxyethyl)benzamide (Compound No. 16), 4-{[7-(Acetylamino)-1H-pyrrolo[2,3-c]pyridin-3-yl]carbonyl}-3,5-dichloro-N-(2-methoxyethyl)benzamide (Compound No. 17), N-[3-(2,6-Dichlorobenzoyl)-1H-pyrrolo[2,3-c]pyridin-5-yl]cyclopropanecarboxamide (Compound No. 18), N-[3-(2-Chloro-6-fluorobenzoyl)-1H-pyrrolo[2,3-c]pyridin-5-yl]cyclopropanecarboxamide (Compound No. 19), 3,5-Dichloro-4-({5-[(cyclopropylcarbonyl)amino]-1H-pyrrolo[2,3-c]pyridin-3-yl}carbonyl)-N-methylbenzamide (Compound No. 20), N-[3-(2,6-Dichloro-4-cyanobenzoyl)-1H-pyrrolo[2,3-c]pyridin-7-yl]acetamide (Compound No. 21), N-[3-(4-Bromo-2,6-dichlorobenzoyl)-1H-pyrrolo[2,3-c]pyridin-7-yl]cyclopropanecarboxamide (Compound No. 22), N-{3-[2,6-Dichloro-4-(3,5-dimethyl-1,2-oxazol-4-yl)benzoyl]-1H-pyrrolo[2,3-c]pyridin-7-yl}cyclopropanecarboxamide (Compound No. 23), N-[3-(4-Bromo-2,6-dichlorobenzoyl)-1H-pyrrolo[2,3-c]pyridin-7-yl]acetamide (Compound No. 24), Methyl 3,5-dichloro-4-({7-[(cyclopropylcarbonyl)amino]-1H-pyrrolo[2,3-c]pyridin-3-yl}carbonyl)benzoate (Compound No. 25), N-[3-(4-Amino-2,6-dichlorobenzoyl)-1H-pyrrolo[2,3-c]pyridin-7-yl]cyclopropanecarboxamide (Compound No. 26), N-{3-[4-(Acetylamino)-2,6-dichlorobenzoyl]-1H-pyrrolo[2,3-c]pyridin-7-yl}cyclopropanecarboxamide (Compound No. 27), N-[3-(2-Chloro-6-fluorobenzoyl)-1H-pyrrolo[2,3-c]pyridin-7-yl]propanamide (Compound No. 28), 3,5-Dichloro-4-({7-[(cyclopropylcarbonyl)amino]-1H-pyrrolo[2,3-c]pyridin-3-yl}carbonyl)-N-[2-(2-hydroxyethoxyl)ethyl]benzamide (Compound No. 29), 3,5-Dichloro-4-({7-[(cyclopropylcarbonyl)amino]-1H-pyrrolo[2,3-c]pyridin-3-yl}carbonyl)-N-(3-hydroxypropyl)benzamide (Compound No. 30), 3,5-Dichloro-4-({7-[(cyclopropylcarbonyl)amino]-1H-pyrrolo[2,3-c]pyridin-3-yl}carbonyl)-N-[3-(morpholin-4-yl)propyl]benzamide (Compound No. 31), 3,5-Dichloro-4-({7-[(cyclopropylcarbonyl)amino]-1H-pyrrolo[2,3-c]pyridin-3-yl}carbonyl)-N-(2,3-dihydroxypropyl)benzamide (Compound No. 32), 3,5-Dichloro-4-({7-[(cyclopropylcarbonyl)amino]-1H-pyrrolo[2,3-c]pyridin-3-yl}carbonyl)-N-[2-(dimethylamino)ethyl]benzamide (Compound No. 33), 3,5-Dichloro-4-({7-[(cyclopropylcarbonyl)amino]-1H-pyrrolo[2,3-c]pyridin-3-yl}carbonyl)-N-[2-(piperidin-1-yl)ethyl]benzamide (Compound No. 34), Methyl N-[3,5-dichloro-4-({7-[(cyclopropylcarbonyl)amino]-1H-pyrrolo[2,3-c]pyridin-3-yl}carbonyl)benzoyl]glycinate (Compound No. 35), N-[3,5-Dichloro-4-({7-[(cyclopropylcarbonyl)amino]-1H-pyrrolo[2,3-c]pyridin-3-yl}carbonyl)benzoyl]glycine (Compound No. 36), N-[3-(2-Chloro-3,6-difluorobenzoyl)-1H-pyrrolo[2,3-c]pyridin-7-yl]cyclopropanecarboxamide (Compound No. 37), 3,5-Dichloro-N-methyl-4-{[7-(propanoylamino)-1H-pyrrolo[2,3-c]pyridin-3-yl]carbonyl}benzamide (Compound No. 38), N-[3-(2,6-Dichloro-4-cyanobenzoyl)-1H-pyrrolo[2,3-c]pyridin-7-yl]cyclopropanecarboxamide (Compound No. 39), 4-{[7-(Acetylamino)-1H-pyrrolo[2,3-c]pyridin-3-yl]carbonyl}-3,5-dichloro-N-[2-(dimethylamino)ethyl]benzamide (Compound No. 40), 4-{[7-(Acetylamino)-1H-pyrrolo[2,3-c]pyridin-3-yl]carbonyl}-3,5-dichloro-N-[2-(2-hydroxyethoxy)ethyl]benzamide (Compound No. 41),
4-{[7-(Acetylamino)-1H-pyrrolo[2,3-c]pyridin-3-yl]carbonyl}-3,5-dichloro-N-[2-(piperidin-1-yl)ethyl]benzamide (Compound No. 42),
4-{[7-(Acetylamino)-1H-pyrrolo[2,3-c]pyridin-3-yl]carbonyl}-3,5-dichloro-N-[2-(morpholin-4-yl)ethyl]benzamide (Compound No. 43),
4-{[7-(Acetylamino)-1H-pyrrolo[2,3-c]pyridin-3-yl]carbonyl}-3,5-dichloro-N-[2-(pyrrolidin-1-yl)ethyl]benzamide (Compound No. 44),
N-[3-(2,4,6-Trichlorobenzoyl)-1H-pyrrolo[2,3-c]pyridin-7-yl]cyclopropanecarboxamide (Compound No. 45),
N-{3-[2,6-Dichloro-4-(3,5-dimethyl-1H-pyrazol-4-yl)benzoyl]-1H-pyrrolo[2,3-c]pyridin-7-yl}cyclopropanecarboxamide (Compound No. 46),
N-{3-[2,6-Dichloro-4-(pyrimidin-5-yl)benzoyl]-1H-pyrrolo[2,3-c]pyridin-7-yl}cyclopropanecarboxamide (Compound No. 47),
N-{3-[2,6-Dichloro-4-(6-methoxypyridin-3-yl)benzoyl]-1H-pyrrolo[2,3-c]pyridin-7-yl}cyclopropanecarboxamide (Compound No. 48),
N-{3-[2,6-Dichloro-4-(6-fluoropyridin-3-yl)benzoyl]-1H-pyrrolo[2,3-c]pyridin-7-yl}cyclopropanecarboxamide (Compound No. 49),
N-{3-[2,6-Dichloro-4-(1-methyl-1H-pyrazol-4-yl)benzoyl]-1H-pyrrolo[2,3-c]pyridin-7-yl}cyclopropanecarboxamide (Compound No. 50),
N-[3-(4-Cyano-2,6-difluorobenzoyl)-1H-pyrrolo[2,3-c]pyridin-7-yl]cyclopropanecarboxamide (Compound No. 51),
Methyl 4-({7-[(cyclopropylcarbonyl)amino]-1H-pyrrolo[2,3-c]pyridin-3-yl}carbonyl)-3,5-difluorobenzoate (Compound No. 52),
N-[3-(4-Cyano-2,6-difluorobenzoyl)-1H-pyrrolo[2,3-c]pyridin-7-yl]acetamide (Compound No. 53),
3,5-Dichloro-N-cyclopropyl-4-({7-[(cyclopropylcarbonyl)amino]-1H-pyrrolo[2,3-c]pyridin-3-yl}carbonyl)benzamide (Compound No. 54),
3,5-Dichloro-4-({7-[(cyclopropylcarbonyl)amino]-1H-pyrrolo[2,3-c]pyridin-3-yl}carbonyl)-N-(cyclopropylmethyl)benzamide (Compound No. 55),
3,5-Dichloro-4-({7-[(cyclopropylcarbonyl)amino]-1H-pyrrolo[2,3-c]pyridin-3-yl}carbonyl)-N-(3-ethoxypropyl)benzamide (Compound No. 56),
N-Butyl-3,5-Dichloro-4-({7-[(cyclopropylcarbonyl)amino]-1H-pyrrolo[2,3-c]pyridin-3-yl}carbonyl)benzamide (Compound No. 57),
N-{3-[2,6-Dichloro-4-(hydroxymethyl)benzoyl]-1H-pyrrolo[2,3-c]pyridin-7-yl}cyclopropanecarboxamide (Compound No. 58),
4-({7-[(Cyclopropylcarbonyl)amino]-1H-pyrrolo[2,3-c]pyridin-3-yl}carbonyl)-3,5-difluoro-N-(2-fluoroethyl)benzamide (Compound No. 59),
4-({7-[(Cyclopropylcarbonyl)amino]-1H-pyrrolo[2,3-c]pyridin-3-yl}carbonyl)-N-ethyl-3,5-difluorobenzamide (Compound No. 60),
4-({7-[(Cyclopropylcarbonyl)amino]-1H-pyrrolo[2,3-c]pyridin-3-yl}carbonyl)-3,5-difluoro-N-methylbenzamide (Compound No. 61),
4-({7-[(Cyclopropylcarbonyl)amino]-1H-pyrrolo[2,3-c]pyridin-3-yl}carbonyl)-3,5-difluoro-N-(3-hydroxypropyl)benzamide (Compound No. 62),
4-({7-[(Cyclopropylcarbonyl)amino]-1H-pyrrolo[2,3-c]pyridin-3-yl}carbonyl)-N-[2-(dimethylamino)ethyl]-3,5-difluorobenzamide (Compound No. 63),
4-({7-[(Cyclopropylcarbonyl)amino]-1H-pyrrolo[2,3-c]pyridin-3-yl}carbonyl)-N-(3-ethoxypropyl)-3,5-difluorobenzamide (Compound No. 64),
N-{3-[4-(3,5-Dimethyl-1,2-oxazol-4-yl)-2,6-difluorobenzoyl]-1H-pyrrolo[2,3-c]pyridin-7-yl}cyclopropanecarboxamide (Compound No. 65),
N-(3-{2,6-Dichloro-4-[(methylamino)methyl]benzoyl}-1H-pyrrolo[2,3-c]pyridin-7-yl)cyclopropanecarboxamide (Compound No. 66),
N-(3-{2,6-Dichloro-4-[(ethylamino)methyl]benzoyl}-1H-pyrrolo[2,3-c]pyridin-7-yl)cyclopropanecarboxamide (Compound No. 67),
N-[3-(2,6-Dichlorobenzoyl)-2-methyl-1H-pyrrolo[2,3-c]pyridin-7-yl]cyclopropanecarboxamide (Compound No. 68),
N-[3-(4-Bromo-2,6-difluorobenzoyl)-1H-pyrrolo[2,3-c]pyridin-7-yl]cyclopropanecarboxamide (Compound No. 69),
N-[3-(2,6-Difluorobenzoyl)-2-methyl-1H-pyrrolo[2,3-c]pyridin-7-yl]cyclopropanecarboxamide (Compound No. 70),
3,5-Dichloro-4-({7-[(cyclopropylcarbonyl)amino]-2-methyl-1H-pyrrolo[2,3-c]pyridin-3-yl}carbonyl)-N-methylbenzamide (Compound No. 71),
3,5-Dichloro-N-methyl-4-(1H-pyrrolo[3,2-c]pyridin-1-ylcarbonyl)benzamide (Compound No. 72),
3,5-Dichloro-N-ethyl-4-(1H-pyrrolo[3,2-c]pyridin-1-ylcarbonyl)benzamide (Compound No. 73),
Methyl[1-(2,6-dichlorobenzoyl)-1H-pyrrolo[3,2-c]pyridin-4-yl]carbamate (Compound No. 74),
3,5-Dichloro-N-(2-hydroxyethyl)-4-(1H-pyrrolo[3,2-c]pyridin-1-ylcarbonyl)benzamide (Compound No. 75),
3,5-Dichloro-N-(cyanomethyl)-4-(1H-pyrrolo[3,2-c]pyridin-1-ylcarbonyl)benzamide (Compound No. 76),
N-[1-(2,6-Dichlorobenzoyl)-1H-pyrrolo[3,2-c]pyridin-4-yl]cyclopropanecarboxamide (Compound No. 77),
1-[3,5-Dichloro-4-(1H-pyrrolo[3,2-c]pyridin-1-ylcarbonyl)phenyl]-3-ethylurea (Compound No. 78),
Methyl[3,5-dichloro-4-(1H-pyrrolo[3,2-c]pyridin-1-ylcarbonyl)phenyl]carbamate (Compound No. 79),
1-[3,5-Dichloro-4-(1H-pyrrolo[3,2-c]pyridin-1-ylcarbonyl)phenyl]-3-(2-hydroxyethyl)urea (Compound No. 80),
3-[3,5-Dichloro-4-(1H-pyrrolo[3,2-c]pyridin-1-ylcarbonyl)phenyl]-1,1-dimethylurea (Compound No. 81),
2-Cyano-N-[3,5-dichloro-4-(1H-pyrrolo[3,2-c]pyridin-1-ylcarbonyl)phenyl]acetamide (Compound No. 82),
(2E)-3-[3,5-Dichloro-4-(1H-pyrrolo[3,2-c]pyridin-1-ylcarbonyl)phenyl]prop-2-enamide (Compound No. 83),
(2E)-3-[3,5-Dichloro-4-(1H-pyrrolo[3,2-c]pyridin-1-ylcarbonyl)phenyl]prop-2-enenitrile (Compound No. 84),
N-(Cyclopropylcarbonyl)-N-[1-(2,6-dichloro-4-cyanobenzoyl)-1H-pyrrolo[3,2-c]pyridin-4-yl]cyclopropanecarboxamide (Compound No. 85),
N-{1-(2,6-Dichloro-4-cyanobenzoyl)-1H-pyrrolo[3,2-c]pyridin-4-yl}cyclopropanecarboxamide (Compound No. 86),
N-{1-[2,6-Dichloro-4-(3,5-dimethyl-1,2-oxazol-4-yl)benzoyl]-1H-pyrrolo[3,2-c]pyridin-4-yl}cyclopropanecarboxamide (Compound No. 87),
N-{1-[2,6-Dichloro-4-(3,5-dimethyl-1H-pyrazol-4-yl)benzoyl]-1H-pyrrolo[3,2-c]pyridin-4-yl}cyclopropanecarboxamide (Compound No. 88)
N-{1-[2,6-Dichloro-4-(pyrimidin-5-yl)benzoyl]-1H-pyrrolo[3,2-c]pyridin-4-yl}cyclopropanecarboxamide (Compound No. 89),
[2,6-Dichloro-4-(hydroxymethyl)phenyl](1H-pyrrolo[3,2-c]pyridin-1-yl)methanone (Compound No. 90),
3,5-Dichloro-4-({4-[(cyclopropylcarbonyl)amino]-1H-pyrrolo[3,2-c]pyridin-1-yl}carbonyl)-N-(2-hydroxyethyl)benzamide (Compound No. 91), 4-{[4-(Acetylamino)-1H-pyrrolo[3,2-c]pyridin-1-yl]carbonyl}-3,5-dichloro-N-ethylbenzamide (Compound No. 92), 3,5-Dichloro-4-({4-[(cyclopropylcarbonyl)amino]-1H-pyrrolo[3,2-c]pyridin-1-yl}carbonyl)-N-ethylbenzamide (Compound No. 93), N-[3,5-Dichloro-4-(1H-pyrrolo[3,2-c]pyridin-1-ylcarbonyl)phenyl]-2-fluoroacetamide (Compound No. 94), 3,5-Dichloro-4-(1H-pyrrolo[3,2-c]pyridin-1-ylcarbonyl)benzonitrile (Compound No. 95), N-{1-[2,6-Dichloro-4-(hydroxymethyl)benzoyl]-1H-pyrrolo[3,2-c]pyridin-4-yl}cyclopropanecarboxamide (Compound No. 96), N-{1-[2,6-Dichloro-4-(hydroxymethyl)benzoyl]-1H-pyrrolo[3,2-c]pyridin-4-yl}acetamide (Compound No. 97), 3,5-Dichloro-4-({4-[(cyclopropylcarbonyl)amino]-1H-pyrrolo[3,2-c]pyridin-1-yl}carbonyl)-N-(2-methoxyethyl)benzamide (Compound No. 98), N-[1-(2,6-Dichloro-4-cyanobenzoyl)-1H-pyrrolo[3,2-c]pyridin-4-yl]acetamide (Compound No. 99), 3,5-Dichloro-4-({4-[(cyclopropylcarbonyl)amino]-1H-pyrrolo[3,2-c]pyridin-1-yl}carbonyl)benzamide (Compound No. 100), 4-{[4-(Acetylamino)-1H-pyrrolo[3,2-c]pyridin-1-yl]carbonyl}-3,5-dichloro-N-(2-methoxyethyl)benzamide (Compound No. 101), Methyl[1-(2-chloro-6-fluorobenzoyl)-1H-pyrrolo[3,2-c]pyridin-4-yl]carbamate (Compound No. 102), N-(1-{2,6-Dichloro-4-[(ethylcarbamoyl)amino]benzoyl}-1H-pyrrolo[3,2-c]pyridin-4-yl)cyclopropanecarboxamide (Compound No. 103), 1-[3,5-Dichloro-4-(1H-pyrrolo[3,2-c]pyridin-1-ylcarbonyl)phenyl]-3-(2-methoxyethyl)urea (Compound No. 104), 4-{[4-(Acetylamino)-1H-pyrrolo[3,2-c]pyridin-1-yl]carbonyl}-3,5-dichloro-N-methylbenzamide (Compound No. 105), 3,5-Dichloro-4-({4-[(cyclopropylcarbonyl)amino]-1H-pyrrolo[3,2-c]pyridin-1-yl}carbonyl)-N-methylbenzamide (Compound No. 106), 3,5-Dichloro-4-({4-[(cyclopropylcarbonyl)amino]-1H-pyrrolo[3,2-c]pyridin-1-yl}carbonyl)-N-(propan-2-yl)benzamide (Compound No. 107), Methyl {1-[2,6-dichloro-4-(ethylcarbamoyl)benzoyl]-1H-pyrrolo[3,2-c]pyridin-4-yl}carbamate (Compound No. 108), N-(1-{2,6-Dichloro-4-[(cyclopropylcarbonyl)amino]benzoyl}-1H-pyrrolo[3,2-c]pyridin-4-yl)cyclopropanecarboxamide (Compound No. 109), N-{1-[4-(Acetylamino)-2,6-dichlorobenzoyl]-1H-pyrrolo[3,2-c]pyridin-4-yl}cyclopropanecarboxamide (Compound No. 110), N-[1-(2,6-Dichloro-4-{[(2-methoxyethyl)carbamoyl]amino}benzoyl)-1H-pyrrolo[3,2-c]pyridin-4-yl]cyclopropanecarboxamide (Compound No. 111), N-[1-(2,6-Dichloro-4-{[(2-hydroxyethyl)(methyl)carbamoyl]amino}benzoyl)-1H-pyrrolo[3,2-c]pyridin-4-yl]cyclopropanecarboxamide (Compound No. 112), N-(1-{2,6-Dichloro-4-[(cyclopropylcarbamoyl)amino]benzoyl}-1H-pyrrolo[3,2-c]pyridin-4-yl)cyclopropanecarboxamide (Compound No. 113), N-(1-{2,6-Dichloro-4-[(cyclopropylcarbamoyl)amino]benzoyl}-1H-pyrrolo[3,2-c]pyridin-4-yl)acetamide (Compound No. 114), N-[1-(2,6-Dichloro-4-{[(2-hydroxyethyl)carbamoyl]amino}benzoyl)-1H-pyrrolo[3,2-c]pyridin-4-yl]cyclopropanecarboxamide (Compound No. 115), N-[1-(2,6-Dichloro-4-{[(2-hydroxyethyl)carbamoyl]amino}benzoyl)-1H-pyrrolo[3,2-c]pyridin-4-yl]acetamide (Compound No. 116), N-(1-{2,6-Dichloro-4-[(ethylcarbamoyl)amino]benzoyl}-1H-pyrrolo[3,2-c]pyridin-4-yl)acetamide (Compound No. 117), 3,5-Dichloro-4-[(3-chloro-1H-pyrrolo[3,2-c]pyridin-1-yl)carbonyl]-N-ethylbenzamide (Compound No. 118), 3,5-Dichloro-4-[(3-chloro-1H-pyrrolo[3,2-c]pyridin-1-yl)carbonyl]benzonitrile (Compound No. 119), N-[1-(2,6-Dichlorobenzoyl)-1H-pyrrolo[3,2-c]pyridin-6-yl]cyclopropanecarboxamide (Compound No. 120), Methyl 3,5-dichloro-4-({4-[(cyclopropylcarbonyl)amino]-1H-pyrrolo[3,2-c]pyridin-1-yl}carbonyl)benzoate (Compound No. 121)

3,5-Dichloro-4-({4-[(cyclopropylcarbonyl)amino]-1H-pyrrolo[3,2-c]pyridin-1-yl}carbonyl)-N-[2-(dimethylamino)ethyl]benzamide (Compound No. 122), 3,5-Dichloro-4-({4-[(cyclopropylcarbonyl)amino]-1H-pyrrolo[3,2-c]pyridin-1-yl}carbonyl)-N-(3-hydroxypropyl)benzamide (Compound No. 123), 3,5-Dichloro-4-({4-[(cyclopropylcarbonyl)amino]-1H-pyrrolo[3,2-c]pyridin-1-yl}carbonyl)-N-[2-(2-hydroxyethoxyl)ethyl]benzamide (Compound No. 124), 3,5-Dichloro-4-({4-[(cyclopropylcarbonyl)amino]-1H-pyrrolo[3,2-c]pyridin-1-yl}carbonyl-N-[2-(morpholin-4-yl)ethyl]benzamide (Compound No. 125), Ethyl N-[3,5-dichloro-4-({4-[(cyclopropylcarbonyl)amino]-1H-pyrrolo[3,2-c]pyridin-1-yl}carbonyl)benzoyl]-b-alaninate (Compound No. 126), N-(2-Aminoethyl)-3,5-dichloro-4-({4-[(cyclopropylcarbonyl)amino]-1H-pyrrolo[3,2-c]pyridin-1-yl}carbonyl)benzamide (Compound No. 127), 4-{[4-(Acetylamino)-1H-pyrrolo[3,2-c]pyridin-1-yl]carbonyl}-3,5-dichloro-N-[2-(dimethylamino)ethyl]benzamide (Compound No. 128), Ethyl N-(4-{[4-(acetylamino)-1H-pyrrolo[3,2-c]pyridin-1-yl]carbonyl}-3,5-dichlorobenzoyl)-b-alaninate (Compound No. 129), 3,5-Dichloro-4-({6-[(cyclopropylcarbonyl)amino]-1H-pyrrolo[3,2-c]pyridin-1-yl}carbonyl)-N-ethylbenzamide (Compound No. 130), 3,5-Dichloro-4-({4-[(cyclopropylcarbonyl)amino]-1H-pyrrolo[3,2-c]pyridin-1-yl}carbonyl)-N-(3-methoxypropyl)benzamide (Compound No. 131), 3,5-Dichloro-N-cyclobutyl-4-({4-[(cyclopropylcarbonyl)amino]-1H-pyrrolo[3,2-c]pyridin-1-yl}carbonyl)benzamide (Compound No. 132), 3,5-Dichloro-4-({4-[(cyclopropylcarbonyl)amino]-1H-pyrrolo[3,2-c]pyridin-1-yl}carbonyl)-N-propylbenzamide (Compound No. 133), 4-{[4-(Acetylamino)-1H-pyrrolo[3,2-c]pyridin-1-yl]carbonyl}-3,5-dichloro-N-(3-methoxypropyl)benzamide (Compound No. 134), N-[3,5-Dichloro-4-({4-[(cyclopropylcarbonyl)amino]-1H-pyrrolo[3,2-c]pyridin-1-yl}carbonyl)benzoyl]-b-alanine (Compound No. 135), 3,5-Dichloro-4-({3-chloro-4-[(cyclopropylcarbonyl)amino]-1H-pyrrolo[3,2-c]pyridin-1-yl}carbonyl)-N-ethylbenzamide (Compound No. 136), N-[1-(2,6-dichloro-4-cyanobenzoyl)-1H-pyrrolo[3,2-c]pyridin-6-yl]cyclopropanecarboxamide (Compound No. 137), 3,5-Dichloro-N-ethyl-4-{[4-(propanoylamino)-1H-pyrrolo[3,2-c]pyridin-1-yl]carbonyl}benzamide (Compound No. 138), 3,5-Dichloro-4-({4-[(cyclopropylcarbonyl)amino]-1H-pyrrolo[3,2-c]pyridin-1-yl}carbonyl)-N-[2-(1H-indol-3-yl)ethyl]benzamide (Compound No. 139), 3,5-Dichloro-N-methyl-4-{[4-(propanoylamino)-1H-pyrrolo[3,2-c]pyridin-1-yl]carbonyl}benzamide (Compound No. 140), Ethyl N-[3,5-dichloro-4-({4-[(cyclopropylcarbonyl)amino]-1H-pyrrolo[3,2-c]pyridin-1-yl}carbonyl)benzoyl]alaninate (Compound No. 141), 3,5-Dichloro-4-({4-[(cyclopropylcarbonyl)amino]-1H-pyrrolo[3,2-c]pyridin-1-yl}carbonyl)-N-[2-(2-oxoimidazolidin-1-yl)ethyl]benzamide (Compound No. 142), 3,5-Dichloro-4-({4-[(cyclopropylcarbonyl)amino]-1H-pyrrolo[3,2-c]pyridin-1-yl}carbonyl)-N-(2,3-dihydroxypropyl)benzamide (Compound No. 143), 3,5-Dichloro-4-({4-[(cyclopropylcarbonyl)amino]-1H-pyrrolo[3,2-c]pyridin-1-yl}carbonyl)-N-[2-(thiophen-2-yl)ethyl]benzamide (Compound No. 144), 3,5-Dichloro-4-({4-[(cyclopropylcarbonyl)amino]-1H-pyrrolo[3,2-c]pyridin-1-yl}carbonyl)-N-[2-(pyridin-4-yl)ethyl]benzamide (Compound No. 145), 3,5-Dichloro-N-cyclopropyl-4-({4-[(cyclopropylcarbonyl)amino]-1H-pyrrolo[3,2-c]pyridin-1-yl}carbonyl)benzamide (Compound No. 146), 3,5-Dichloro-4-({4-[(cyclopropylcarbonyl)amino]-1H-pyrrolo[3,2-c]pyridin-1-yl}carbonyl)-N-(pyridin-2-ylmethyl)benzamide (Compound No. 147), 3,5-Dichloro-4-({4-[(cyclopropylcarbonyl)amino]-1H-pyrrolo[3,2-c]pyridin-1-yl}carbonyl)-N-[2-(pyrrolidin-1-yl)ethyl]benzamide (Compound No. 148), 3,5-Dichloro-4-({4-[(cyclopropylcarbonyl)amino]-1H-pyrrolo[3,2-c]pyridin-1-yl}carbonyl)-N-[3-(morpholin-4-yl)propyl]benzamide (Compound No. 149), 3,5-Dichloro-4-({4-[(cyclopropylcarbonyl)amino]-1H-pyrrolo[3,2-c]pyridin-1-yl}carbonyl)-N-[2-(piperidin-1-yl)ethyl]benzamide (Compound No. 150), 3,5-Dichloro-4-({4-[(cyclopropylcarbonyl)amino]-1H-pyrrolo[3,2-c]pyridin-1-yl}carbonyl)-N-(1-hydroxypropan-2-yl)benzamide (Compound No. 151), N-[3,5-Dichloro-4-({4-[(cyclopropylcarbonyl)amino]-1H-pyrrolo[3,2-c]pyridin-1-yl}carbonyl)benzoyl]-L-alanine (Compound No. 152), 3,5-Dichloro-4-({3-chloro-4-[(cyclopropylcarbonyl)amino]-1H-pyrrolo[3,2-c]pyridin-1-yl}carbonyl)-N-methylbenzamide (Compound No. 153), 3,5-Dichloro-4-({4-[(cyclopropylcarbonyl)amino]-1H-pyrrolo[3,2-c]pyridin-1-yl}carbonyl)-N-(2-fluoroethyl)benzamide (Compound No. 154), 3,5-Dichloro-4-({4-[(cyclopropylcarbonyl)amino]-1H-pyrrolo[3,2-c]pyridin-1-yl}carbonyl)-N-(2,2,2-trifluoroethyl)benzamide (Compound No. 155), 3,5-Dichloro-4-({4-[(cyclopropylcarbonyl)amino]-1H-pyrrolo[3,2-c]pyridin-1-yl}carbonyl)-N-(3-ethoxypropyl)benzamide (Compound No. 156), 4-{[4-(Acetylamino)-1H-pyrrolo[3,2-c]pyridin-1-yl]carbonyl}-3,5-dichloro-N-(2-fluoroethyl)benzamide (Compound No. 157), 4-{[4-(Acetylamino)-1H-pyrrolo[3,2-c]pyridin-1-yl]carbonyl}-3,5-dichloro-N-[2-(1H-indol-3-yl)ethyl]benzamide (Compound No. 158), 3,5-Dichloro-4-({4-[(cyclopropylcarbonyl)amino]-1H-pyrrolo[3,2-c]pyridin-1-yl}carbonyl)-N-[(2R)-1-methoxypropan-2-yl]benzamide (Compound No. 159), 4-{[4-(Acetylamino)-1H-pyrrolo[3,2-c]pyridin-1-yl]carbonyl}-3,5-dichloro-N-(pyridin-2-ylmethyl)benzamide (Compound No. 160), 4-{[4-(Acetylamino)-1H-pyrrolo[3,2-c]pyridin-1-yl]carbonyl}-3,5-dichloro-N-[2-(pyridin-2-yl)ethyl]benzamide (Compound No. 161), 4-{[4-(Acetylamino)-1H-pyrrolo[3,2-c]pyridin-1-yl]carbonyl}-3,5-dichloro-N-[3-(morpholin-4-yl)propyl]benzamide (Compound No. 162), N-(1-{2,6-Dichloro-4-[(methylamino)methyl]benzoyl}-1H-pyrrolo[3,2-c]pyridin-4-yl)cyclopropanecarboxamide (Compound No. 163), N-(1-{2,6-Dichloro-4-[(ethylamino)methyl]benzoyl}-1H-pyrrolo[3,2-c]pyridin-4-yl)cyclopropanecarboxamide (Compound No. 164), N-{1-[2,6-Dichloro-4-({[2-(2-oxoimidazolidin-1-yl)ethyl]amino}methyl)benzoyl]-1H-pyrrolo[3,2-c]pyridin-4-yl}cyclopropanecarboxamide (Compound No. 165), N-{1-[2,6-Dichloro-4-({[3-(morpholin-4-yl)propyl]amino}methyl)benzoyl]-1H-pyrrolo[3,2-c]pyridin-4-yl}cyclopropanecarboxamide (Compound No. 166), N-[1-(2,6-Dichloro-4-{[(3-hydroxypropyl)amino]methyl}benzoyl)-1H-pyrrolo[3,2-c]pyridin-4-yl]cyclopropanecarboxamide (Compound No. 167), 3,5-Dichloro-4-({4-[(cyclopropylcarbonyl)amino]-1H-pyrrolo[3,2-c]pyridin-1-yl}carbonyl)-N-[2-(1H-pyrrol-1-yl)ethyl]benzamide (Compound No. 168), 3,5-Dichloro-4-({4-[(cyclopropylcarbonyl)amino]-1H-pyrrolo[3,2-c]pyridin-1-yl}carbonyl)-N-[2-(pyridin-3-yl)ethyl]benzamide (Compound No. 169), 3,5-Dichloro-4-({4-[(cyclopropylcarbonyl)amino]-1H-pyrrolo[3,2-c]pyridin-1-yl}carbonyl)-N-(cyclopropylmethyl)benzamide (Compound No. 170), 3,5-Dichloro-4-({4-[(cyclopropylcarbonyl)amino]-1H-pyrrolo[3,2-c]pyridin-1-yl}carbonyl)-N-(piperidin-3-ylmethyl)benzamide (Compound No. 171), N-[1-(2,6-Dichlorobenzoyl)-1H-pyrrolo[3,2-c]pyridin-4-yl]acetamide (Compound No. 172), or a pharmaceutically acceptable salt thereof, a prodrug thereof or a hydrate thereof.

The present invention provides a pharmaceutical composition comprising a compound of formula (I), a pharmaceutically acceptable salt thereof, a prodrug thereof, a hydrate thereof as its active ingredient and one or more pharmaceutically acceptable excipient(s).

Another aspect of the present invention provides a use of a compound of formula (I) or a pharmaceutically acceptable salt thereof, a prodrug thereof or a hydrate thereof, for the manufacture of a medicament for treating or preventing disease, condition or disorder responsive to the inhibition of signal transduction pathway mediated at least in part by protein kinase activity.

In another aspect, there is provided a method for treating or preventing a disease, condition or disorder responsive to the inhibition of signal transduction pathway mediated at least in part by protein kinase activity in a patient comprising the steps of administering to the said patient a therapeutically effective amount of a compound of formula (I), a pharmaceutically acceptable salt thereof, a prodrug thereof, a hydrate thereof or a pharmaceutical composition thereof.

The present invention also provides a method for treating or preventing autoimmune, inflammatory or proliferative disease, condition or disorder.

In certain embodiments, the protein kinase is Janus kinase. In another embodiment, Janus kinase represents JAK1, JAK2, JAK3, TYK2 or combination thereof.

In a preferred embodiment, there is provided a method for treating or preventing a disease, condition or disorder mediated by JAK1, JAK2, JAK3, TYK2 or combination thereof, in a patient comprising the steps of administering to the said patient a therapeutically effective amount of a compound of formula (I), a pharmaceutically acceptable salt thereof, or a pharmaceutical composition thereof.

In yet another embodiment the disease is auto-immune or inflammatory disease selected from, but not limited to, asthma, rheumatoid arthritis, psoriasis, multiple sclerosis, chronic obstructive pulmonary disease or inflammatory bowel disease.

The present invention provides a compound of formula (I), or a pharmaceutically acceptable salt thereof, a prodrug thereof or a hydrate thereof for use in a method of treating or preventing disease, condition or disorder associated with protein kinase.

The present invention also provides processes and intermediates disclosed herein that are useful for preparing compounds of formula (I) and salts thereof.

The aforementioned aspects and embodiments, and other aspects, objects, features and advantages of the present invention will be apparent from the following detailed description and the appended claims thereof.

DETAILED DESCRIPTION OF THE INVENTION

As used herein the following definitions apply unless clearly indicated otherwise.

It should be understood that unless expressly stated to the contrary, "a compound of general formula (I)" refers to and includes any and all compounds described by formula (I), its embodiments, as well as subgenuses, inclusive of all salts, prodrugs and hydrates thereof. It should also be noted that the singular forms "a" "an" and "the" include plural reference unless the context clearly dictates otherwise.

The term "halo" or "halogen" as used herein alone or in combination refers to fluorine, chlorine, bromine, and iodine.

The term "alkyl" as used herein alone or in combination refers to alkane-derived radical containing from 1 to 15 carbon atoms that includes a straight alkyl or branched alkyl. The straight chain or branched alkyl group is attached at any available point to produce a stable compound. In many embodiments, alkyl is a straight or branched alkyl group containing from 1-6, 1-4, or 1-3 carbon atoms, such as methyl, ethyl, propyl, isopropyl, butyl, t-butyl, and the like. A "substituted alkyl" denotes alkyl that is independently substituted, unless indicated otherwise, with one or more, preferably 1, 2, 3, 4 or 5, more preferably 1, 2 or 3 substituents, attached at any available atom to produce a stable compound, wherein the substituents are selected from, but are not limited to, Cl, F, Br, —NO$_2$, —CN, —OR$^f$, —SR$^f$, —C(O)R$^f$, —C(S) R$^f$, —C(O)OR$^f$, C(S)OR$^f$, (CH)$_r$NR$^f$R$^g$, —C(O)NR$^f$R$^g$, —C(S)NR$^f$R$^g$, —C(NH)NR$^f$R$^g$, —NR$^f$C(O)R$^g$, —NR$^f$C(S) R$^g$, —NR$^f$C(O)NR$^g$R$^h$, —NR$^f$C(S)NR$^g$R$^h$, —NR$^f$S(O)$_2$R$^g$, —NR$^f$S(O)$_2$NR$^g$R$^h$, —NR$^f$C(O)OR$^g$, —CONR$^f$R$^g$, —OC (O)R$^f$, —OC(S)R$^f$, —(CH)$_r$halo, —S(O)$_p$R$^f$, —S(O)$_p$NR$^f$R$^g$, R$^i$ or R$^j$.

The term "alkenyl" as used herein alone or in combination refers to straight or branched hydrocarbon containing 2 to 10 carbon atoms and at least one, preferably 1-3, more preferably 1-2, most preferably one, carbon to carbon double bond, which may be present either in straight chain or branched chain. Examples of alkenyl include, but are not limited to, ethenyl, propenyl, isopropenyl, butenyl, and the like. A "substituted alkenyl" denotes alkenyl that is independently substituted, unless indicated otherwise, with one or more, preferably 1, 2, 3, 4 or 5, more preferably 1, 2 or 3 substituents, attached at any available atom to produce a stable compound, wherein the substituents are selected from, but are not limited to, Cl, F, Br, —NO$_2$, —CN, —OR$^f$, —SR$^f$, —C(O)R$^f$, —C(S) R$^f$, —C(O)OR$^f$, —C(S)OR$^f$, —(CH)$_r$NR$^f$R$^g$, —C(O)NR$^f$R$^g$, —C(S)NR$^f$R$^g$, —C(NH)NR$^f$R$^g$, —NR$^f$C(O)R$^g$, NR$^f$C(S)R$^g$, —NR$^f$C(O)NR$^g$R$^h$, —NR$^f$C(S)NR$^g$R$^h$, —NR$^f$S(O)$_2$R$^g$, —NR$^f$S(O)$_2$NR$^g$R$^h$, —NR$^f$C(O)OR$^g$, CONR$^f$R$^g$, —OC(O) R$^f$, —OC(S)R$^f$, —(CH)$_r$halo, —S(O)$_p$R$^f$, —S(O)$_p$NR$^f$R$^g$, R$^i$ or R$^j$.

The term "alkynyl" as used herein alone or in combination refers to straight or branched hydrocarbon containing 2 to 10 carbon atoms and at least one, preferably one carbon to carbon triple bond, which may be present either in straight chain or branched chain. Examples of alkynyl include, but are not limited to, ethynyl, propynyl, butyryl, and the like. A "substituted alkynyl" denotes alkynyl that is independently substituted, unless indicated otherwise, with one or more, preferably 1, 2, 3, 4 or 5, more preferably 1, 2 or 3 substituents, attached at any available atom to produce a stable compound, wherein the substituents are selected from, but are not limited to, Cl, F, Br, —NO$_2$, —CN, —OR$^f$, —SR$^f$, —C(O)R$^f$, —C(S) R$^f$, —C(O)OR$^f$, —C(S)OR$^f$, —(CH)$_r$NR$^f$R$^g$, —C(O)NR$^f$R$^g$, —C(S)NR$^f$R$^g$, —C(NH)NR$^f$R$^g$, —NR$^f$C(O)R$^g$, —NR$^f$C(S) R$^g$, —NR$^f$C(O)NR$^g$R$^h$, —NR$^f$C(S)NR$^g$R$^h$, —NR$^f$S(O)$_2$R$^g$, —NR$^f$S(O)$_2$NR$^g$R$^h$, —NR$^f$C(O)OR$^g$, —CONR$^f$R$^g$, —OC (O)R$^f$, —OC(S)R$^f$, —(CH)$_r$halo, —S(O)$_p$R$^f$, —S(O)$_p$NR$^f$R$^g$, R$^i$, or R$^j$.

The term "alkoxy" as used herein alone or in combination refers to alkyl or substituted alkyl, as defined above, bonded to an oxygen atom. Representative examples of alkoxy group include, but are not limited to methoxy, ethoxy, tert-butoxy, trifluoromethoxy, etc.

The term "cycloalkyl" as used herein refers to saturated or unsaturated non-aromatic monocyclic, bicyclic or tricyclic carbon ring systems of 3 to 10, preferably 3 to 8, more preferably 3 to 6 ring members per ring. Examples of cycloalkyl include, but are not limited to, cyclopropyl, cyclobutyl, cyclopentyl, cyclohexyl, adamantly, and the like. A "substituted cycloalkyl" denotes cycloalkyl that is independently substituted, unless indicated otherwise, with one or more, preferably 1, 2, 3, 4 or 5, more preferably 1, 2 or 3 substituents, attached at any available atom to produce a stable compound, wherein the substituents are selected from, but are not limited to, Cl, F, Br, —NO$_2$, —CN, —OR$^f$, —SR$^f$, —C(O)R$^f$, —C(S) R$^f$, —C(O)OR$^f$, —C(S)OR$^f$, —(CH)$_r$NR$^f$R$^g$, —C(O)NR$^f$R$^g$, —C(S)NR$^f$R$^g$, —C(NH)NR$^f$R$^g$, —NR$^f$C(O)R$^g$, —NR$^f$C(S) R$^g$, —NR$^f$C(O)NR$^g$R$^h$, —NR$^f$C(S)NR$^g$R$^h$, —NR$^f$S(O)$_2$R$^g$, —NR$^f$S(O)$_2$NR$^g$R$^h$, —NR$^f$C(O)OR$^g$, —CONR$^f$R$^g$, —OC (O)R$^f$, —OC(S)R$^f$, —(CH)$_r$halo, —S(O)$_p$R$^f$, —S(O)$_p$NR$^f$R$^g$, R$^i$ or R$^j$.

The term "heterocycloalkyl" as used herein refers to a saturated or unsaturated non-aromatic mono or polycyclic cycloalkyl group in which from 1 to 3 carbon atoms in the ring are replaced by heteroatom selected from oxygen, sulphur, phosphorus or nitrogen. Heterocycloalkyl is also intended to include oxidized S or N, such as sulfinyl, sulfonyl, and N-oxide of tertiary ring nitrogen. Heterocycloalkyl is also intended to include compounds, in which a ring carbon may be oxo substituted, i.e., the ring carbon is carbonyl group, such as lacyones and lactams. Heterocycloalkyl is also intended to include fused, bridged and spiro ring system. Preferably, heterocycloalkyl rings are optionally fused with benzo or 5 to 6 membered heteroaryl ring. The point of attachment of the heterocycloalkyl ring is at a carbon or nitrogen atom such that a stable ring is retained. Examples of heterocycloalkyl include, but are not limited to, oxiranyl, thiaarnyl, aziridinyl, oxetanyl, thiatanyl, azetidinyl, tetrahydrofuranyl, tetrahydrothiophenyl, pyrrolidinyl, tetrahydropyranyl, pyranyl, tetrahydrothiopyranyl, thiopyranyl, piperidinyl, 1,4-dioxanyl, 1,4-oxathianyl, morpholinyl, thiomorpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-azaphosphinanyl, 1,4-diazepanyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, chromanyl, chromenyl, isooxazolidinyl, 1,3-oxazolidin-3-yl, isothiazolidinyl, 1,3-thiazolidin-3-yl, 1,2-pyrazolidin-2-yl, 1,3-pyrazolidin-1-yl, 7-oxa-1-aza-spiro[4,4]nonanyl, 3-azabicyclo[3.1.0]hexanyl, indolinyl, dihydroindolinyl, octahydro-1H-indolyl, octahydro-2H-pyrido[1,2-a]pyrazinyl, 3-azabicyclo[4.1.0]heptanyl, 3,4-dihydro-2H-pyranyl, 1,2,3,4-tetrahydropyridinyl, 1,2,5,6-tetrahydropyridinyl, or tetrahydro-1H-benzo[d]azepinyl, etc. A "substituted heterocycloalkyl" denotes heterocycloalkyl that is independently substituted, unless indicated otherwise, with one or more, preferably 1, 2, 3, 4 or 5, more preferably 1, 2 or 3 substituents, attached at any available atom to produce a stable compound, wherein the substituents are selected from, but are not limited to, Cl, F, Br, —$NO_2$, —CN, —$OR^f$, —$SR^f$, —$C(O)R^f$, —$C(S)R^f$, —$C(O)OR^f$, —$C(S)OR^f$, —$(CH)_r NR^f R^g$, —$C(O)NR^f R^g$, —$C(S)NR^f R^g$, —$C(NH)NR^f R^g$, —$NR^f C(O)R^g$, $NR^f C(S)R^g$, —$NR^f C(O)NR^g R^h$, —$NR^f C(S)NR^g R^h$, —$NR^f S(O)_2 R^g$, —$NR^f S(O)_2 NR^g R^h$, —$NR^f C(O)OR^g$, —$CONR^f R^g$, —$OC(O)R^f$, —$OC(S)R^f$, —$(CH)_r halo$, —$S(O)_p R^f$, —$S(O)_p NR^f R^g$, $R^i$ or $R^j$.

The term "heterocycloalkylalkyl" as used herein refers to alkyl group, as defined above, having a heterocycloalkyl group, as defined above, as a substituent. Examples include, but are not limited to, piperidinylmethyl, pyrrolidinylethyl, etc.

The term "aryl" as used herein alone or in combination refers to monocyclic and polycyclic aromatic hydrocarbon ring systems containing the requisite number of carbon atoms as described above. Representative examples include, but not limited to, phenyl, naphhthyl, etc. A "substituted aryl" denotes aryl that is independently substituted, unless indicated otherwise, with one or more, preferably 1, 2, 3, 4 or 5, more preferably 1, 2 or 3 substituents, attached at any available atom to produce a stable compound, wherein the substituents are selected from, but are not limited to, Cl, F, Br, —$NO_2$, —CN, —$OR^f$, —$SR^f$, —$C(O)R^f$, —$C(S)R^f$, —$C(O)OR^f$, —$C(S)OR^f$, —$(CH)_r NR^f R^g$, —$C(O)NR^f R^g$, —$C(S)NR^f R^g$, —$C(NH)NR^f R^g$, —$NR^f C(O)R^g$, —$NR^f C(S)R^g$, —$NR^f C(O)NR^g R^h$, —$NR^f C(S)NR^g R^h$, —$NR^f S(O)_2 R^g$, —$NR^f S(O)_2 NR^g R^h$, —$NR^f C(O)OR^g$, —$CONR^f R^g$, —$OC(O)R^f$, —$OC(S)R^f$, —$(CH)_r halo$, —$S(O)_p R^f$, —$S(O)_p NR^f R^g$, $R^i$ or $R^j$.

The term "aralkyl" as used herein alone or in combination refers to alkyl, as defined above, having aryl group, as defined above, as a substituent, for example, benzyl, phenylethyl, etc.

The term "heteroaryl" as used herein alone or in combination refers to monocyclic or polycyclic aromatic ring systems containing requisite number of carbon atoms, and at least one heteroatom selected from N, O or S. polycyclic ring systems may contain aromatic portions, while other portions of the ring system may be fully saturated or non-aromatic. Representative examples of heteroaryl include, but are not limited to pyrrolyl, furanyl, thiophenyl, thienyl, pyrazolyl, imidazolyl, isoxazolyl, oxazolyl, isothiazolyl, thiazolyl, 1,2,3-triazolyl, 1,2,4-triazolyl, tetrazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridinyl, pyridazinyl, pyrimidinyl, pyrazinyl, 1,2,3-triazinyl, pyrazolo[3,4-b]pyridinyl, cinnolinyl, pteridinyl, purinyl, 6,7-dihydro-5H-[1]pyrindinyl, benzo[b]thiophenyl, benzoxazolyl, benzothiazolyl, benzoisothiazolyl, benzoisoxazolyl, benzimidazolyl, benzofuranyl, isobenzofuranyl, isoindolyl, indolyl, indolizinyl, indazolyl, isoquinolinyl, quinolinyl, phthalazinyl, quinoxalinyl, quinazolinyl, benzoxazinyl, and the like. A "substituted heteroaryl" denotes heteroaryl that is independently substituted, unless indicated otherwise, with one or more, preferably 1, 2, 3, 4 or 5, more preferably 1, 2 or 3 substituents, attached at any available atom to produce a stable compound, wherein the substituents are selected from, but are not limited to, Cl, F, Br, —$NO_2$, —CN, —$OR^f$, —$SR^f$, —$C(O)R^f$, —$C(S)R^f$, —$C(O)OR^f$, —$C(S)OR^f$, —$(CH)_r NR^f R^g$, —$C(O)NR^f R^g$, —$C(S)NR^f R^g$, —$C(NH)NR^f R^g$, —$NR^f C(O)R^g$, —$NR^f C(S)R^g$, —$NR^f C(O)NR^g R^h$, —$NR^f C(S)NR^g R^h$, —$NR^f S(O)_2 R^g$, —$NR^f S(O)_2 NR^g R^h$, —$NR^f C(O)OR^g$, —$CONR^f R^g$, —$OC(O)R^f$, —$OC(S)R^f$, —$(CH)_r halo$, —$S(O)_p R^f$, —$S(O)_p NR^f R^g$, $R^i$ or $R^j$.

The term "heteroarylalkyl" as used herein refers to alkyl group, as defined above, having a heteroaryl group, as defined above, as a substituent. Examples include, but are not limited to, pyridinylmethyl, pyrrolidinylethyl, etc.

The term "optionally substituted alkyl, alkenyl, alkenyl, cycloalkyl, aryl and heteroaryl" as used herein refers to alkyl, alkenyl, alkenyl, cycloalkyl, aryl and heteroaryl optionally substituted with one or more substituent(s) independently selected from, but are not limited to, halogen, —$NO_2$, —CN, —$OR^f$, —$SR^f$, —$C(O)R^f$, —$C(S)R^f$, —$C(O)OR^f$, $C(S)OR^f$, —$(CH)_r NR^f R^g$, —$C(O)NR^f R^g$, —$C(S)NR^f R^g$, —$C(NH)NR^f R^g$, —$NR^f C(O)R^g$, —$NR^f C(S)R^g$, —$NR^f C(O)NR^g R^h$, —$NR^f C(S)NR^g R^h$, —$NR^f S(O)_2 R^g$, —$NR^f S(O)_2 NR^g R^h$, —$NR^f C(O)OR^g$, —$CONR^f R^g$, —$OC(O)R^f$, —$OC(S)R^f$, —$(CH)_r halo$, —$S(O)_p R^f$, —$S(O)_p NR^f R^g$, $R^i$ or $R^j$. In a preferred embodiment, one or more substituents are selected from $C_1$-$C_6$ alkyl, halogen, —$NO_2$, —CN, —$OR^f$, —$C(O)R^f$ or —$NR^f R^g$, $C(O)NR^f R^g$, —$NR^f C(O)R^g$ or heteroaryl.

The variables $R^f$, $R^g$, $R^h$, $R^i$ and $R^j$ as used in the description of optional substituents for alkyl, alkynyl, cycloalkyl, heterocycloalkyl, aryl, and heteroaryl are as follows.

$R^f$, $R^g$ and $R^h$ independently represent H, $R^i$ or $R^j$. $R^f$ and $R^g$ or $R^g$ and $R^h$ along with nitrogen atom to which they are attached form 3-8 membered optionally substituted heterocyclyl group, optionally containing one or more heteroatom(s) selected from N, O or S.

$R^i$ represents alkyl, alkenyl, alkynyl or cycloalkyl, wherein alkyl, alkenyl, alkynyl or cycloalkyl is optionally substituted with one or more, preferably 1, 2 or 3 substitutents selected from, but are not limited to, halogen, —$NO_2$, —CN, —$OR^f$, —$SR^f$, —$C(O)R^f$, —$C(S)R^f$, —$C(O)OR^f$, —$C(S)OR^f$, —$(CH)_r NR^f R^g$, —$C(O)NR^f R^g$, —$C(S)NR^f R^g$, —$C(NH)NR^f R^g$, —$NR^f C(O)R^g$, —$NR^f C(S)R^g$, —$NR^f C(O)NR^g R^h$, —$NR^f C(S)NR^g R^h$, —$NR^f S(O)_2 R^g$, —$NR^f S(O)_2 NR^g R^h$, —$NR^f C(O)OR^g$, —$CONR^f R^g$, —$OC(O)R^f$, $OC(S)R^f$, —$(CH)_r halo$, —$S(O)_p R^f$ or —$S(O)_p NR^f R^g$, wherein $R^f$, $R^g$ and $R^h$ are as defined hereinbefore.

$R^j$ represents aryl, heteroaryl and heterocyclyl wherein aryl, heteroaryl or heterocyclyl is optionally substituted with one or more, preferably 1, 2, 3, 4 or 5, more preferably 1, 2 or 3, most preferably 1 or 2 substituents selected from, but are not limited to, halogen, —$NO_2$, —CN, —$OR^f$, —$SR^f$, —$C(O)R^f$, —$C(S)R^f$, —$C(O)OR^f$, —$C(S)OR^f$, —$(CH)_r NR^f R^g$, —$C(O)NR^f R^g$, —$C(S)NR^f R^g$, —$C(NH)NR^f R^g$, —$NR^f C(O)R^g$, —$NR^f C(S)R^g$, —$NR^f C(O)NR^g R^h$, —$NR^f C(S)NR^g R^h$, —$NR^f S(O)_2 R^g$, —$NR^f S(O)_2 NR^g R^h$, —$NR^f C(O)OR^g$, —$CONR^f R^g$, —$OC(O)R^f$, —$OC(S)R^f$, —$(CH)_r halo$, —$S(O)_p R^f$ or —$S(O)_p NR^f R^g$, wherein $R^f$, $R^g$ and $R^h$ are as defined hereinbefore.

Preferred substituents in the heterocyclic compounds of formula (I) according to the present invention are described hereinafter.

The values for $R^1$ include, but are not limited to, H, methyl, ethyl, propyl or —COR⁴, wherein $R^4$ is phenyl optionally substituted with two or more substituents independently selected from $R^5$, $R^6$, $R^7$, $R^8$ or $R^9$.

The values for $R^2$ include, but are not limited to, H, methyl, ethyl, propyl or isopropyl.

The values for $R^3$ include, but are not limited to H, methyl, ethyl, propyl, Cl, Br, F or —COR⁴, wherein $R^4$ is phenyl optionally substituted with two or more substituents selected from $R^5$, $R^6$, $R^7$, $R^8$ or $R^9$.

$R^5$, $R^6$, $R^7$, $R^8$ and $R^9$ independently represent H, alkyl, alkenyl, alkynyl, cycloalkyl, aryl, aralkyl, heteroaryl, heteroarylalkyl, heterocyclyl, heterocyclylalkyl, alkoxy, halo, —NO₂, —(CH₂)$_q$C(O)NR$^c$R$^d$, —(CH₂)$_q$NR$^c$COR$^d$, —(CH₂)$_q$NR$^c$CONR$^c$R$^d$, —(CH₂)$_q$NR$^c$C(O)OR$^d$, —(CH₂)$_q$NR$^c$R$^d$, —(CH═CH)—(CH₂)$_s$C(O)OR$^e$, —(CH═CH)—(CH₂)$_s$CONR$^c$R$^d$, —(CH═CH)—(CH₂)$_s$CN, —(CH═CH)—(CH₂)$_s$R$^e$, —(CH₂)$_s$C(O)OR$^e$, —(CH)$_r$CN, —(CH₂)$_r$OR$^e$, —(CH₂)$_r$R$^e$, —(CH₂)$_r$C(O)OR$^e$, —(CH)$_r$halo, —S(O)$_p$R$^e$, —S(O)$_p$NR$^c$R$^d$, —NR$^c$S(O)$_p$R$^d$, and wherein alkyl, alkenyl, alkynyl, cycloalkyl, aryl, heteroaryl heterocyclyl are optionally substituted and R$^c$, R$^d$, R$^e$, p, q, r and s are as defined hereinbefore.

In one embodiment, $R^5$ and $R^6$ independently represent, but are not limited to, H, Cl, Br, F, —CN, —NO₂, —NH₂, —CH₃, —C₂H₅, —OCF₃, —OCH₃, —CH₂OH or —COOH. In a preferred embodiment, $R^5$ and $R^6$ independently represent H, Cl, Br, F, —CN, —NO₂, —NH₂, —CH₃ or —OCH₃.

In another embodiment, $R^7$ and $R^8$ independently represent, but are not limited to, H, Cl, Br, F, —CN, —NO₂, —NH₂, NHCOCH₃ or NHCOC₂H₅.

In another embodiment, $R^9$ represents, but are not limited to, H, Cl, Br, —CN, —NO₂, —NH₂, —CH₃, —C₂H₅, —OCF₃, —OCH₃, —CH₂OH, —COOH, —C(O)OCH₃, —(CH═CH)—COOH, —(CH═CH)—CH₂COOH, —(CH═CH)—CONH₂, —(CH═CH)—CH₂CONH₂, —(CH═CH)CN, —(CH═CH)CH₂CN, —CO(heterocyclyl), —CH₂CH₂CN, —CH₂CN, —(CH═CH)—CONHC₂H₅, —(CH═CH)phenyl, —(CH═CH)CH₂phenyl, —CH₂CH₂C(O)OC₂H₅, —CH₂CH₂CONHC₂H₅, —CH₂CH₂CONH₂, —CH₂CH₂COOH, —CH₂CH₂CN, —(CH₂)₃(morpholinyl), —CH₂NH(CH₂)₃OH or —CH₂NHC₂H₅.

In another embodiment, $R^9$ represents, but are not limited to, —CONH₂, —CONHCH₃, —CON(CH₃)₂, —CONHC₂H₅, —CONHC₃H₇, —CONHC(CH₃)₂, —CONHCH₂CH₂OH, —CONHCH₂CH₂OCH₃, —CONHCH₂CN, —CONH(cycloalkyl), —CONHCH₂C(CH₃)₂, —CON(C₂H₅)₂, —CONHCH₂CH₂OCH₂CH₂OH, —CONH(CH₂)₁₋₃(heterocyclyl), —CONH(CH₂)₁₋₃(heteroaryl), —CONHCH₂CH(OH)CH₂OH, —CONHCH₂CH₂N(CH₃)₂, —CONH(CH₂)₁₋₃C(O)OCH₃, —CONH(CH₂)₁₋₃C(O)OC₂H₅, —CONHCH(CH₃)C(O)OC₂H₅, —CONHCH(CH₃)C₃H₇, —CONHCH(CH₃)CH₂OH, —CONHCH(CH₃)COOH, —CONH(CH₂)₁₋₃COOH, —CONHCH(CH₃)CH₂OCH₃, —CONHCH₂(cycloalkyl), —CONH(CH₂)₁₋₃OCH₃, —CONH(CH₂)₁₋₃OC₂H₅, —CONH(CH₂)₃CH₃, —CONHCH₂CH₂F, —CONHCH₂CF₃, —CONHCH₂CH₂NH₂, wherein cycloalkyl, heterocyclyl and heteroaryl are optionally substituted.

In another embodiment, $R^9$ represents, but are not limited to, —N(CH₃)₂, —NHCONHC₂H₅, —NHC(O)OCH₃, —NHC(O)O(tert-butyl), —N(benzyl)C(O)O(tert-butyl), NHCONHCH₂CH₂OH, —NHCONHCH₂CH₂OCH₃, —NHCON(CH₃)₂, —NH(heteroaryl), —NHCH₂phenyl, —NHCOCH₂CN, —NHCO(cycloalkyl), —NHCOCH₂OH, —NHCOCH₃, —NHCOC₂H₅, —NHCOCH₂F, —NHCOCH₂Cl, —NHCOCH₂(heteroaryl), —NH(SO₂)CH₃, —NHC(O)OC(CH₃)₃, —NHCH₃, —NH(cycloalkyl), —NHCON(CH₃)CH₂CH₂OH, —NHCONH(cycloalkyl), —NHCONHC₃H₇, —NHCONHC₂H₅, —N(CH₃)CH₂C(O)OCH₃ or —NCH₃CH₂C(O)OH, wherein cycloalkyl, phenyl, heteroaryl and heterocyclyl are optionally substituted.

In another embodiment, $R^9$ represents, but are not limited to, cyclopropyl, cyclobutyl, cyclopentyl, cyclohexyl, morpholinyl, piperazinyl, pyrrolidinyl, azetidinyl, pyrazolyl, imidazolyl, isoxazolyl, oxazolyl, isothiazolyl, thiazolyl, pyridinyl, pyridazinyl, pyrimidinyl or pyrazinyl ring, wherein the ring is optionally substituted with halo, alkyl or alkoxy.

Preferred values for the descriptors R, R' and R" include, but are not limited to, H, Cl, Br, F, —CN, —NH₂, —NHC₂H₅, —NHCH₃, —NH(heteroaryl), —NH(aryl), —NHC(O)OCH₃, —NHCOCH₂Cl, —NHCOCH₂F, —NHCOCH₂CF₃, —CONH₂, —NHCOCH₃, —NHCO-cyclopropyl, —NHCO-cyclobutyl, —NHCO-cyclopentyl, —NHCO-cyclohexyl, —N(CO-cyclopropyl)₂, —NHC(O)OC₂H₅, —NHCONHC₂H₅, —NHCOC(CH₃)₂, —NHCOC(CH₃)₃ or —NH—(C₁-C₉) alkyl, wherein alkyl, aryl and heteroaryl are optionally substituted. In particular, R' and R" are selected from, but are not limited, to, H, —NHC(O)OCH₃, —NHC(O)OC₂H₅, —NHCOCH₂Cl, —NHCOCH₂F, —NHCOCH₃, —NHCOC₂H₅, —NHCO-cyclopropyl or —NHCO-cyclobutyl.

According to another preferred embodiment of the present invention, there is provided a compound of formula (I), a pharmaceutically acceptable salt thereof, a prodrug thereof or a hydrate thereof, wherein $R^4$ represents a group selected from:

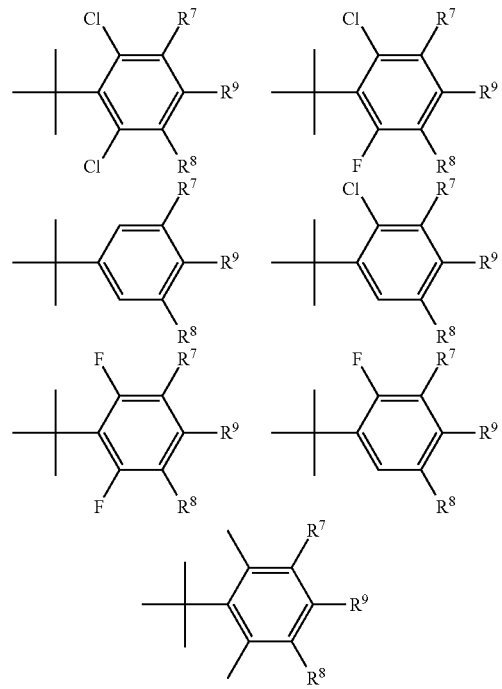

wherein:

$R^7$ and $R^8$ independently represent, but are not limited to, H, Cl, Br, —CN, —NO₂, —NH₂, —NHCOCH₃ or —NHCOC₂H₅;

$R^9$ represents H, alkyl, alkenyl, alkynyl, cycloalkyl, aryl, aralkyl, heteroaryl, heteroarylalkyl, heterocyclyl, heterocyclylalkyl, alkoxy, halo, —NO$_2$, —(CH$_2$)$_q$C(O)NR$^c$R$^d$, —(CH$_2$)$_q$NR$^c$COR$^d$, —(CH$_2$)$_q$NR$^c$CONR$^c$R$^d$, —(CH$_2$)$_q$NR$^c$C(O)OR$^d$, —(CH$_2$)$_q$NR$^c$R$^d$, —(CH=CH)—(CH$_2$)$_s$C(O)OR$^e$, —(CH=CH)—(CH$_2$)$_s$CONR$^c$R$^d$, —(CH=CH)—(CH$_2$)$_s$CN, —(CH=CH)—(CH$_2$)$_s$R$^e$, —(CH$_2$)$_s$C(O)OR$^e$, —(CH)$_r$CN, —(CH$_2$)$_r$OR$^e$, —(CH$_2$)$_r$R$^e$, —(CH$_2$)$_r$C(O)OR$^e$, —(CH)$_r$halo, —S(O)$_p$R$^e$, —S(O)$_p$NR$^c$R$^d$, —NR$^c$S(O)$_p$R$^d$, and wherein alkyl, alkenyl, alkynyl, cycloalkyl, aryl, heteroaryl heterocyclyl are optionally substituted; and R$^a$, R$^b$, R$^c$, R$^d$, R$^e$, p, q, r and s are as defined hereinbefore.

Yet another embodiment of the present invention provides a compound having the structure of formula (IA),

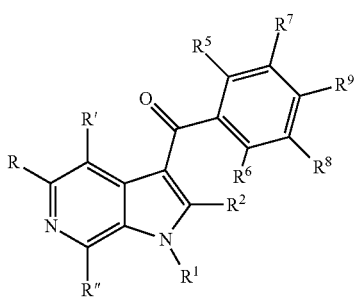
(IA)

a pharmaceutically acceptable salt thereof, a prodrug thereof or a hydrate thereof, wherein:
R and R' independently represent H, (C$_1$-C$_6$) alkyl, halogen, —CN, —NR$^a$R$^b$, —NR$^a$COR$^b$ or —CONR$^a$R$^b$;
R" represents H, halogen or —NR$^a$COR$^b$;
R$^1$ and R$^2$ are independently represent H or (C$_1$-C$_3$) alkyl;
R$^5$ and R$^6$ independently represent H, Cl, Br, F, —CN, —NO$_2$, —NH$_2$, —CH$_3$, —C$_2$H$_5$, —OCF$_3$, —OCH$_3$, —CH$_2$OH or —COOH;
R$^7$ and R$^8$ independently represent H, Cl, Br, —CN, —NO$_2$, —NH$_2$, —NHCOCH$_3$ or —NHCOC$_2$H$_5$;
R$^9$ represents H, alkyl, alkenyl, alkynyl, cycloalkyl, aryl, aralkyl, heteroaryl, heteroarylalkyl, heterocyclyl, heterocyclylalkyl, alkoxy, halo, —NO$_2$, —(CH$_2$)$_q$C(O)NR$^c$R$^d$, —(CH$_2$)$_q$NR$^c$COR$^d$, —(CH$_2$)$_q$NR$^c$CONR$^c$R$^d$, —(CH$_2$)$_q$NR$^c$C(O)OR$^d$, —(CH$_2$)$_q$NR$^c$R$^d$, —(CH=CH)—(CH$_2$)$_s$C(O)OR$^e$, —(CH=CH)—(CH$_2$)$_s$CONR$^c$R$^d$, —(CH=CH)—(CH$_2$)$_s$CN, —(CH=CH)—(CH$_2$)$_s$R$^e$, —(CH$_2$)$_s$C(O)OR$^e$, —(CH)$_r$CN, —(CH$_2$)$_r$OR$^e$, —(CH$_2$)$_r$R$^e$, —(CH$_2$)$_r$C(O)OR$^e$, —(CH)$_r$halo, —S(O)$_p$R$^e$, —S(O)$_p$NR$^c$R$^d$, —NR$^c$S(O)$_p$R$^d$, and wherein alkyl, alkenyl, alkynyl, cycloalkyl, aryl, heteroaryl heterocyclyl are optionally substituted; and R$^a$, R$^b$, R$^c$, R$^d$, R$^e$, p, q, r and s are as defined hereinbefore.

Yet another embodiment of the present invention provides a compound having the structure of formula (IB),

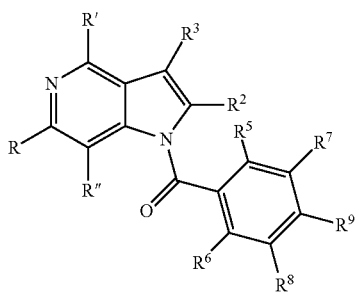
(IB)

R and R" independently represent H, (C$_1$-C$_6$) alkyl, halogen, —CN, —NR$^a$R$^b$, —NR$^a$COR$^b$ or —CONR$^a$R$^b$;
R' represents H, halogen or —NR$^a$COR$^b$;
R$^2$ represents H or (C$_1$-C$_3$) alkyl;
R$^3$ represents H, halo, —CN or (C$_1$-C$_3$) alkyl;
R$^5$ and R$^6$ independently represent H, Cl, Br, F, —CN, —NO$_2$, —NH$_2$, —CH$_3$, —C$_2$H$_5$, —OCF$_3$, —OCH$_3$, —CH$_2$OH or —COOH.
R$^7$ and R$^8$ independently represent H, Cl, Br, F, —CN, —NO$_2$, —NH$_2$, —NHCOCH$_3$ or —NHCOC$_2$H$_5$.
R$^9$ represents H, alkyl, alkenyl, alkynyl, cycloalkyl, aryl, aralkyl, heteroaryl, heteroarylalkyl, heterocyclyl, heterocyclylalkyl, alkoxy, halo, —NO$_2$, —(CH$_2$)$_q$C(O)NR$^c$R$^d$, —(CH$_2$)$_q$NR$^c$COR$^d$, —(CH$_2$)$_q$NR$^c$CONR$^c$R$^d$, —(CH$_2$)$_q$N-R$^c$C(O)OR$^d$, —(CH$_2$)$_q$NR$^c$R$^d$, —(CH=CH)—(CH$_2$)$_s$C(O)OR$^e$, —(CH=CH)—(CH$_2$)$_s$CONR$^c$R$^d$, —(CH=CH)—(CH$_2$)$_s$CN, —(CH=CH)—(CH$_2$)$_s$R$^e$, —(CH$_2$)$_s$C(O)OR$^e$, —(CH)$_r$CN, —(CH$_2$)$_r$OR$^e$, —(CH$_2$)$_r$R$^e$, —(CH$_2$)$_r$C(O)OR$^e$, —(CH)$_r$halo, —S(O)$_p$R$^e$, —S(O)$_p$NR$^c$R$^d$, —NR$^c$S(O)$_p$R$^d$, and wherein alkyl, alkenyl, alkynyl, cycloalkyl, aryl, heteroaryl heterocyclyl are optionally substituted; and R$^a$, R$^b$, R$^c$, R$^d$, R$^e$, p, q, r and s are as defined hereinbefore.

In certain embodiments, the compound of formula (IA) is represented by following formulae:

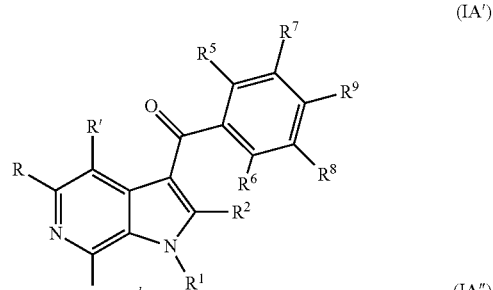
(IA')

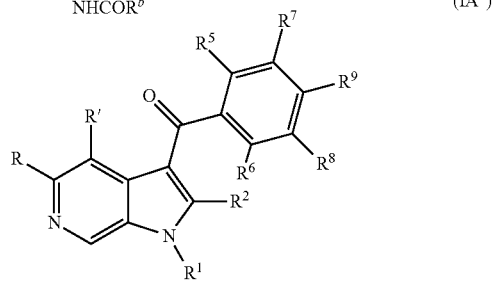
(IA")

wherein R, R', R$^1$, R$^5$, R$^6$, R$^7$, R$^8$ and R$^9$ are as defined for formula (IA) and R$^b$ represents —(CH$_2$)$_r$OR$^e$, —(CH$_2$)$_r$R$^e$, —(CH)$_r$halo, alkyl or cycloalkyl.

In certain embodiments, the compound of formula (IA) is represented by following formulae:

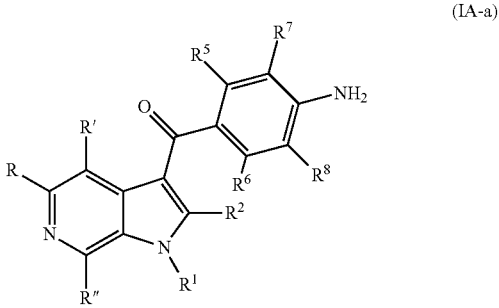
(IA-a)

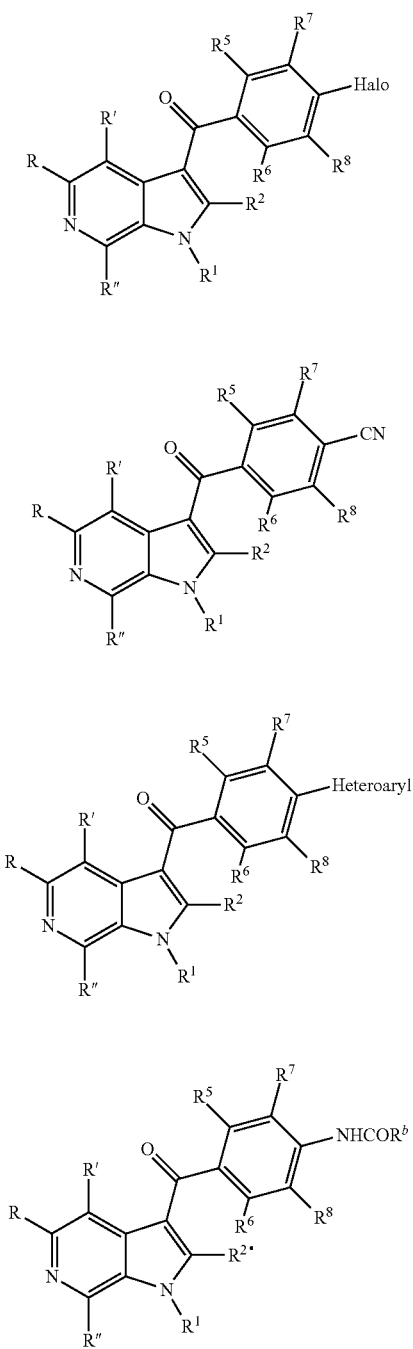
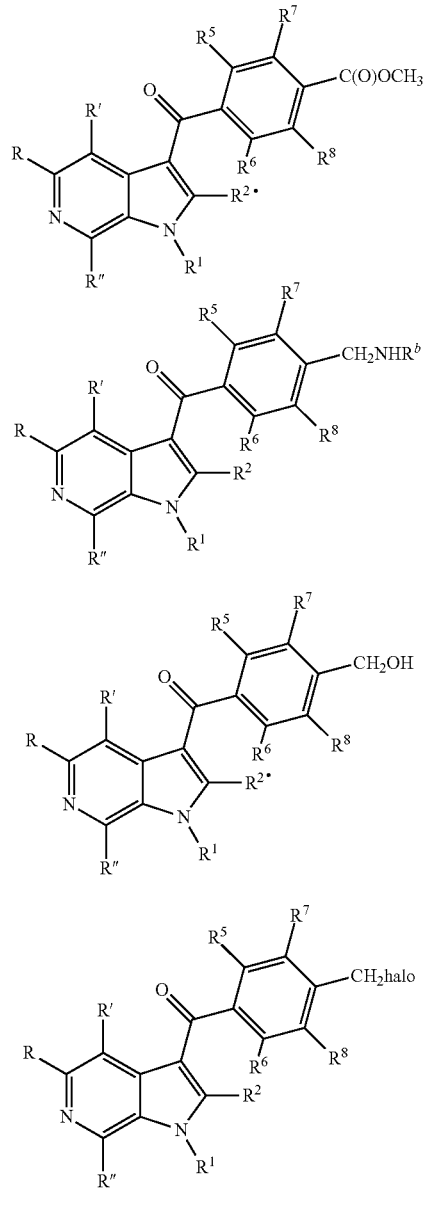
wherein R, R', R", $R^1$, $R^2$, $R^5$, $R^6$, $R^7$ and $R^8$ are as defined for formula (I).
In certain embodiments, the compound of formula (IB) is represented by following formulae:
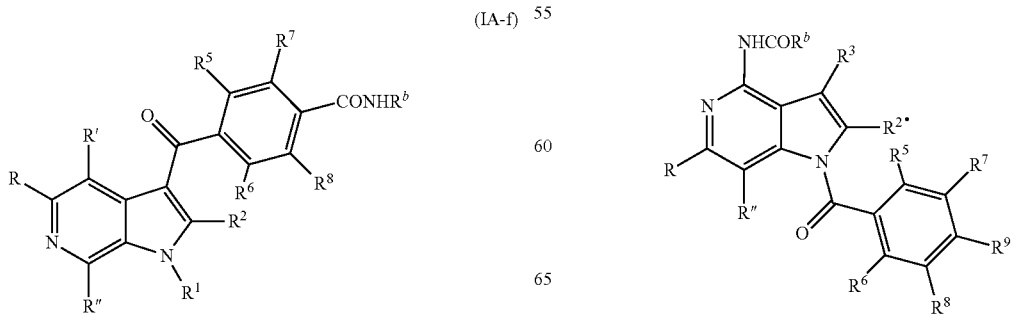

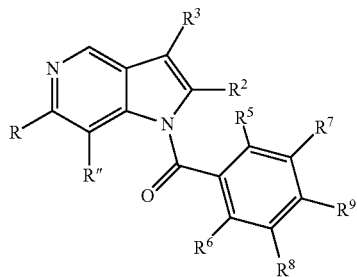
(IB″)
wherein R, R″, R², R³, R⁵, R⁶, R⁷, R⁸ and R⁹ are as defined for formula (IB) and $R^b$ represents —(CH$_2$)$_r$OR$^e$, —(CH$_2$)$_r$R$^e$, —(CH)$_r$halo, alkyl or cycloalkyl.
In certain embodiments, the compound of formula (IB) is represented by following formulae:
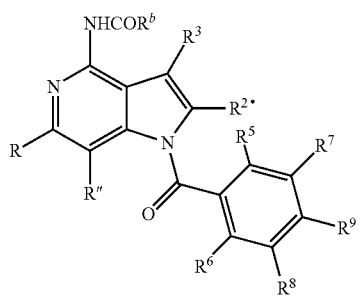
(IB-a)
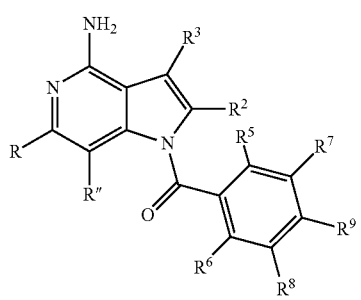
(IB-b)
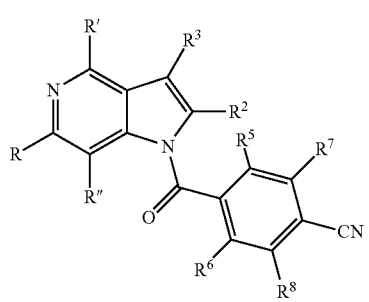
(IB-c1)
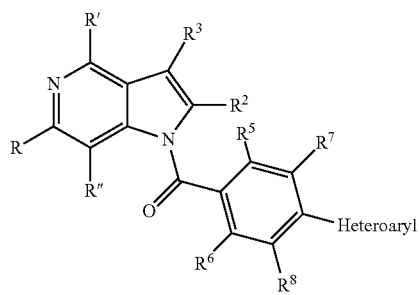
(IB-c2)
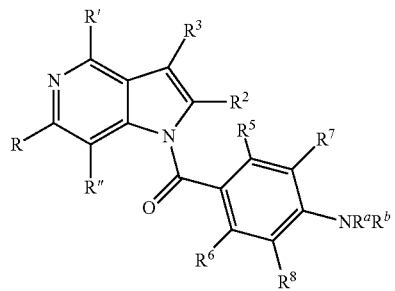
(IB-c3)
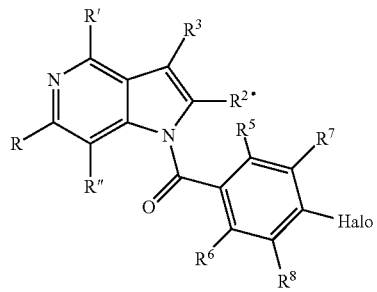
(IB-d)
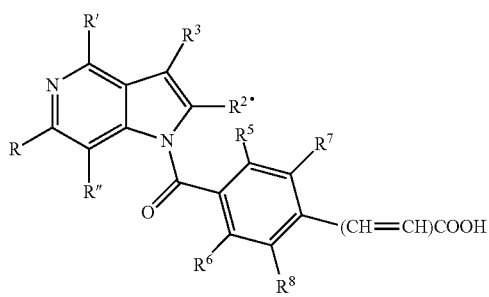
(IB-e1)
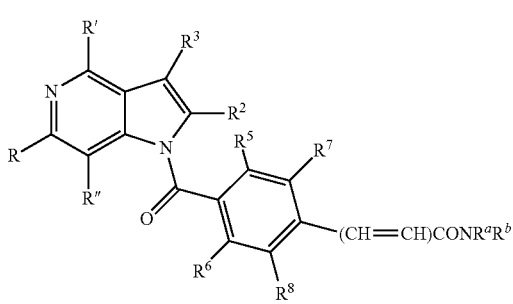
(IB-e2)

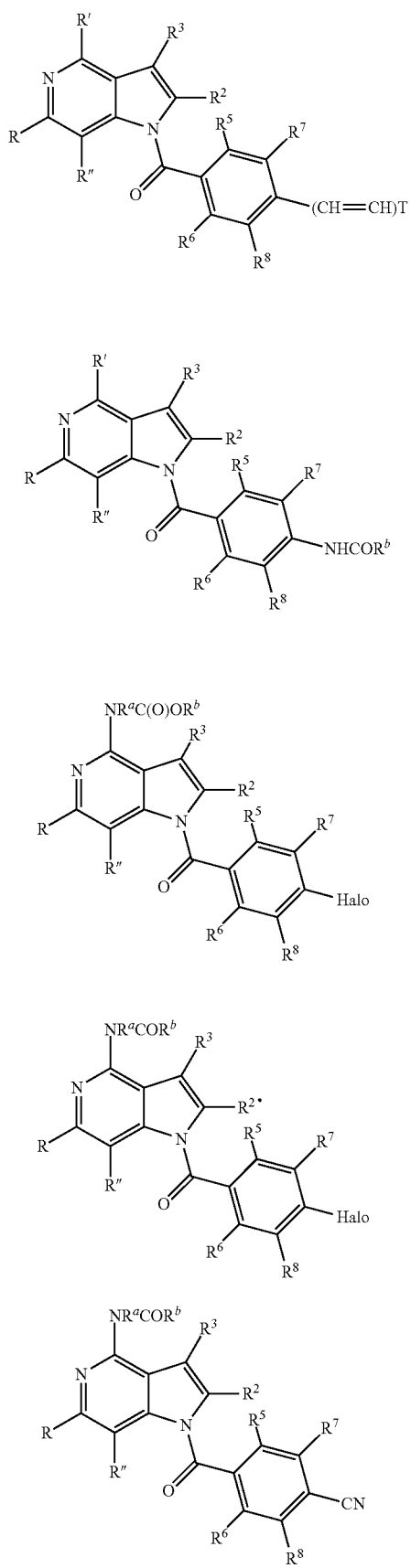
wherein $R^a$, $R^b$, R, R', R", $R^1$, $R^2$, $R^3$, $R^5$, $R^6$, $R^7$, $R^8$ and $R^9$ are as defined for formula (I) and T represents CN or $CONH_2$.
The compounds of formula (I) including their embodiments, subgenuses and intermediates described herein may be isolated in the form of a pharmaceutically acceptable salt. It should be understood that the term "pharmaceutically acceptable salt" as used herein refers to salts that are chemically and/or physically compatible with other ingredients comprising a formulation, and/or are physiologically compatible with the recipient thereof. The pharmaceutically acceptable salts are however not limited to the salts approved by a regulatory authority such as FDA for clinical or therapeutic use in humans. It should be understood that all salts known to a person of ordinary skill in the art including mixed salt forms are within the scope of the instant application. The pharmaceutically salts of the compounds of the present invention can be prepared in situ during the isolation and/or purification of a compound, or by separately reacting the compound with a suitable organic or inorganic acid or base and isolating the salt thus formed. The compounds of the present invention have a basic group such as an amino group or an acidic group such as carboxylic group and accordingly their salts can be prepared by reacting with an acid or base, respectively. The salts may be precipitated (with or without the addition of one or more so-solvents and/or anti-solvents) and collected by filtration or the salts may be recovered by evaporation of solvents(s). The salts of the present invention may also be formed via a "salt switch" or ion exchange/double displacement reaction. It should also be understood that the salts may be prepared and/or isolated using a single method or a combination of methods.

Representative salts include, but are not limited to, acetate, ascorbate, aspartate, benzoate, besylate, bicarbonate, carbonate, bisulfate, sulfate, borate, camsylate, citrate, edisylate, esylate, formate, fumarate, gluconate, glucuronate, glutamate, hexafluorophosphate, chloride, bromide, iodide, lactate, malate, maleate, malonate, mesylate, methanesulfonate, ethanesulfonate, benzenesulfonate, p-toluenesulfonate, methylsulphate, nicotinate, nitrate, bisulphate, oxalate, palmitate, pamoate, hydrogen phosphate, dihydrogen phosphate, phosphate, stearate, saccharate, succinate, salicylate, tartrate, bitartrate, tannate, tosylate or trifluoroacetate. Other examples of representative salts include alkali or alkaline earth metal cations such as sodium, lithium, potassium, calcium, magnesium, and the like, as well as non-toxic ammonium, quaternary ammonium and amine cations including, but are not limited to, ammonium, tetramethylammonium, tetraethylammonium, lysine, arginine, benzathine, choline, tromethamine, diolamine, glycine, meglumine, olamine, and the like.

The term "prodrug" as used herein refers to a compound that is transformed in vivo to yield the parent compound, wherein the in vivo transformation may occur by various mechanisms such as hydrolysis by the gastric acid under the physiological condition or enzymatic hydrolysis. Examples of prodrugs are compounds, wherein the amino group or hydroxyl group in a compound of the present invention is acylated, alkylated, phosphorylated or sulphonated, glycosylated or wherein the carboxyl group is esterified or amidated. A prodrug of a compound of formula (I) may be formed in a conventional manner, for example, if a compound of formula (I) contains a carboxylic acid functional group, a prodrug can be formed by replacement of a hydrogen atom of the acid group with a group such as alkyl or aryl. Similarly, a prodrug may be formed by any methods well known in the art.

Discussion regarding prodrugs and their use can be found in, for example, see Stella et al., "Prodrugs: A Chemical Approach to Targeted Drug Delivery," Directed Drug Delivery, Borchardt et al., (ed), pp. 247-267, Hamana Press (1985); Bioreversible Carriers in Drug Design, Pergamon Press, 1987 (ed. E B Roche, American Pharmaceutical Association).

The term "bioavailability" as used herein refers to the systemic availability of a given amount of a drug administered to a patient. It is an absolute term that indicates measurement of both the time and total amount of drug that reaches the general circulation from an administered dosage form.

The term "pharmaceutically acceptable" as used herein refers to a compound of formula (I) or pharmaceutical composition thereof is suitable for administration to humans. Preferably, this term means approved by a regulatory agencies such as EMEA (Europe) and/or FDA and/or any other National Regulatory Agency for use in animals, preferably humans.

The term "patient" as used herein refers to human subjects and other animal subjects. In this context, the terms "subject", "animal subject", and the like refer to human such as men and women, and non-human vertebrates, for example mammals such as non-human primates, sports and commercial animals, and pets (e.g., canines and felines). Preferably, the patient is human subject.

The term "hydrate" as used herein refers to hydrate formed by the association of one or more water molecules to a compound of formula (I). The water molecule may be bounded or freely available on to the surface of a compound of formula (I). Representative examples of hydrate, but are not limited to, monohydrate, dehydrate, trihydrate, tetrahydrate, and the like. Certain compounds of the present invention can also exist in a solvate form, wherein the term "solvate" refers to association of solvent molecules with a compound of formula (I). The solvent may be organic, inorganic or combination of both. All such solvate forms of a compound of formula (I) are considered to be within the scope of the present invention.

The term "therapeutically effective amount" as used herein refers to an amount of a compound of formula (I) sufficient to treat or prevent a specific disease, disorder, condition or one or more of its symptoms. The amount of a compound which constitutes an effective amount will vary depending on the various factors including for example, the compound being used, the disease state and its severity, the age of the patient to be treated, and the like. The said effective amount can be determined routinely by a person of ordinary skill in the art.

The present invention also intends to encompass the metabolites of a compound of formula (I). The term "metabolites" means all molecules derived from any of the compounds of formula (I) in a cell or organism, preferably mammal. The structure of the metabolites of the compounds according to the present invention will be understood by any person having ordinary skill in the art, using the various appropriate methods.

Certain compounds of the present invention may have one or more asymmetric centers and therefore can exist in a number of stereoisomeric and diastereomeric configurations. All such configurations are within the scope of the present invention. Where the compound of formula (I) contain asymmetric centers, such compounds can be synthesized and/or isolated as mixtures of enantiomers and/or as individual enantiomers, as well as diastereomers and mixtures of different diastereomers.

In practice, resolution and isolation of pure enantiomers can be achieved using methods well known in the art. The examples include, but are not limited to, (a) by formation of diastereomeric salts which may be separated, for example, by crystallization; (b) by formation diastereomeric derivatives or complexes which may be separated, for example, by crystallization, gas-liquid or liquid chromatography; (c) by selective reaction of one enantiomer with an enantiomer specific reagent, for example enzymatic esterification; (d) by using an optically active starting material; (e) by asymmetric synthesis using optically active reagents, substrates, catalysts or solvents; or (f) by converting one stereoisomer into the other by asymmetric transformation or inversion. It will be appreciated and understood by one of ordinary skill in the art that where the desired stereoisomer is converted into another chemical entity by one of the separation procedures described above, one or more steps may additionally be required to liberate the desired enantiomeric form.

Certain compounds of the present invention may have one or more olefinic double bonds or other centers of geometric asymmetry. Unless specified otherwise, it is intended that both E and Z geometric isomers of such compounds are within the scope of the present invention.

The compounds of the present invention have utility over a wide range of therapeutic applications and may be used to treat or prevent a variety of diseases, conditions and/or disorders responsive to the inhibition of signal transduction pathway mediated at least in part by protein activity, in a patient including men and women, as well as a mammal in general. For example, such diseases and disorders include, but are not limited to, those associated with cardiovascular disease, proliferative disease, inflammatory disease or autoimmune disease. The term protein kinase is preferably meant to include Janus kinase, wherein Janus kinase is selected from JAK1, JAK2, JAK3, TYK2 or combination thereof.

As shown in the specification, the compounds of the present invention were tested for their selectivity for TYK2 over other kinases such as JAK1, JAK2 and JAK3. In certain embodiments, the compounds of the instant invention bind TYK2 more selectively than JAK1, JAK2 or JAK3. As a result of these findings, the compounds of the present invention are considered to be useful for the prevention and/or treatment of diseases and/or disorders associated with TYK2, for example inflammatory, autoimmune, proliferative diseases (such as cancer), Transplant rejection or Graft-versus-host disease.

Thus, one object of the present invention is to provide a method for treating or preventing a disease, condition or disorder associated with protein kinase activity.

Another object of the present invention is to provide a method for treating or preventing a disease, condition or disorder associated with Janus kinase activity, preferably JAK1, JAK2, JAK3, TYK2 or combination thereof, and most preferably with TYK2.

According to another object of the present invention, there is provided a method for treating or preventing inflammatory disease, condition or disorder.

In another object there is provided a method for treating or preventing autoimmune disease, condition or disorder.

In yet another object there is provided a method for treating or preventing proliferative disease, condition or disorder.

The term "inflammatory disease" as used herein refers to the inflammation of tissues and organs which results from activation of the cytokine family of receptors. The inflammatory diseases or disorders associated with activation of TYK2 include, but are not limited to, skin inflammation, skin inflammation due to radiation exposure, asthma, chronic obstructive pulmonary disease, allergic inflammation and chronic inflammation.

The term "autoimmune disease" as used herein refers to a disease which is partially provoked by an immune reaction of the body against own components, for example DNA, lipids, protein, and the like. The autoimmune disease could be organ-specific or non-organ specific. Representative examples of organic-specific include, but are not limited to, insulin-dependent diabetes (Type I), celiac disease, psoriasis, inflammatory bowel disease, chronic active hepatitis, polycystic ovary syndrome, pernicious anemia, ankylosing spondylitis, Hashimoto's thyroiditis and Graves' disease which affects the thyroid gland, Cushing's disease and Addison's disease which affect the adrenal glands, and the like. The non-limiting examples of non-organ specific autoimmune disease include rheumatoid arthritis, multiple sclerosis, systemic lupus erythmetosus or myasthenia gravis.

The proliferative disease or disorder refers to increased cell multiplication as observed in myeloproliferative disorders such as polycythemia vera.

Cancer comprises a group of diseases characterized by uncontrolled growth and spread of abnormal cells. Typically, cancers are classified as hematological cancers (e.g., leukemias or lymphomas) and solid cancers such as sarcomas and carcinomas (e.g., cancer of the breast, brain, lung, colon, stomach, liver, pancreas, prostate or ovary). In particular, cancers in which the JAK-STAT signal transduction pathway is activated. For example due to activation of TYK2 are expected to respond to treatment with TYK2 inhibitors.

Transplant rejection (allograft transplant rejection) includes, but is not limited to, acute and chronic allograft rejection following for example transplantation of kidney, heart, liver, lung, bone marrow, skin and cornea. It is known that T cells play a central role in the specific immune response of allograft rejection.

Graft-versus-host disease (GVDH) is a major complication in allogenic bone marrow transplantation. It is caused by donor T cells that recognize and react to recipient differences in the histocompatibility complex system, resulting in significant morbidity and mortality.

Inflammatory bowel disease (IBD) is characterized by a chronic relapsing intestinal inflammation. It is subdivided into Crohn's disease and ulcerative colitis phenotypes. Psoriasis is a chronic inflammatory dermatosis that affects approximately 2% of the population. Multiple sclerosis is an inflammatory and demyelating neurological disease. Rheumatoid arthritis is a chronic progressive, debilitating inflammatory disease that affects approximately 1% of the world's population.

In certain embodiments, the disease, disorder or condition is selected from, but are not limited to, skin inflammation due to radiation exposure, asthma, chronic obstructive pulmonary disease, allergic inflammation, chronic inflammation, allergic disease, insulin-dependent diabetes (Type I), celiac disease, psoriasis, inflammatory bowel disease, chronic active hepatitis, polycystic ovary syndrome, pernicious anemia, ankylosing spondylitis, Hashimoto's thyroiditis and Graves' disease which affects the thyroid gland, Cushing's disease and Addison's disease which affect the adrenal glands, rheumatoid arthritis, multiple sclerosis, systemic lupus erythmetosus, myasthenia gravis, Crohn's disease, myeloproliferative disorders (polycythemia vera), acute allograft rejection, chronic allograft rejection, Graft-versus-host disease, cancer (e.g., breast, ovary, cervix, stomach, lung, melanoma, small cell lung, and the like), stroke, cardiovascular disease, atherosclerosis, retenosis, immunodeficiency disorders, destructive bone disorders, infectious diseases, CNS disorders, hormone-related disease, and the like.

In particular, the disease, disorder or condition is selected from asthma, chronic obstructive pulmonary disease, insulin-dependent diabetes (Type I), psoriasis, inflammatory bowel disease, rheumatoid arthritis, multiple sclerosis, systemic lupus, myeloproliferative disorders, cancer, and the like.

In a preferred embodiment of the present invention, there is provided a method for treating or prevention rheumatoid arthritis.

In another preferred embodiment of the present invention, there is provided a method for treating or preventing psoriasis.

In another preferred embodiment of the present invention, there is provided a method for treating or preventing multiple sclerosis.

In another preferred embodiment of the present invention, there is provided a method for treating or preventing chronic obstructive pulmonary disease.

In yet another preferred embodiment of the present invention there is provided a method for treating or preventing inflammatory bowel disease.

In certain embodiments, the compound of the present invention is about 100 fold or about 50 fold or about 10 to 25 fold more selective in inhibiting TYK2 activity over inhibiting JAK1, JAK2 or JAK3. In one preferred embodiment, the compound of the present invention is more than about 100 fold selective in inhibiting TYK2 activity over inhibiting JAK1, JAK2 or JAK3.

The compound alone or in the form of a pharmaceutical composition will typically be used in therapy for human subjects. However, they may also be used to prevent or treat similar indications in other animal subjects as described herein. Thus, for therapy a suitable dosage form may be required. Suitable dosage forms will depend upon the use or the route of administration. It should be understood that such dosage forms should allow the compound to reach target cells. Other factors are well known in the art, and include considerations such as toxicity and dosage forms that retard the compound or composition from exerting its effect. Techniques and formulations generally may be found in *The Science and Practice of Pharmacy*, $21^{st}$ edition, Lippincott, Willams and Wilkins, Philadelphia, Pa., 2005 (incorporated herein by reference).

Thus, in another object of the present invention, there is provided a pharmaceutical composition comprising a compound of formula (I) and one or more pharmaceutically acceptable excipient(s).

The compound of formula (I), a pharmaceutically acceptable salt thereof, a prodrug thereof or a hydrate thereof, may be administered as a formulation, i.e., pharmaceutical composition, in association with one or more pharmaceutically acceptable excipient(s). The term "excipient" as used herein refers to any ingredient in the formulation other than the compound of formula (I). The examples of an excipient includes, but are not limited to, carrier, vehicle, solvent, adjuvant, lubricant, surfactant, binder, buffer, diluent, flavouring agent, coloring agent, disintegrant, emulsifying agent, suspending agent, plasticizer, solubilizer, filler or bulking agent. The choice of excipient(s) will largely depend on factors such as the particular mode of administration, the effect of the excipients on solubility, stability, and release profile, and the nature of the dosage form. The compound of formula (I) may be generally referred to as the active ingredient(s) in a formulation or pharmaceutical composition. A pharmaceutical composition suitable for the delivery of a compound of formula (I) and methods for their preparation will be readily apparent to those skilled in the art. Such compositions and methods for their preparation may be found, for example, in *Remington's Pharmaceutical Sciences*, $19^{th}$ ed., (Mack Publishing Company, 1995).

The compounds can be administered by different routes including, for example intravenous, intraperitoneal, subcutaneous, intramuscular, oral, transmucosal, rectal, transdermal, or inhalant. Oral administration is preferred. For oral administration, for example, the compounds can be formulated into conventional oral dosage forms such as a tablet, capsule (hard or soft filled), pill, powder, sustain or immediate release formulations, solution, suspension; for parenteral injection as a sterile solution, suspension or emulsion; for topical administration as an ointment or cream.

The amount of active ingredient(s) and excipient(s) to be present in formulation or pharmaceutical composition can be determined by standard procedures taking into account factors such as the compound $IC_{50}$, the biological half life of the compound, the age, size, and weight of the patient, and the disorder associated with the patient. The importance of these and other factors are well known to those of ordinary skill in the art. Generally, a dose will be between about 0.01 and 100 mg/Kg, preferably 0.1 to 50 mg/Kg, even more preferably 0.1 to 20 mg/Kg of the patient being treated. Multiple doses may be used. The person skilled in the art would appreciate that the dose is adjusted in accordance with the methods well know in the therapeutic arts. That is, the maximum tolerable dose can be readily established, and the effective amount providing a detectable therapeutic benefit to the patient may also be determined. Accordingly, while certain dose and administration regimens are exemplified herein, however, these do not in any way limit the dose and administration regimen that may be provided to the patient in practicing the present invention.

General Methods for Preparation of a Compound of Formula (I)

In general, compounds of the formula (I) can be prepared by following the processes described in the methods, schemes and specific examples of the present application and/or by additional or alternative processes and procedures known in the art in combination with the knowledge of ordinary skill in the art. It should be understood that the methods set forth in the following descriptions, reaction schemes, methods, and experimental part are intended for illustrative purposes and are not to be construed as limiting the scope of the disclosure. Alternative reagents, intermediates, starting materials, synthetic routes and methods can be used or adapted in practice, particularly in light of the scope of the present disclosure in combination with the knowledge of one of ordinary skill in the art. Such alternatives and modifications should be understood as being within the spirit and scope of the present application and the claims. Unless otherwise indicated, the variables R, R', R", $R^a$, $R^b$, $R^1$, $R^2$, $R^3$, $R^4$, $R^5$, $R^6$, $R^7$, $R^8$ and $R^9$ shown or referenced in the methods and schemes are defined as above or as defined herein the specification including claims. The compound of formula (I) may be prepared from commercially available starting materials using the general methods illustrated herein below.

It should also be appreciated and understood that where appropriate functional groups exist, compounds of methods (1-15) including intermediates may be further derivatized by using one or more synthetic methods known in the art including for example oxidation, reduction, substitution, condensation or cleavage reactions. In particular, the introduction of functional groups such as halo group, nitro group, amino group, amide group, urea group, carboxylic group, hydroxyl group or alkoxy group, in the compounds of the present invention may be achieved by following the procedures well known in the art. For example, the procedures described hereinafter.

Method (1)

A compound of formula (IA) [formula (I), wherein A represents CR, B represents N; $R^3$ represents $—COR^4$, wherein $R^4$ is optionally substituted phenyl] can be prepared by reacting a compound of formula (a) or salt thereof, with a compound of formula (b) according to the Freidel-Crafts acylation as shown in the reaction Scheme 1.

Scheme 1

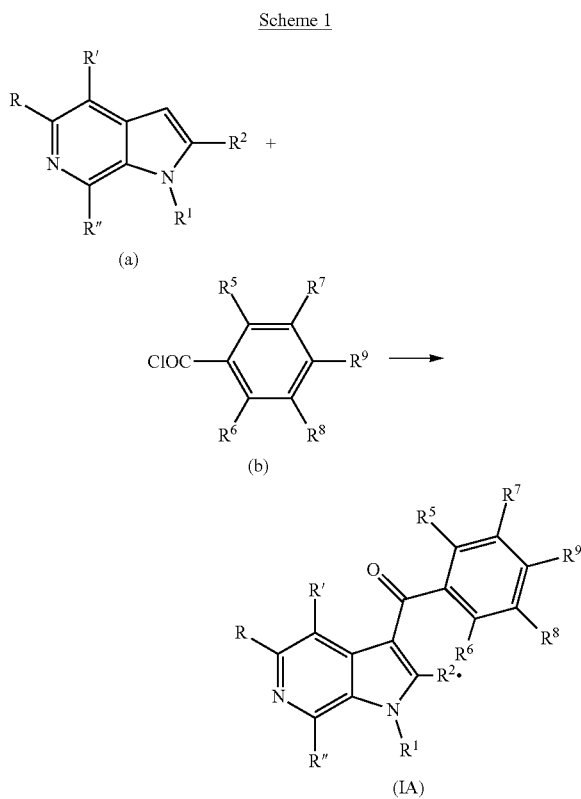

wherein R, R', R", $R^1$, $R^2$, $R^5$, $R^6$, $R^7$, $R^8$ and $R^9$ are as defined herein.

The reaction is performed using the procedure well known in the art. In particular, the reaction is carried out in a chlorinated solvent such as dichloromethane, and in the presence of a metal halide such as aluminium chloride. The compound of formula (b) can be prepared by heating acid derivative of formula (b) with thionyl chloride in presence or absence of a suitable chlorinated solvent such as dichloromethane. The compound of formula (b) can also be prepared by treating acid derivative of formula (b) with oxalyl chloride in presence of a suitable solvent such as dichloromethane, dimethylformamide or mixture thereof.

Method (2)

A compound of formula (IA-a) [formula IA, wherein $R^9$ represents amino] can be prepared from a halo compound of formula (IA-b) [formula IA, wherein R, R', R", $R^1$, $R^2$, $R^5$, $R^6$, $R^7$ and $R^8$ are as defined herein and $R^9$ represents halo such as bromo).

The reaction is performed by reacting compound of formula (IA-b) with metal azide such as sodium azide and metal iodide such as cuprous iodide, in a suitable protic solvent such as water, methanol, ethanol or isopropanol, or an aprotic solvent such as dimethylformamide or dimethylsulfoxide or a mixture thereof, in the presence of an organic base, for example, dimethylaminopyridine, N,N-diisopropylethylamine, triethylamine, pyridine or N,N-dimethylethylenediamine, in a temperature range of about 75° C. to about 150° C.

Method (3)

A compound of formula (IA-c) [formula IA, wherein $R^9$ represents CN] can be prepared from a halo compound of formula (IA-b).

The cyanation reaction is carried out following procedures well known in the art. For example, the reaction is performed in an appropriate solvent such as tetrahydrofuran, dioxane, ether or dimethylformamide in the presence of metal cyanide such as cuprous cyanide or zinc cyanide. The palladium catalyst such as tris(dibenzylideneacetone)dipalladium(0) and a ligand such as 1,1'-bis(diphenylphosphino)ferrocene are used for this reaction. Such a palladium catalyzed cyanation reaction is performed in a temperature range of about 100° C. to about 150° C.

Method (4)

The compound of formula (IA-d) [formula IA, wherein $R^9$ represents heteroaryl] can be prepared from a halo compound of formula (IA-b).

The reaction is performed by reacting a compound of formula (IA-b) with a borate ester of formula $R^9B(OH)_2$ (wherein $R^9$ represents aryl such as phenyl or heteroaryl such as pyrrolyl) or a boronic acid, in an appropriate solvent such as water, acetonitrile, 1,4-dioxane, dimethylformamide, toluene or a mixture thereof, in the presence of a palladium complex such as dichloro[1,1'-bis(diphenylphosphino)ferrocene]palladium(II) and a base such as potassium carbonate, cesium carbonate or sodium carbonate. Such a reaction is optionally performed under heating system well known in the art including, for example, microwave heating system, in a temperature range of about 80° C. to about 110° C.

Method (5)

The compound of formula (IA-e) [formula IA, wherein $R^9$ represents —$NHCOR^b$] can be prepared from an amino compound of formula (IA-a).

The compound of formula (IA-a) is reacted with a compound of formula $R^bCOCl$ in an appropriate solvent such as methylene chloride, chloroform or carbon tetrachloride, in the presence of a base such as triethylamine, N,N-diisopropylethylamine, pyridine, 2,6-dialkylpyridine (e.g., 2,6-lutidine or 2,6-di-tert-butylpyridine) to give a compound of formula (IA-e).

Method (6)

The compound of formula (IA-f) [formula IA, wherein $R^9$ represents —$CONHR^b$] can be prepared from a compound of formula (IA-g) [formula IA, wherein R, R', R", $R^1$, $R^2$, $R^5$, $R^6$, $R^7$ and $R^8$ are as defined herein and $R^9$ represents —$COOCH_3$).

The compound of formula (IA-f) can be prepared by following any methods well known in the art including the methods described herein. For instant, said compound is prepared by hydrolyzing a compound of formula (IA-g) under basic condition (e.g., sodium hydroxide) in a suitable solvent such as water, tetrahydrofuran, dioxane or mixture thereof, followed by reacting with an amine compound of formula $R^bNH_2$ in presence of a coupling agent and a suitable solvent such as dimethylformamide or dimethylsulfoxide.

Method (7)

The compound of formula (IA-h) [formula IA, wherein $R^9$ represents —$CH_2NHR^b$] can be prepared from a compound of formula (IA-g) by following the steps (i), (ii) and (iii).

(i) The compound of formula (IA-g) is subjected to reduction using an appropriate reducing agent such as sodium borohydride and a suitable solvent such as water, tetrahydrofuran, methanol, dioxane or mixture thereof, to give a compound of formula (IA-i) [formula IA, wherein R, R', R", $R^1$, $R^2$, $R^5$, $R^6$, $R^7$ and $R^8$ are as defined herein and $R^9$ represents —$CH_2OH$].

(ii) The compound of formula (IA-i) is brominated using an appropriate brominating agent such as phosphorous tribromide, in a suitable solvent such as methylene chloride, chloroform, carbon tetrachloride or mixture thereof, to give a compound of formula (IA-j) [formula IA, wherein R, R', R", $R^1$, $R^2$, $R^5$, $R^6$, $NR^7$ and $R^8$ are as defined herein and $R^9$ represents —CH$_2$halo such as —CH$_2$Br).

(iii) The compound of formula (IA-j) is finally reacted with an amine compound $R^bNH_2$ in an appropriate solvent such as acetonitrile, in the presence of a base such as cesium carbonate to give a compound of formula (IA-h).

Method (8)

A compound of formula (IB) [formula (I), wherein A represents N, B represents CR, $R^1$ represents —COR$^4$, wherein $R^4$ is optionally substituted phenyl] can be prepared by reacting a compound of formula (d) or salt thereof, with a compound of formula (e) according to the reaction Scheme 2.

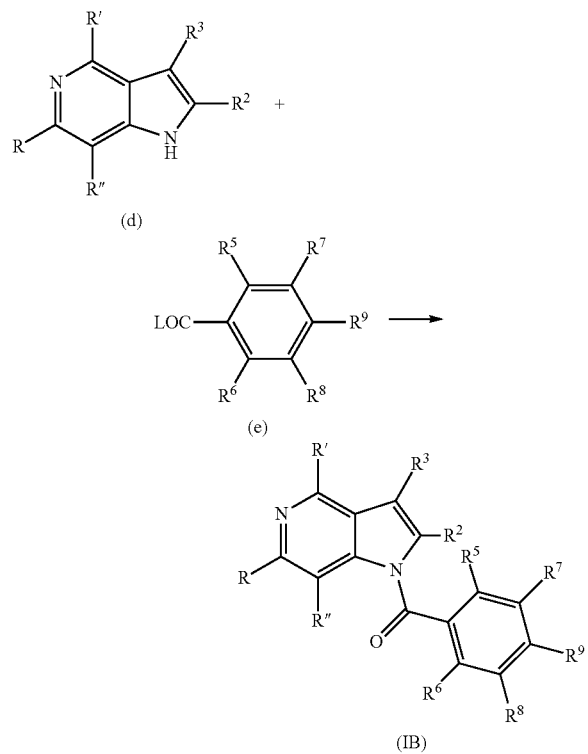

Scheme 2 wherein R, R', R", $R^2$, $R^3$, $R^5$, $R^6$, $R^7$, $R^8$ and $R^9$ are as defined herein. The reaction (when L is OH) is performed in an appropriate solvent such as dimethylformamide, dimethylacetamide, ethyl acetate, acetonitrile, in the presence of a coupling agent and a base such as dimethylaminopyridine (DMAP) or N,N-diisopropylethylamine (DIPEA). The examples of coupling agents include, but are not limited to, 2-(1H-7-azabenzotriazol-1-yl)-1,1,3,3-tetramethyl uronium hexafluorophosphate methanaminium (HATU) or 1-hydroxy-7-azabenzotriazole (HOAt) or mixture thereof.

In Scheme 2, when L is halo such as chloro, the reaction is performed i) in an appropriate solvent such as tetrahydrofuran, ether, dioxane, methylene chloride, chloroform or carbon tetrachloride, in the presence of a base, for example, N,N-diisopropylethylamine (Hünig's base), triethylamine, diethylamine or pyridine or ii) in an appropriate solvent such as dimethylformamide or dimethylsulfoxide, in the presence of a metal hydride such as sodium hydride or potassium hydride. Such a reaction is performed in a temperature range of 0° C. to 80° C., preferably from 0° C. to an ambient temperature.

Method (9)

A compound of formula (IB-a) [formula IB, wherein R' represents —NHCOR$^b$] can be prepared from a compound of formula (IB-b) [formula IB, wherein R, R", $R^2$, $R^3$, $R^5$, $R^6$, $R^7$, $R^8$ and $R^9$ are as defined and R' represents —NH$_2$).

The compound of formula (IB-b) is reacted with a compound of formula $R^bCOCl$ in an appropriate solvent such as diethyl ether, tetrahydrofuran or dioxane, dichloromethane in the presence of a base such as triethylamine, diethylamine, pyridine or diisopropylethylamine, at an ambient temperature, followed by treatment with an inorganic base such as potassium carbonate or sodium carbonate, in a suitable solvent such as methanol or ethanol, at the same temperature.

The compound of formula (IB-b) can be prepared by following any methods well known in the art including the methods described herein. For example, the N-oxidation of a compound of formula (IB, wherein R' is H), followed by reaction with a compound of formula R'"NH$_2$ (wherein R'" is alkyl such as tert-butyl or tert-octyl) in a suitable solvent such as chloroform, dichloromethane or carbon tetrachloride, in the presence of p-toluenesulfonyl chloride or methanesulfonyl chloride, in a temperature range of 0° C. to an ambient temperature gives an intermediate compound which upon treatment with an acid, in a suitable solvent such as chloroform, dichloromethane or carbon tetrachloride gives (IB-b). The examples of acids include, but are not limited to, acetic acid, trichloroacetic acid, trifluoroacetic acid or difluoroacetic acid, preferably trifluoroacetic acid. The N-oxidation can be carried out in an appropriate solvent such as chloroform, dichloromethane or carbon tetrachloride, in presence of an oxidizing agent such as hydrogen peroxide, peracetic acid, potassium peroxymonosulfate (oxone) or meta-chloroperbenzoic acid, preferably m-chloroperbenzoic acid, in a temperature range of 0° C. to an ambient temperature. The N-oxide product thus formed is halogenated in a temperature range of ambient temperature to about 70° C. The examples of halogenating agents include, but are not limited to, thionyl chloride, phosphorous trichloride or phosphoryl chloride.

Method (10)

A compound of formula (IB-c) [formula IB, wherein $R^9$ represents CN, heteroaryl or —NR$^a$R$^b$] can be prepared from a compound of formula (IB-d) [formula IB, wherein R, R', R", $R^2$, $R^3$, $R^5$, $R^6$, $R^7$ and $R^8$ are as defined herein and $R^9$ represents halo such as bromo).

The compound of formula (IB-d) is subjected to a palladium catalyzed cyanation procedures well known in the art, to give a compound of formula (IB-c1, wherein $R^9$ represents CN). For example, the reaction is performed in an appropriate solvent such as tetrahydrofuran, dioxane or ether, in the presence of metal cyanide such as cuprous cyanide or zinc cyanide and a base such as potassium carbonate, cesium carbonate or sodium carbonate. The palladium catalyst such as tris(dibenzylideneacetone)dipalladium(0) and a ligand such as 1,1'-bis(diphenylphosphino)ferrocene are used for this reaction. Such a palladium catalyzed cyanation reaction is performed in a temperature range of about 70° C. to about 100° C.

The compound of formula (IB-d) is reacted with borate esters of formula $R^9B(OH)_2$ (wherein $R^9$ is heteroaryl such as pyrrolyl) in an appropriate solvent such as water, acetonitrile, dimethylformamide, toluene or a mixture thereof, in the presence of a palladium complex such as dichloro[1,1'-bis(diphenylphosphino)ferrocene]palladium(II) and a base such as potassium carbonate, cesium carbonate or sodium carbonate, to give a compound of formula (IB-c2, wherein $R^9$ is heteroaryl). Such a reaction is performed under heating system well known in the art including, for example, microwave heating system, in a temperature range of about 75° C. to about 100° C.

The compound of formula (IB-d) is reacted with an amine compound of formula —NR$^a$R$^b$ in a suitable solvent such as toluene or xylene, in the presence of a palladium catalyst and ligand such as 4,5-bis(diphenylphosphino)-9,9-dimethylxanthene or 2,2'-bis(diphenylphosphino)-1,1'-binaphthyl, and a base such as potassium carbonate, cesium carbonate or sodium carbonate, to give a compound of formula (IB-c3, wherein R$^9$ represents —NR$^a$R$^b$. The examples of palladium catalysts include, but are not limited to, palladium (II) acetate or tris(dibenzylideneacetone)dipalladium(0). Such a palladium catalyzed reaction is performed in the temperature range of about 80° C. to about 100° C.

Method (11)

A compound of formula (IB-e) [formula IB, wherein R$^9$ represents —(CH═CH)COOH or —(CH═CH)CONR$^a$R$^b$] can be prepared from a compound of formula (IB-f) [formula IB, wherein R, R', R", R$^2$, R$^3$, R$^5$, R$^6$, R$^7$ and R$^8$ are as defined herein and R$^9$ represents —CH═CH-T, wherein T is COO-ethyl).

The compound of formula (IB-f) is hydrolyzed in an appropriate solvent such as water, tetrahydrofuran, ether or a mixture thereof, in the presence of metal hydroxide such as lithium hydroxide, potassium hydroxide, sodium hydroxide, magnesium hydroxide or calcium hydroxide, and in a temperature range of ambient temperature to about 80° C., preferably ambient temperature to give a compound of formula [IB-e1, wherein R$^9$ represents —(CH═CH)COOH], which upon reacting with an amine compound (—NR$^a$R$^b$) in an appropriate solvent such as dimethylformamide or dimethylsulfoxide, in the presence of a coupling agent and optionally in the presence of a base such as triethylamine, N,N-diisopropylethylamine, pyridine, 2,6-dialkylpyridine (e.g., 2,6-lutidine or 2,6-di-tert-butylpyridine) gives a compound of formula [IB-e2, wherein R$^9$ represents —(CH═CH)CONR$^a$R$^b$].

A standard coupling agent well known in the art can be used. In particular, a coupling agent such as carbonyldiimidazole, dicyclohexyl-carbodiimidazole, 1-ethyl-3-(3-dimethylaminopropyl)carbodiimide hydrochloride or a combination thereof can be used. Such a coupling reaction can optionally be performed in the presence of a catalyst such as 1-hydroxy-benzotriazole.

Method (12)

The compound of formula (IB-g) [formula IB, wherein R, R', R", R$^2$, R$^3$, R$^5$, R$^6$, R$^7$ and R$^8$ are as defined herein and R$^9$ represents —NHCOR$^b$] can be prepared by following the procedures (i), (ii) or (iii).

(i) The compound of formula (IB-c3, wherein R$^9$ represents —NR$^a$R$^b$; both R$^a$ and R$^b$ represent H) is subjected to a coupling reaction with a compound of formula R$^b$COOH in a reaction condition described in Method (11).

(ii) The compound of formula (IB-c3, wherein R$^9$ represents —NR$^a$R$^b$; both R$^a$ and R$^b$ represent H) is reacted with a compound of formula R$^b$COCl in an appropriate solvent such as methylene chloride, chloroform or carbon tetrachloride, in the presence of a base such as triethylamine, N,N-diisopropylethylamine, pyridine, 2,6-dialkylpyridine (e.g., 2,6-lutidine or 2,6-di-tert-butylpyridine).

(iii) The compound of formula (IB-c3, wherein R$^9$ represents —NR$^a$R$^b$; both R$^a$ and R$^b$ represent H) is reacted with phenyl chloroformate in an appropriate solvent such as tetrahydrofuran, ether or dioxane, in the presence of a base such as triethylamine, N,N-diisopropylethylamine, pyridine, 2,6-dialkylpyridine (e.g., 2,6-lutidine or 2,6-di-tert-butylpyridine), followed by reaction with a compound of formula R$^b$NH$_2$ in a suitable solvent such as methanol, ethanol or isopropanol.

Method (13)

A compound of formula (IB-h) [formula IB, wherein R$^9$ represents halo, —CN and R' represents —NR$^a$COR$^b$ or —NR$^a$C(O)OR$^b$ or both R$^9$ and R' represent —NR$^a$COR$^b$] can be prepared from a compound of formula (IB-i, wherein R, R', R", R$^2$, R$^3$, R$^5$, R$^6$, R$^7$ and R$^8$ are as defined herein and R$^9$ represents halo such as bromo).

(i) The compound of formula (IB-h1, wherein R$^9$ represents halo and R' represents —NR$^a$C(O)OR$^b$] can be prepared by treating a compound of formula (IB-i1, wherein R$^9$ represents halo and R' represents amino) with phenyl chloroformate as defined herein.

(ii) The compound of formula (IB-h2, wherein R$^9$ represents halo and R' represents —NR$^a$COR$^b$] can be prepared by following the standard methods known in the art.

(iii) The compound of formula (IB-h3, wherein R$^9$ represents CN and R' represents —NR$^a$COR$^b$] can be prepared by treating an amine compound with a compound of formula R$^b$COCl in a reaction condition as mentioned herein, followed by a palladium catalyzed cyanation procedures well known in the art including, for example, the use of a combination of 1,1'-bis(diphenylphosphino)ferrocene and tris(dibenzylideneacetone)dipalladium(0). The palladium catalyzed cyanation is performed in a suitable solvent such as tetrahydrofuran, dioxane or ether, in the presence of a metal cyanide such as cuprous cyanide or zinc cyanide and a base such as potassium carbonate, cesium carbonate or sodium carbonate, in a temperature range of about 75° C. to about 100° C.

(iv) The compound of formula (IB-h4, wherein both R$^9$ and R' represent —NR$^a$COR$^b$] can be prepared by reacting an amine compound with a compound of formula R$^b$COCl in a reaction condition well known in the art, for example, the process described herein.

Method (14)

A compound of formula (IB-j) [formula IB, wherein R$^9$ represents —CONR$^a$R$^b$] can be prepared from a compound of formula (IB-k, wherein R, R', R", R$^2$, R$^3$, R$^5$, R$^6$, R$^7$ and R$^8$ are as defined herein and R$^9$ represents —COOCH$_3$). The compound of formula (IB-j) can be prepared by following any methods well known in the art including the methods described herein, for example Method (6).

Method (15)

The compound of formula (IB-l) [formula IB, wherein R$^9$ represents —CH$_2$NHR$^b$] can be prepared from a compound of formula (IB-k) by following steps as described in Method (7).

One of ordinary skill in the art will appreciate that in some cases protecting groups may be required during the reaction in any of the methods described herein. The term "protecting group" as used herein refers to a group used to mask or block a particular site/functional group in the preparation for a chemical transformation at a different site/functional group in a molecule. After a particular target or transformation is complete or at some specific step later in a synthetic route, the protecting group can be removed using methods well known in the art. The introduction, use and removal of protecting group have been described in "Protective Groups in Organic Synthesis", (3$^{rd}$ Ed., John Wiley & Sons, 1999). For example, the reaction of a compound of formula (1) and a compound of formula (2) (wherein R, R', R", R$^1$, R$^2$, R$^3$, R$^4$, R$^5$, R$^6$, R$^7$, R$^8$ or R$^9$ is NH-protected) is performed in a suitable solvent such as methylene chloride, chloroform or carbon tetrachloride, in the presence of a base such as dimethylaminopyridine, and a coupling agent such as 1-ethyl-3-(3-dimethylaminopropyl) carbodiimide hydrochloride. The protecting group is then removed by treating the compound thus formed with an acid such as trifluoroacetic acid in a suitable solvent such as methylene dichloride. The examples of N-protecting groups include, but are not limited to, acetyl, benzyl, benzyloxycarbonyl or tert-butyloxycarbonyl.

One of ordinary skill in the art will also appreciate that in some cases leaving group may be required during the reaction in any of the methods described herein. The examples of leaving groups include, but are not limited to, halogen, aryl or alkyl sulfonates, phosphonates, azides and $-S(O)_{0-2}R^h$, wherein $R^h$ is alkyl, aryl or heteroaryl (wherein alkyl, aryl or heteroaryl are optionally substituted). The person of ordinary skill in the art of organic synthesis will readily identify suitable leaving group to perform a desired reaction under different reaction conditions.

During the course of synthetic reactions, the oxidizing agents may be required, which include, but are not limited to, Dess-Martin reagent, TEMPO (2,2,6,6-Tetramethylpiperidine-N-oxide), DDQ (2,3-Dichloro-5,6-dicyano-1,4-benzoquinone), PDC (Pyridinium Dichromate), pyridine.$SO_3$, chromium trioxide, sodium chlorite, p-nitroperbenzoic acid, magnesium monoperoxyphythalate, sodium periodate, potassium periodate, hydrogen peroxide, urea peroxide, alkali metal borates, cumene hydroperoxide, tert-butyl peroxide, peracids such as perbenzoic acid, m-chloroperbenzoic acid, o-carboxyperbenzoic acid and the like; sodium metaperiodate, dichromic acid, dichromates such as sodium dichromate, potassium dichromate; permanganic acid; permanganates such as potassium permanganate, sodium permanganate; and lead salts such as lead tetraacetate.

Similarly, the reducing agents may also be required, which include, but are not limited to, catalytic reducing agents using hydrogen and transition metal catalysts (e.g., palladium, platinum or rhodium); a mixture of trifluoracetic acid triethylsilane, borane tetrahydrofuran complex, diborane, borane dimethylsulfide complex, and a combination of sodium borohydride and boron trifluoride; metal hydrogen complex compounds such as alkali metal borohydrides (e.g., potassium borohydride, sodium borohydride, lithium borohydride, zinc borohydride or sodium triacetoxyborohydride), aluminium lithium hydride; metal hydrides such as sodium hydride; and metal slats such as nickel compounds, zinc compounds, tin compounds (e.g., tin(II) chloride).

According to the present invention, the solvents, unless otherwise indicated, include polar and non-polar solvents well known in the art including polar aprotic and polar protic solvents. The examples of polar solvents include, but are not limited to, methanol, ethanol, isopropyl alcohol, tert-butanol, n-butanol, acetic acid, formic acid or water, or aprotic solvent such as tetrahydrofuran, acetonitrile, dioxane, methylene chloride, di methylsulfoxide, acetone, N,N-dimethylformamide, N,N-dimethylacetamide, ethyl acetate, 1,2-dimethoxyethane, 1,2-dichloroethane, chloroform or pyridine. Polar solvent also include a mixture of water with any of the above, or a mixture of any two or more of the above solvents. The examples of non-polar solvents include, but are not limited to, toluene, benzene, chlorobenzene, xylenes and hexanes.

According to the present invention, the coupling agents may be required which include, but are not limited to, tetramethylfluoroformamidium hexafluorophosphate (TFFH), benzyltriphenylphosphonium dihydrogen trifluoride (PTF), 2-(1H-7-azabenzotriazol-1-yl)-1,1,3,3-tetramethyl uronium hexafluorophosphate methanaminium (HATU) or 1-hydroxy-7-azabenzotriazole (HOAt), 1-hydroxybenzotriazole (HOBt), 1-ethyl-3-(3-dimethylaminopropyl)carbodiimide (EDCl), 1-ethyl-3-(3-dimethylaminopropyl)carbodiimide hydrochloride (EDCl.HCl), diphenylphosphoryl azide (DPPA), diethylpyrocarbonate (DEPC), pentafluorophenyl diphenylphosphinate (FDDP), (2-(1H-benzotriazole-1-yl)-1,1,3,3-tetramethyluronium hexafluorophosphate (HBTU), benzotriazole-1-yl-oxy-tris-(dimethylamino)-phosphonium hexafluorophosphate (BOP), 1-(t-butyldimethylsilyloxy) benzotriazole (TBDMS-OBt) or 1-(t-butyldiphenylsilyloxy) benzotriazole (TBDPS-OBt). The coupling agent may be optionally used in combination with one or more base(s) selected from, but are not limited to, N,N-diisopropylethylamine, diethylamine, triethylamine, dicyclohexylamine, pyridine, dimethylaminopyridine, collidine (e.g., 2,4,6-trimethylpyridine) or lutidine (e.g., 2,3-dimethylpyridine). The coupling agent also includes a mixture of any of the above, for example, a mixture of TFFH and HOAt or a mixture of EDCl and HOAt or HOBt.

According to the present invention, the palladium complex, unless otherwise indicated, includes, but are not limited to, dichloro[1,1'-bis(diphenylphosphino)ferrocene]palladium(II), 1,1'-bis(diphenylphosphino)ferrocene-palladium (11)dichloride dichloromethane, dichloro{bis-2-(3,5-dimethylpyrazolyl-1-carbonyl)furan}palladium (II), dichloro{bis-2-(3,5-dimethylpyrazolyl-1-carbonyl) thiophene}palladium(II), dichloro{bis2-(3,5-di-tert-butylpyrazolyl-1-carbonyl)furan}palladium (II), dichloro{bis-2-(3,5-di-tert-butylpyrazolyl-1-carbonyl) thiophene}palladium(II), dichloro{bis-2-(3-methylpyrazolyl-1-carbonyl)-furan}palladium(II), dichloro{bis-2-(pyrazolyl-1-carbonyl)furan}palladium (II), dichloro{bis-2-(3,5-diphenylpyrazolyl-1-carbonyl) furan}palladium(II) or dichloro{bis-2-(3,5-diphenylpyrazolyl-1-carbonyl)thiophene}palladium (II).

In certain embodiments, it is to be understood that in place of oxidizing agent, reducing agent, coupling agent, solvent and base, optionally indicated in one or more methods described herein, any other oxidizing agent, reducing agent, coupling agent, solvent and base, as described herein, can also be employed.

In certain embodiments, it is desirable to separate the reaction products from one another and/or from starting materials to get the desired products in the purified forms. Such a separation can be performed by using techniques well known in the art. For example, multiphase extraction, crystallization from a solvent or solvent mixture, distillation, sublimation or chromatography. One skilled in the art will apply the techniques most likely to achieve the desired purification.

In certain embodiments, the present invention encompasses isotopically labeled compounds of the formula (I). All isotopes of any particular atom or element as specified are contemplated within the scope of the present invention. The examples of isotopes that can be incorporated into compounds of the present invention include, but are not limited to, isotopes of hydrogen (e.g., $^2H$ or $^3H$), carbon (e.g., $^{13}C$ or $^{14}C$), nitrogen (e.g., $^{13}N$ or $^{15}N$), oxygen (e.g., $^{15}O$, $^{17}O$ or $^{18}O$), phosphorous (e.g., $^{32}P$ or $^{33}P$), sulphur (e.g., $^{35}S$), halogen (e.g., $^{18}F$, $^{36}Cl$, $^{123}I$ or $^{125}I$). Isotopically labeled compounds of formula (I) can be prepared by following the methods (1-15) by using isotopically labeled reagents. Isotopically labeled of the present invention may be useful in compound and/or substrate tissue distribution assays. Such applications of isotopically labeled compounds are well known to person skill in the art, and are therefore within the scope of the present invention.

EXPERIMENTAL PROCEDURES

It should be understood that the procedures set forth below are intended for illustrative purposes and are not to be construed as limiting the scope of the disclosure. Any modification in the procedures described herein, other synthetic procedures and modification thereon can be employed or adapted. All such modifications and alternative procedures are within the spirit and scope of the present application. In examples mentioned below, the term intermediate in some cases may refer to starting material for the synthesis of final compound.

PREPARATION OF INTERMEDIATES

Intermediate 1: Synthesis of 7-chloro-1H-pyrrolo[2,3-c]pyridine

A solution of 2-chloro-3-nitropyridine (1 g, 6.3 mmol) in dry tetrahydrofuran (100 mL) was treated with vinyl magnesium bromide (60 mL, 60 mmol) at −78° C. in a drop-wise manner under inert atmosphere. The resulting reaction mixture was stirred at the same temperature for 2 hours followed by stirring at −20° C. for 8 hours. The reaction was quenched slowly with aqueous ammonium chloride solution (20 mL), extracted with ethyl acetate (3×50 mL) and the combined organic layer dried over anhydrous sodium sulfate, filtered and concentrated. The crude product was purified by silica gel (100-200) column chromatography using ethyl acetate and hexane gradient elution to afford 7-chloro-1H-pyrrolo[2,3-c]pyridine (0.350 g, 36.45%).
$^1$H NMR (400 MHz, CHCl$_3$-d): δ 8.04 (d, J=5.46 Hz, 1H), 7.50 (dd, J=5.46, 0.75 Hz, 1H) 7.43 (dd, J=3.11, 2.54 Hz, 1H), 6.64 (dd, J=3.14, 2.07 Hz, 1H). MS: 152.98 (M$^+$).

7-Bromo-1H-pyrrolo[2,3-c]pyridine (Intermediate 2) was synthesized from 2-bromo-3-nitropyridine (18.55%) in an analogous manner.
$^1$H NMR (400 MHz, CHCl$_3$-d): δ 7.99-8.06 (m, 1H), 7.48-7.54 (m, 1H), 7.41-7.45 (m, 1H), 6.64-6.69 (m, 1H). MS: 197.40 (M$^+$).

Intermediate 3: Synthesis of Cyclopropanecarboxamide

Ammonia was purged through a well-stirred solution of cyclopropane carbonyl chloride (1 g, 9.61 mmol) in dichloromethane (10 mL) for 2 hours at room temperature. Solvent was removed under vacuum, the residue was taken up in ethyl acetate and filtered. The filtrate was concentrated to afford pure cyclopropanecarboxamide as a crystalline solid (0.81 g, 100%).
$^1$H NMR (400 MHz, CHCl$_3$-d): δ 5.63-5.91 (br. s, 2H), 1.43 (m, 1H), 0.98 (dd, J=4.42, 2.98 Hz, 2H), 0.79 (dd, J=7.91, 2.95 Hz, 2H). MS: 85.91 (M+1).

Intermediate 4: Synthesis of Cyclobutane Carboxmide

A solution of cyclobutyl carbonyl chloride (5 g, 42.37 mmol) in dichloromethane (20 mL) was treated with aqueous ammonia solution (20 mL) at −20° C. The resulting reaction mixture was stirred overnight at room temperature. Volatiles were removed under vacuum. The precipitated solid was filtered and dried under vacuum to afford the cyclobutane carboxamide (3 g, 71.77%).
$^1$H NMR (400 MHz, DMSO-d$_6$): δ 7.02-7.16 (m, 1H), 6.65 (br. s., 1H), 2.95 (quind, J=8.43, 8.43, 8.43, 8.43, 0.85 Hz, 1H), 1.61-2.18 (m, 6H).

Intermediate 5: Synthesis of N-(1H-pyrrolo[2,3-c]pyridin-7-yl)cyclobutanecarboxamide To a solution of 7-bromo-1H-pyrrolo[2,3-c]pyridine (500 mg, 2.53 mmol) in toluene were added tris (dibenzylidene acetone)dipalladium (116.20 mg, 0.126 mmol), Xantphos (32.98 mg, 0.057 mmol), cesium carbonate (896 mg, 2.75 mmol), and cyclobutanecarboxamide (251 mg, 2.96 mmol, Intermediate 4). The resulting reaction mixture was heated to 120° C. and stirred for 8 hours. After cooling to room temperature a saturated aqueous sodium bicarbonate solution (20 mL) was added to the reaction mixture and extracted with ethyl acetate (3×50 mL). The combined organic layer was dried over anhydrous sodium sulfate, filtered and concentrated. The crude product was purified by silica gel (100-200) column chromatography to afford N-(1H-pyrrolo[2,3-c]pyridin-7-yl)cyclopropane carboxamide (200 mg, 36% yield).
$^1$H NMR (400 MHz, CHCl$_3$-d): δ 7.72-7.79 (m, 1H), 7.45-7.54 (m, 1H), 7.38-7.45 (m, 1H), 6.58-6.63 (m, 1H), 3.47-3.51 (m, 1H), 2.29-2.51 (m, 2H), 1.88-2.14 (m, 2H), 1.21-1.31 (m, 2H). MS: 216.56 (M+1).

The following intermediates were prepared in an analogous manner.

N-(1H-Pyrrolo[2,3-c]pyridin-7-yl)acetamide (Intermediate 6, yield: 8.69%) was synthesized from 7-chloro-1H-pyrrolo[2,3-c]pyridine using acetamide.
$^1$H NMR (400 MHz, CHCl$_3$-d): δ 7.81-7.88 (m, 1H), 7.34-7.43 (m, 2H), 6.56 (d, J=3.01 Hz, 1H), 2.31 (s, 3H).

N-(1H-pyrrolo[2,3-c]pyridin-7-yl)cyclopropanecarboxamide (Intermediate 7, yield: 7.59%) was synthesized from 7-chloro-1H-pyrrolo[2,3-c]pyridine using cyclopropanamide.
$^1$H NMR (400 MHz, CHCl$_3$-d): δ 8.01-8.06 (m, 1H), 7.82-7.87 (m, 1H), 7.36 (d, J=5.58 Hz, 2H), 6.55 (d, J=2.95 Hz, 1H), 1.59-1.61 (m, 1H), 1.16 (d, J=4.39 Hz, 2H), 0.94-1.00 (m, 2H). MS: 202.22 (M+1).

N-(1H-pyrrolo[2,3-c]pyridin-7-yl)propanamide (Intermediate 8, yield: 15%) was synthesized from 7-chloro-1H-pyrrolo[2,3-c]pyridine using propanamide.
$^1$H NMR (400 MHz, DMSO-d6): δ 11.01 (s, 1H), 10.49 (br s, 1H), 7.82 (d, J=5.6 Hz, 1H), 7.69 (d, J=2.4 Hz), 1H), 7.36 (d, J=5.6 Hz, 1H), 2.47-2.53 (m, 2H), 1.12-1.16 (t, J=7.2 Hz, 3H). MS: 190.55 (M+1).

Intermediate 9: Synthesis of 4-bromo-2,6-dichlorobenzoic acid

Step a: Synthesis of 2,6-dichloro-3-nitrobenzoic acid 2,6-Dichlorobenzoic acid (10 g, 52 mmol) was added portion wise to a previously stirred mixture of nitric acid (15 mL) and sulfuric acid (30 mL) at 55° C. and stirred for 30 minutes followed by stirring at room temperature for 0.5 hour. The reaction mixture was poured into crushed ice and the precipitated off white solid was filtered, washed with water, and dried under vacuum to afford 2,6-dichloro-3-nitrobenzoic acid (7 g, 57%).
$^1$H NMR (400 MHz, MeOH-d$_4$): δ 7.98 (d, J=8.81H), 7.67 (d, J=8.81H).

Step b: Synthesis of 3-amino-2,6-dichlorobenzoic acid 2,6-Dichloro-3-nitro-benzoic acid (10 g, 42 mmol, Step a) was added to concentrated hydrochloric acid (100 mL), followed by stannous chloride dihydrate (38 g, 169 mmol). The reaction mixture was heated at 60° C. for 1 hour. The reaction mixture was diluted with water (500 mL) and extracted with ethyl acetate (2×300 mL). The combined organic layer was dried over anhydrous sodium sulfate and concentrated under vacuum to afford the crude product (sticky material). The crude material was dissolved in water (200 mL, turbid solution) and treated slowly with aqueous sodium hydroxide (20%) solution till precipitation while maintaining the pH 1-2 (dense precipitate was observed). The precipitate was filtered and filtrate was extracted with ethyl acetate (2×200 mL) and dried over anhydrous sodium sulfate and concentrated under vacuum to yield 3-amino-2,6-dichloro-benzoic acid as a creamish solid (6 gm, 69%).

$^1$H NMR (400 MHz, MeOH-d$_4$): δ 7.11 (d, J=8.81H), 6.85 (d, J=8.81H).

Step c: Synthesis of 3-amino-4-bromo-2,6-dichlorobenzoic acid

A mixture of 3-amino-2,6-dichlorobenzoic acid (5 g, 24 mmol, Step b) in acetonitrile (50 mL) was treated with N-bromosuccinimide (5.1 g, 29 mmol) and the reaction mixture was stirred at 90° C. for 45 minutes. Acetonitrile was removed in vaccuo and the residue was partitioned between water (200 mL) and ethyl acetate (200 mL). The organic layer was separated and the aqueous layer was again extracted with ethyl acetate (2×100 mL). The combined organics were dried over anhydrous sodium sulfate and concentrated to afford 3-amino-4-bromo-2,6-dichloro-benzoic acid (5 g, 73%).

$^1$H NMR (400 MHz, MeOH-d$_4$): δ 7.49 (s, 1H) and 7.11 (d, J=8.81H).

Step d: Synthesis of 4-bromo-2,6-dichlorobenzoic acid

An aqueous solution of sodium nitrite (3.64 g dissolved in 4 mL of water, 52 mmol) was added drop wise to the concentrated hydrochloric acid (15 mL) cooled to −10 to −5° C. 3-Amino-4-bromo-2,6-dichlorobenzoic acid (5 g, 17 mmol, Step c) was added to the above solution portion-wise while maintaining the temperature around −5° C. The reaction mixture was stirred at this temperature for about 2 hours. Then hypophosphorous acid (9 mL, 170 moles) was added very slowly over a period of 1 hour at the same temperature. The reaction mixture was stirred at the same temperature for about 3 hours and then kept in refrigerator overnight. A precipitate was observed at this stage. The reaction mixture was allowed to warm to room temperature and kept for another 2 hours at room temperature. The reaction mixture was filtered, the residue was washed with cold water and dried to obtain 4-bromo-2,6-dichloro benzoic acid as a yellowish solid (2 g, 42%).

$^1$H NMR (400 MHz, MeOH-d$_4$): δ 7.69 (s, 2H).

Intermediate 10: Synthesis of 4-bromo-2,6-dichlorobenzoyl chloride

A solution of 4-bromo-2,6-dichlorobenzoic acid (2 g, 7.4 mmol), and thionyl chloride (5.5 mL, 74 mmol) in dichloromethane (30 mL) was heated under refluxed for 5 hours. The reaction mixture was cooled to room temperature and concentrated under vacuum. The resulting mass was taken up in dichloromethane (20 mL) and concentrated under vacuum. The process was repeated 2-3 times to remove excess thionyl chloride. 4-Bromo-2,6-dichlorobenzoyl chloride (2.2 g, 100%) thus formed was used as such for the next step.

Intermediate 11: Synthesis of N-(1H-pyrrolo[2,3-c]pyridin-5-yl)acetamide

Step a: Synthesis of N-(4-methyl-5-nitropyridin-2-yl)acetamide

A mixture of 4-methyl-5-nitropyridin-2-amine (5 g, 32 mmol) and acetic anhydride (20 mL) was heated at 90° C. for 4 hours. After cooling the solvent was evaporated under vacuum. The concentrated mass was dissolved in toluene and evaporated under vacuum. The resulting solid was triturated with diethyl ether and filtered to afford N-(4-methyl-5-nitropyridin-2-yl)acetamide (5.5 g, 87%).

Step b: Synthesis of N-{4-[(Z)-2-(dimethylamino) ethenyl]-5-nitropyridin-2-yl}acetamide To a solution of N-(4-methyl-5-nitropyridin-2-yl)acetamide (1 g, 5 mmol, Step a) in dry dimethylformamide (10 mL), dimethylformamide dimethyl acetal (1.5 mL, 11 mmol) was added and the resulting reaction mixture was heated at 90° C. for 3 hours. The reaction mixture was cooled to room temperature, toluene was added and evaporated under vacuum followed by triturating with diethyl ether and filtration to afford N-{4-[(Z)-2-(dimethylamino)ethenyl]-5-nitropyridin-2-yl}acetamide (0.8 g, 63%).

Step c: Synthesis of N-(1H-pyrrolo[2,3-c]pyridin-5-yl)acetamide

To a solution of N-{4-[(Z)-2-(dimethylamino)ethenyl]-5-nitropyridin-2-yl}acetamide (0.7 g, 3 mmol, Step b) in methanol and dichloromethane (5:1, 120 mL), palladium on carbon (0.4 g) was added followed by addition of acetic acid (7 mL). The reaction mixture was then purged with hydrogen gas and stirred overnight at room temperature. The resulting mixture was filtered over celite bed, and the residue was washed with methanol (100 mL). The combined filtrate was concentrated under vacuum and purified by silica gel column chromatography using methanol in dichloromethane (2%) to afford N-(1H-pyrrolo[2,3-c]pyridin-5-yl)acetamide (0.35 g, 71%).

$^1$H NMR (400 MHz, DMSO-d$_6$): δ 11.43 (br. s., 1H), 10.13 (s, 1H), 8.46 (s, 1H), 8.21, (s, 1H), 7.56 (t, J=2.76 Hz, 1H), 6.45 (t, J=1.88 Hz, 1H), 2.06 (s, 3H). MS: 176.44 (M+1).

Intermediate 12: Synthesis of N-(1H-pyrrolo[2,3-c] pyridin-5-yl)cyclopropanecarboxamide

Step a: Synthesis of N-(4-methyl-5-nitropyridin-2-yl)cyclopropanecarboxamide An ice-cooled mixture of 4-methyl-5-nitropyridin-2-amine (1 g, 6.5 mmol), triethylamine (1.31 g, 13 mmol) in tetrahydrofuran (20 mL) was treated with cyclopropyl acetyl chloride (0.75 g, 7.1 mmol) drop wise. After complete addition the reaction mixture was stirred at room temperature for 1 hour, cooled to 0° C. and added cyclopropyl acetyl chloride (0.75 g, 7.1 mmol) followed by stirring at room temperature for 1 hour. The solvent was evaporated under vacuum and water (100 mL) was poured into the reaction mixture and extracted with ethyl acetate (2×150 mL). The organic layer was washed with aqueous sodium bicarbonate solution, dried over anhydrous sodium sulfate and concentrated under vacuum. The residue (1.5 g) was taken-up in methanol and water (4:1, 40 mL). Potassium carbonate was added to it and stirred at room temperature for 20 hours. The mixture was concentrated under vacuum. Residue was taken up in water (100 mL) and extracted with ethyl acetate (2×150 mL). The organic layer was dried over anhydrous sodium sulfate and concentrated under vacuum to get the crude compound, which upon purification by silica gel column chromatography using methanol in dichloromethane (1%) as eluent afforded N-(4-methyl-5-nitropyridin-2-yl)cyclopropanecarboxamide (0.6 g, 52%).

Step b: Synthesis of N-{4-[(Z)-2-(dimethylamino) ethenyl]-5-nitropyridin-2-yl}cyclopropanecarboxamide N-{4-[(Z)-2-(dimethylamino)ethenyl]-5-nitropyridin-2-yl}cyclopropanecarboxamide was prepared in an analogous manner as in intermediate 11, Step b.

Step c: Synthesis of N-(1H-pyrrolo[2,3-c]pyridin-5-yl)cyclopropanecarboxamide N-(1H-pyrrolo[2,3-c]pyridin-5-yl)cyclopropanecarboxamide was prepared following a procedure similar to N-(1H-pyrrolo[2,3-c]pyridin-5-yl)acetamide (Intermediate 11, Step c).

$^1$H NMR (400 MHz, DMSO-$d_6$): δ 11.43 (br. s., 1H), 10.41 (s, 1H), 8.47 (s, 1H), 8.19 (s, 1H), 7.56 (t, J=2.76 Hz, 1H), 6.43 (td, J=1.82, 0.88 Hz, 1H), 1.99 (s, 1H), 0.65-0.88 (m, 4H). MS: 202.51 (M+1).

Intermediate 13: Synthesis of 3,5-dichloro-4-(methoxycarbonyl)benzoic acid

Step a: Synthesis of dimethyl 2-amino-3,5-dichlorobenzene-1,4-dicarboxylate Sulfuryl chloride (8.5 mL, 10.5 mmol) was added to a round bottom flask containing diethyl ether (150 mL) at 0° C. Dimethyl 2-aminobenzene-1,4-dicarboxylate (10 g, 47.8 mmol) was added portion-wise while maintaining the temperature at 0° C. After complete addition, reaction mixture was stirred at room temperature for 15 hours. The reaction mixture was neutralized using saturated aqueous sodium bicarbonate solution under ice-cooled condition, diluted with water (100 mL) and then extracted with ethyl acetate (2×800 mL). The combined organic layer was washed with brine, dried over anhydrous sodium sulfate and concentrated under vacuum to afford dimethyl 2-amino-3,5-dichlorobenzene-1,4-dicarboxylate as a brownish liquid (12.9 g, 97%).

$^1$H NMR (400 MHz, DMSO-$d_6$): δ 7.82 (s, 2H), 6.95-7.37 (m, 2H), 3.93 (s, 3H), 3.86 (s, 3H). MS: 278.09 (M$^+$), 280.07 (M+2).

Step b: Synthesis of dimethyl 2,6-dichlorobenzene-1,4-dicarboxylate

In a round bottom flask containing concentrated sulfuric acid (10 mL) was added ice-cold water (10 mL) while maintaining the temperature around 0° C. Sodium nitrite (3.7 g, 53 mmol) was added portion wise followed by the drop wise addition of hypophosphorous acid (8 mL). This was followed by drop wise addition of a solution of dimethyl 2-amino-3,5-dichlorobenzene-1,4-dicarboxylate (5 g, 17.9 mmol, Step a) in acetic acid (10 mL). The resulting reaction mixture was stirred at 0° C. for 2 hours and then stored in a refrigerator at −10° C. for 15 hours. The reaction mixture was stirred at room temperature for additional 2 hours. The reaction mixture was again cooled to 0° C. and neutralized with aqueous ammonia solution, partitioned with ethyl acetate (2×15 mL). The combined organic layer was washed with brine, dried over anhydrous sodium sulfate, filtered and concentrated. The crude product was purified by silica gel column chromatography using ethyl acetate in hexane (4%) to yield dimethyl 2,6-dichlorobenzene-1,4-dicarboxylate as a pale yellow crystalline solid (3.8 g, 79%).

$^1$H NMR (400 MHz, DMSO-$d_6$): δ 8.04 (s, 2H), 3.96 (s, 3H), 3.90 (s, 3H).

Step c: Synthesis of 3,5-dichloro-4-(methoxycarbonyl)benzoic acid

To the stirred solution of dimethyl 2,6-dichlorobenzene-1,4-dicarboxylate (2 g, 7.6 mmol, Step b) in tetrahydrofuran and water (1:1, 20 mL), sodium hydroxide (304 mg, 7.6 mmol) was added and the reaction mixture was stirred at room temperature for 16 hours. The reaction mixture was concentrated under vacuum and the residue was neutralized using cold hydrochloric acid (1N). The precipitated solid was filtered under suction, washed with hexane and dried to afford 3,5-dichloro-4-(methoxycarbonyl)benzoic acid as an white solid (1.5 g, 85%).

$^1$H NMR (400 MHz, DMSO-$d_6$): δ 7.93 (s, 2H), 3.94 (s, 3H). MS: 247.6 (M−2), 249.6 (M$^-$).

Intermediate 14: Synthesis of 2,6-dichloro-4-(methylcarbamoyl)benzoyl chloride

Synthesis of 2,6-dichloro-4-(methylcarbamoyl)benzoyl chloride

A mixture of 2,6-dichloro-4-(methylcarbamoyl)benzoic acid (400 mg, 1.6 mmol) and thionyl chloride (1.91 g, 16 mmol) in dichloromethane (10 mL) was stirred at 50° C. for 5 hours. The reaction mixture was concentrated under rotary evaporator and used as such for next step.

The following intermediates were prepared in an analogous manner using appropriate starting materials. These intermediates are used as such for next step.

2,6-Dichloro-4-(ethylcarbamoyl)benzene carbonyl chloride (Intermediate 15).
2,6-Dichloro-4-(2-methoxyethylcarbamoyl)benzene carbonyl chloride (Intermediate 16).
2,6-Dichloro-4-(carbamoyl)benzene carbonyl chloride (Intermediate 17).

Intermediate 18: Synthesis of methyl-4-(chlorocarbonyl) 3,5-difluoro-benzoate

Step a: Synthesis of methyl-3,5-difluorobenzoate

To a solution of 3,5-difluorobenzoic acid (10 gm, 63.2 mmol) in dichloromethane (100 mL) was added oxalyl chloride (11.96 gm, 94.9 mmol) at 0° C. followed by addition of dimethylformamide (2 mL). The resulting reaction mixture was stirred for about 3 hours at room temperature. Methanol (100 mL) was added to the reaction mass and stirring was continued further for 20-30 minutes. Solvents were evaporated to obtain an oily mass which was further purified by column chromatography over silica gel (100-200) using ethyl acetate/hexane gradient elution to afford colorless methyl 3,5-difluorobenzoate (10 gm, 91.91%).

$^1$H NMR (400 MHz, CHCl$_3$-d): δ 7.52-7.59 (m, 1H), 6.97-7.06 (m, 1H), 3.94 (s, 3H).

Step b: Synthesis of methyl-3,5-difluoro-4-formyl benzoate

To a solution of methyl 3,5-difluorobenzoate (1 gm, 5.8 mmol) in dry tetrahydrofuran (20 mL), lithium diisopropylamide (0.621 gm, 5.8 mmol, 15% solution in tetrahydrofuran and heptane) was added at −78° C. The resulting reaction mixture was stirred for about 1 hour. Dimethylformamide (0.51 g, 6.9 mmol) was added drop wise to the reaction mixture and stirring was continued for about 3 hours at −78° C. The reaction was warm up to room temperature. Saturated aqueous ammonium chloride solution (20 mL) was added to quench the reaction mass. The aqueous phase was extracted with ethyl acetate (3×50 mL) and the combined organic layer dried over anhydrous sodium sulfate, filtered and concentrated. The crude product was purified by column chromatography over silica gel (100-200) using ethyl acetate/hexane gradient elution to afford methyl 3,5-difluoro-4-formylbenzoate (0.5 gm, 31.25%).

$^1$H NMR (400 MHz, CHCl$_3$-d): δ 10.39 (s, 1H), 7.55-7.83 (m, 2H), 3.98 (s, 3H).

Step c: Synthesis of 2,6-difluoro-4-(methoxycarbonyl)benzoic acid

To a solution of 3,5-difluoro-4-formylbenzoate (2.5 gm, 12.5 mmol) in dimethylsulfoxide (10 mL) were added potassium dihydrogen phosphate (4.25 gm, 31.2 mmol), sodium chlorite (2.26 gm, 25 mmol), sulfamic acid (1.21 gm, 12.5 mmol) and water (5 mL) in one lot at an ambient temperature. The resulting reaction mixture was stirred for about 3 hours. The reaction mass was diluted with water (100 mL). The aqueous phase was extracted with ethyl acetate (3×100 mL) and the combined organic layer dried over anhydrous sodium sulfate, filtered and concentrated to afford 2,6-difluoro-4-(methoxycarbonyl)benzoic acid (1.6 gm, 89.88%).

$^1$H NMR (400 MHz, DMSO-d6): δ 7.55-7.56 (m, 2H), 3.89 (s, 3H).

Step d: Synthesis of methyl-4-(chlorocarbonyl) 3,5-difluoro-benzoate

To a solution of 2,6-difluoro-4-(methoxycarbonyl)benzoic acid (1.6 gm, 7.4 mmol) in dichloromethane (25 mL), oxalyl chloride (2.33 gm, 18.5 mmol) was added at 0° C. followed by addition of dimethylformamide (1 mL). The resulting reaction mixture was stirred for about 3 hours at an ambient temperature. Solvents were evaporated to afford crude solid methyl 4-(chlorocarbonyl)-3,5-difluorobenzoate (1.6 gm, 94.11% Yield). The resulting product was used as such for next step.

Intermediate 19: Synthesis of 4-cyano-2,6-difluorobenzoyl chloride

Step a: Synthesis of 3,5-difluoro-4-formylbenzonitrile

To a solution of 3,5-difluorobenzonitrile (1 gm, 7.1 mmol) in dry tetrahydrofuran (20 mL), lithium diisopropylamide (0.769 gm, 7.1 mmol) was added at −78° C. The resulting reaction mixture was stirred for about 1 hour. Dimethylformamide (0.62 g, 8.5 mmol) was added dropwise to the reaction mixture and stirring was continued for about 45 minutes. Acetic acid (1.5 mL) and water (40 mL) were added to the cold solution of reaction mixture. The aqueous phase was extracted with diethyl ether (4×50 mL). The combined organic layer was dried over anhydrous sodium sulfate, filtered and concentrated. The crude product was purified by silica gel (100-200) column chromatography using hexane and ethyl acetate as gradient system to afford pure 3,5-difluoro-4-formylbenzonitrile (0.5 gm, 31.25%).

$^1$H NMR (400 MHz, DMSO-d6): δ 10.20 (s, 1H), 7.91-8.04 (m, 2H).

Step b: Synthesis of 4-cyano-2,6-difluoro benzoic acid

To a solution of 3,5-difluoro-4-formylbenzonitrile (0.2 g, 1.1 mmol) in dimethylsulfoxide (10 mL), were added a aqueous solution of potassium dihydrogen phosphate (0.41 g, 2.9 mmol in 0.4 mL of water), sodium chlorite (0.216 g, 2.3 mmol in 4 mL of water) in one lot at an ambient temperature. The resulting reaction mixture was stirred for about 1 hour. The reaction mass was diluted with water (100 mL). The aqueous phase was extracted with ethyl acetate (3×100 mL). The combined organic layer dried over anhydrous sodium sulfate, filtered and concentrated to afford 4-cyano-2,6-difluorobenzoic acid (200 mg, 91.32%).

$^1$H NMR (400 MHz, DMSO-d$_6$): δ 7.95 (d, J=7.53 Hz, 2H).

Step c: Synthesis of 4-cyano-2,6-difluorobenzoyl chloride

A mixture of 4-cyano-2,6-difluorobenzoic acid (0.3 gm, 0.5 mmol) and thionyl chloride (5 mL) were refluxed for about 3 hours. The reaction mixture was cooled to ambient temperature, and concentrated under vacuum at 50° C. to afford 4-cyano-2,6-difluorobenzoyl chloride (0.3 gm, 91.18%).

The resulting product was used as such for further reaction.

Intermediate 20: Synthesis of 4-bromo-2,6-difluorobenzoic acid

To a solution of 1-bromo-3,5-difluorobenzene (1 g, 5.2 mmol) in dry tetrahydrofuran (50 mL), was added lithium diisopropylamide (0.557 g, 5.2 mmol) at −78° C. The resulting reaction mixture was stirred at an ambient temperature for about 1.5 hours. A cooled reaction mixture was poured onto dry ice and left for about 20 minutes, followed by mixing with aqueous hydrochloric acid (6N, 10 mL). The acidic aqueous phase was extracted with ethyl acetate (3×100 mL). The combined organic layer dried over anhydrous sodium sulfate, filtered and concentrated to afford 4-bromo-2,6-difluorobenzoic acid (800 mg, 66.66%).

$^1$H NMR (400 MHz, DMSO-d$_6$): Shift 13.80-14.46 (m, 1H), 7.59-7.67 (m, 2H).

Intermediate 21: Synthesis of N-(2-methyl-1H-pyrrolo[2,3-c]pyridin-7-yl)cycloprobanecarboxamide Step a: Synthesis of 7-chloro-1-(phenylsulfonyl)-1H-pyrrolo[2,3-c]pyridine 7-Chloro-1-(phenylsulfonyl)-1H-pyrrolo[2,3-c]pyridine was prepared following the method described in US 2010/0292262.

$^1$H NMR (400 MHz, DMSO-d6): δ 8.29 (d, J=3.76 Hz, 1H), 8.17 (d, J=5.02 Hz, 1H), 7.93 (dd, J=1.13, 8.41 Hz, 2H), 7.73-7.79 (m, 2H), 7.67 (d, J=8.28 Hz, 2H), 7.08 (d, J=3.51 Hz, 1H). MS: 292.96 (M+1).

Step b: Synthesis of 7-chloro-2-methyl-1-(phenylsulfonyl)-1H-pyrrolo[2,3-c]pyridine 7-chloro-2-methyl-1-(phenylsulfonyl)-1H-pyrrolo[2,3-c] pyridine was prepared following the method described in Synthesis 2005 No. 20 pp 3581-3588.

$^1$H NMR (400 MHz, CHCl$_3$-d): δ 8.14 (d, J=5.02 Hz, 1H), 7.84-7.86 (m, 2H), 7.60-7.66 (m, 1H), 7.49-7.56 (m, 2H), 7.30 (d, J=5.02 Hz, 1H), 6.49 (d, J=1.00 Hz, 1H), 2.75 (d, J=1.25 Hz, 3H). MS: 307.35 (M+1).

Step c: Synthesis of 7-chloro-2-methyl-1H-pyrrolo[2,3-c]pyridine

To a solution of 7-chloro-2-methyl-1-(phenylsulfonyl)-1H-pyrrolo[2,3-c]pyridine (220 mg, 0.71 mmol) in ethanol (10 mL), a solution of sodium hydroxide (10%, 6 mL) was added and the reaction mixture was stirred at room temperature for about 16 hours. The solvent was removed under vacuum. The residue was taken up in ethyl acetate washed with water and brine, dried over anhydrous sodium sulfate & concentrated under vacuum to give 7-chloro-2-methyl-1H-pyrrolo[2,3-c]pyridine (110 mg, 92% yield).
$^1$H NMR (400 MHz, CHCl$_3$-d): δ 8.47 (br. s, 1H), 7.97 (d, J=5.27 Hz, 1H), 7.35 (d, J=5.52 Hz, 1H), 6.30 (dd, J=1.00, 2.01 Hz, 1H), 2.48 (d, J=0.75 Hz, 3H). MS: 167.14 (M+1).

Step d: Synthesis of N-(2-methyl-1H-pyrrolo[2,3-c]pyridin-7-yl)cyclopropanecarboxamide To a solution of 7-chloro-2-methyl-1H-pyrrolo[2,3-c]pyridine (1.1 g, 06 mmol) in toluene were added tris (dibenzylidene acetone)dipalladium (302 mg, 0.3 mmol), Xantphos (0.286 g, 0.49 mmol), cesium carbonate (4.3 g, 13.2 mmol), and cyclopropanecarboxamide (0.842 g, 9 mmol). The resulting reaction mixture was heated to 110° C. and stirred for about 4 hours. The reaction mixture cooled to room temperature diluted with water and extracted with ethyl acetate. The combined organic layer was dried over anhydrous sodium sulfate, filtered and concentrated. The crude product was purified by silica gel (100-200) column chromatography to afford N-(2-methyl-1H-pyrrolo[2,3-c]pyridin-7-yl)cyclopropanecarboxamide (0.45 g, 40% yield).
$^1$H NMR (400 MHz, CHCl$_3$-d): δ 11.01 (brs, 1H), 10.3 (brs, 1H), 7.75 (d, J=5.52 Hz, 1H), 7.23 (d, J=5.77 Hz, 1H), 6.24 (s, 1H), 2.43 (s, 3H), 1.86 (m, 1H), 1.14-1.25 (m, 2H), 0.94-1.12 (m, 2H). MS: 216.06 (M+1).

Intermediate 22: Synthesis of 1H-pyrrolo[3,2-c]pyridine

Step a: Synthesis of 3-methylpyridine 1-oxide

3-Methylpyridine (20 g, 21.5 mmol) was added into a round bottom flask containing acetic acid (60 mL). The mixture was treated with ice-cooled hydrogen peroxide (19 mL, 50% solution, 27.6 mmol) and the resulting reaction mixture was heated at 70° C. for 20 hours. The reaction mixture was concentrated under vacuum and the residue was treated with aqueous sodium hydroxide solution (40%) while maintaining the temperature at 0° C. The mixture was then extracted with dichloromethane. The combined organic layer was washed with brine, dried over anhydrous sodium sulfate and concentrated under vacuum to get 3-methylpyridine 1-oxide (24 g, 100%) as oil.
$^1$H NMR (400 MHz, DMSO-d$_6$): δ 8.09-8.15 (m, 1H), 8.05 (dd, J=6.37, 0.78 Hz, 1H), 7.27-7.34 (m, 1H), 7.18 (dt, J=7.81, 0.74 Hz, 1H), 2.51 (m, 3H).

Step b: Synthesis of 3-methyl-4-nitropyridine 1-oxide

3-Methylpyridine 1-oxide (2 g, 18.3 mmol, Step a) was added slowly to the round bottom flask containing sulfuric acid (7 mL, 128 mmol). The mixture was cooled to 0° C. and nitric acid (5.7 mL, 128 mmol) was added drop wise. The resulting reaction mixture was heated at 90-100° C. for 2 hours. The reaction mixture was poured onto crushed ice and sodium carbonate was added portion wise. The aqueous phase was extracted with chloroform. The combined organic layer was washed with brine, dried over anhydrous sodium sulfate and concentrated under vacuum to get 3-methyl-4-nitropyridine 1-oxide (1.4 g, 50%).
$^1$H NMR (400 MHz, CHCl$_3$-d): δ 8.09-8.17 (m, 2H), 8.02 (d, J=7.09 Hz, 1H), 2.62 (s, 3H).

Step c: Synthesis of (E)-N,N-dimethyl-2-(4-nitro-1-oxidopyridin-3-yl)ethenamine

To the stirred solution of 3-methyl-4-nitropyridine 1-oxide (600 mg, 3.8 mmol, Step b) in dimethylformamide was added dimethylformamide and dimethylamine (1.14 mL, 8.5 mmol) drop wise at room temperature. After complete addition, the reaction mixture was stirred at 90° C. for 15 hours. The reaction mixture was poured on cold water and the precipitated solid was filtered, washed with water and dried to get (E)-N,N-dimethyl-2-(4-nitro-1-oxidopyridin-3-yl)ethenamine (470 mg, 50%).
$^1$H NMR (400 MHz, DMSO-d$_6$): δ 8.68 (d, J=1.88 Hz, 1H), 7.82-7.92 (m, 2H), 7.61 (dd, J=7.22, 1.94 Hz, 1H), 5.84 (d, J=13.30 Hz, 1H), 2.98 (br. s., 6H).

Step d: Synthesis of 1H-pyrrolo[3,2-c]pyridine

To a suspension of (E)-N,N-dimethyl-2-(4-nitro-1-oxidopyridin-3-yl)ethenamine (400 mg, Step c) in methanol was added palladium on carbon (50 mg, 10% wet) and the reaction mixture was stirred under hydrogen atmosphere for 2 hours. The reaction mixture was filtered through celite and the filtrate was concentrated to get 1H-pyrrolo[3,2-c]pyridine (98 mg, 44%) as off-white solid.
$^1$H NMR (400 MHz, DMSO-d$_6$): δ 8.83 (s, 1H) and 11.50 (br. s., 1H), 8.15 (d, J=5.71 Hz, 1H), 7.29-7.56 (m, 2H), 6.55-6.59 (m, 1H).

Intermediate 23: Synthesis of benzyl 4-amino-1H-pyrrolo[3,2-c]pyridine-1-carboxylate Step a: Synthesis of benzyl 1H-pyrrolo[3,2-c]pyridine-1-carboxylate To a stirred solution of 1H-pyrrolo[3,2-c]pyridine (500 mg, 4.2 mmol) in dichloromethane (6 mL), triethylamine (1.2 mL, 8.4 mmol) was added. The mixture was cooled to 0° C. and benzyl chloroformate (1.6 mL, 50% solution in dichloromethane, 4.6 mmol) was added drop wise. After complete addition, the reaction mixture was stirred at room temperature for about 1 hour. On completion, the reaction was quenched by addition of saturated aqueous sodium bicarbonate solution and the organic layer was separated, washed with brine, dried over anhydrous sodium sulfate and concentrated under vacuum to afford benzyl 4-amino-1H-pyrrolo[3,2-c]pyridine-1-carboxylate (1 g, 100%) as viscous liquid.
$^1$H NMR (400 MHz, DMSO-d$_6$): δ 8.93 (d, J=1.00 Hz, 1H), 8.45 (d, J=5.77 Hz, 1H), 7.56 (dd, J=8.06, 1.47 Hz, 1H), 7.97 (d, J=5.71 Hz, 1H), 7.82 (d, J=3.76 Hz, 1H), 7.32-7.48 (m, 4H), 6.89 (dd, J=3.76, 0.82 Hz, 1H), 5.51 (s, 2H).

Step b: Synthesis of benzyl 1H-pyrrolo[3,2-c]pyridine-1-carboxylate 5-oxide

A stirred suspension of benzyl 4-amino-1H-pyrrolo[3,2-c]pyridine-1-carboxylate (1 g, 3.9 mmol, Step a)) in a mixture of dichloromethane and dimethyl ether (10:1 mL) was treated portion wise with 3-chloroperoxybenzoic acid (0.85 g, 4.9 mmol) followed by stirring at room temperature for 4 hours. The reaction was neutralized with saturated aqueous sodium bicarbonate solution. The organic layer was separated, dried over anhydrous sodium sulfate and concentrated to yield benzyl 1H-pyrrolo[3,2-c]pyridine-1-carboxylate 5-oxide (1 g, 99%).

Step c: Synthesis of benzyl 4-[(2,4,4-trimethylpentan-2-yl)amino]-1H-pyrrolo[3,2-c]pyridine-1-carboxylate A solution of benzyl 1H-pyrrolo[3,2-c]pyridine-1-carboxylate 5-oxide (500 mg, 1.9 mmol, Step b) in chloroform was treated dropwise with 2,4,4-trimethylpentan-2-amine (1.57 mL, 8.5 mmol) and stirred for about 15 minutes. The mixture was cooled to 0° C. followed by the portion wise addition of p-toluenesulphonyl chloride (745 mg, 4.2 mmol). The reaction mixture was then stirred at room temperature for 1 hour, diluted with dichloromethane and washed with saturated sodium bicarbonate solution. The organic layer was separated, dried over anhydrous sodium sulfate and concentrated under vacuum to yield viscous oil. The crude product was purified by silica gel (100-200 mesh) column chromatography using ethyl acetate in hexane (1.5%) as eluent to yield benzyl 4-[(2,4,4-trimethylpentan-2-yl)amino]-1H-pyrrolo[3,2-c]pyridine-1-carboxylate (390 mg, 43%) as a pale yellow solid.

$^1$H NMR (400 MHz, CHCl$_3$-d): δ 7.95 (d, J=5.90 Hz, 1H), 7.27-7.50 (m, 7H), 6.37 (dd, J=3.76, 0.56 Hz, 1H), 5.44 (s, 2H), 4.42 (s, 1H), 1.96 (s, 2H), 1.59 (s, 6H), 0.99 (s, 9H).

Step d: Synthesis of benzyl 4-amino-1H-pyrrolo[3,2-c]pyridine-1-carboxylate

Trifluoroacetic acid (10 ml) was added drop wise to an ice-cooled suspension of benzyl 4-[(2,4,4-trimethylpentan-2-yl)amino]-1H-pyrrolo[3,2-c]pyridine-1-carboxylate (5 g, 9.7 mmol, Step c) in dichloromethane (30 mL). The reaction mixture was stirred at room temperature for 4 hours. Upon completion, the reaction mixture was concentrated under vacuum and the residue was stirred in excess aqueous ammonia solution. The precipitated solid was filtered under suction, washed with water and dried to yield benzyl 4-amino-1H-pyrrolo[3,2-c]pyridine-1-carboxylate (2.5 g, 95%) as off-white solid.

$^1$H NMR (400 MHz, DMSO-d$_6$): δ 7.77 (d, J=6.40 Hz, 1H), 7.66 (d, J=3.76 Hz, 1H), 7.51-7.56 (m, 2H), 7.36-7.48 (m, 3H), 7.30 (d, J=6.34 Hz, 1H), 7.19 (br. s., 2H), 6.98-7.03 (m, 1H).

Intermediate 24: Synthesis of N-(1H-pyrrolo[3,2-c]pyridin-4-yl)cyclopropanecarboxamide To a stirred solution of benzyl 4-amino-1H-pyrrolo[3,2-c]pyridine-1-carboxylate (1 g, 3.5 mmol) in tetrahydrofuran was added triethylamine (1 mL, 7 mmol). The mixture was cooled to −10° C. and cyclopropanecarbonyl chloride (0.53 mL, 5.3 mmol) was added drop wise. The reaction mixture was stirred at room temperature for 1 hour, followed by concentration under vacuum to remove tetrahydrofuran. The residue was dissolved in ethyl acetate and organic layer was washed with water, dried over anhydrous sodium sulfate and concentrated to give the crude mixture of benzyl 4-[bis(cyclopropylcarbonyl)amino]-1H-pyrrolo[3,2-c]pyridine-1-carboxylate and benzyl 4-[(cyclopropylcarbonyl)amino]-1H-pyrrolo[3,2-c]pyridine-1-carboxylate. The mixture was treated with a saturated potassium carbonate solution in methanol and stirred at room temperature followed by removal of methanol under vacuum at the same temperature. The residue was treated drop wise with saturated aqueous sodium bicarbonate solution and the precipitated solid was filtered, washed with water and dried to yield N-(1H-pyrrolo[3,2-c]pyridin-4-yl)cyclopropanecarboxamide (0.5 g, 69%) as a pale yellow solid.

$^1$H NMR (400 MHz, DMSO-d$_6$): δ 7.91 (d, J=5.96 Hz, 1H), 7.43 (br. s., 1H), 7.30 (d, J=5.96 Hz, 1H), 6.74 (br. s., 1H), 2.10-2.20 (m, 1H), 0.84-0.93 (m, 4H). MS: 201.1 (M$^+$).

N-(1H-pyrrolo[3,2-c]pyridin-4-yl)acetamide (Intermediate 25) was prepared from benzyl 4-amino-1H-pyrrolo[3,2-c]pyridine-1-carboxylate in an analogous manner using acetyl chloride.

$^1$H NMR (400 MHz, DMSO-d$_6$): δ 9.57 (d, J=0.76 Hz, 1H), 8.40 (d, J=0.82 Hz, 1H), 7.55 (d, J=9.03 Hz, 2H), 7.37 (d, J=8.97 Hz, 2H), 2.23 (s, 3H).

N-(1H-pyrrolo[3,2-c]pyridin-4-yl)propanamide (Intermediate 26) was prepared from benzyl 4-amino-1H-pyrrolo[3,2-c]pyridine-1-carboxylate in an analogous manner using propanoyl chloride.

$^1$H NMR (400 MHz, DMSO-d$_6$): δ 9.5 (s, 1H), 8.40 (d, J=0.82 Hz, 1H), 7.55 (d, J=9.03 Hz, 2H), 7.37 (d, J=8.97 Hz, 2H), 2.43-2.55 (m, 2H), 1.15-1.23 (t, J=7.2 Hz, 3H).

Intermediate 27: Synthesis of methyl 1H-pyrrolo[3,2-c]pyridin-4-ylcarbamate

Step a: Synthesis of benzyl 4-[(methoxycarbonyl)amino]-1H-pyrrolo[3,2-c]pyridine-1-carboxylate A well stirred mixture of a solution of benzyl 4-amino-1H-pyrrolo[3,2-c]pyridine-1-carboxylate (464 mg, 1.74 mmol) and triethylamine (0.49 mL, 3.47 mmol) in tetrahydrofuran was cooled to −10° C. and treated drop wise with methyl carbonochloridate (0.15 mL, 1.92 mmol). The reaction mixture was stirred at room temperature for 30 minutes followed by removal of volatiles under vacuum. The residue was dissolved in ethyl acetate and organic layer was washed with water, dried over anhydrous sodium sulfate and concentrated to yield benzyl 4-[(methoxycarbonyl)amino]-1H-pyrrolo[3,2-c]pyridine-1-carboxylate (278 mg, 49.13%).

MS: 325.33 (M$^+$).

Step b: Synthesis of methyl 1H-pyrrolo[3,2-c]pyridin-4-ylcarbamate

To a stirred solution of benzyl 4-[(methoxycarbonyl)amino]-1H-pyrrolo[3,2-c]pyridine-1-carboxylate (264 mg, 0.82 mmol, Step a) in ethanol (10 mL) was added catalytic amount of palladium on carbon (10% wet). The reaction mixture was stirred under an atmosphere of hydrogen gas (atmospheric pressure) for 1 hour. The reaction mixture was filtered over celite and the residue washed with ethanol. The filtrate was concentrated to yield methyl 1H-pyrrolo[3,2-c]pyridin-4-ylcarbamate as a white powder (141 mg, 90.75%).

$^1$H NMR (400 MHz, DMSO-d$_6$): δ 11.49 (br. s., 1H), 9.55-10.05 (m, 1H), 7.86 (d, J=5.77 Hz, 1H), 7.33 (dd,

J=2.42, 3.04 Hz, 1H), 7.17 (d, J=5.71 Hz, 1H), 6.59 (td, J=1.05, 2.04 Hz, 1H), 3.67 (s, 3H). MS: 191.19 (M+).

Intermediate 28: Synthesis of 2,6-dichloro-4-(methylcarbamoyl)benzoic acid

Step a: Synthesis of methyl 2,6-dichloro-4-(methylcarbamoyl)benzoate

A solution of 3,5-dichloro-4-(methoxycarbonyl)benzoic acid (400 mg, 1.6 mmol) in dimethylformamide and dichloromethane was treated with oxalyl chloride (0.16 ml, 1.9 mmol) drop wise at room temperature followed by stirring at same temperature for 30 minutes. The reaction mixture was concentrated under vacuum. The residue was dissolved in dichloromethane, cooled to 0° C. and methylamine hydrochloride (118 mg, 1.7 mmol) was added followed by the drop wise addition of triethylamine (0.33 ml, 2.4 mmol) at the same temperature. The reaction mixture was allowed to warm to room temperature, stirred for 1 hour and concentrated under vacuum. The residue was treated with ice-cooled aqueous sodium bicarbonate solution (5%). The precipitated solid was filtered, washed with water, and dried to yield methyl 2,6-dichloro-4-(methylcarbamoyl)benzoate (340 mg, 70%) as a pale yellow solid.

Step b: Synthesis of 2,6-dichloro-4-(methylcarbamoyl)benzoic acid

A well stirred mixture of methyl 2,6-dichloro-4-(methylcarbamoyl)benzoate (280 mg, 1 mmol, Step a) and anhydrous lithium iodide (429 mg, 3.2 mmol) in pyridine (3 mL) was heated under reflux for 3 hours. The reaction mixture was concentrated under vacuum to remove pyridine. The residue was acidified using ice-cooled dilute hydrochloric acid solution and partitioned with ethyl acetate. The combined organic layer was washed with brine, dried over sodium sulfate, and concentrated under vacuum to obtain a solid that upon triturating with cold diethyl ether yielded pure 2,6-dichloro-4-(methylcarbamoyl)benzoic acid (200 mg, 75%).

$^1$H NMR (400 MHz, DMSO-$d_6$): δ 8.73 (d, J=4.58 Hz, 1H), 7.93 (s, 2H), 2.79 (d, J=4.58 Hz, 3H). MS: 248.2 (M+).

The following intermediates (starting materials) were prepared in an analogous manner using the appropriate amines.

2,6-Dichloro-4-(ethylcarbamoyl)benzoic acid (Intermediate 29)

$^1$H NMR (400 MHz, DMSO-$d_6$): δ 8.74 (s, 1H), 7.95 (s, 2H), 3.24-3.31 (m, 2H), 1.13 (t, J=7.23 Hz, 3H). MS: 262.00 (M+).

4-Carbamoyl-2,6-dichlorobenzoic acid (Intermediate 30)

$^1$H NMR (400 MHz, DMSO-$d_6$): δ 8.23 (s, 1H), 7.97 (s, 3H), 7.77 (s, 1H). MS: 234.23 (M+).

2,6-Dichloro-4-[(2-hydroxyethyl)carbamoyl]benzoic acid (Intermediate 31)

$^1$H NMR (400 MHz, DMSO-$d_6$): δ 8.75 (t, J=5.52 Hz, 1H), 7.96 (s, 2H), 4.76 (s, 1H), 3.51 (d, J=4.71 Hz, 2H). MS: 278.18 (M+).

2,6-Dichloro-4-[(2-methoxyethyl)carbamoyl]benzoic acid (Intermediate 32)

$^1$H NMR (400 MHz, DMSO-$d_6$): δ 8.75-8.90 (m, 1H), 7.97 (s, 2H), 3.40-3.50 (m, 5H), 3.29-3.38 (m, 2H). MS: 292.14 (M+).

2,6-Dichloro-4-(dimethylcarbamoyl)benzoic acid (Intermediate 33)

$^1$H NMR (400 MHz, DMSO-$d_6$): δ 7.60 (s, 2H), 2.98 (s, 3H), 2.89 (s, 3H).

2,6-Dichloro-4-[(cyanomethyl)carbamoyl]benzoic acid (Intermediate 34)

$^1$H NMR (400 MHz, DMSO-$d_6$): δ 9.52 (t, J=5.36 Hz, 1H), 7.99 (s, 2H), 4.36 (d, J=5.40 Hz, 2H).

2,6-Dichloro-4-[(2-methylpropyl)carbamoyl]benzoic acid (Intermediate 35)

$^1$H NMR (400 MHz, DMSO-$d_6$): δ 8.73 (s, 1H), 7.95 (s, 2H), 3.09 (t, J=6.38 Hz, 2H), 1.77-1.92 (m, 1H), 0.89 (d, J=6.69 Hz, 6H). MS: 290.16 (M+).

2,6-dichloro-4-(cyclopropylcarbamoyl)benzoic acid (Intermediate 36)

$^1$H NMR (400 MHz, DMSO-$d_6$): δ 8.69 (d, J=4.11 Hz, 1H), 7.92 (s, 2H), 2.86 (dd, J=7.52, 3.54 Hz, 1H), 0.67-0.75 (m, 2H), 0.54-0.63 (m, 2H). MS: 274.19 (M+).

2,6-Dichloro-4-(morpholin-4-ylcarbonyl)benzoic acid (Intermediate 37)

$^1$H NMR (400 MHz, DMSO-$d_6$): δ 7.62 (s, 2H), 3.50-3.70 (m, 6H). MS: 304.14 (M+).

2,6-Dichloro-4-(propan-2-ylcarbamoyl)benzoic acid (Intermediate 38) and 2,6-dichloro-4-(piperidin-1-ylcarbonyl)benzoic acid (Intermediate 39)

Intermediate 40: Synthesis of 2,6-dichloro-4-cyanobenzoic acid

Step a: Synthesis of methyl 2,6-dichloro-4-cyanobenzoate

To a solution of methyl 4-carbamoyl-2,6-dichlorobenzoate (100 mg, 0.4 mmol) in pyridine (2 mL) trifluoro-acetic anhydride (0.11 ml, 0.8 mmol) was added drop wise at 0° C. The reaction mixture was allowed to warm to room temperature and stirred for 1 hour. The contents were poured into ice cold water and the precipitated solid was filtered, washed with water and dried to yield methyl 2,6-dichloro-4-cyanobenzoate (55 mg, 88%) as an off-white solid.

Step b: Synthesis of 2,6-dichloro-4-cyanobenzoic acid

A suspension of methyl 2,6-dichloro-4-cyanobenzoate (620 mg, 2.6 mmol) in pyridine (5 mL) was treated with anhydrous lithium iodide (1000 mg, 8 mmol). The resulting reaction mixture was stirred at reflux for 1 hour and concentrated under vacuum to remove pyridine. The residue was acidified with hydrochloric acid (2N) under ice-cold condition to adjust the pH between 2 to 3. The precipitated solid was filtered, washed with water and dried to yield 2,6-dichloro-4-cyanobenzoic acid (380 mg, 86%) as a pale brown solid.

$^1$H NMR (400 MHz, DMSO-d$_6$): δ 8.23 (s, 2H).

Intermediate 41: Synthesis of 2,6-dichloro-4-(hydroxymethyl)benzoic acid

Step a: Synthesis of methyl 2,6-dichloro-4-(hydroxymethyl)benzoate

A solution of dimethyl 2,6-dichlorobenzene-1,4-dicarboxylate (2.3 g, 8.7 mmol) in tetrahydrofuran (10 mL) was treated with sodium borohydride (0.496 g, 13 mmol) and heated to refluxing temperature. The reaction mixture was then treated drop wise with methanol (1 mL) and continued refluxing for about 2 hours. The reaction mixture was warmed to room temperature and quenched with saturated aqueous ammonium chloride solution followed by partitioning with ethyl acetate. The combined organic layer was washed with brine, dried over sodium sulfate, filtered and concentrated. The crude product was purified by silica gel column chromatography using ethyl acetate in hexane (10%) as an eluant to yield methyl 2,6-dichloro-4-(hydroxymethyl)benzoate as a colorless liquid (1.6 g, 80%).

Step b: Synthesis of 2,6-dichloro-4-(hydroxymethyl)benzoic acid

A suspension of methyl 2,6-dichloro-4-(hydroxymethyl) benzoate (5.3 g, 22 mmol) in pyridine (20 mL) was treated with anhydrous lithium iodide (9 g, 67 mmol). The resulting reaction mixture was heated to reflux for 5 hours, cooled to room temperature and concentrated under vacuum. The residue was diluted with water and acidified with dilute hydrochloric acid (pH 2-3) and partitioned with ethyl acetate. The combined organic layer was washed with brine, dried over sodium sulfate, concentrated and the residue obtained upon triturating with diethyl ether afforded 2,6-dichloro-4-(hydroxymethyl)benzoic acid as a pale yellow solid (3.5 g, 70%).

$^1$H NMR (400 MHz, DMSO-d$_6$): δ 7.44 (s, 2H), 4.52 (d, J=5.15 Hz, 2H), 5.50 (t, J=5.71 Hz, 1H).

Intermediate 42: Synthesis of 4-bromo-2,6-dichlorobenzoic acid

Step a: Synthesis of 2,6-dichloro-3-nitro-benzoic acid 2,6-Dichloro-benzoic acid (10 g, 52 mmol) was treated with a previously stirred mixture of nitric acid (15 mL) and sulfuric acid (30 mL) at 55° C. for 30 minutes followed by stirring at room temperature for 30 minutes. The reaction mixture was poured in ice cold water (1 L) and the solid obtained was filtered and dried to afford the product (9 gm). The filtrate was extracted with ethyl acetate (2×200 mL). The combined organic layer was dried over anhydrous sodium sulphate and concentrated to dryness to yield more product (2 gm). (11 g, 88%).

$^1$H NMR (400 MHz, MeOH-d$_4$): δ 7.98 (d, J=8.81H), 7.67 (d, J=8.81H).

Step b: Synthesis of 3-amino-2,6-dichloro-benzoic acid 2,6-Dichloro-3-nitro-benzoic acid (10 g, 42 mmol, Step a) was added to concentrated hydrochloric acid (100 mL) followed by stannous chloride dihydrate (38 g, 169 mmol). The reaction mixture was heated at 60° C. for 1 hour. The reaction mixture was diluted with water (500 mL) and extracted with ethyl acetate (2×300 mL). The combined organic layer was dried over anhydrous sodium sulphate and concentrated under vacuum to afford the sticky material. The sticky material (crude product) was dissolved in water (turbid solution, 200 mL) and treated slowly with aqueous sodium hydroxide (20%) solution till precipitation while maintaining the pH 1-2 (dense precipitate was observed). The precipitate was filtered and the filtrate was extracted with ethyl acetate (2×200 mL) and dried over anhydrous sodium sulphate and concentrated under vacuum to yield 3-amino-2,6-dichlorobenzoic acid as a creamish solid (6 gm, 69%).

$^1$H NMR (400 MHz, MeOH-d$_4$): δ 7.11 (d, J=8.81H), 6.85 (d, J=8.81H).

Step c: Synthesis of 3-amino-4-bromo-2,6-dichloro-benzoic acid

A mixture of 3-amino-2,6-dichloro-benzoic acid (5 g, 24 mmol, Step b) in acetonitrile (50 mL) was treated with N-bromosuccinimide (5.1 g, 29 mmol) and the reaction mixture was stirred at 90° C. for 45 minutes. Acetonitrile was removed under vacuum and the residue was partitioned between water (200 mL) and ethyl acetate (200 mL). Organic layer was separated and the aqueous layer was again extracted with ethyl acetate (2×100 mL). The combined organic layer was dried over anhydrous sodium sulphate and concentrated to yield 3-amino-4-bromo-2,6-dichloro-benzoic acid (5 g, 73%).

$^1$H NMR (400 MHz, MeOH-d$_4$): δ 7.49 (s, 1H), 7.11 (d, J=8.81H).

Step d: Synthesis of 4-bromo-2,6-dichloro-benzoic acid

An aqueous solution of sodium nitrite (3.64 g, dissolved in 4 mL of water, 52 mmol) was added drop wise to the concentrated hydrochloric acid (15 mL), cooled to −10° C. to −5° C. 3-Amino-4-bromo-2,6-dichloro-benzoic acid (5 g, 17 mmol, Step c) was added to the above solution portion-wise while maintaining the temperature at about −5° C. The reaction mixture was stirred at the same temperature for about 2 hours. Hypophosphorous acid (9 mL, 170 mmol) was added very slowly over a period of 1 hour at the same temperature. The reaction mixture was stirred at the same temperature for about 3 hours and kept in refrigerator overnight. A precipitate was observed at this stage. The reaction mixture was allowed to warm to room temperature and kept for another 2 hours at the same temperature. The reaction mixture was filtered, the residue was washed with cold water and dried to yield 4-bromo-2,6-dichloro-benzoic acid as a yellowish solid (2 g, 42%).

$^1$H NMR (400 MHz, MeOH-d$_4$): δ 7.69 (s, 2H).

Intermediate 43: Synthesis of (2,6-dichloro-phenyl)-(5-oxy-pyrrolo[3,2-c]pyridin-1-yl)-methanone To a stirred solution of (2,6-dichloro-phenyl)-pyrrolo[3,2-c]pyridin-1-yl-methanone (221 mg, 0.76 mmol) in dichloromethane (5.0 mL) was added m-chloroperbezoic acid (296 mg, 1.72 mmol) in 2 portions at 0° C. After stirring at room temperature for 2 hours, saturated sodium bicarbonate solution was added, and extracted with dichloromethane. The organic layer was dried over magnesium sulfate and concentrated. The residue was purified by flash chromatography (linear gradient: 0 to 5%, methanol in chloroform) to give (2,6-dichloro-phenyl)-(5-oxy-pyrrolo[3,2-c]pyridin-1-yl)-methanone (204 mg, 0.66 mmol, 87%) as a white solid.

$^1$H NMR (CDCl$_3$): δ 8.57 (d, J=1.4 Hz, 1H), 8.47 (d, J=7.5 Hz, 1H), 8.29 (dd, J=7.5, 1.4 Hz, 1H), 7.48 (m, 3H), 6.99 (d, J=4.0 Hz, 1H), 6.61 (d, J=4.0 Hz, 1H).

Intermediate 44: Synthesis of 3-chloro-1H-pyrrolo[3,2-c]pyridine

A solution of 1H-pyrrolo[3,2-c]pyridine (200 mg, 1.69 mmol) in dichloromethane (10 ml) was treated with N-chlorosuccinimide (339 mg, 2.5 mmol) and stirred at room temperature for 5 hours. The reaction mixture was diluted with dichloromethane and washed with aqueous sodium hydrogen carbonate solution, brine, dried over anhydrous sodium sulfate and concentrated. Purification from silica gel column chromatography using methanol and dichloromethane gradient afforded 3-chloro-1H-pyrrolo[3,2-c]pyridine (98 mg, 40%).

$^1$H NMR (400 MHz, MeOH-d$_4$): δ 8.75-8.80 (m, 1H), 8.19-8.24 (m, 1H), 7.42-7.47 (m, 2H). MS: 152.28 (M$^+$).

Intermediate 45: Synthesis of N-(3-chloro-1H-pyrrolo[3,2-c]pyridin-4-yl)cyclopropane carboxamide Step a: Synthesis of 3-chloro-1H-pyrrolo[3,2-c]pyridine A solution of 1H-pyrrolo[3,2-c]pyridine (200 mg, 1.69 mmol) in dichloromethane (10 mL) was treated with N-chlorosuccinimide (332 mg, 2.5 mmol) and stirred at room temperature for about 5 hours. The reaction mixture was diluted with dichloromethane and washed with aq. sodium hydrogen carbonate solution, brine, dried over anhydrous sodium sulphate and concentrated. Purification by silica gel (100-200) column chromatography using methanol and dichloromethane gradient as eluent afforded 3-chloro-1H-pyrrolo[3,2-c]pyridine (103 mg, 40%).

$^1$H NMR (400 MHz, MeOH-d$_4$): δ 8.75-8.80 (m, 1H), 8.19-8.24 (m, 1H), 7.42-7.47 (m, 2H). MS: 152.58 (M$^+$).

Step b: Synthesis of benzyl 3-chloro-1H-pyrrolo[3,2-c]pyridine-1-carboxylate

To a stirred solution of 3-chloro-1H-pyrrolo[3,2-c]pyridine (1 g, 6.55 mmol) in dichloromethane (10 mL), triethylamine (2.3 ml, 16.38 mmol) was added. The mixture was cooled to 0° C. and benzyl chloroformate (2.3 mL, 50% solution in dichloromethane, 9.83 mmol) was added drop wise. After complete addition, the reaction mixture was stirred at room temperature for about 1 hour. On completion, the reaction was quenched by addition of saturated aq. sodium bicarbonate solution and the organic layer was separated, washed with brine, dried over anhydrous sodium sulfate and concentrated under vacuum to afford benzyl 3-chloro-1H-pyrrolo[3,2-c]pyridine-1-carboxylate (2.42 g, 100%) as viscous liquid.

$^1$H NMR (400 MHz, DMSO-d$_6$): δ 8.90 (d, J=1.00 Hz, 1H), 8.57 (d, J=5.77 Hz, 1H), 8.09 (s, 1H), 8.01 (dd, J=1.00, 5.77 Hz, 1H), 7.53-7.62 (m, 2H), 7.26-7.50 (m, 3H), 5.51 (s, 2H). MS: 286.72 (M$^+$).

Step c: Synthesis of benzyl 3-chloro-1H-pyrrolo[3,2-c]pyridine-1-carboxylate 5-oxide A stirred suspension of benzyl 3-chloro-1H-pyrrolo[3,2-c]pyridine-1-carboxylate (2.4 g, 8.37 mmol) in dichloromethane (20 mL) was treated portion wise with 3-chloroperoxybenzoic acid (2.165 g, 12.55 mmol) followed by stirring at room temperature for about 1.5 hours. The reaction was neutralized with saturated aq. sodium bicarbonate solution. The organic layer was separated, dried over anhydrous sodium sulfate and concentrated to afford benzyl 3-chloro-1H-pyrrolo[3,2-c]pyridine-1-carboxylate 5-oxide (2.45 g, 99%).

$^1$H NMR (400 MHz, DMSO-d$_6$): δ 8.56 (d, J=1.00 Hz, 1H), 8.22 (d, J=5.77 Hz, 1H), 8.19 (s, 1H), 7.87-7.92 (m, 3H), 7.68-7.74 (m, 1H), 7.29-7.33 (m, 2H), 5.49 (s, 2H). MS: 302.72 (M$^+$).

Step d: Synthesis of benzyl 3-chloro-4-[(2,4,4-trimethylpentan-2-yl)amino]-1H-pyrrolo[3,2-c]pyridine-1-carboxylate A solution of benzyl 3-chloro-1H-pyrrolo[3,2-c]pyridine-1-carboxylate 5-oxide (2.6 g, 8.53 mmol) in chloroform was treated dropwise with 2,4,4-trimethylpentan-2-amine (6.026 mL, 37.54 mmol) and stirred for about 15 minutes. The mixture was cooled to 0° C. followed by the portion wise addition of p-toluenesulphonyl chloride (3.578 g, 18.77 mmol). The reaction mixture was then stirred at room temperature for about 1 hour, diluted with dichloromethane and washed with saturated aq. sodium bicarbonate solution. The organic layer was separated, dried over anhydrous sodium sulfate and concentrated under vacuum to get viscous oil. The crude product was purified by silica gel column chromatography using ethyl acetate and hexane (1%) to yield benzyl 3-chloro-4-[(2,4,4-trimethylpentan-2-yl)amino]-1H-pyrrolo[3,2-c]pyridine-1-carboxylate (610.8 mg, 43%) as a pale yellow solid.

$^1$H NMR (400 MHz, DMSO-d$_6$): δ 7.90 (d, J=5.77 Hz, 1H), 7.75 (s, 1H), 7.50-7.57 (m, 2H), 7.36-7.47 (m, 3H), 7.22 (d, J=5.77 Hz, 1H), 5.46 (s, 2H), 1.96 (s, 2H), 1.53 (s, 6H), 0.93 (s, 9H). MS: 413.95 (M$^+$).

Step e: Synthesis of benzyl 4-amino-3-chloro-1H-pyrrolo[3,2-c]pyridine-1-carboxylate Trifluoroacetic acid (1.5 mL) was added drop wise to an ice-cooled suspension of benzyl 3-chloro-4-[(2,4,4-trimethylpentan-2-yl)amino]-1H-pyrrolo[3,2-c]pyridine-1-carboxylate (610 mg) in dichloromethane (10 mL). The reaction mixture was stirred at room temperature for about 4 hours. Upon completion, the reaction mixture was concentrated under vacuum and the residue was stirred in excess aqueous ammonia solution. The precipitated solid was filtered under suction, washed with water and dried to afford benzyl 4-amino-3-chloro-1H-pyrrolo[3,2-c]pyridine-1-carboxylate (354.8 mg, 95%) as an off-white solid.

$^1$H NMR (400 MHz, DMSO-d$_6$): δ 7.84 (d, J=6.02 Hz, 1H), 7.74 (s, 1H), 7.53 (d, J=6.78 Hz, 1H), 7.36-7.48 (m, 2H), 7.36-7.47 (m, 3H), 7.26 (d, J=6.02 Hz, 1H), 7.07 (br. s., 2H), 5.46 (s, 2H). MS: 301.73 (M$^+$).

Step f: Synthesis of N-(3-chloro-1H-pyrrolo[3,2-c]pyridin-4-yl)cyclopropane carboxamide Benzyl 4-amino-3-chloro-1H-pyrrolo[3,2-c]pyridine-1-carboxylate (350 mg, 1.16 mmol) was stirred in tetrahydrofuran and triethylamine (0.32 mL, 2.3 mmol) was added. The mixture was cooled to −10° C. and cyclopropanecarbonyl chloride (0.2 mL, 1.73 mmol) was added drop wise. The reaction mixture was stirred at room temperature for about 1 hour, followed by concentration under vacuum to remove tetrahydrofuran. The residue was dissolved in ethyl acetate and organic layer was washed with water, dried over anhydrous sodium sulfate and concentrated to give the crude mixture of benzyl 4-[bis(cyclopropylcarbonyl)amino]-3-chloro1H-pyrrolo[3,2-c]pyridine-1-carboxylate and benzyl 4-[(cyclopropylcarbonyl)amino]-3-chloro1H-pyrrolo[3,2-c]pyridine-1-carboxylate. The mixture was treated with saturated potassium carbonate solution in methanol (1 mL) and stirred at room temperature. After completion, methanol was removed under vacuum at room temperature. The residue was treated drop wise with saturated aq. sodium bicarbonate solution and the precipitated solid was filtered, washed with water and dried to obtain N-(3-chloro-1H-pyrrolo[3,2-c]pyridin-4-yl)cyclopropanecarboxamide (176 mg, 69%) as a white solid.

$^1$H NMR (400 MHz, DMSO-$d_6$): δ 11.81 (br. s., 1H), 10.21 (s, 1H), 8.18 (d, J=5.77 Hz, 1H), 8.00 (d, J=5.77 Hz, 1H), 7.71 (s, 1H), 7.52 (s, 1H), 7.26-7.34 (m, 1H), 1.82-2.01 (m, 1H), 0.75-0.84 (m, 4H). MS: 235.67 (M$^+$).

EXAMPLES

Example 1

Synthesis of (2,6-dichlorophenyl)(1H-pyrrolo[2,3-c]pyridin-3-yl)methanone

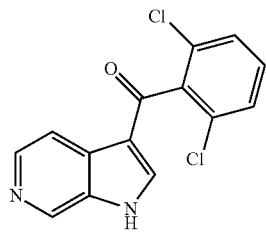 [SMILES: O=C(c1c(Cl)cccc1Cl)c1c[nH]c2cnccc12]

1H-Pyrrolo[2,3-c]pyridine (0.5 g, 4.2 mmol) was added to a stirred suspension of aluminium chloride (2.82 g, 21.1 mmol) in dry dichloromethane (100 mL) and the mixture was stirred at room temperature for 1 hour. This was followed by drop-wise addition of 2,6-dichloro benzoyl chloride (4.42 g, 21.1 mmol). The resulting reaction mixture was stirred at room temperature for 8 hours. Methanol (25 mL) was added cautiously to quench the reaction mass followed by concentration under vacuum. The resulting residue was neutralized using aqueous sodium bicarbonate solution followed by partitioning with ethyl acetate (3×100 mL). The combined organic layer was dried over anhydrous sodium sulfate, filtered and concentrated. Purification by silica gel column chromatography using ethyl acetate and hexane gradient as eluent afforded (2,6-dichlorophenyl)(1H-pyrrolo[2,3-c]pyridin-3-yl)methanone (0.5 g, 41.66%).

$^1$H NMR (400 MHz, CHCl$_3$-d): δ 9.81 (s, 1H), 8.71 (br. s., 1H), 8.36 (d, J=6.34 Hz, 1H), 8.11 (s, 1H), 7.39-7.47 (m, 3H). MS: 291.06 (M+1).

The following compounds were prepared in an analogous manner (2-Chloro-6-fluorophenyl)(1H-pyrrolo[2,3-c]pyridine-3-yl)methanone was prepared from 1H-Pyrrolo[2,3-c]pyridine and 2-chloro-6-fluoro benzoyl chloride (Compound No. 1).

$^1$H NMR (400 MHz, DMSO-$d_6$): δ 12.73 (br. s., 1H), 8.88 (d, J=1.00 Hz, 1H), 8.36 (d, J=5.52 Hz, 1H), 8.11 (s, 1H), 7.93 (br. s., 1H), 7.61 (td, J=8.28, 6.27 Hz, 1H), 7.49 (d, J=8.28 Hz, 1H), 7.38-7.45 (m, 1H). MS: 275.1 (M+1).

3,5-Dichloro-N-ethyl-4-(1H-pyrrolo[2,3-c]pyridin-3-yl-carbonyl)benzamide was prepared from 1H-Pyrrolo[2,3-c]pyridine and 2,6-dichloro-4-(ethylcarbamoyl)benzene carbonyl chloride (Compound No. 2).

$^1$H NMR (400 MHz, DMSO-$d_6$): δ 12.83 (br. s., 1H), 8.89 (s, 1H), 8.81 (t, J=5.02 Hz, 1H), 8.36 (d, J=4.77 Hz, 1H), 8.16 (br. s., 1H), 8.04 (s, 2H), 3.30-3.41 (m, 2H), 1.16 (t, J=7.15 Hz, 3H). MS: 361.90 (M$^+$), 363.87 (M+2).

N-[3-(2,6-Dichlorobenzoyl)-1H-pyrrolo[2,3-c]pyridin-7-yl]cyclopropanecarboxamide was similarly synthesized from N-(1H-pyrrolo[2,3-c]pyridin-7-yl)cyclopropane carboxamide and 2,6-dichloro benzoyl chloride (Compound No. 5).

$^1$H NMR (400 MHz, DMSO-$d_6$): δ 11.85-11.96 (m, 1H), 11.06-11.19 (m, 2H), 8.11 (d, J=5.14 Hz, 1H), 7.54-7.66 (m, 3H), 2.08-2.19 (m, 1H), 0.88-0.96 (m, 4H). MS: 373.87 (M+1).

4-{[7-(Acetylamino)-1H-pyrrolo[2,3-c]pyridin-3-yl]carbonyl}-3,5-dichloro-N-methylbenzamide was similarly synthesized from N-(1H-pyrrolo[2,3-c]pyridin-7-yl)acetamide and 2,6-dichloro-4-(methylcarbamoyl)benzene carbonyl chloride (Compound No. 7).

$^1$H NMR (400 MHz, DMSO-$d_6$): δ 12.00 (br. s., 1H), 10.75 (br. s., 1H), 8.80 (d, J=4.27 Hz, 1H), 8.13 (d, J=5.02 Hz, 1H), 8.03 (s, 2H), 7.93 (br. s., 1H), 2.83 (d, J=4.52 Hz, 3H), 2.19 (s, 3H). MS: 404.84 (M$^+$), 406.82 (M+2).

N-[3-(2-Chloro-6-fluorobenzoyl)-1H-pyrrolo[2,3-c]pyridin-7-yl]acetamide was prepared analogously using N-(1H-pyrrolo[2,3-c]pyridin-7-yl)acetamide and 2-chloro-6-fluoro benzoyl chloride (Compound No. 8).

$^1$H NMR (400 MHz, DMSO-$d_6$): δ 11.97 (br. s., 1H), 10.76 (br. s., 1H), 8.12 (d, J=5.27 Hz, 1H), 7.89 (s, 1H), 7.85 (br. s., 1H), 7.61 (td, J=8.28, 6.27 Hz, 1H), 7.50 (d, J=8.03 Hz, 1H), 7.43 (t, J=8.66 Hz, 1H), 2.01 (s, 3H). MS: 331.9 (M$^+$), 333.88 (M+2).

4-{[7-(Acetylamino)-1H-pyrrolo[2,3-c]pyridin-3-yl]carbonyl}-3,5-dichloro-N-ethylbenzamide was prepared from N-(1H-pyrrolo[2,3-c]pyridin-7-yl)acetamide and 2,6-dichloro-4-(ethylcarbamoyl)benzene carbonyl chloride (Compound No. 9).

$^1$H NMR (400 MHz, DMSO-$d_6$): δ 12.00 (br. s., 1H), 10.75 (br. s., 1H), 8.81 (t, J=5.40 Hz, 1H), 8.13 (d, J=4.77 Hz, 1H), 8.04 (s, 2H), 7.93 (br. s., 1H), 3.30-3.36 (m, 2H), 2.19 (s, 3H), 1.16 (t, J=7.28 Hz, 3H). MS: 418.82 (M$^+$), 420.80 (M+2).

(4-Bromo-2,6-dichlorophenyl)(1H-pyrrolo[2,3-c]pyridin-3-yl)methanone was prepared from 1H-Pyrrolo[2,3-c]pyridine and 4-bromo-2,6-dichloro benzoyl chloride (Compound No. 10).

$^1$H NMR (400 MHz, DMSO-$d_6$): δ 12.87 (br. s, 1H), 8.82-8.87 (m, 1H), 8.12-8.35 (m, 3H), 8.18 (br. s, 1H), 7.97 (s, 2H). MS: 371 (M+1), 372.9 (M+2).

N-[3-(2-Chloro-6-fluorobenzoyl)-1H-pyrrolo[2,3-c]pyridin-7-yl]cyclopropanecarboxamide was similarly synthesized from N-(1H-pyrrolo[2,3-c]pyridin-7-yl)cyclopropane carboxamide and 2-chloro-6-fluoro benzoyl chloride (Compound No. 11).

$^1$H NMR (400 MHz, DMSO-$d_6$): δ 11.93 (br. s., 1H), 11.14 (s, 1H), 8.13 (d, J=5.27 Hz, 1H), 7.82 (d, J=2.76 Hz, 2H), 7.61 (d, J=6.27 Hz, 1H), 7.50 (d, J=8.03 Hz, 1H), 7.43 (s, 1H), 2.07-2.19 (m, 1H), 0.87-0.97 (m, 4H). MS: 358.15 (M$^+$), 360.15 (M+2).

3,5-Dichloro-4-({7-[(cyclopropylcarbonyl)amino]-1H-pyrrolo[2,3-c]pyridin-3-yl}carbonyl)-N-methylbenzamide was similarly synthesized from N-(1H-pyrrolo[2,3-c]pyridin-7-yl)cyclopropane carboxamide and 2,6-dichloro-4-(methylcarbamoyl)benzene carbonyl chloride (Compound No. 12).

$^1$H NMR (400 MHz, DMSO-$d_6$): δ 11.94 (br. s., 1H), 11.11 (br. 5.1H), 8.79 (d, J=4.52 Hz, 1H), 8.13 (d, J=5.02 Hz, 1H), 8.02 (s, 2H), 7.85 (br. s., 1H), 2.81 (d, J=4.4 Hz, 3H), 2.07-2.12 (m, 1H), 0.88-0.96 (m, 4H). MS: 431.11 (M+), 433.13 (M+2).

3,5-Dichloro-4-({7-[(cyclopropylcarbonyl)amino]-1H-pyrrolo[2,3-c]pyridin-3-yl}carbonyl)-N-ethylbenzamide was similarly synthesized from N-(1-methyl-1H-pyrrolo[2,3-c]pyridin-7-yl)cyclopropane carboxamide and 2,6-dichloro-4-(ethylcarbamoyl)benzene carbonyl chloride (Compound No. 13).

$^1$H NMR (400 MHz, DMSO-d$_6$): δ 11.96 (br. s., 1H), 11.12 (br. s., 1H), 8.81 (t, J=5.40 Hz, 1H), 8.13 (d, J=5.02 Hz, 1H), 8.04 (s, 2H), 7.85 (br. s., 1H), 3.29-3.36 (m, 2H), 2.09-2.17 (m, 1H), 1.16 (t, J=7.28 Hz, 3H), 0.87-0.96 (m, 4H). MS: 445.15 (M+), 447.13 (M+2).

3,5-Dichloro-N-(2-methoxyethyl)-4-(1H-pyrrolo[2,3-c]pyridin-3-ylcarbonyl)benzamide was prepared from 1H-Pyrrolo[2,3-c]pyridine and 2,6-dichloro-4-(2-methoxyethylcarbamoyl)benzene carbonyl chloride (Compound No. 14).

$^1$H NMR (400 MHz, DMSO-d$_6$): δ 12.79 (br. s., 1H), 8.88 (s, 2H), 8.36 (d, J=5.02 Hz, 1H), 8.15 (br. s., 1H), 8.06 (s, 2H), 3.45-3.52 (m, 4H), 3.33 (s., 3H). MS: 392.63 (M+), 394.64 (M+2).

4-{[7-(Acetylamino)-1H-pyrrolo[2,3-c]pyridin-3-yl]carbonyl}-3,5-dichloro-N-propylbenzamide was prepared from N-(1H-pyrrolo[2,3-c]pyridin-7-yl)acetamide and 2,6-dichloro-4-(1-propylcarbamoyl)benzene carbonyl chloride (Compound No. 15).

$^1$H NMR (400 MHz, DMSO-d$_6$): δ 12.00 (br. s., 1H), 10.75 (br. s., 1H), 8.79 (t, J=5.52 Hz, 1H), 8.13 (d, J=5.02 Hz, 1H), 8.04 (s, 2H), 7.92 (dd, J=6.15, 3.39 Hz, 1H), 3.22-3.30 (m, 2H), 2.19 (s, 3H), 1.53-1.61 (m, 2H), 0.92 (t, J=7.40 Hz, 3H). MS: 433.75 (M+), 435.74 (M+2).

3,5-Dichloro-4-({7-[(cyclopropylcarbonyl)amino]-1H-pyrrolo[2,3-c]pyridin-3-yl}carbonyl)-N-(2-methoxyethyl)benzamide was prepared analogously using N-(1H-pyrrolo[2,3-c]pyridin-7-yl)cyclopropane carboxamide and 2,6-dichloro-4-(2-methoxyethylcarbamoyl)benzene carbonyl chloride (Compound No. 16).

$^1$H NMR: (400 MHz, DMSO-d$_6$): δ 11.95 (br. s., 1H), 11.11 (s, 1H), 8.85-8.93 (m, 1H), 8.13 (d, J=5.02 Hz, 1H), 8.06 (s, 2H), 7.85 (d, J=9.79 Hz, 1H), 3.45-3.51 (m, 4H), 3.29 (s, 3H), 2.08-2.17 (m, 1H), 0.86-0.97 (m, 4H). MS: 475.75 (M+), 477.72 (M+2).

4-{[7-(Acetylamino)-1H-pyrrolo[2,3-c]pyridin-3-yl]carbonyl}-3,5-dichloro-N-(2-methoxyethyl)benzamide was prepared analogously using N-(1H-pyrrolo[2,3-c]pyridin-7-yl)acetamide and 2,6-dichloro-4-(2-methoxyethylcarbamoyl)benzene carbonyl chloride (Compound No. 17).

$^1$H NMR (400 MHz, DMSO-d$_6$): δ 12.00 (br. s., 1H), 10.75 (br. s., 1H), 8.84-8.93 (m, 1H), 8.13 (d, J=5.27 Hz, 1H), 8.06 (s, 2H), 7.94 (br. s., 1H), 3.45-3.51 (m, 4H), 3.29 (s, 3H), 2.19 (s, 3H). MS: 449.81 (M+), 451.78 (M+2).

N-[3-(2,6-Dichlorobenzoyl)-1H-pyrrolo[2,3-c]pyridin-5-yl]cyclopropanecarboxamide was prepared using N-(1H-pyrrolo[2,3-c]pyridin-5-yl)cyclopropane carboxamide and 2,6-dichloro benzoyl chloride (Compound No. 18).

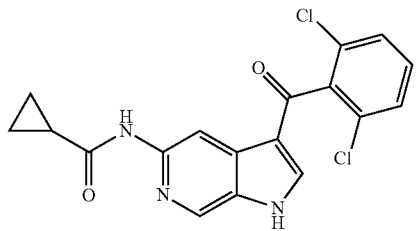 [SMILES: O=C(c1c(Cl)cccc1Cl)c1c[nH]c2cnc(NC(=O)C3CC3)cc12]

$^1$H NMR (400 MHz, DMSO-d$_6$): δ 12.53 (br. s., 1H), 10.65 (s, 1H), 8.77 (br. s., 1H), 8.57 (d, J=1.00 Hz, 1H), 7.94 (br. s., 1H), 7.57-7.64 (m, 2H), 7.50-7.57 (m, 1H), 1.98-2.07 (m, 1H), 0.73-0.87 (m, 4H). MS: 374.70 (M+), 376.70 (M+2).

N-[3-(2-Chloro-6-fluorobenzoyl)-1H-pyrrolo[2,3-c]pyridin-5-yl]cyclopropanecarboxamide was prepared using N-(1H-pyrrolo[2,3-c]pyridin-5-yl)cyclopropane carboxamide and 2-chloro-6-fluoro benzoyl chloride (Compound No. 19).

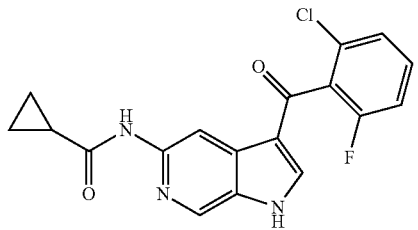 [SMILES: O=C(c1c(F)cccc1Cl)c1c[nH]c2cnc(NC(=O)C3CC3)cc12]

$^1$H NMR (400 MHz, DMSO-d$_6$): δ 12.56 (br. s., 1H), 10.66 (s, 1H), 8.79 (br. s., 1H), 8.58 (s, 1H), 8.00 (s, 1H), 7.54-7.63 (m, 1H), 7.47 (d, J=8.03 Hz, 1H), 7.40 (t, J=8.53 Hz, 1H), 1.94-2.07 (m, 1H), 0.74-0.89 (m, 4H). MS: 358.75 (M+1).

3,5-Dichloro-4-({5-[(cyclopropylcarbonyl)amino]-1H-pyrrolo[2,3-c]pyridin-3-yl}carbonyl)-N-methylbenzamide was prepared using N-(1H-pyrrolo[2,3-c]pyridin-5-yl)cyclopropane carboxamide and 2,6-dichloro-4-(methylcarbamoyl)benzene carbonyl chloride (Compound No. 20).

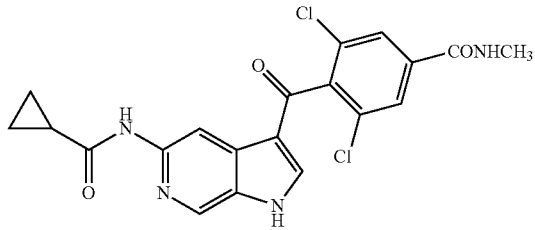

$^1$H NMR (400 MHz, DMSO-d$_6$): δ 12.61 (br. s., 1H), 10.67 (br. s., 1H), 8.74-8.77 (m, 1H), 8.58 (s, 1H), 8.01 (s, 2H), 7.85-7.95 (m, 1H), 2.83 (d, J=4.27 Hz, 3H), 2.02 (br. s., 1H), 0.75-0.88 (m, 4H). MS: 431.70 (M+1), 433.69 (M+2).

N-[3-(2-Chloro-6-fluorobenzoyl)-1H-pyrrolo[2,3-c]pyridin-7-yl]propanamide was synthesized using N-(1H-pyrrolo[2,3-c]pyridin-7-yl)propanamide and 2-chloro-6-fluoro benzoyl chloride (Compound No. 28).

$^1$H NMR (400 MHz, DMSO-d$_6$): δ 11.97 (br. s., 1H), 10.73 (s, 1H), 8.12 (d, J=5.27 Hz, 1H), 7.87 (br. s., 1H), 7.85 (br. s., 1H), 7.61 (td, J=8.22, 6.40 Hz, 1H), 7.38-7.53 (m, 2H) 2.45-2.54 (m, 2H merged with DMSO), 1.14 (t, J=7.53 Hz, 3H). MS: 346.79 (M+1), 348.81 (M+3).

N-[3-(2-Chloro-3,6-difluorobenzoyl)-1H-pyrrolo[2,3-c]pyridin-7-yl]cyclopropanecarboxamide was prepared using N-(1H-pyrrolo[2,3-c]pyridin-5-yl)cyclopropane carboxamide and 2-chloro-3,6-difluorobenzoyl chloride (Compound No. 37).

$^1$H NMR (400 MHz, CDCl3-d1): δ 12.14 (br. s., 1H), 9.13 (br. s., 1H), 8.11-8.33 (m, 2H), 7.56 (s, 1H), 7.21-7.26 (m, 1H), 7.07-7.12 (m, 1H), 2.17 (m, 1H), 0.98-1.03 (m, 2H), 1.14-1.62 (m, 2H). MS: 376.83 (M+1).

N-[3-(2,4,6-Trichlorobenzoyl)-1H-pyrrolo[2,3-c]pyridin-7-yl]cyclopropanecarboxamide (Compound No. 45) was prepared using N-(1H-pyrrolo[2,3-c]pyridin-5-yl)cyclopropane carboxamide and 2,4,6-trichlorobenzoyl chloride.

$^1$H NMR (400 MHz, DMSO-$d_6$): δ 12.12 (br. s., 1H), 11.25 (br. s., 1H), 8.13 (d, J=5.27 Hz, 1H), 7.98 (br. s., 1H), 7.88 (s, 2H), 7.80 (s, 1H), 2.09-2.17 (m, 1H), 0.89-0.98 (m, 4H). MS: 469.15 (M+1).

3,5-Dichloro-4-({5-[(cyclopropylcarbonyl)amino]-1H-pyrrolo[2,3-c]pyridin-3-yl}carbonyl)-N-ethylbenzamide $^1$H NMR (400 MHz, DMSO-$d_6$): δ 12.60 (br. s., 1H), 10.67 (br. s., 1H), 8.79 (t, J=5.52 Hz, 1H), 8.57 (d, J=1.25 Hz, 1H), 8.03 (s, 2H), 3.29-3.37 (m, 2H), 2.02 (br. s., 1H), 1.16 (t, J=7.15 Hz, 3H), 0.72-0.88 (m, 4H).

Example 2

Synthesis of (4-amino-2,6-dichlorophenyl)(1H-pyrrolo[2,3-c]pyridin-3-yl)methanone (Compound No. 3)

A mixture of 4-bromo-2,6-dichlorophenyl)(1H-pyrrolo[2,3-c]pyridin-3-yl)methanone (50 mg, 0.13 mmol, Compound No. 28), sodium azide (85 mg, 0.54 mmol), copper iodide (7.7 mg, 0.04 mmol) and N,N'-dimethyl ethylenediamine (19 mg, 0.24 mmol) in dimethylsulfoxide (2 mL) was heated at 100° C. for 24 hours. The reaction mixture was cooled to room temperature and treated cautiously with saturated aqueous ammonium chloride solution (10 mL) followed by partitioning with ethyl acetate (3×50 mL). The combined organic layer was dried over anhydrous sodium sulfate, filtered and concentrated. The crude product was purified by silica gel (100-200) column chromatography to afford pure (4-amino-2,6-dichlorophenyl)(1H-pyrrolo[2,3-c]pyridin-3-yl)methanone (11.2 mg, 26.82%).

$^1$H NMR (400 MHz, CHCl$_3$-d+DMSO-$d_6$): δ 8.71-8.77 (m, 1H), 8.28-8.35 (m, 1H), 7.76-8.15 (m, 1H), 7.55-7.65 (m, 1H), 6.69 (s, 2H). MS: 306.06 (M$^+$).

Example 3

Synthesis of [2,6-dichloro-4-(3,5-dimethyl-1H-pyrazol-4-yl)phenyl](1H-pyrrolo[2,3-c]pyridin-3-yl)methanone

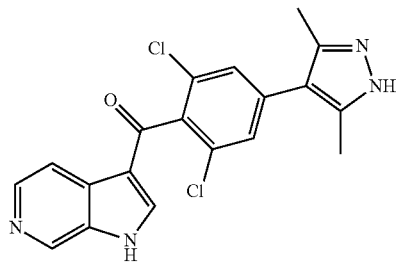 [SMILES: Cc1n[nH]c(C)c1-c1cc(Cl)c(C(=O)c2c[nH]c3cnccc23)c(Cl)c1]

A mixture of (4-bromo-2,6-dichlorophenyl)(1H-pyrrolo[2,3-c]pyridin-3-yl)methanone (50 mg, 0.135 mmol), [1-(tert-butoxycarbonyl)-3,5-dimethyl-1H-pyrazol-4-yl]boronic acid (52 mg, 0.162 mmol), potassium carbonate (55 mg, 0.4 mmol), water (0.5 mL) and 1,1'(diphenylphosphino)ferrocene]dichloropalladium (II) (11 mg, 0.0135 mmol) in 1,4 dioxane (2 mL) was heated at 100° C. for 2 hours in a sealed vial. The reaction mixture was cooled to room temperature, diluted with water (10 mL) and extracted with ethyl acetate (2×50 mL). The combined organic layer was dried over anhydrous sodium sulfate and concentrated under vacuum. The resulting crude mass was purified by preparative thin layer chromatography using methanol in dichloromethane (10%) to afford [2,6-dichloro-4-(3,5-dimethyl-M-pyrazol-4-yl)phenyl](1H-pyrrolo[2,3-c]pyridin-3-yl)methanone (0.012 g, 23%).

$^1$H NMR (400 MHz, DMSO-$d_6$): δ 12.69 (br. s., 1H), 12.51 (br. s., 1H), 8.88 (s, 1H), 8.36 (d, J=5.27 Hz, 1H), 8.15 (br. s., 1H), 7.71-8.05 (m, 1H), 7.49 (s, 2H), 2.29 (s., 6H). MS: 385.01 (M$^+$), 387.03 (M+2).

The following compound was prepared from 4-bromo-2,6-dichlorophenyl)(1H-pyrrolo[2,3-c]pyridin-3-yl)methanone by an analogous procedure using appropriate starting material.

[2,6-Dichloro-4-(2-methoxypyrimidin-5-yl)phenyl](1H-pyrrolo[2,3-c]pyridin-3-yl)methanone (Compound No. 4).

$^1$H NMR (400 MHz, DMSO-$d_6$): δ 12.76 (br. s., 1H), 9.11 (s, 2H), 8.88 (s, 1H), 8.37 (br. s., 1H), 8.15 (br. s., 1H), 8.08 (s, 2H), 4.00 (s, 3H). MS: 400.86 (M+1).

Example 4

Synthesis of 3,5-dichloro-4-(1H-pyrrolo[2,3-c]pyridin-3-ylcarbonyl)benzonitrile (Compound No. 6)

A mixture of (4-bromo-2,6-dichlorophenyl)(1H-pyrrolo[2,3-c]pyridin-3-yl)methanone (100 mg, 0.27 mmol) in dimethylformamide (3 mL) was treated with zinc cyanide (25.2 mg, 0.21 mmol), tris(dibenzylideneacetone)dipalladium (0) (6.21 mg, 0.006 mmol) and 1,1'-bis(diphenylphosphino)ferrocene (5.6 mg, 0.01 mmol) followed by heating at 130° C. for 16 hours. The reaction mixture was diluted with ethyl acetate, filtered over celite, and the filtrate was concentrated under vacuum. The crude compound was purified by LC-MS to afford 3,5-dichloro-4-(1H-pyrrolo[2,3-c]pyridin-3-ylcarbonyl)benzonitrile (2 mg, 2%).

$^1$H NMR (400 MHz, CHCl$_3$-d): δ 8.61 (s, 1H) 8.41 (m, 1H), 8.21 (m, 1H), 7.48-7.56 (m, 3H). MS: 316.62 (M+1).

Example 5

Synthesis of N-{3-[2,6-dichloro-4-(3,5-dimethyl-1,2-oxazol-4-yl)benzoyl]-1H-pyrrolo[2,3-c]pyridin-7-yl}cyclopropanecarboxamide (Compound No. 23)

A mixture of N-[3-(4-bromo-2,6-dichlorobenzoyl)-1H-pyrrolo[2,3-c]pyridin-7-yl]cyclopropanecarboxamide (0.1 g, 0.2 mmol) and (3,5-dimethyl-1,2-oxazol-4-yl)boronic acid (0.037 g, 0.26 mmol) was taken in a vial. To the reaction mixture, 1,4 dioxane (3 mL), potassium carbonate (0.091 g, 0.6 mmol) and water (0.5 mL) were added. The whole reaction mixture was stirred with argon gas for about five minutes. Finally dichloro[1,1'-bis(diphenylphosphino)ferrocene]palladium(II) (0.018 g, 0.02 mmol) was added to the reaction mixture, the vial was sealed properly and heated at 90° C. for about 4 hours. The reaction mixture was cooled to room temperature, followed by addition of water (25 mL), extracted with ethyl acetate (2×50 mL). The organic layer was dried over anhydrous sodium sulphate and concentrated under vacuum to get the crude. The crude was purified by preparative thin layer chloromatography using methanol (6%) in dicloromethane to obtain N-{3-[2,6-dichloro-4-(3,5-dimethyl-1,2-oxazol-4-yl)benzoyl]-1H-pyrrolo[2,3-c]pyridin-7-yl}cyclopropanecarboxamide (0.015 g, 15%).

$^1$H NMR (400 MHz, CHCl$_3$-d): δ 12.16 (br. s., 1H), 9.18 (br. s., 1H), 8.11 (d, J=5.02 Hz, 1H), 7.99-8.08 (m, 1H), 7.61 (br. s., 1H), 7.29 (s, 2H), 2.49 (s, 3H), 2.34 (s, 3H), 1.75 (dt, J=7.65, 3.70 Hz, 1H), 1.12-1.19 (m, 2H), 0.89-1.01 (m, 2H). MS: 469.78 (M$^+$), 471.79 (M+2).

N-{3-[2,6-Dichloro-4-(3,5-dimethyl-1H-pyrazol-4-yl) benzoyl]-1H-pyrrolo[2,3-c]pyridin-7-yl}cyclopropanecarboxamide (Compound No. 46) was analogously synthesized from N-[3-(4-bromo-2,6-dichlorobenzoyl)-1H-pyrrolo[2,3-c]pyridin-7-yl]cyclopropanecarboxamide and [1-(tert-butoxycarbonyl)-3,5-dimethyl-1H-pyrazol-4-yl]boronic acid.

$^1$H NMR (400 MHz, DMSO-d$_6$): δ 12.68 (br. s., 1H), 11.91 (br. s., 1H), 11.14 (br. s., 1H), 8.12 (d, J=5.27 Hz, 1H), 7.88 (br. s., 1H), 7.50 (s, 2H), 2.29 (s, 6H), 2.12-2.17 (m, 1H), 0.88-0.97 (m, 4H). MS: 408.8 (M$^+$) and 410.8 (M+2).

Example 6

Synthesis of N-{3-[2,6-dichloro-4-(pyrimidin-5-yl) benzoyl]-1H-pyrrolo[2,3-c]pyridin-7-yl}cyclopropanecarboxamide (Compound No. 47)

A mixture of N-[3-(4-bromo-2,6-dichlorobenzoyl)-1H-pyrrolo[2,3-c]pyridin-7-yl]cyclopropanecarboxamide (108 mg, 0.23 mmol), pyrimidin-5-yl-boronic acid (42 mg, 0.34 mmol), potassium carbonate (95.22 mg, 0.69 mmol), water (0.5 mL) and dichloro[1,1'-bis(diphenylphosphino)ferrocene]palladium(II) (34.8 mg, 0.047 mmol) in 1,4 dioxane (3 mL) was heated overnight at 100° C. in a sealed vial. The reaction mixture was cooled to room temperature, diluted with water (10 mL) and extracted with ethyl acetate (2×50 mL). The combined organic layer was dried over anhydrous sodium sulphate and concentrated under vacuum. The resulting crude mass was purified by preparative thin layer chloromatography using 10% methanol in dichloromethane to afford N-{3-[2,6-dichloro-4-(pyrimidin-5-yl)benzoyl]-1H-pyrrolo[2,3-c]pyridin-7yl}cyclopropane carboxamide (15 mg, 14.01%).

$^1$H NMR (400 MHz, DMSO-d$_6$): δ11.95 (br. s., 1H), 11.13 (s, 1H), 9.32 (s, 2H), 9.28 (s, 1H), 8.18 (s, 2H), 8.14 (d, J=5.02 Hz, 1H), 7.88 (br. s., 1H), 2.09-2.17 (m, 1H), 0.88-0.96 (m, 4H). MS: 451.09 (M$^+$).

The following compound was synthesized following a similar procedure using N-[3-(4-bromo-2,6-dichlorobenzoyl)-1H-pyrrolo[2,3-c]pyridin-7-yl]cyclopropane carboxamide and an appropriate boronic acids.

N-{3-[2,6-Dichloro-4-(6-methoxypyridin-3-yl)benzoyl]-1H-pyrrolo[2,3-c]pyridin-7-yl}cyclopropanecarboxamide (Compound No. 48)

$^1$H NMR (400 MHz, DMSO-d$_6$): δ 11.92 (br. s., 1H), 11.13 (s, 1H), 8.68 (d, J=2.26 Hz, 1H), 8.23 (d, J=2.51 Hz, 1H), 8.21 (d, J=2.76 Hz, 1H), 8.13 (d, J=5.02 Hz, 1H), 7.98 (s, 2H), 7.86 (br. s., 1H), 6.97 (d, J=8.78 Hz, 1H), 3.93 (s, 3H), 1.98-2.13 (m, 1H), 0.86-0.98 (m, 4H). MS: 481.14 (M$^+$).

N-{3-[2,6-Dichloro-4-(6-fluoropyridin-3-yl)benzoyl]-1H-pyrrolo[2,3-c]pyridin-7-yl}cyclopropanecarboxamide (Compound No. 49)

$^1$H NMR (400 MHz, DMSO-d6): δ 11.94 (br. s., 1H), 11.13 (s, 1H), 8.76 (d, J=2.26 Hz, 1H), 8.45-8.54 (m, 1H), 8.13 (d, J=5.02 Hz, 1H), 8.07 (s, 2H), 7.84-7.90 (m, 1H), 7.37 (dd, J=2.76, 8.53 Hz, 1H), 2.01-2.15 (m, 1H), 0.87-0.96 (m, 4H). MS: 469.12 (M$^+$).

N-{3-[2,6-Dichloro-4-(1-methyl-1H-pyrazol-4-yl) benzoyl]-1H-pyrrolo[2,3-c]pyridin-7-yl}cyclopropanecarboxamide. (Compound No. 50)

$^1$H NMR (400 MHz, DMSO-d6): δ 11.90 (br. s., 1H), 11.11 (s, 1H), 8.41 (s, 1H), 8.11 (s, 2H), 7.83-7.89 (m, 4H), 3.89 (s, 3H), 2.04-2.19 (m, 1H), 0.86-0.97 (m, 4H). MS: 454.15 (M$^+$).

N-{3-[4-(3,5-Dimethyl-1,2-oxazol-4-yl)-2,6-difluorobenzoyl]-1H-pyrrolo[2,3-c]pyridin-7-yl}cyclopropanecarboxamide (Compound No. 65)

$^1$H NMR (400 MHz, DMSO-d$_6$): δ 11.96 (br. s., 1H), 11.14 (br. s., 1H), 8.15 (d, J=5.27 Hz, 1H), 8.02 (s, 1H), 7.94 (d, J=5.27 Hz, 1H), 7.40 (d, J=8.28 Hz, 2H), 3.35 (s, 3H), 2.33 (s, 3H), 2.04-2.13 (m, 1H), 0.87-0.98 (m, 4H). MS: 436.41 (M$^+$).

Example 7

Synthesis of N-{3-[4-(acetylamino)-2,6-dichlorobenzoyl]-1H-pyrrolo[2,3-c]pyridin-7-yl}cyclopropanecarboxamide. (Compound No. 27)

Step a: Synthesis of N-[3-(4-bromo-2,6-dichlorobenzoyl)-1H-pyrrolo[2,3-c]pyridin-7-yl]cyclopropanecarboxamide (Compound No. 22)

Aluminium chloride (4.3 g, 32.2 mmol) was added to a solution of N-(1H-pyrrolo[2,3-c]pyridin-7-yl)cyclopropanecarboxamide (0.65 g, 3.2 mmol) in dichloromethane (100 mL) under Argon atmosphere. The mixture was stirred at room temperature under inert atmosphere for about 1 hour, followed by drop wise addition of 4-bromo-2,6-dichlorobenzoyl chloride (4.6 g, 15.9 mmol) in dichloromethane (20 mL). After complete addition the reaction mixture was stirred at room temperature for about 16 hours. Methanol (100 mL) was poured in the reaction mixture and stirred well. Solvent was evaporated under vacuum, water (250 mL) was added and extracted with ethyl acetate (3×200 mL). The organic layer was washed with aqueous sodium bicarbonate (10%) solution. The organic layer was dried over anhydrous sodium sulfate and concentrated under vacuum. The crude product was purified by silica gel (100-200 mesh) column chromatography using 2% methanol in dichloromethane as an eluant to afford N-[3-(4-bromo-2,6-dichlorobenzoyl)-1H-pyrrolo [2,3-c]pyridin-7-yl]cyclopropanecarboxamide (0.8 g, 54%).

$^1$H NMR (400 MHz, DMSO-d$_6$): δ 11.94 (br. s., 1H), 11.10 (s, 1H), 8.13 (d, J=5.52 Hz, 1H), 7.97 (s, 2H), 7.90 (br. s., 1H), 2.12 (br. s., 1H), 0.88-0.97 (m, 4H). MS: 452.64 (M−1), 454.65 (M+1), 456.64 (M+3).

Step b: Synthesis of N-[3-(4-amino-2,6-dichlorobenzoyl)-1H-pyrrolo[2,3-c]pyridin-7-yl]cyclopropanecarboxamide (Compound No. 26)

N-[3-(4-Bromo-2,6-dichlorobenzoyl)-1H-pyrrolo[2,3-c] pyridin-7-yl]cyclopropanecarboxamide (0.5 g, 1.1 mmol)

was taken in a reaction vial, followed by addition of sodium azide (0.286 g, 4.4 mmol), cuprous iodide (0.063 g, 0.3 mmol), N,N'-dimethylethane-1,2-diamine (0.058 g, 0.6 mmol) and dimethylsulfoxide (12 mL). The vial was sealed properly and heated at 110° C. for overnight. The reaction mixture was cooled to room temperature and water (100 mL) was added, extracted with ethyl acetate (3×150 mL). The organic layer was dried over anhydrous sodium sulfate and concentrated under vacuum. The crude product was purified by silica gel (100-200 mesh) column chromatography using 2% methanol in dichloromethane to afford pure N-[3-(4-amino-2,6-dichlorobenzoyl)-1H-pyrrolo[2,3-c]pyridin-7-yl] cyclopropanecarboxamide (0.23 g, 47%).

$^1$H NMR (400 MHz, DMSO-d$_6$): δ 11.79 (br. s., 1H), 11.10 (s, 1H), 8.08 (d, J=5.27 Hz, 1H), 7.73 (br. s., 1H), 6.67 (s, 2H), 5.97 (s, 2H), 2.13 (m, 1H), 0.81-0.99 (m, 4H). MS: 389.87 (M$^+$), 391.88 (M+2).

Step c: Synthesis of N-{3-[4-(acetylamino)-2,6-dichlorobenzoyl]-1H-pyrrolo[2,3-c]pyridin-7-yl}cyclopropanecarboxamide To a solution of N-[3-(4-amino-2,6-dichlorobenzoyl)-1H-pyrrolo[2,3-c]pyridin-7-yl]cyclopropanecarboxamide (0.2 g, 0.5 mmol) in dichloromethane (10 mL), pyridine (0.081 g, 1 mmol) was added followed by addition of acetyl chloride (0.044 g, 0.56 mmol) at 0° C. After stirring at 0° C. for about 0.5 hour, the reaction was kept at room temperature for about 2 hours. Dichloromethane was evaporated; water (50 mL) was added to the reaction mixture, extracted with ethyl acetate (2×100 mL). The organic layer was dried over anhydrous sodium sulfate and concentrated under vacuum. The crude product was purified by silica gel (100-200 mesh) column chromatography. Elution with 2.5% methanol in dichloromethane afforded N-{3-[4-(acetylamino)-2,6-dichlorobenzoyl]-1H-pyrrolo[2,3-c]pyridin-7-yl}cyclopropanecarboxamide (0.06 g, 27%).

$^1$H NMR (400 MHz, DMSO-d$_6$): δ 11.89 (br. s., 1H), 11.11 (s, 1H), 10.44 (s, 1H), 8.11 (d, J=5.27 Hz, 1H), 7.65-7.98 (m, 4H), 2.02-2.18 (m, 4H), 0.87-0.98 (m, 4H). MS: 431.87 (M$^+$), 433.89 (M+2).

Example 8

Synthesis of N-[3-(2,6-dichloro-4-cyanobenzoyl)-1H-pyrrolo[2,3-c]pyridin-7-yl]cyclopropanecarboxamide (Compound No. 39)

N-(1H-pyrrolo[2,3-c]pyridin-7-yl)cyclopropanecarboxamide (1 g, 4.9 mmol) was added to a stirred suspension of aluminium chloride (3.30 g, 24.8 mmol) in dry dichloromethane (100 mL) and the mixture was stirred at room temperature for about 1 hour, followed by drop-wise addition of 2,6-dichloro-4-cyanobenzoyl chloride (1.16 g, 4.9 mmol). The resulting reaction mixture was stirred at room temperature for about 8 hours. Methanol (25 mL) was added cautiously to quench the reaction mass followed by concentration under vacuum. The resulting residue was taken up in water followed by partitioning with ethyl acetate. The combined organic layer was dried over anhydrous sodium sulfate, filtered and concentrated. The crude product was purified by silica gel (100-200) column chromatography using ethyl acetate and hexane gradient elution to afford N-[3-(2,6-dichloro-4-cyanobenzoyl)-1H-pyrrolo[2,3-c]pyridin-7yl]cyclopropane carboxamide (0.75 g, 37.87%).

$^1$H NMR (400 MHz, DMSO-d$_6$): δ 11.98 (br. s., 1H), 11.10 (s, 1H), 8.28-8.33 (m, 2H), 8.14 (d, J=5.52 Hz, 1H), 7.89-8.04 (m, 2H), 2.07-2.18 (m, 1H), 0.83-0.98 (m, 4H).

The following compounds were prepared in an analogous manner:

N-[3-(4-Cyano-2,6-difluorobenzoyl)-1H-pyrrolo[2,3-c]pyridin-7-yl]cyclopropane carboxamide (Compound No. 51) was prepared from N-(1H-pyrrolo[2,3-c]pyridin-7-yl)cyclopropanecarboxamide and 4-cyano-2,6-difluorobenzoyl chloride.

$^1$H NMR (400 MHz, DMSO-d6): δ12.03 (br. s., 1H), 10.93-11.23 (m, 1H), 8.16 (d, J=5.27 Hz, 1H), 8.07 (d, J=3.26 Hz, 1H), 8.01-8.05 (m, 2H), 7.93 (d, J=5.52 Hz, 1H), 2.01-2.22 (m, 1H), 0.88-0.97 (m, 4H). MS: 367.19 (M$^+$).

Methyl 4-({7-[(cyclopropylcarbonyl)amino]-1H-pyrrolo[2,3-c]pyridin-3-yl}carbonyl)-3,5-difluorobenzoate (Compound No. 52) was prepared from N-(1H-pyrrolo[2,3-c]pyridin-7-yl)cyclopropanecarboxamide and methyl-4-(chlorocarbonyl) 3,5-difluoro benzoate.

$^1$H NMR (400 MHz, DMSO-d$_6$): δ 12.00 (br. s., 1H), 11.13 (s, 1H), 8.15 (d, J=5.27 Hz, 1H), 8.00 (s, 1H), 7.92 (d, J=5.02 Hz, 1H), 7.79 (d, J=7.28 Hz, 2H), 3.93 (s, 3H), 2.02-2.2 (m, 1H), 0.84-0.99 (m, 4H). MS: 400.19 (M$^+$).

N-[3-(4-Cyano-2,6-difluorobenzoyl)-1H-pyrrolo[2,3-c]pyridin-7-yl]acetamide (Compound No. 53) was prepared from N-(1H-pyrrolo[2,3-c]pyridin-7-yl)acetamide and 4-cyano-2,6-difluoro benzoyl chloride.

$^1$H NMR (400 MHz, DMSO-d$_6$): δ 12.10 (br. s., 1H), 10.76 (br. s., 1H), 8.10-8.21 (m, 2H), 8.00-8.07 (m, 2H), 7.94 (dd, J=1.88, 5.40 Hz, 1H), 2.14-2.22 (m, 3H). MS: 341.08 (M$^+$).

N-[3-(2,6-Dichloro-4-cyanobenzoyl)-1H-pyrrolo[2,3-c]pyridin-7-yl]acetamide (Compound No. 21) was prepared from N-(1H-pyrrolo[2,3-c]pyridin-7-yl)acetamide and 4-cyano-2,6-dichloro benzoyl chloride.

$^1$H NMR (400 MHz, DMSO-d$_6$): δ 12.00 (br. s., 1H), 10.74 (br. s., 1H), 8.30 (s, 1H), 8.13 (s, 1H), 8.07 (s, 2H), 2.18 (s, 3H). MS: 371.76 (M+1).

N-[3-(4-Bromo-2,6-difluorobenzoyl)-1H-pyrrolo[2,3-c]pyridin-7-yl]cyclopropane carboxamide (Compound No. 69) was prepared from N-(1H-pyrrolo[2,3-c]pyridin-7-yl)cyclopropane carboxamide and 4-bromo-2,6-difluorobenzoyl chloride $^1$H NMR (400 MHz, DMSO-d$_6$): δ 11.97 (br. s, 1H), 11.13 (br. s, 1H), 8.13-8.15 (m, 1H), 8.02 (s, 1H), 7.89-7.97 (m, 1H), 7.70 (d, J=7.03 Hz, 2H), 2.09-2.18 (m, 1H), 0.94 (br. s., 4H). MS: 419.86 (M$^+$), 421.85 (M+2).

Methyl 3,5-dichloro-4-({7-[(cyclopropylcarbonyl)amino]-1H-pyrrolo[2,3-c]pyridin-3-yl}carbonyl)benzoate (Compound No. 25) was analogously prepared from N-(1H-pyrrolo[2,3-c]pyridin-7-yl)cyclopropanecarboxamide and methyl-4(chlorocarbonyl)3,5-dichloro benzoate.

$^1$H NMR (400 MHz, DMSO-d$_6$): δ 11.97 (br. s., 1H), 11.11 (s, 1H), 8.13 (d, J=5.02 Hz, 1H), 8.08 (s, 2H), 7.87-7.90 (m, 2H), 3.93 (s, 3H), 2.07-2.16 (m, 1H), 0.88-0.95 (m, 4H). MS: 432.88 (M$^+$).

3,5-Dichloro-N-methyl-4-{[7-(propanoylamino)-1H-pyrrolo[2,3-c]pyridin-3-yl]carbonyl}benzamide (Compound No. 38) was similarly prepared from N-(1H-pyrrolo[2,3-c]pyridin-7-yl)propanamide and 2,6-dichloro-4-(methylcarbamoyl)benzene carbonyl chloride.

$^1$H NMR (400 MHz, DMSO-d$_6$): δ 12.00 (br. s., 1H), 10.72 (br. s., 1H), 8.81 (d, J=4.52 Hz, 1H), 8.12 (d, J=4.77 Hz, 1H), 8.03 (s, 2H), 7.95 (d, J=7.03 Hz, 1H), 2.83 (d, J=4.52 Hz, 3H), 2.54 (qt, 2H merged with DMSO), 1.14 (t, J=7.53 Hz, 3H). MS: 419.84 (M$^+$), 421.84 (M+2).

N-[3-(4-Bromo-2,6-dichlorobenzoyl)-1H-pyrrolo[2,3-c]pyridin-7-yl]acetamide (Compound No. 24) was analogously synthesized from N-(1H-pyrrolo[2,3-c]pyridin-7-yl)acetamide and 4-Bromo-2,6-dichlorobenzoyl chloride.

$^1$H NMR (400 MHz, DMSO-d$_6$): δ 12.00 (br. s., 1H), 10.74 (br. s., 1H), 8.12 (d, J=5.27 Hz, 1H), 7.97 (s, 2H), 7.70-7.90 (m, 2H), 2.19 (s, 3H). MS: 428.64 (M+1).

N-[3-(2-Chloro-4-cyano-6-fluorobenzoyl)-1H-pyrrolo[2,3-c]pyridin-7-yl]cyclopropanecarboxamide $^1$H NMR (400 MHz, DMSO-d$_6$): δ 11.81 (br. s., 1H), 11.09 (br. s., 1H), 8.10 (d, J=5.52 Hz, 1H), 7.73-7.88 (m, 2H), 7.60 (s, 1H), 7.26 (s, 1H), 2.02-2.13 (m., 1H), 0.81-1.02 (m, 4H). MS: 383.05 (M+1).

Example 9

Synthesis of 3,5-dichloro-4-({7-[(cyclopropylcarbonyl)amino]-1H-pyrrolo[2,3-c]pyridin-3-yl}carbonyl)-N-[2,3-dihydroxypropyl]benzamide (Compound No. 32)

Step a: Synthesis of 3,5-dichloro-4-({7-[(cyclopropylcarbonyl)amino]-1H-pyrrolo[2,3-c]pyridin-3-yl}carbonyl)benzoic acid A mixture of methyl 3,5-dichloro-4-({7-[(cyclopropylcarbonyl)amino]-1H-pyrrolo[2,3-c]pyridin-3-yl}carbonyl)benzoate, (30 mg, 0.06 mmol) and sodium hydroxide (27 mg, 0.06 mmol) were stirred in tetrahydrofuran and water (1:1, 6 mL) solution for about 2 hours, followed by slowly addition of aqueous hydrochloric acid till pH 4-5. The precipitated product was filtered and dried under vacuum to afford 3,5-dichloro-4-({7-[(cyclopropylcarbonyl)amino]-1H-pyrrolo[2,3-c]pyridin-3-yl}carbonyl)benzoic acid (20 mg, 62.5%).

$^1$H NMR (400 MHz, DMSO-d$_6$): δ 8.44-8.52 (m, 1H), 8.12 (d, J=6.27 Hz, 1H), 8.06 (s, 2H), 2.24-2.35 (m, 1H), 0.90-1.20 (m, 4H). MS: 416.89 (M$^-$).

The following compound was prepared in a similar fashion starting from N-[3,5-dichloro-4-({7-[(cyclopropylcarbonyl)amino]-1H-pyrrolo[2,3-c]pyridin-3-yl}carbonyl)benzoyl] glycine ethyl ester.

N-[3,5-Dichloro-4-({7-[(cyclopropylcarbonyl)amino]-1H-pyrrolo[2,3-c]pyridin-3-yl}carbonyl)benzoyl]glycine (Compound No. 36)

$^1$H NMR (400 MHz, DMSO-d6): δ 12.83 (br. s, 1H), 12.05 (br s., 1H), 11.08-11.52 (m, 1H), 9.25 (t, J=5.77 Hz, 1H), 8.13 (d, J=5.52 Hz, 1H), 8.08 (s, 2H), 8.00 (br. s., 1H), 3.95-4.01 (m, 2H), 2.09-2.17 (m, 1H), 0.89-0.99 (m, 4H). MS: 474.96 (M$^+$).

Step b: Synthesis of 3,5-dichloro-4-({7-[(cyclopropylcarbonyl)amino]-1H-pyrrolo[2,3-c]pyridin-3-yl}carbonyl)-N-(-2,3-dihydroxypropyl)benzamide To a solution of 3,5-dichloro-4-({7-[(cyclopropylcarbonyl)amino]-1H-pyrrolo[2,3-c]pyridin-3-yl}carbonyl)benzoic acid (50 mg, 0.11 mmol) in dimethylformamide (3 mL), 1-ethyl-3-(3-dimethylaminopropyl)carbodiimide (27.4 mg, 0.14 mmol), 1-hydroxybenzotriazole (19.37 mg, 0.14 mmol) and 3-aminopropane-1,2-diol (13 mg, 0.14 mmol) were added in one lot at room temperature. The resulting reaction mixture was stirred at room temperature for about 5 hours. Saturated aquoues sodium bicarbonate solution (20 mL) was added to quench the reaction mass. The aquoues phase was extracted with ethyl acetate and the combined organic layer dried over anhydrous sodium sulfate, filtered and concentrated. The crude product was purified by silica gel (100-200) column chromatography using ethyl acetate and hexane gradient elution to afford 3,5-dichloro-4-({7-[(cyclopropylcarbonyl)amino]-1H-pyrrolo[2,3-c]pyridin-3-yl}carbonyl)-N-(2,3-dihydroxypropyl)benzamide (30 mg, 51.72%).

$^1$H NMR (400 MHz, MeOH-d$_4$): δ 8.11 (d, J=5.02 Hz, 1H), 7.98 (s, 2H), 7.77 (br. s., 1H), 5.49 (s, 1H), 3.81-3.90 (m, 1H), 3.52-3.62 (m, 3H), 3.37-3.47 (m, 1H), 1.96-2.05 (m, 1H), 1.05-1.11 (m, 2H), 0.92-1.00 (m, 2H). MS: 490 (M$^+$).

The following compounds were analogously prepared by treating 3,5-dichloro-4-({7-[(cyclopropylcarbonyl)amino]-1H-pyrrolo[2,3-c]pyridin-3-yl}carbonyl)benzoic acid with appropriate amines.

3,5-Dichloro-4-({7-[(cyclopropylcarbonyl)amino]-1H-pyrrolo[2,3-c]pyridin-3-yl}carbonyl)-N-[2-(2-hydroxyethoxy)ethyl]benzamide (Compound No. 29)

$^1$H NMR (400 MHz, DMSO-d$_6$): δ11.95 (br. s., 1H), 11.11 (br. s., 1H), 8.88 (br. s., 1H), 8.13 (br. s., 1H), 8.05 (s, 2H), 7.86 (br. s., 1H), 4.62 (br. s., 1H), 3.42-3.61 (m, 8H), 2.12 (br. s., 1H), 0.86-0.98 (m, 4H). MS: 505.93 (M$^+$).

3,5-Dichloro-4-({7-[(cyclopropylcarbonyl)amino]-1H-pyrrolo[2,3-c]pyridin-3-yl}carbonyl)-N-(3-hydroxypropyl)benzamide (Compound No. 30)

$^1$H NMR (400 MHz, DMSO-d$_6$): δ 11.95 (br. s., 1H), 11.12 (br. s., 1H), 8.79 (br. s., 1H), 8.13 (br. s., 1H), 8.04 (s, 2H), 7.85 (br. s., 1H), 4.51 (br. s., 1H), 3.50 (d, J=7.53 Hz, 2H), 2.12 (br. s., 1H), 1.62-1.77 (m, 2H), 0.83-0.99 (m, 4H). MS: 475.89 (M$^+$).

3,5-Dichloro-4-({7-[(cyclopropylcarbonyl)amino]-1H-pyrrolo[2,3-c]pyridin-3-yl}carbonyl)-N-[3-(morpholin-4-yl)propyl]benzamide (Compound No. 31)

$^1$H NMR (400 MHz, DMSO-d$_6$): δ 11.95 (br. s., 1H), 11.12 (s, 1H), 8.82 (t, J=5.40 Hz, 1H), 8.13 (d, J=4.77 Hz, 1H), 8.03 (s, 2H), 7.85 (br. s., 1H),), 3.58 (t, J=4.39 Hz, 4H), 2.36 (d, J=5.02 Hz, 5H), 2.07-2.16 (m, 1H), 1.71 (quin, J=7.03 Hz, 2H), 0.85-0.97 (m, 4H). MS: 545.04 (M+1).

3,5-Dichloro-4-({7-[(cyclopropylcarbonyl)amino]-1H-pyrrolo[2,3-c]pyridin-3-yl}carbonyl)-N-[2-(dimethylamino)ethyl]benzamide (Compound No. 33)

$^1$H NMR (400 MHz, DMSO-d$_6$): δ 11.88-12.04 (m, 1H), 11.12 (br. s., 1H), 8.83 (br. s., 1H), 8.13 (d, J=5.02 Hz, 1H), 8.05 (s, 2H), 7.81-7.89 (m, 1H), 3.40-3.51 (m, 2H), 2.58-2.63 (m, 2H), 2.33 (s., 6H), 2.02-2.14 (m, 1H), 0.84-0.98 (m, 4H). MS: 489 (M+1).

3,5-Dichloro-4-({7-[(cyclopropylcarbonyl)amino]-1H-pyrrolo[2,3-c]pyridin-3-yl}carbonyl)-N-[2-(piperidin-1-yl)ethyl]benzamide (Compound No. 34)

$^1$H NMR (400 MHz, DMSO-d6): δ 11.88-12.02 (m, 1H), 11.12 (br. s., 1H), 8.10-8.20 (m, 1H), 8.04 (s, 2H), 7.79-7.91 (m, 1H), 3.44-3.58 (m, 2H), 3.38 (d, J=7.03 Hz, 1H), 2.55-2.74 (m, 2H), 2.08-2.17 (m, 1H), 2.06-2.20 (m, 1H), 1.59 (br. s., 3H), 1.39-1.50 (m, 2H), 1.09 (t, J=7.03 Hz, 1H), 0.80-1.01 (m, 4H), 0.80-0.99 (m, 4H). MS: 529.05 (M+1).

Methyl N-[3,5-dichloro-4-({7-[(cyclopropylcarbonyl)amino]-1H-pyrrolo[2,3-c]pyridin-3-yl}carbonyl)benzoyl]glycinate (Compound No. 35)

$^1$H NMR (400 MHz, DMSO-d$_6$): δ 11.96 (br. s., 1H), 11.11 (br. s., 1H), 9.35 (t, J=5.77 Hz, 1H), 8.13 (d, J=5.02 Hz, 1H), 8.07 (s, 2H), 7.85-7.95 (m, 1H), 4.08 (d, J=5.77 Hz, 2H), 3.69 (s, 3H), 2.12 (br. s., 1H), 0.87-0.97 (m, 4H). MS: 490.07 (M+1).

4-({7-[(Cyclopropylcarbonyl)amino]-1H-pyrrolo[2,3-c]pyridin-3-yl}carbonyl)-3,5-difluoro-N-(2-fluoroethyl)benzamide (Compound No. 59)

$^1$H NMR (400 MHz, DMSO-d$_6$): δ 11.13 (s, 1H), 9.02 (t, J=5.65 Hz, 1H), 8.15 (d, J=5.27 Hz, 1H), 7.98 (s, 1H), 7.91 (d, J=5.02 Hz, 1H), 7.76 (d, J=8.03 Hz, 2H), 4.63 (t, J=5.02 Hz, 1H), 4.51 (t, J=5.02 Hz, 1H), 3.65 (q, J=5.19 Hz, 1H), 3.58 (q, J=5.27 Hz, 1H), 2.08-2.17 (m, 1H), 0.88-0.98 (m, 4H). MS: 431.13 (M+1).

4-({7-[(Cyclopropylcarbonyl)amino]-1H-pyrrolo[2,3-c]pyridin-3-yl}carbonyl)-N-ethyl-3,5-difluorobenzamide (Compound No. 60)

$^1$H NMR (400 MHz, DMSO-d6): δ11.98 (br. s., 1H), 11.13 (s, 1H), 8.76 (t, J=5.52 Hz, 1H), 8.15 (d, J=5.52 Hz, 1H), 7.97 (s, 1H), 7.91 (d, J=5.27 Hz, 1H), 7.73 (d, J=8.03 Hz, 2H), 2.08-2.17 (m, 1H), 1.15 (t, J=7.28 Hz, 3H), 0.87-0.97 (m, 4H). MS: 413.13 (M+1).

4-({7-[(Cyclopropylcarbonyl)amino]-1H-pyrrolo[2,3-c]pyridin-3-yl}carbonyl)-3,5-difluoro-N-methylbenzamide (Compound No. 61)

$^1$H NMR (400 MHz, DMSO-d$_6$): δ11.98 (br. s., 1H), 11.13 (s, 1H), 8.74-8.75 (d, J=8 Hz, 1H), 8.14-8.15 (d, J=5.2 Hz, 1H), 7.96 (Unresolved S, 1H), 7.90 (d, J=5.2 Hz, 1H), 7.69-7.71 (m, 2H), 2.83 (d, J=4.52 Hz, 3H), 2.08-2.17 (m, 1H), 0.88-0.97 (m, 4H). MS: 399.1 (M$^+$).

4-({7-[(Cyclopropylcarbonyl)amino]-1H-pyrrolo[2,3-c]pyridin-3-yl}carbonyl)-3,5-difluoro-N-(3-hydroxypropyl)benzamide (Compound No. 62)

$^1$H NMR (400 MHz, DMSO-d$_6$): δ11.98 (br. s., 1H), 11.13 (s, 1H), 8.74 (t, J=5.52 Hz, 1H), 8.15 (d, J=5.27 Hz, 1H), 7.97 (s, 1H), 7.91 (d, J=5.27 Hz, 1H), 7.73 (d, J=8.03 Hz, 2H), 4.51 (br. s., 1H), 3.48 (d, J=3.01 Hz, 2H), 3.36-3.40 (m, 2H), 2.09-2.17 (m, 1H), 1.71 (quin, J=6.71 Hz, 2H), 0.87-0.97 (m, 4H). MS: 443.15 (M+1).

4-({7-[(Cyclopropylcarbonyl)amino]-1H-pyrrolo[2,3-c]pyridin-3-yl}carbonyl)-N-[2-(dimethylamino)ethyl]-3,5-difluorobenzamide (Compound No. 63)

$^1$H NMR (400 MHz, DMSO-d$_6$): δ 11.98 (br. s., 1H), 11.13 (br. s., 1H), 8.73 (t, J=5.52 Hz, 1H), 8.15 (d, J=5.52 Hz, 1H), 7.98 (s, 1H), 7.91 (d, J=5.02 Hz, 1H), 7.73 (d, J=8.28 Hz, 2H), 3.41 (q, J=6.53 Hz, 2H), 2.24 (s, 6H), 2.10-2.18 (m, 1H), 0.88-0.98 (m, 4H). MS: 456.26 (M+1).

4-({7-[(Cyclopropylcarbonyl)amino]-1H-pyrrolo[2,3-c]pyridin-3-yl}carbonyl)-N-(3-ethoxypropyl)-3,5-difluorobenzamide (Compound No. 64)

$^1$H NMR (400 MHz, DMSO-d$_6$): δ11.98 (br. s., 1H), 11.13 (s, 1H), 8.75 (t, J=5.52 Hz, 1H), 8.15 (d, J=5.52 Hz, 1H), 7.97 (s, 1H), 7.91 (d, J=5.27 Hz, 1H), 7.72 (d, J=8.03 Hz, 2H), 3.39-3.46 (m, 4H), 3.34-3.39 (m, 2H), 2.02-2.13 (m, 1H), 1.78 (q, 2H), 1.12 (t, J=7.03 Hz, 3H), 0.87-0.98 (m, 4H). MS: 471.23 (M+1).

3,5-Dichloro-N-cyclopropyl-4-({7-[(cyclopropylcarbonyl)amino]-1H-pyrrolo[2,3-c]pyridin-3-yl}carbonyl)benzamide (Compound No. 54)

$^1$H NMR (400 MHz, DMSO-d$_6$): δ 11.94 (br. s., 1H), 11.11 (s, 1H), 8.76 (d, J=4.04 Hz, 1H), 8.12 (d, J=4.80 Hz, 1H), 8.01 (s, 2H), 7.83 (br. s., 1H), 2.89 (dt, J=3.66, 7.26 Hz, 1H), 2.12 (d, J=4.29 Hz, 1H), 0.86-0.98 (m, 4H), 0.52-0.79 (m, 4H). MS: 457.12 (M+1).

3,5-Dichloro-4-({7-[(cyclopropylcarbonyl)amino]-1H-pyrrolo[2,3-c]pyridin-3-yl}carbonyl)-N-(cyclopropylmethyl)benzamide (Compound No. 55)

$^1$H NMR (400 MHz, DMSO-d$_6$): δ 11.94 (br. s., 1H), 11.11 (br. s., 1H), 8.92 (m, 1H), 8.12 (m, 1H), 8.06 (s, 2H), 7.85 (br. s., 1H), 3.16-3.20 (m, 2H), 2.09-2.18 (m, 1H), 0.86-0.98 (m, 5H), 0.46-0.49 (m, 2H), 0.25-0.27 (m, 2H). MS: 471.13 (M$^+$).

3,5-Dichloro-4-({7-[(cyclopropylcarbonyl)amino]-1H-pyrrolo[2,3-c]pyridin-3-yl}carbonyl)-N-(3-ethoxypropyl)benzamide (Compound No. 56)

$^1$H NMR (400 MHz, DMSO-d$_6$): δ 11.94 (br. s., 1H), 11.11 (br. s., 1H), 8.79 (m, 1H), 8.13 (d, J=4.80 Hz, 1H), 8.03 (s, 2H), 7.84 (br. s., 1H), 3.41-3.43 (m, 4H), 2.12 (br. s., 1H), 1.79 (m, 2H), 1.09-1.13 (m, 3H), 0.87-0.98 (m, 4H). MS: 503.14 (M+1).

N-Butyl-3,5-dichloro-4-({7-[(cyclopropylcarbonyl)amino]-1H-pyrrolo[2,3-c]pyridin-3-yl}carbonyl)benzamide (Compound No. 57)

$^1$H NMR (400 MHz, DMSO-d$_6$): δ 11.96 (br. s., 1H), 11.13 (br. s., 1H), 8.78 (t, J=5.27 Hz, 1H), 8.13 (d, J=5.02 Hz, 1H), 8.04 (s, 1H), 7.91-7.98 (m, 1H), 7.79-7.90 (m, 1H), 3.03-3.11 (m, 1H), 2.13 (br. s., 1H), 1.53 (td, J=7.03, 14.56 Hz, 2H), 1.36 (td, J=7.31, 14.74 Hz, 2H), 1.20-1.31 (m, 2H), 0.79-0.99 (m, 7H). MS: 473.19 (M$^+$).

Example 10

4-{[7-(Acetylamino)-1H-pyrrolo[2,3-c]pyridin-3-yl]carbonyl}-3,5-dichloro-N-[2-(2-hydroxyethoxyl)ethyl]benzamide (Compound No. 41)

4-{[7-(Acetylamino)-1H-pyrrolo[2,3-c]pyridin-3-yl]carbonyl}-3,5-dichlorobenzoic acid (0.1 g, 0.25 mmol) was taken in a reaction vial. To it 2-(2-aminoethoxyl)ethanol (0.029 g, 2.8 mmol), 1-ethyl-3-(3-dimethylaminopropyl)carbodiimide (0.073 g, 3.8 mmol), 1-hydroxybenzotriazole (0.051 g, 3.8 mmol) and dimethylformamide (2 mL) were added. The whole reaction mixture was stirred at room temperature for overnight. Water (20 mL) was added to the reaction mixture, extracted with ethyl acetate (3×50 mL). The organic layer was dried over anhydrous sodium sulfate and concentrated under vacuum to get the crude mass which was purified by flash column chromatography to get 4-{[7-(acetylamino)-1H-pyrrolo[2,3-c]pyridin-3-yl]carbonyl}-3,5-dichloro-N-[2-(2-hydroxyethoxyl)ethyl]benzamide (0.035 g, 29%).

¹H NMR (400 MHz, DMSO-d₆): δ 12.00 (br. s., 1H), 10.75 (br. s., 1H), 8.87 (t, J=5.27 Hz, 1H), 8.13 (d, J=5.02 Hz, 1H), 8.05 (s, 2H), 7.94 (br. s., 1H), 4.62 (br. s., 1H), 3.55-3.60 (m, 2H), 3.45-3.54 (m, 6H), 2.19 (s, 3H). MS: 480.07 (M+1), 482.07 (M+3).

The following compounds were synthesized following a similar procedure while using appropriate amines.

4-{[7-(Acetylamino)-1H-pyrrolo[2,3-c]pyridin-3-yl]carbonyl}-3,5-dichloro-N-[2-(dimethylamino)ethyl]benzamide (Compound No. 40)

¹H NMR (400 MHz, DMSO-d₆): δ 12.01 (br. s., 1H), 10.75 (br. s., 1H), 8.77 (t, J=5.43 Hz, 1H), 8.13 (d, J=4.55 Hz, 1H), 8.04 (s, 2H), 7.94 (br. s., 1H), 3.38-3.43 (m, 2H), 2.43 (t, J=6.69 Hz, 2H), 2.20 (s, 6H), 2.01-2.19 (m, 3H). MS: 463.12 (M+1).

4-{[7-(Acetylamino)-1H-pyrrolo[2,3-c]pyridin-3-yl]carbonyl}-3,5-dichloro-N-[2-(piperidin-1-yl)ethyl]benzamide (Compound No. 42)

¹H NMR (400 MHz, DMSO-d₆): δ 12.00 (br. s., 1H), 10.75 (br. s., 1H), 8.74-8.82 (m, 1H), 8.13 (d, J=5.02 Hz, 1H), 8.03 (s, 2H), 7.94 (br. s., 1H), 3.37 (br. s., 4H), 2.45 (br. s., 4H), 2.19 (s, 3H), 1.36-1.56 (m, 6H). MS: 503.18 (M+1), 505.18 (M+3).

4-{[7-(Acetylamino)-1H-pyrrolo[2,3-c]pyridin-3-yl]carbonyl}-3,5-dichloro-N-[2-(morpholin-4-yl)ethyl]benzamide (Compound No. 43)

¹H NMR (400 MHz, DMSO-d₆): δ 12.00 (br. s., 1H), 10.75 (br. s., 1H), 8.79 (t, J=5.52 Hz, 1H), 8.13 (d, J=4.77 Hz, 1H), 8.01-8.07 (m, 2H), 7.94 (br. s., 1H), 3.58 (t, J=4.52 Hz, 4H), 2.43 (br. s., 4H), 2.19 (s, 3H). MS: 505.16 (M+1), 507.16 (M+3).

4-{[7-(Acetylamino)-1H-pyrrolo[2,3-c]pyridin-3-yl]carbonyl}-3,5-dichloro-N-[2-(pyrrolidin-1-yl)ethyl]benzamide (Compound No. 44)

¹H NMR (400 MHz, DMSO-d₆): δ12.01 (br. s., 1H), 10.76 (br. s., 1H), 8.88 (br. s., 1H), 8.13 (d, J=5.27 Hz, 1H), 8.06 (s, 2H), 7.93 (br. s., 1H), 3.47 (d, J=6.02 Hz, 2H), 2.56-2.86 (m, 6H), 2.19 (s, 3H), 1.75 (br. s., 4H). MS: 489.13 (M+1), 491.15 (M+3).

Example 11

Synthesis of N-(3-{2,6-dichloro-4-[(methylamino)methyl]benzoyl}-1H-pyrrolo[2,3-c]pyridin-7-yl)cyclopropanecarboxamide (Compound No. 66)

Step a: Synthesis of N-{3-[2,6-dichloro-4-(hydroxymethyobenzoyl]-1H-pyrrolo[2,3-c]pyridin-7-yl}cyclopropanecarboxamide (Compound No. 58)

To a solution of methyl 3,5-dichloro-4-({7-[(cyclopropylcarbonyl)amino]-1H-pyrrolo[2,3-c]pyridin-3-yl}carbonyl)benzoate (100 mg, 2.31 mmol) in 1,4-dioxane and water (3:1), sodium borohydride (27 mg, 6.944 mmol) was added portion wise over a period of about 15 minutes, followed by heating the reaction mixture at 60° C. until starting material was consumed (approximately 3 hours) The reaction mixture was cooled to room temperature and quenched by the addition of saturated aq. ammonium chloride solution and extracted with ethyl acetate. Organic layer was separated, washed with brine, dried over sodium sulfate and concentrated under vacuum. Purification by silica gel (100-200) column chromatography using dichloromethane and methanol gradient as eluent afforded N-{3-[2,6-dichloro-4-(hydroxymethyl)benzoyl]-1H-pyrrolo[2,3-c]pyridin-7-yl}cyclopropane carboxamide (20 mg, 22%).

¹H NMR (400 MHz, DMSO-d6): δ 11.91 (br. s, 1H), 11.12 (br. s, 1H), 8.05-8.11 (m, 1H), 7.66-7.82 (m, 1H), 7.53 (s, 2H), 5.57 (m, 1H), 4.59-4.66 (m, 2H), 2.13 (m, 1H), 0.89-0.93 (m, 4H). MS: 403.97 (M⁺).

Step b—Synthesis of N-{3-[4-(bromomethyl)-2,6-dichlorobenzoyl]-1H-pyrrolo[2,3-c]pyridin-7-yl}cyclopropanecarboxamide To a solution of N-{3-[2,6-dichloro-4-(hydroxymethyl)benzoyl]-1H-pyrrolo[2,3-c]pyridin-7-yl}cyclopropanecarboxamide (900 mg, 2.23 mmol) in dichloromethane and carbon tetrachloride (2:1) at 0° C., phosphorus tribromide (1200 mg, 0.42 mL, 4.455 mmol) was added drop wise over a period of few minutes, stirred the mixture at 0° C. to room temperature. On completion, the reaction was quenched by adding saturated solution of sodium bicarbonate and extracted with dichloromethane. Organic layer was separated, washed with brine, dried over sodium sulfate and concentrated under vacuum. Purification by silica gel (100-200) column chromatography using dichloromethane and methanol gradient as eluent afforded N-{3-[4-(bromomethyl)-2,6-dichlorobenzoyl]-1H-pyrrolo[2,3-c]pyridin-7-yl}cyclopropanecarboxamide (330 mg, 33%).

¹H NMR (400 MHz, DMSO-d₆): δ 11.92 (br. s, 1H), 11.12 (br. s, 1H), 8.11-8.12 (m, 1H), 7.79 (m, 1H), 7.73 (s, 2H), 4.77 (s, 2H), 1.95-2.13 (m, 1H), 0.85-0.93 (m, 4H). MS: 467.81 (M+1).

Step c: Synthesis of N-(3-{2,6-dichloro-4-[(methylamino)methyl]benzoyl}-1H-pyrrolo[2,3-c]pyridin-7-yl)cyclopropanecarboxamide To a solution of N-{3-[4-(bromomethyl)-2,6-dichlorobenzoyl]-1H-pyrrolo[2,3-c]pyridin-7-yl}cyclopropanecarboxamide (50 mg, 0.11 mmol) in acetonitrile, cesium carbonate (70 mg, 0.21 mmol) was added and stirred at same temperature. Methyl amine (6.8 mg, 0.21 mmol) was added at 0° C. The reaction mixture was then stirred at room temperature for 3 h. On completion, the reaction mixture was diluted with water and extracted with ethyl acetate, organic layer was separated, washed with brine, dried over sodium sulfate and concentrated under vacuum. Purification by silica gel (100-200) column chromatography using dichloromethane and methanol gradient as eluent afforded N-(3-{2,6-dichloro-4-[(methylamino)methyl]benzoyl}-1H-pyrrolo[2,3-c]pyridin-7-yl)cyclopropanecarboxamide (7.2 mg, 16%).

¹H NMR (400 MHz, DMSO-d₆): δ 11.13 (br. s., 1H), 8.11 (d, J=5.02 Hz, 1H), 7.75 (br. s., 2H), 7.62 (s, 2H), 3.86-3.95 (m, 2H), 2.37-2.43 (m, 3H), 2.13 (d, J=5.02 Hz, 1H), 0.9-0.92 (m, 4H). MS: 415.08 (M⁺).

The following compound was synthesized in a similar fashion by treating N-{3-[4-(bromomethyl)-2,6-dichlorobenzoyl]-1H-pyrrolo[2,3-c]pyridin-7-yl}cyclopropane carboxamide with ethylamine N-(3-{2,6-Dichloro-4-[(ethylamino)methyl]benzoyl}-1H-pyrrolo[2,3-c]pyridin-7-yl)cyclopropanecarboxamide (Compound No. 67)

¹H NMR (400 MHz, DMSO-d₆): δ 11.97 (br. s., 1H), 11.12 (br. s., 1H), 8.02-8.16 (m, 1H), 7.70-7.83 (m, 2H), 7.59 (s, 2H), 3.82 (s, 2H), 2.3-2.52 (m, 2H, merged), 2.07-2.20 (m, 1H), 1.07 (t, J=7.15 Hz, 3H), 0.85-0.98 (m, 4H). MS: 431.22 (M⁺).

Example 12

Synthesis of N-[3-(2,6-dichlorobenzoyl)-2-methyl-1H-pyrrolo[2,3-c]pyridin-7-yl]cyclopropanecarboxamide (Compound No. 68)

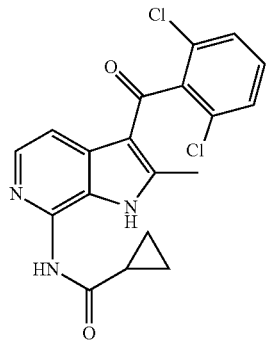 [SMILES: Cc1[nH]c2c(NC(=O)C3CC3)nccc2c1C(=O)c1c(Cl)cccc1Cl]

N-(2-Methyl-1H-pyrrolo[2,3-c]pyridin-7yl)cyclopropanecarboxamide (100 mg, 0.46 mmol) was added to a stirred suspension of aluminium chloride (620 mg, 4.65 mmol) in dry dichloromethane (5 mL) and the mixture was stirred at room temperature for about 1 hour under argon atmosphere. This was followed by drop wise addition of a solution of 2,6-dichlorobenzoyl chloride (194 mg, 0.93 mmol) in dichloromethane and stirring overnight at room temperature. After completion, methanol (10 mL) was added cautiously to quench the reaction mass followed by concentration under vacuum. The residual mass was diluted with water and extracted with ethyl acetate. The combined organic layer was neutralized using aq. sodium bicarbonate solution, washed with brine, dried over anhydrous sodium sulfate and concentrated. Purification by silica gel (100-200) column chromatography using dichloromethane and methanol gradient as eluent afforded N-[3-(2,6-dichlorobenzoyl)-2-methyl-1H-pyrrolo[2,3-c]pyridin-7-yl]cyclopropanecarboxamide (70 mg, 39%).

$^1$H NMR (400 MHz, DMSO-$d_6$): δ 8.11-8.14 (m, 1H), 7.53-7.55 (m, 1H), 7.43-7.51 (m, 3H), 2.87-2.92 (m, 1.5H), 2.1-2.15 (m, 1H), 2.02-2.09 (m, 1.5H), 0.89-0.98 (m, 4H). MS: 388.2 (M$^+$), 390.04 (M+2).

Example 13

Synthesis of N-[3-(2,6-difluorobenzoyl)-2-methyl-1H-pyrrolo[2,3-c]pyridin-7-yl]cyclopropanecarboxamide (Compound No. 70)

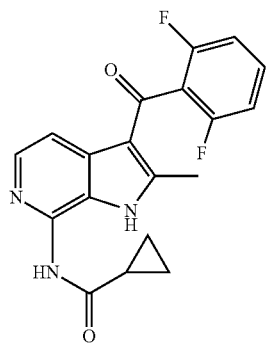 [SMILES: Cc1[nH]c2c(NC(=O)C3CC3)nccc2c1C(=O)c1c(F)cccc1F]

To a solution of 2,6-difluorobenzoic acid (176 mg, 1.15 mmol) in dry dichloromethane, was added thionyl chloride (5 mL) and heated at 100° C. for about 3 hours. The reaction mass was concentrated under vacuum. The residual mass was dissolved in dry dichloromethane (3 mL) and added to a well stirred solution of N-(2-methyl-1H-pyrrolo[2,3-c]pyridin-7-yl)cyclopropanecarboxamide (120 mg, 0.55 mmol) in aluminium chloride (743 mg, 5.57 mmol) drop wise. The resulting reaction mixture was stirred overnight at room temperature. After completion, methanol (10 mL) was added cautiously to quench the reaction mass followed by concentration under vacuum. The reaction mass was diluted with water and extracted with ethyl acetate. The combined organic layer was neutralized using aq. sodium bicarbonate solution, washed with brine, dried over anhydrous sodium sulfate, and concentrated. Purification by silica gel (100-200) column chromatography using dichloromethane and methanol gradient as eluent afforded N-[3-(2,6-difluorobenzoyl)-2-methyl-1H-pyrrolo[2,3-c]pyridin-7-yl]cyclopropanecarboxamide (80 mg, 42%).

$^1$H NMR (400 MHz, DMSO-$d_6$) δ: 11.80 (br. s., 1H), 10.91 (br. s., 1H), 7.96 (d, J=5.52 Hz, 1H), 7.57-7.74 (m, 1H), 7.24-7.35 (m, 2H), 7.03 (br. s., 1H), 2.47 (s, 3H), 1.99-2.11 (m, 1H), 0.86-0.97 (m, 4H). MS: 356.13 (M+1)

Example 14

Synthesis of 3,5-dichloro-4-({7-[(cyclopropylcarbonyl)amino]-2-methyl-1H-pyrrolo[2,3-c]pyridin-3-yl}carbonyl)-N-methylbenzamide (Compound No. 71)

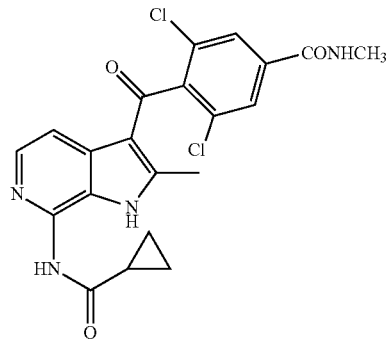

To a solution of 2,6-dichloro-4-(methylcarbamoyl)benzoic acid (276 mg, 1.1 mmol) in dry dichloromethane, was added thionyl chloride (5 mL) and heated at 100° C. for about 3 hours. The mixture was concentrated under vacuum. The residue was dissolved in dry dichloromethane (3 mL) and added to the stirred solution of N-(2-methyl-1H-pyrrolo[2,3-c]pyridin-7-yl)cyclopropanecarboxamide (120 mg, 0.55 mmol) in aluminium chloride (743 mg, 5.57 mmol) drop wise. The resulting reaction mixture was stirred overnight at room temperature. After completion, methanol (10 mL) was added cautiously to quench the reaction mass followed by concentration under vacuum. The reaction mass was diluted with water and extracted with ethyl acetate. The combined organic layer was washed with aq. sodium bicarbonate solution, brine, dried over anhydrous sodium sulfate, and concentrated. Purification by silica gel (100-200) column chromatography using dichloromethane and methanol gradient as eluent afforded 3,5-dichloro-4-({7-[(cyclopropylcarbonyl)

amino]-2-methyl-1H-pyrrolo[2,3-c]pyridin-3-yl}carbonyl)-N-methylbenzamide (70 mg, 29%).

$^1$H NMR (400 MHz, DMSO-d$_6$): δ 11.74 (br, s., 1H), 10.91 (br. s., 1H), 8.82 (dd, J=4.52, 16.56 Hz, 1H), 8.00-8.11 (m, 2H), 2.78-2.91 (m, 3H), 2.07 (d, J=4.77 Hz, 1H), 1.99 (d, J=2.26 Hz, 3H), 0.85-0.97 (m, 4H). MS: 445.1 (M+1).

Example 15

Synthesis of methyl[1-(2,6-dichlorobenzoyl)-1H-pyrrolo[3,2-c]pyridin-4-yl]carbamate (Compound No. 74)

A solution of (4-amino-1H-pyrrolo[3,2-c]pyridin-1-yl)(2,6-dichlorophenyl)methanone (50 mg, 0.16 mmol) and triethylamine (0.013 mL, 0.18 mmol) in anhydrous tetrahydrofuran was cooled to 0° C. and treated drop wise with methyl chloroformate (0.05 mL, 0.33 mL) and stirred at room temperature for 2 hours. The reaction mixture was poured onto cold water and the precipitated solid was filtered off, washed with hexane and dried to afford methyl[1-(2,6-dichlorobenzoyl)-1H-pyrrolo[3,2-c]pyridin-4-yl]carbamate (35 mg, 60%).

$^1$H NMR (400 MHz, MeOH-d$_4$): δ 8.28 (d, J=5.27 Hz, 2H), 7.61 (s, 3H), 7.05 (d, J=3.89 Hz, 1H), 6.91 (d, J=3.83 Hz, 1H), 3.80 (s, 3H). MS: 364 (M$^+$).

Example 16

Synthesis of N-[1-(2,6-dichlorobenzoyl)-1H-pyrrolo[3,2-c]pyridin-4-yl]acetamide (Compound No 172)

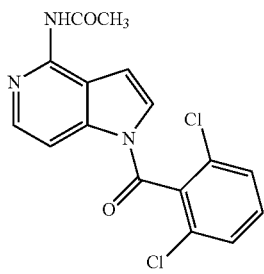

To an ice-cooled solution of (4-amino-1H-pyrrolo[3,2-c]pyridin-1-yl)(2,6-dichlorophenyl)methanone (50 mg, 0.16 mmol) and triethylamine (0.05 ml, 0.32 mmol) in tetrahydrofuran (5 mL) was added acetyl chloride (0.01 ml, 0.15 mmol) drop wise and stirred at room temperature for about 1 hour. Ethyl acetate was added and washed with saturated aqueous sodium hydrogen carbonate solution, dried over anhydrous sodium sulfate and concentrated. The residue was taken up in methanol (5 mL), potassium carbonate (50 mg) was added and stirred for 10 minutes. The solvent was removed on a rotary evaporator at 20° C. and the residue was dissolved in dichloromethane, washed with water and brine, dried and concentrated to afford the crude product. Purification by silica gel column chromatography using ethyl acetate and dichloromethane gradient as eluent yielded N-[1-(2,6-dichlorobenzoyl)-1H-pyrrolo[3,2-c]pyridin-4-yl]acetamide (45 mg, 81%).

$^1$H NMR (400 MHz, DMSO-d$_6$): δ 10.62 (s, 1H), 8.35 (d, J=5.65 Hz, 1H), 8.21 (d, J=5.58 Hz, 1H), 7.66-7.79 (m, 3H), 7.21 (d, J=3.89 Hz, 1H), 6.79 (d, J=3.70 Hz, 1H), 2.17 (s, 3H). MS: 348.05 (M$^+$).

The following compound was prepared following similar method while using appropriate starting material:

N-[1-(2,6-Dichlorobenzoyl)-1H-pyrrolo[3,2-c]pyridin-4-yl]cyclopropanecarboxamide (Compound No. 77)

$^1$H NMR (400 MHz, DMSO-d$_6$): δ 10.89 (s, 1H), 8.36 (d, J=5.65 Hz, 1H), 8.21 (d, J=5.65 Hz, 1H), 7.64-7.77 (m, 3H), 7.17 (d, J=3.89 Hz, 1H), 6.72 (d, J=3.45 Hz, 1H), 2.01-2.10 (m, 1H), 0.85 (d, J=6.21 Hz, 4H). MS: 374.07 (M$^+$).

Example 17

Synthesis of 3,5-dichloro-4-({4-[(cyclopropylcarbonyl)amino]-1H-pyrrolo[3,2-c]pyridin-1-yl}carbonyl)-N-ethylbenzamide (Compound No. 93)

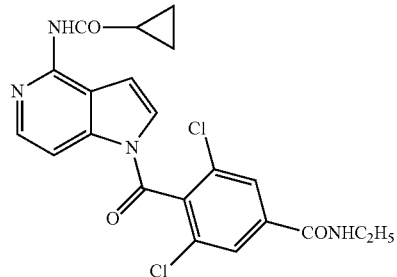

A well stirred mixture of 2,6-dichloro-4-(ethylcarbamoyl)benzoic acid (84.6 mg, 0.42 mmol), 1-hydroxy-7-azabenzotriazole (77 mg, 0.57 mmol), N,N-dimethyl aminopyridine (22 mg, 0.11 mmol) and 2-(1H-7-azabenzotriazol-1-yl)-1,1,3,3-tetramethyl uronium hexafluorophosphate methanaminium (216 mg, 0.57 mmol) in N,N-dimethylaniline was treated with N-(1H-pyrrolo[3,2-c]pyridin-4-yl)cyclopropanecarboxamide (100 mg, 0.38 mmol) and N,N-diisopropylethylamine (0.1 ml, 0.95 mmol). The reaction was stirred overnight at room temperature. The contents were diluted with water and extracted with ethyl acetate. The combined organic portion was washed with brine, dried over anhydrous sodium sulfate, filtered and concentrated. The crude product was purified by silica gel column chromatography using methanol in dichloromethane (3%) as eluent to yield 3,5-dichloro-4-({4-[(cyclopropylcarbonyl)amino]-1H-pyrrolo[3,2-c]pyridin-1-yl}carbonyl)-N-ethylbenzamide (45 mg, 26%) as an off white solid.

$^1$H NMR (400 MHz, DMSO-d$_6$): δ 10.89 (s, 1H), 8.86 (t, J=5.36 Hz, 1H), 8.37 (d, J=5.65 Hz, 1H), 8.21 (d, J=6.27 Hz, 1H), 8.12 (s, 2H), 7.28 (d, J=3.89 Hz, 1H), 6.72 (d, J=3.89 Hz, 1H), 3.35 (q, 2H, merged), 2.00-2.10 (m, 1H), 1.15 (t, J=7.22 Hz, 3H), 0.85 (d, J=6.15 Hz, 4H). MS: 444.86 (M$^+$).

The following compounds were prepared in an analogous manner using appropriately substituted starting materials.

3,5-Dichloro-4-(1H-pyrrolo[3,2-c]pyridin-1-ylcarbonyl)benzonitrile (Compound No. 95) was prepared using 1H-pyrrolo[3,2-c]pyridine and 2,6-dichloro-4-cyanobenzoic acid.

$^1$H NMR (400 MHz, DMSO-d$_6$): δ 9.00 (d, J=1.07 Hz, 1H), 8.61 (d, J=5.65 Hz, 1H), 8.43 (s, 2H), 8.33 (dt, J=5.62, 0.89 Hz, 1H), 7.52 (d, J=3.89 Hz, 1H), 6.98 (dd, J=3.86, 0.72 Hz, 1H). MS: 315.89 (M$^+$).

N-[1-(2,6-Dichloro-4-cyanobenzoyl)-1H-pyrrolo[3,2-c]pyridin-4-yl]acetamide (Compound No. 99) was prepared using N-(1H-pyrrolo[3,2-c]pyridin-4-yl)acetamide and 2,6-dichloro-4-cyanobenzoic acid.

$^1$H NMR (400 MHz, DMSO-d$_6$): δ 10.60 (s, 1H), 8.40 (s, 2H), 8.35 (d, J=5.65 Hz, 1H), 8.19 (d, J=5.65 Hz, 1H), 7.36 (d, J=3.95 Hz, 1H), 6.81 (d, J=3.89 Hz, 1H), 2.17 (s, 3H). MS: 373.06 (M$^+$).

3,5-Dichloro-N-methyl-4-(1H-pyrrolo[3,2-c]pyridin-1-ylcarbonyl)benzamide (Compound No. 72) was prepared using 1H-pyrrolo[3,2-c]pyridine and 2,6-dichloro-4-(methylcarbamoyl)benzoic acid.

$^1$H NMR (400 MHz, DMSO-d$_6$) δ: 9.00 (s, 1H), 8.85 (d, J=4.64 Hz, 1H), 8.61 (d, J=5.58 Hz, 1H), 8.35 (d, J=5.65 Hz, 1H), 8.11 (s, 2H), 7.42 (d, J=3.83 Hz, 1H), 6.95 (dd, J=3.83, 0.69 Hz, 1H), 2.84 (d, J=4.58 Hz, 3H). MS: 348.11 (M$^+$).

3,5-Dichloro-N-ethyl-4-(1H-pyrrolo[3,2-c]pyridin-1-ylcarbonyl)benzamide (Compound No. 73) was prepared using 1H-pyrrolo[3,2-c]pyridine and 2,6-dichloro-4-(ethylcarbamoyl)benzoic acid.

$^1$H NMR (400 MHz, DMSO-d$_6$) δ: 9.00 (s, 1H), 8.87 (s, 1H), 8.60 (d, J=5.65 Hz, 1H), 8.35 (d, J=5.58 Hz, 1H), 8.13 (s, 2H), 7.43 (d, J=3.89 Hz, 1H), 6.95 (dd, J=3.83, 0.75 Hz, 1H), 1.16 (t, J=7.22 Hz, 3H). MS: 362.09 (M$^+$).

3,5-Dichloro-N-(2-hydroxyethyl)-4-(1H-pyrrolo[3,2-c]pyridin-1-ylcarbonyl)benzamide (Compound No. 75) was prepared using 1H-pyrrolo[3,2-c]pyridine and 2,6-dichloro-4-[(2-hydroxyethyl)carbamoyl]benzoic acid.

$^1$H NMR (400 MHz, DMSO-d$_6$): δ 9.00 (d, J=0.94 Hz, 1H), 8.86 (t, J=5.55 Hz, 1H), 8.61 (d, J=5.58 Hz, 1H), 8.32-8.38 (m, 1H), 8.15 (s, 2H), 7.42 (d, J=3.83 Hz, 1H), 6.95 (dd, J=3.89, 0.69 Hz, 1H), 4.80 (t, J=5.65 Hz, 1H), 3.54 (q, J=5.92 Hz, 2H), 3.36-3.40 (m, 2H). MS: 378.20 (M$^+$).

3,5-Dichloro-N-(cyanomethyl)-4-(1H-pyrrolo[3,2-c]pyridin-1-ylcarbonyl)benzamide (Compound No. 76) was prepared using 1H-pyrrolo[3,2-c]pyridine and 2,6-dichloro-4-[(cyanomethyl)carbamoyl]benzoic acid.

$^1$H NMR (400 MHz, DMSO-d$_6$): δ 9.64 (t, J=5.43 Hz, 1H), 9.00 (d, J=0.75 Hz, 1H), 8.61 (d, J=5.65 Hz, 1H), 8.35 (d, J=5.58 Hz, 1H), 8.16 (s, 2H), 7.45 (d, J=3.89 Hz, 1H), 6.96 (dd, J=3.86, 0.66 Hz, 1H), 4.41 (d, J=5.40 Hz, 2H).

3,5-Dichloro-4-({4-[(cyclopropylcarbonyl)amino]-1H-pyrrolo[3,2-c]pyridin-1-yl}carbonyl)benzamide (Compound No. 100) was prepared using N-(1H-pyrrolo[3,2-c]pyridin-4-yl)cyclopropane carboxamide and 2,6-dichloro-4-carbamoyl benzoic acid.

$^1$H NMR (400 MHz, DMSO-d$_6$): δ 10.89 (s, 1H), 8.37 (d, J=5.65 Hz, 1H), 8.33-8.35 (m, 1H), 8.21 (d, J=5.96 Hz, 1H), 8.15 (s, 2H), 7.78-7.89 (m, 1H), 7.29 (d, J=3.89 Hz, 1H), 6.72 (d, J=3.95 Hz, 1H), 1.95-2.10 (m, 1H), 0.83-0.95 (m, 4H). MS: 416.91 (M$^+$).

3,5-Dichloro-4-({4-[(cyclopropylcarbonyl)amino]-1H-pyrrolo[3,2-c]pyridin-1-yl}carbonyl)-N-methylbenzamide (Compound No. 107) was prepared using N-(1H-pyrrolo[3,2-c]pyridin-4-yl)cyclopropane carboxamide and 2,6-dichloro-4-(methyl carbamoyl)benzoic acid.

$^1$H NMR (400 MHz, DMSO-d$_6$): δ 10.89 (s, 1H), 8.84 (d, J=4.45 Hz, 1H), 8.37 (d, J=5.65 Hz, 1H), 8.21 (d, J=5.65 Hz, 1H), 8.11 (s, 2H), 7.28 (d, J=3.95 Hz, 1H), 6.72 (d, J=3.89 Hz, 1H), 2.84 (d, J=4.52 Hz, 3H), 2.01-2.11 (m, 1H), 0.85 (d, J=6.09 Hz, 4H). MS: 430.82 (M$^+$).

3,5-Dichloro-4-({4-[(cyclopropylcarbonyl)amino]-1H-pyrrolo[3,2-c]pyridin-1-yl}carbonyl)-N-(2-hydroxyethyl)benzamide (Compound No. 91) was prepared using N-(1H-pyrrolo[3,2-c]pyridin-4-yl)cyclopropane carboxamide and 2,6-dichloro-4-[(2-hydroxyethyl)carbamoyl]benzoic acid.

$^1$H NMR (400 MHz, MeOH-d$_4$): δ 8.34 (s, 2H), 8.05 (s, 2H), 7.01 (d, J=3.95 Hz, 1H), 6.80 (d, J=3.89 Hz, 1H), 3.75 (t, J=5.65 Hz, 2H), 3.49-3.58 (m, 2H), 2.02-2.15 (m, 1H), 0.89-0.95 (m, 4H). MS (m/z): 461.00 (M$^+$).

3,5-Dichloro-4-({4-[(cyclopropylcarbonyl)amino]-1H-pyrrolo[3,2-c]pyridin-1-yl}carbonyl)-N-(2-methoxyethyl)benzamide (Compound No. 98) was prepared using N-(1H-pyrrolo[3,2-c]pyridin-4-yl)cyclopropane carboxamide and 2,6-dichloro-4-[(2-methoxyethyl)carbamoyl]benzoic acid.

$^1$H NMR (400 MHz, DMSO-d$_6$): δ 10.89 (s, 1H), 8.89-8.99 (m, 1H), 8.37 (d, J=5.65 Hz, 1H), 8.21 (d, J=5.27 Hz, 1H), 8.14 (s, 2H), 7.30 (d, J=3.89 Hz, 1H), 6.72 (d, J=3.95 Hz, 1H), 3.48 (s, 3H), 3.28 (s, 3H), 2.01-2.09 (m, 1H), 0.85-1.01 (m, 4H). MS (m/z): 474.93 (M$^+$).

3,5-Dichloro-4-({4-[(cyclopropylcarbonyl)amino]-1H-pyrrolo[3,2-c]pyridin-1-yl}carbonyl)-N-(propan-2-yl)benzamide (Compound No. 106) was prepared using N-(1H-pyrrolo[3,2-c]pyridin-4-yl)cyclopropane carboxamide and 2,6-dichloro-4-[(propan-2-yl)carbamoyl]benzoic acid.

$^1$H NMR (400 MHz, DMSO-d$_6$): δ 10.89 (s, 1H), 8.62 (d, J=7.40 Hz, 1H), 8.37 (d, J=5.58 Hz, 1H), 8.21 (d, J=5.52 Hz, 1H), 8.14 (s, 2H), 7.27 (d, J=3.89 Hz, 1H), 6.72 (d, J=3.58 Hz, 1H), 4.07-4.17 (m, 1H), 2.04-2.33 (m, 1H), 1.20 (d, J=6.59 Hz, 6H), 0.85-0.95 (m, 4H). MS (m/z): 458.84 (M$^+$).

4-{[4-(Acetylamino)-1H-pyrrolo[3,2-c]pyridin-1-yl]carbonyl}-3,5-dichloro-N-methylbenzamide (Compound No. 105) was prepared using N-(1H-pyrrolo[3,2-c]pyridin-4-yl)acetamide and 2,6-dichloro-4-(methylcarbamoyl)benzoic acid.

$^1$H NMR (400 MHz, DMSO-d$_6$): δ 10.60 (s, 1H), 8.84 (d, J=4.64 Hz, 1H), 8.36 (d, J=5.65 Hz, 1H), 8.20 (d, J=5.58 Hz, 1H), 8.11 (s, 2H), 7.30 (d, J=3.89 Hz, 1H), 6.78 (d, J=3.83 Hz, 1H), 2.84 (d, J=4.52 Hz, 3H), 2.16 (s, 3H). MS (m/z): 404.84 (M$^+$).

4-{[4-(Acetylamino)-1H-pyrrolo[3,2-c]pyridin-1-yl]carbonyl}-3,5-dichloro-N-ethylbenzamide (Compound No. 92) was prepared using N-(1H-pyrrolo[3,2-c]pyridin-4-yl)acetamide and 2,6-dichloro-4-(ethylcarbamoyl)benzoic acid.

$^1$H NMR (400 MHz, DMSO-d$_6$): δ 10.60 (s, 1H), 8.86 (t, J=5.33 Hz, 1H), 8.36 (d, J=5.65 Hz, 1H), 8.20 (d, J=5.58 Hz, 1H), 8.13 (s, 2H), 7.30 (d, J=3.89 Hz, 1H), 6.78 (d, J=3.83 Hz, 1H), 3.3 (q, 2H, merged), 2.16 (s, 3H), 1.16 (t, J=7.22 Hz, 3H). MS (m/z): 419.08 (M$^+$).

4-{[4-(Acetylamino)-1H-pyrrolo[3,2-c]pyridin-1-yl]carbonyl}-3,5-dichloro-N-(2-methoxyethyl)benzamide (Compound No. 101) was prepared using N-(1H-pyrrolo[3,2-c]pyridin-4-yl)acetamide and 2,6-dichloro-4-[(2-methoxyethyl)carbamoyl]benzoic acid.

$^1$H NMR (400 MHz, DMSO-d$_6$): δ 10.60 (s, 1H), 8.93-8.96 (m, 1H), 8.36 (d, J=5.65 Hz, 1H), 8.20 (d, J=6.15 Hz, 1H), 8.15 (s, 2H), 7.32 (d, J=3.89 Hz, 1H), 6.78 (d, J=3.89 Hz, 1H), 3.45-3.55 (m, 4H), 3.28 (s, 3H), 2.16 (s, 3H). MS (m/z): 448.88 ((M$^+$).

Methyl {1-[2,6-dichloro-4-(ethylcarbamoyl)benzoyl]-1H-pyrrolo[3,2-c]pyridin-4-yl}carbamate (Compound No. 108) was prepared using methyl 1H-pyrrolo[3,2-c]pyridin-4-ylcarbamate and 2,6-dichloro-4-[ethylcarbamoyl]benzoic acid.

$^1$H NMR (400 MHz, DMSO-d$_6$): δ 10.24 (s, 1H), 8.86 (t, J=5.43 Hz, 1H), 8.33 (d, J=5.71 Hz, 1H), 8.11-8.20 (m, 3H), 7.32 (d, J=3.95 Hz, 1H), 6.85-6.88 (m, 1H), 3.70 (s, 3H), 3.34-3.41 (m, 2H) and 1.16 (t, J=7.22 Hz, 3H). MS (m/z): 435.27 (M$^+$).

3,5-Dichloro-4-[(3-chloro-1H-pyrrolo[3,2-c]pyridin-1-yl)carbonyl]-N-ethylbenzamide (Compound No. 118) was prepared using 3-chloro-1H-pyrrolo[3,2-c]pyridine and 2,6-dichloro-4-[ethylcarbamoyl]benzoic acid.

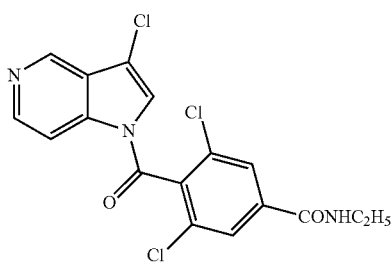

¹H NMR (400 MHz, DMSO-d₆): δ 8.97-9.00 (m, 1H), 8.84-8.89 (m, 1H), 8.71-8.75 (m, 1H), 8.38-8.43 (m, 1H), 8.13 (s, 2H), 7.94 (s, 1H), 3.36 (q, 2H, merged) and 1.05-1.26 (m, 3H). MS (m/z): 396.66 (M⁺).

3,5-Dichloro-4-[(3-chloro-1H-pyrrolo[3,2-c]pyridin-1-yl)carbonyl]benzonitrile (Compound No. 119) was prepared using 3-chloro-1H-pyrrolo[3,2-c]pyridine and 2,6-dichloro-4-cyanobenzoic acid.

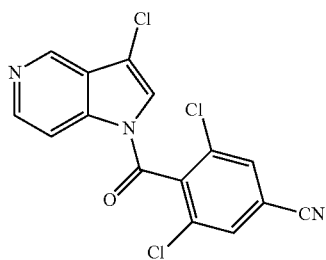 [SMILES: N#Cc1cc(Cl)c(C(=O)n2cc(Cl)c3cnccc32)c(Cl)c1]

¹H NMR (400 MHz, DMSO-d₆): δ 8.97-9.02 (m, 1H), 8.71-8.77 (m, 1H), 8.45 (s, 3H), 7.99-8.03 (m, 1H). MS (m/z): 350.59 (M⁺).

3,5-Dichloro-4-(1H-pyrrolo[3,2-c]pyridin-1-ylcarbonyl)benzamide was prepared using 1H-pyrrolo[3,2-c]pyridine and 2,6-dichloro-4-carbamoyl benzoic acid.

¹H NMR (400 MHz, MeOH-d₄): δ 8.93 (d, J=0.94 Hz, 1H), 8.54-8.58 (m, 1H), 8.46-8.52 (m, 1H), 8.09 (s, 2H), 7.23 (d, J=3.83 Hz, 1H), 6.90 (dd, J=3.83, 0.63 Hz, 1H). MS: 334.07 (M⁺).

3,5-Dichloro-N-cyclopropyl-4-(1H-pyrrolo[3,2-c]pyridin-1-ylcarbonyl)benzamide was prepared using 1H-pyrrolo[3,2-c]pyridine and 2,6-dichloro-4-(cycloproylcarbamoyl) benzoic acid.

¹H NMR (400 MHz, DMSO-d₆): δ 9.00 (d, J=1.00 Hz, 1H), 8.81 (d, J=4.20 Hz, 1H), 8.60 (d, J=5.58 Hz, 2H), 8.31-8.37 (m, 1H), 8.10 (s, 2H), 7.40 (d, J=3.83 Hz, 1H), 6.94 (dd, J=3.86, 0.72 Hz, 2H), 2.86-2.94 (m, 1H), 0.72-0.78 (m, 2H), 0.59-0.64 (m, 2H). MS: 374.21 (M⁺)

Example 18

Synthesis of N-{1-[2,6-dichloro-4-(hydroxymethyl)benzoyl]-1H-pyrrolo[3,2-c]pyridin-4-yl}cyclopropanecarboxamide (Compound No. 96)

To a stirred solution of 2,6-dichloro-4-(hydroxymethyl) benzoic acid (219 mg, 0.99 mmol), 1-hydroxy-7-azabenzotriazole (202 mg, 1.48 mmol), dimethylaminopyridine (60 mg, 0.49 mmol) and 2-(1H-7-azabenzotriazol-1-yl)-1,1,3,3-tetramethyl uronium hexafluorophosphate methanaminium (567 mg, 1.48 mmol) in N,N-dimethylaniline, N-(1H-pyrrolo[3,2-c]pyridin-4-yl)cyclopropanecarboxamide (200 mg, 0.99 mmol) was added followed by N,N-diisopropylethylamine (0.25 ml, 1.48 mmol). The reaction mixture was stirred at room temperature for 15 hours. The contents were diluted with water and extracted with ethyl acetate. The combined organic layer was washed with brine, dried over anhydrous sodium sulfate, filtered and concentrated. The crude compound was purified by silica gel column chromatography using methanol in dichloromethane (3%) as eluent to yield N-{1-[2,6-dichloro-4-(hydroxymethyl)benzoyl]-1H-pyrrolo[3,2-c]pyridin-4-yl}cyclopropanecarboxamide (45 mg, 11°/o).

¹H NMR (400 MHz, DMSO-d₆): δ 8.36 (d, J=5.58 Hz, 1H), 8.20 (d, J=5.65 Hz, 1H), 7.63 (s, 2H), 7.16 (d, J=3.89 Hz, 1H), 6.71 (d, J=3.95 Hz, 1H), 5.65 (t, J=5.77 Hz, 1H), 4.62 (d, J=5.84 Hz, 2H), 2.02-2.08 (m, 1H), 0.85 (d, J=6.21 Hz, 4H). MS (m/z): 404.07 (M⁺).

The following compounds were prepared in a similar manner using appropriately substituted starting materials.

[2,6-Dichloro-4-(hydroxymethyl)phenyl](1H-pyrrolo[3,2-c]pyridin-1-yl)methanone (Compound No. 90) was synthesized from N-(1H-pyrrolo[3,2-c]pyridine and 2,6-dichloro-4-(hydroxymethyl)benzoic acid.

¹H NMR (400 MHz, DMSO-d₆): δ 9.00 (s, 1H), 8.59 (d, J=5.62 Hz, 1H), 8.34 (d, J=5.68 Hz, 1H), 7.63 (s, 2H), 7.30 (d, J=3.79 Hz, 1H), 6.93 (d, J=3.79 Hz, 1H), 5.65 (t, J=5.78 Hz, 1H), 4.63 (d, J=5.75 Hz, 2H). MS (m/z): 321.18 (M⁺).

N-{1-[2,6-Dichloro-4-(hydroxymethyl)benzoyl]-1H-pyrrolo[3,2-c]pyridin-4-yl}acetamide (Compound No. 97) was synthesized from N-(1H-pyrrolo[3,2-c]pyridin-4-yl)acetamide and 2,6-dichloro-4-(hydroxymethyl)benzoic acid ¹H NMR (400 MHz, DMSO-d₆): δ 10.59 (s, 1H), 8.35 (d, J=5.65 Hz, 1H), 8.20 (d, J=5.65 Hz, 1H), 7.63 (s, 2H), 7.18 (d, J=3.89 Hz, 1H), 6.77 (d, J=3.64 Hz, 1H), 5.65 (t, J=5.80 Hz, 1H), 4.62 (d, J=5.84 Hz, 2H), 2.16 (s, 3H). MS (m/z): 378.04 (M⁺).

Example 19

Synthesis of [2,6-dichloro-4-(pyridin-3-yl)phenyl](1H-pyrrolo[3,2-c]pyridin-1-yl)methanone

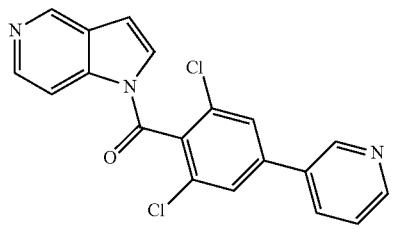 [SMILES: O=C(c1c(Cl)cc(-c2cccnc2)cc1Cl)n1ccc2cnccc21]

A mixture of (4-bromo-2,6-dichlorophenyl)(1H-pyrrolo[3,2-c]pyridin-1-yl)methanone (0.05 g, 0.135 mmol), [1,1-bis(diphenylphosphino)ferrocene]dichloropalladium(II) (0.011 g, 0.0135 mmol), potassium carbonate (0.055 g, 0.40 mmol), pyridine-3-boronic acid (1.1 equiv) and water (0.5 mL) in acetonitrile (2.5 mL) was heated in a sealed vial under microwave irradiation at 110° C. for 25 minutes. Acetonitrile was removed under vacuum and the residue was diluted with water (25 mL) and extracted with ethyl acetate (2×25 mL). The combined organic layer was washed with water, dried over anhydrous sodium sulphate and concentrated to give crude product which was purified by silica gel column chromatography using ethyl acetate and hexane as eluent to yield [2,6-dichloro-4-(pyridin-3-yl)phenyl](1H-pyrrolo[3,2-c]pyridin-1-yl)methanone.

¹H NMR (400 MHz, MeOH-d₄): δ 8.88-8.96 (m, 2H), 8.65 (dd, J=4.93, 1.47 Hz, 1H), 8.53-8.58 (m, 1H), 8.51 (d, J=5.71 Hz, 1H), 8.21-8.26 (m, 1H), 7.99 (s, 2H), 7.61 (dd, J=7.97, 4.89 Hz, 1H), 7.30 (d, J=3.76 Hz, 1H), 6.91 (d, J=3.76 Hz, 1H). MS (m/z): 368.02 (M⁺).

The following compounds were prepared in an analogous manner using (4-bromo-2,6-dichlorophenyl)(1H-pyrrolo[3,2-c]pyridin-1-yl)methanone and appropriate boronic acid or bispinacolatoboranes as starting materials.

N-{1-[2,6-Dichloro-4-(3,5-dimethyl-1,2-oxazol-4-yl)benzoyl]-1H-pyrrolo[3,2-c]pyridin-4-yl}cyclopropanecarboxamide (Compound No. 87) was synthesized in an analogous manner from N-[1-(4-bromo-2,6-dichlorobenzoyl)-1H-pyrrolo[3,2-c]pyridin-4-yl]-N-(cyclopropylcarbonyl)cyclopropanecarboxamide and (3,5-dimethyl-1,2-oxazol-4-yl)boronic acid.

¹H NMR (400 MHz, MeOH-d₄): δ 8.35 (s, 2H), 7.63 (s, 2H), 7.18-7.22 (m, 1H), 6.79 (d, J=3.89 Hz, 1H), 2.50 (s, 3H), 2.34 (s, 3H), 1.93-2.00 (m, 1H), 0.99-1.06 (m, 2H), 0.91-0.97 (m, 2H). MS (m/z): 468.92 (M⁺).

N-{1-[2,6-Dichloro-4-(3,5-dimethyl-1H-pyrazol-4-yl)benzoyl]-1H-pyrrolo[3,2-c]pyridin-4-yl}cyclopropanecarboxamide (Compound No. 88) was synthesized in an analogous manner from N-[1-(4-bromo-2,6-dichlorobenzoyl)-1H-pyrrolo[3,2-c]pyridin-4-yl]-N-(cyclopropylcarbonyl)cyclopropanecarboxamide and [1-(-tert-butoxycarbonyl)-3,5-dimethyl-1H-pyrazol-4-yl]boronic acid.

¹H NMR (400 MHz, MeOH-d₄): δ 8.35 (s, 2H), 7.53 (s, 2H), 7.18 (d, J=3.89 Hz, 1H), 6.79 (d, J=3.76 Hz, 1H), 2.19 (s, 6H), 1.97 (tt, J=8.06, 4.24 Hz, 1H), 1.03 (t, J=3.61 Hz, 2H), 0.91-0.97 (m, 2H). MS (m/z): 467.98 (M⁺).

N-{1-[2,6-Dichloro-4-(pyrimidin-5-yl)benzoyl]-1H-pyrrolo[3,2-c]pyridin-4-yl}cyclopropanecarboxamide (Compound No. 89) was synthesized in an analogous manner from N-[1-(4-bromo-2,6-dichlorobenzoyl)-1H-pyrrolo[3,2-c]pyridin-4-yl]-N-(cyclopropylcarbonyl)cyclopropanecarboxamide and pyrimidin-5-yl-boronic acid.

¹H NMR (400 MHz, MeOH-d₄): δ 9.25 (s, 1H), 9.20 (s, 2H), 8.35 (s, 2H), 8.05 (s, 2H), 7.20 (d, J=3.89 Hz, 1H), 6.79 (d, J=3.89 Hz, 1H), 1.92-2.01 (m, 1H), 0.99-1.06 (m, 2H), 0.91-0.97 (m, 2H). MS (m/z): 451.99 (M⁺).

[2,6-Dichloro-4-(3,5-dimethyl-1,2-oxazol-4-yl)phenyl](1H-pyrrolo[3,2-c]pyridin-1-yl)methanone ¹H NMR (400 MHz, methanol-d₄): δ 8.93 (s, 1H), 8.48-8.57 (m, 2H), 7.64 (s, 2H), 7.31 (d, J=3.89 Hz, 1H), 6.91 (d, J=3.89 Hz, 1H), 2.51 (s, 3H), 2.34 (s, 3H). MS: 386.15 (M⁺).

[2,6-Dichloro-4-(pyrimidin-5-yl)phenyl](1H-pyrrolo[3,2-c]pyridin-1-yl)methanone

¹H NMR (400 MHz, DMSO-d₆): δ 9.30-9.33 (m, 3H), 9.01 (d, J=1.00 Hz, 1H), 8.61 (d, J=5.65 Hz, 1H), 8.35-8.39 (m, 1H), 8.30 (s, 2H), 7.45 (d, J=3.83 Hz, 1H), 6.97 (dd, J=0.69, 3.83 Hz, 1H). MS: 369.21 (M⁺).

Example 20

Synthesis of 1-[3,5-dichloro-4-(1H-pyrrolo[3,2-c]pyridin-1-ylcarbonyl)phenyl]-3-ethylurea (Compound No. 78)

Step a: Synthesis of (4-amino-2,6-dichlorophenyl)(1H-pyrrolo[3,2-c]pyridin-1-yl)methanone A mixture of (4-bromo-2,6-dichlorophenyl)(1H-pyrrolo[3,2-c]pyridin-1-yl)methanone (200 mg, 0.54 mmol), sodium azide (105 mg, 1.62 mmol), copper (II) iodide (30 mg, 0.16) and N,N'-dimethylethane-1,2-diamine (26 mg, 0.32 moles) in ethanol (2 mL) and water (0.5 mL) was heated in a sealed vial at 90° C. for 16 hours. The reaction mixture was concentrated to remove ethanol and the residue was diluted with water (50 mL) and extracted with ethyl acetate (2×50 mL). The combined organic portion was dried over anhydrous sodium sulphate and concentrated under vacuum to give the crude product which was purified by silica gel column chromatography using ethyl acetate and hexane as eluent to yield (4-amino-2,6-dichlorophenyl)(1H-pyrrolo[3,2-c]pyridin-1-yl)methanone (75 mg, 45%).

(4-Amino-2,6-dichlorophenyl){4-[(2,4,4-trimethylpentan-2-yl)amino]-1H-pyrrolo[3,2-c]pyridin-1-yl}methanone was synthesized from (4-bromo-2,6-dichlorophenyl){4-[(2,4,4-trimethylpentan-2-yl)amino]-1H-pyrrolo[3,2-c]pyridin-1-yl}methanone following an analogous procedure.

Step b: Synthesis of 1-[3,5-dichloro-4-(1H-pyrrolo[3,2-c]pyridin-1-ylcarbonyl)phenyl]-3-ethylurea A mixture of (4-amino-2,6-dichlorophenyl)(1H-pyrrolo[3,2-c]pyridin-1-yl)methanone (100 mg, 0.33 mmol, Step a) in anhydrous tetrahydrofuran (5 mL) was treated with phenyl chloroformate (74 mg, 0.49 mmol), and pyridine (38 mg, 0.49 mmol) and stirred at room temperature for 1 hour. Tetrahydrofuran was removed under vacuum; the residue was diluted with water (25 mL) followed by partitioning with ethyl acetate (2×25 mL). The combined organic layer was washed with water (30 mL), dried over anhydrous sodium sulphate and stripped of solvent to give the crude carbamate which was dissolved in ethanol (5 mL) treated with ethyl amine (1.65 mL, 2M solution in tetrahydrofuran, 3.3 mmol) and heated at 80° C. for 4 hours. Ethanol was removed under vacuum and residue was diluted with water (25 mL) and extracted with ethyl acetate (2×25 mL). The combined organic layer was washed with water (30 mL), dried over anhydrous sodium sulphate and concentrated to give the crude product which was purified by silica gel column chromatography using ethyl acetate and hexane gradient as an eluent to yield pure 1-[3,5-dichloro-4-(1H-pyrrolo[3,2-c]pyridin-1-ylcarbonyl)phenyl]-3-ethylurea (25 mg).

¹H NMR (400 MHz, MeOH-d₄): δ 8.88 (s, 1H), 8.43-8.52 (m, 2H), 7.64 (s, 2H), 7.17 (d, J=3.83 Hz, 1H), 6.84 (d, J=3.83 Hz, 1H), 3.23 (q, J=7.24 Hz, 2H), 1.15 (t, J=7.22 Hz, 3H). MS (m/z): 377.15 (M⁺)

The following compounds were prepared by treating 4-amino-2,6-dichlorophenyl)(1H-pyrrolo[3,2-c]pyridin-1-yl)methanone with appropriate amines in an analogous manner.

1-[3,5-Dichloro-4-(1H-pyrrolo[3,2-c]pyridin-1-ylcarbonyl)phenyl]-3-(2-hydroxyethyl)urea (Compound No. 80)

¹H NMR (400 MHz, MeOH-d4): δ 8.90 (s, 1H), 8.45-8.54 (m, 2H), 7.67 (s, 2H), 7.20 (d, J=3.60 Hz, 1H), 6.86 (d, J=3.22 Hz, 1H), 3.65 (t, J=5.31 Hz, 2H), 3.28-3.36 (m, 2H). MS (m/z): 393.04 (M⁺).

1-[3,5-Dichloro-4-(1H-pyrrolo[3,2-c]pyridin-1-ylcarbonyl)phenyl]-3-(2-methoxyethyl)urea (Compound No. 104)

¹H NMR (400 MHz, MeOH-d₄): δ 8.90 (s, 1H), 8.45-8.55 (m, 2H), 7.66 (s, 2H), 7.20 (d, J=3.83 Hz, 1H), 6.86 (d, J=3.76 Hz, 1H), 3.47-3.53 (m, 2H), 3.36-3.43 (m, 5H). MS (m/z): 406.98 (M⁺).

3-[3,5-Dichloro-4-(1H-pyrrolo[3,2-c]pyridin-1-yl-carbonyl)phenyl]-1,1-dimethylurea (Compound No. 81)

$^1$H NMR (400 MHz, DMSO-d$_6$): δ 8.97 (d, J=19.26 Hz, 2H), 8.58 (d, J=5.56 Hz, 1H), 8.33 (d, J=5.68 Hz, 1H), 7.89 (s, 2H), 7.35 (d, J=3.79 Hz, 1H), 6.92 (d, J=3.60 Hz, 1H), 2.97 (s, 6H). MS (m/z): 377.05 (M$^+$).

Example 21

Synthesis of 2-cyano-N-[3,5-dichloro-4-(1H-pyrrolo[3,2-c]pyridin-1-ylcarbonyl)phenyl]acetamide (Compound No. 82)

To a solution of (4-amino-2,6-dichlorophenyl)(1H-pyrrolo[3,2-c]pyridin-1-yl)methanone (60 mg, 0.19 mmol) in dimethylformamide (1 mL) was added cyanoacetic acid (25 mg, 0.29 mmol), hydroxybenzotriazole (39.73 mg, 0.29 mmol), 1-ethyl-3-(3-dimethylaminopropyl)carbodiimide (56.17 mg, 0.29 mmol) and N,N-diisopropylethyl amine (0.06 mL, 0.31 mmol) in the same order. The reaction mixture was stirred at room temperature for 20 hours. The reaction mixture was poured onto water (10 mL) and extracted with ethyl acetate (2×50 mL). The combined organic layer was washed with saturated aqueous solution of sodium bicarbonate, dried over anhydrous sodium sulphate, filtered and the solvent was removed under rotary evaporator. The product was purified by silica gel column chromatography using dichloromethane and methanol (1.5-2%) as eluant to yield 2-cyano-N-[3,5-dichloro-4-(1H-pyrrolo[3,2-c]pyridin-1-ylcarbonyl)phenyl]acetamide (8.7 mg, 12%).

$^1$H NMR (400 MHz, DMSO-d$_6$): δ 10.92 (s, 1H), 8.94-9.01 (m, 1H), 8.56-8.61 (m, 1H), 8.31-8.35 (m, 1H), 7.83 (s, 2H), 7.40 (br. s., 1H), 6.83-6.93 (m, 1H), 4.04 (s, 2H). MS (m/z): 373.20 (M$^+$).

The following compounds were prepared in a similar manner from (4-amino-2,6-dichlorophenyl)(1H-pyrrolo[3,2-c]pyridin-1-yl)methanone and appropriate starting materials.

N-[3,5-Dichloro-4-(1H-pyrrolo[3,2-c]pyridin-1-ylcarbonyl)phenyl]-2-fluoroacetamide (Compound No. 94) was similarly prepared using fluoroacetic acid instead of cyanoacetic acid.

$^1$H NMR (400 MHz, DMSO-d$_6$): δ 10.71 (s, 1H), 8.99 (d, J=0.75 Hz, 1H), 8.59 (d, J=5.58 Hz, 1H), 8.34 (s, 1H), 8.02 (s, 2H), 7.38-7.42 (m, 1H), 6.90-6.95 (m, 1H), 5.15 (s, 1H), 5.04 (s, 1H). MS (m/z): 366.18 (M$^+$).

Example 22

Synthesis of N-[3,5-dichloro-4-(1H-pyrrolo[3,2-c]pyridin-1-ylcarbonyl)phenyl]propanamide

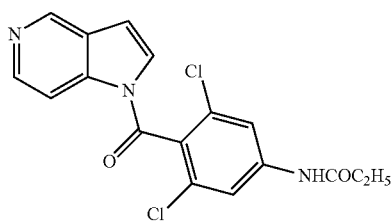

To a stirred solution of (4-amino-2,6-dichlorophenyl)(1H-pyrrolo[3,2-c]pyridin-1-yl)methanone (45 mg, 0.15 mmol) and triethylamine (0.04 mL, 0.29 mmol) in tetrahydrofuran (1 mL), propanoyl chloride (0.014 mL, 0.16 mmol) was added drop wise at 0° C. The resulting reaction mixture was stirred at room temperature for 30 minutes and concentrated under vacuum. The residue was diluted with water, extracted with ethyl acetate (2×20 mL). The combined organic portion was washed with brine, dried over anhydrous sodium sulphate and concentrated on rotary evaporator. The residue was taken up in methanol (2 mL), potassium carbonate (25 mg) was added and stirred at room temperature for 10 minutes, concentrated on a rotary evaporator, diluted with water (10 mL) and extracted with ethyl acetate. The combined organic layer was washed with saturated aqueous sodium bicarbonate solution, water and brine, dried over anhydrous sodium sulphate and concentrated on rotary evaporator. N-[3,5-dichloro-4-(1H-pyrrolo[3,2-c]pyridin-1-ylcarbonyl)phenyl]propanamide (7.4 mg, 14%) was isolated by silica gel column chromatography using dichloromethane and methanol gradient as eluent.

$^1$H NMR (400 MHz, DMSO-d$_6$): δ 10.50 (br. s., 1H), 8.97-9.01 (m, 1H), 8.56-8.61 (m, 1H), 8.31-8.36 (m, 1H), 7.88-7.92 (m, 2H), 7.36-7.40 (m, 1H), 6.90-6.94 (m, 1H), 2.40-2.42 (m, 2H), 1.1.08-1.17 (m, 3H). MS (m/z): 362.21 (M$^+$).

Methyl[3,5-dichloro-4-(1H-pyrrolo[3,2-c]pyridin-1-ylcarbonyl)phenyl]carbamate (Compound No. 79) was prepared by treating (4-amino-2,6-dichlorophenyl)(1H-pyrrolo[3,2-c]pyridin-1-yl)methanone with methylchloroformate following a procedure similar to the one used for methyl[1-(2,6-dichlorobenzoyl)-1H-pyrrolo[3,2-c]pyridin-4-yl]carbamate (Compound No. 74).

$^1$H NMR (400 MHz, MeOH-d$_4$): δ 7.43 (br. s., 1H), 6.97-7.08 (m, 2H), 6.25 (s, 2H), 5.70-5.75 (m, 1H), 5.39 (br. s., 1H), 2.32 (s, 3H). MS (m/z): 364.02 (M$^+$).

Example 23

Synthesis of ethyl(2E)-3-[3,5-dichloro-4-(1H-pyrrolo[3,2-c]pyridin-1-ylcarbonyl)phenyl]prop-2-enoate A solution of (4-bromo-2,6-dichlorophenyl)(1H-pyrrolo[3,2-c]pyridin-1-yl)methanone (100 mg, 0.27 mmol) and ethyl acrylate (3.06 mL, 30.58 mmol) in dimethylformamide (3 mL) was stirred at room temperature. Triethylamine (0.15 mL, 1.08 mmol) was added followed by triphenylphosphine (42.6 mg, 0.16 mmol) and palladium acetate (18.16 mg, 0.008 mmol). The reaction mixture was purged with argon and heated under reflux for about 20 hours. The reaction mixture was cooled to room temperature and the residue was poured into water and extracted with ethyl acetate. The combined organic layer was dried over anhydrous sodium sulfate, filtered and the solvent was removed under rotary evaporator. Ethyl(2E)-3-[3,5-dichloro-4-(1H-pyrrolo[3,2-c]pyridin-1-ylcarbonyl)phenyl]prop-2-enoate (64.8 mg, 61.59%) was isolated by silica gel column chromatography using ethyl acetate in hexane (15-17%) as eluant.

$^1$H NMR (400 MHz, MeOH-d$_4$): δ 8.92-8.94 (m, 1H), 8.53-8.56 (m, 1H), 8.50 (br. s., 1H), 7.91 (s, 2H), 7.69 (d, J=17.00 Hz, 1H), 7.21-7.25 (m, 1H), 6.89 (br. s., 1H), 6.77 (d, J=16.12 Hz, 1H), 4.23-4.33 (m, 2H), 1.31-1.37 (m, 3H). MS (m/z): 389.24 (M$^+$).

The following compounds were prepared from (4-bromo-2,6-dichlorophenyl)(1H-pyrrolo[3,2-c]pyridin-1-yl)methanone following a similar procedure while using appropriate starting materials.

(2E)-3-[3,5-Dichloro-4-(1H-pyrrolo[3,2-c]pyridin-1-ylcarbonyl)phenyl]prop-2-enenitrile (Compound No. 84)

$^1$H NMR (400 MHz, DMSO-d$_6$): δ 9.00 (d, J=0.88 Hz, 1H), 8.58-8.61 (m, 1H), 8.32-8.35 (m, 1H), 8.08 (s, 2H), 7.71-7.77 (m, 1H), 7.44 (d, J=4 Hz, 1H), 6.94 (d, J=3.83 Hz, 1H), 6.84 (d, J=16.69 Hz, 1H). MS (m/z): 342.19 (M$^+$).

(2E)-3-[3,5-Dichloro-4-(1H-pyrrolo[3,2-c]pyridin-1-ylcarbonyl)phenyl]prop-2-enamide (Compound No. 83)

$^1$H NMR (400 MHz, DMSO-d$_6$): δ 9.00 (d, J=0.94 Hz, 1H), 8.60 (d, J=5.65 Hz, 1H), 8.35 (s, 1H), 7.94 (s, 2H), 7.57-7.60 (m, 1H), 7.47 (d, J=15.87 Hz, 1H), 7.43 (d, J=3.83 Hz, 1H), 7.32-7.34 (m, 1H), 6.94 (dd, J=0.66, 3.80 Hz, 1H), 6.86 (d, J=15.87 Hz, 1H). MS (m/z): 360.20 (M$^+$).

Example 24

Synthesis of N-(cyclopropylcarbonyl)-N-[1-(2,6-dichloro-4-cyanobenzoyl)-1H-pyrrolo[3,2-c]pyridin-4-yl]cyclopropanecarboxamide (Compound No. 85) and N-[1-(2,6-dichloro-4-cyanobenzoyl)-1H-pyrrolo[3,2-c]pyridin-4-yl]cyclopropanecarboxamide (Compound No. 86)

Step a: N-[1-(4-bromo-2,6-dichlorobenzoyl)-1H-pyrrolo[3,2-c]pyridin-4-yl]-N-(cyclopropylcarbonyl)cyclopropanecarboxamide A solution of (4-amino-1H-pyrrolo[3,2-c]pyridin-1-yl)(4-bromo-2,6-dichlorophenyl)methanone (40 mg, 0.113 mmol) and triethylamine (0.23 mL, 0.206 mmol) in anhydrous tetrahydrofuran was treated dropwise with cyclopropane carbonyl chloride (0.01 mL, 0.11 mmol) under ice-cooled condition and stirred at room temperature for 1 hour. Ethyl acetate was added and washed with saturated aqueous sodium hydrogen carbonate solution, dried over anhydrous sodium sulphate and concentrated to afford N-[1-(4-bromo-2,6-dichlorobenzoyl)-1H-pyrrolo[3,2-c]pyridin-4-yl]-N-(cyclopropylcarbonyl)cyclopropanecarboxamide.

Step b: N-(cyclopropylcarbonyl)-N-[1-(2,6-dichloro-4-cyanobenzoyl)-1H-pyrrolo[3,2-c]pyridin-4-yl]cyclopropanecarboxamide A mixture of N-[1-(4-bromo-2,6-dichlorobenzoyl)-1H-pyrrolo[3,2-c]pyridin-4-yl]-N-(cyclopropylcarbonyl)cyclopropanecarboxamide (40 mg, 0.11 mmol), dppf (10 mg, 0.018 mmol), copper cyanide (41 mg, 0.45 mmol) and cesium carbonate (110 mg, 0.33 mmol) in 1,4-dioxane (2 mL) was heated in a sealed vial at 90° C. for 4 hours. Ethyl acetate was added and washed with saturated aqueous sodium hydrogen carbonate solution, dried over anhydrous sodium sulphate and concentrated to get the crude residue which was purified by silica gel column chromatography to afford N-(cyclopropylcarbonyl)-N-[1-(2,6-dichloro-4-cyanobenzoyl)-1H-pyrrolo[3,2-c]pyridin-4-yl]cyclopropanecarboxamide and N-[1-(2,6-dichloro-4-cyanobenzoyl)-1H-pyrrolo[3,2-c]pyridin-4-yl]cyclopropanecarboxamide.

N-(Cyclopropylcarbonyl)-N-[1-(2,6-dichloro-4-cyanobenzoyl)-1H-pyrrolo[3,2-c]pyridin-4-yl]cyclopropanecarboxamide (Compound No. 85)

$^1$H NMR (400 MHz, DMSO-d$_6$): δ 8.58 (d, J=5.62 Hz, 1H), 8.39-8.48 (m, 3H), 7.65 (d, J=3.98 Hz, 1H), 6.79 (dd, J=3.92, 0.69 Hz, 1H), 1.84-2.00 (m, 2H), 0.94-1.00 (m, 4H), 0.90 (dt, J=7.85, 3.24 Hz, 4H). MS (m/z): 467.04 (M$^+$).

N-[1-(2,6-Dichloro-4-cyanobenzoyl)-1H-pyrrolo[3,2-c]pyridin-4-yl]cyclopropane carboxamide (Compound No. 86)

$^1$H NMR (400 MHz, DMSO-d$_6$): δ 10.92 (s, 1H), 8.44 (s, 2H), 8.37 (d, J=5.68 Hz, 1H), 8.20 (d, J=5.68 Hz, 1H), 7.39 (d, J=3.92 Hz, 1H), 6.75 (d, J=3.85 Hz, 1H), 2.01-2.09 (m, 1H), 0.84-0.95 (m, 4H). MS (m/z): 399.04 (M$^+$).

Example 25

Synthesis of N-(1-{2,6-dichloro-4-[(cyclopropylcarbonyl)amino]benzoyl}-1H-pyrrolo[3,2-c]pyridin-4-yl)cyclopropanecarboxamide (Compound No. 109)

This compound was synthesized from N-{4-[(4-amino-1H-pyrrolo[3,2-c]pyridin-1-yl)carbonyl]-3,5-dichlorophenyl}cyclopropanecarboxamide and cyclopropane carbonyl chloride following a procedure similar to one described for N-[1-(2,6-dichlorobenzoyl)-1H-pyrrolo[3,2-c]pyridin-4-yl]acetamide.

$^1$H NMR (400 MHz, DMSO-d$_6$): δ 8.32-8.36 (m, 1H), 8.19-8.24 (m, 1H), 7.89 (s, 2H), 7.25-7.29 (d, 1H), 6.85-6.95 (d, 1H) 2.03-2.09 (m, 1H), 1.78-1.83 (m, 1H), 0.82-0.96 (m, 8H). MS (m/z): 457.32 (M$^+$).

The following compounds were prepared following a similar procedure.

N-{1-[4-(Acetylamino)-2,6-dichlorobenzoyl]-1H-pyrrolo[3,2-c]pyridin-4-yl}cyclopropanecarboxamide (Compound No. 110) was synthesized using N-{4-[(4-amino-1H-pyrrolo[3,2-c]pyridin-1-yl)carbonyl]-3,5-dichlorophenyl}acetamide and cyclopropane carbonyl chloride.

$^1$H NMR (400 MHz, DMSO-d$_6$): δ 10.86 (s, 1H), 10.53-10.58 (m, 1H), 8.31-8.37 (m, 1H), 8.19 (d, J=5.65 Hz, 1H), 7.87 (s, 2H), 7.23 (d, J=3.89 Hz, 1H), 6.70 (d, J=3.83 Hz, 1H), 2.13 (s, 3H), 2.02-2.07 (m, 1H), 0.86 (s, 4H). MS (m/z): 431.28 (M$^+$).

N-(1-{2,6-Dichloro-4-[(ethylcarbamoyl)amino]benzoyl}-1H-pyrrolo[3,2-c]pyridin-4-yl)cyclopropanecarboxamide (Compound No. 103) was prepared following an analogous procedure starting from 1-{4-[(4-amino-1H-pyrrolo[3,2-c]pyridin-1-yl)carbonyl]-3,5-dichlorophenyl}-3-(ethyl)urea and cyclopropane carbonyl chloride.

$^1$H NMR (400 MHz, MeOH-d$_4$): δ 8.32 (s, 2H), 7.65 (s, 2H), 7.10 (d, J=3.89 Hz, 1H), 6.75 (d, J=3.83 Hz, 1H), 3.24 (q, J=7.24 Hz, 2H), 1.93-1.99 (m, 1H), 1.15-1.19 (m, 3H), 1.00-1.04 (m, 2H), 0.91-0.96 (m, 2H). MS (m/z): 459.96 (M$^+$).

N-[1-(2,6-Dichloro-4-{[(2-methoxyethyl)carbamoyl]amino}benzoyl)-1H-pyrrolo[3,2-c]pyridin-4-yl]cyclopropanecarboxamide (Compound No. 111) was prepared following an analogous procedure starting from 1-{4-[(4-amino-1H-pyrrolo[3,2-c]pyridin-1-yl)carbonyl]-3,5-dichlorophenyl}-3-(2-methoxyethyl)urea and cyclopropane carbonyl chloride.

$^1$H NMR (400 MHz, MeOH-d$_4$): δ 8.31-8.33 (m, 2H), 7.60-7.68 (m, 2H), 7.05-7.15 (m, 1H), 6.92 (s, 1H), 3.49 (br. s., 2H), 3.34-3.43 (m, 6H), 1.24-1.32 (m, 1H), 0.96-1.06 (m, 4H). MS (m/z): 489.81 (M$^+$).

N-[1-(2,6-Dichloro-4-{[(2-hydroxyethyl)(methyl)carbamoyl]amino}benzoyl)-1H-pyrrolo[3,2-c]pyridin-4-yl]cyclopropanecarboxamide (Compound No. 112) was prepared in analogous manner from 3-{4-[(4-amino-1H-pyrrolo[3,2-c]pyridin-1-yl)carbonyl]-3,5-dichlorophenyl}-1-(2-hydroxyethyl)-1-methylurea.

$^1$H NMR (400 MHz, MeOH-d$_4$): δ 8.32 (s, 2H), 7.68 (s, 2H), 7.10 (d, J=3.83 Hz, 1H), 6.75 (d, J=3.89 Hz, 1H), 3.74-3.80 (m, 2H), 3.48-3.56 (m, 2H), 3.08 (s, 3H cyclopropane carbonyl chloride), 1.93-2.01 (m, 1H), 0.84-0.98 (m, 4H). MS (m/z): 490.35 (M$^+$).

N-(1-{2,6-Dichloro-4-[(cyclopropylcarbamoyl)amino]benzoyl}-1H-pyrrolo[3,2-c]pyridin-4-yl)cyclopropanecarboxamide (Compound No. 113) was prepared from 1-{4-[(4-amino-1H-pyrrolo[3,2-c]pyridin-1-yl)carbonyl]-3,5-dichlorophenyl}-3-cyclopropylurea and cyclopropane carbonyl chloride.

$^1$H NMR (400 MHz, MeOH-d$_4$): δ 8.32 (s, 2H), 7.69 (s, 2H), 7.10 (d, J=3.83 Hz, 1H), 6.73-6.78 (m, 1H), 2.57-2.65 (m, 1H), 1.91-2.00 (m, 1H), 0.84-0.99 (m, 4H), 0.73-0.81 (m, 2H), 0.50-0.57 (m, 2H). MS (m/z): 472.33 (M$^+$).

N-(1-{2,6-Dichloro-4-[(cyclopropylcarbamoyl)amino]benzoyl}-1H-pyrrolo[3,2-c]pyridin-4-yl)acetamide (Compound No. 114) was prepared from 1-{4-[(4-amino-1H-pyrrolo[3,2-c]pyridin-1-yl)carbonyl]-3,5-dichlorophenyl}-3-cyclopropylurea and acetyl chloride following a similar procedure.

$^1$H NMR (400 MHz, MeOH-d$_4$): δ 8.29-8.36 (m, 6H), 7.69 (s, 5H), 7.11 (d, J=3.95 Hz, 3H), 6.79 (d, J=3.89 Hz, 3H), 2.57-2.64 (m, 1H), 2.22-2.27 (m, 3H), 0.73-0.80 (m, 2H), 0.50-0.57 (m, 2H). MS (m/z): 446.30 (M$^+$).

N-[1-(2,6-Dichloro-4-{[(2-hydroxyethyl)carbamoyl]amino}benzoyl)-1H-pyrrolo[3,2-c]pyridin-4-yl]cyclopropanecarboxamide (Compound No. 115) was prepared from 1-{4-[(4-amino-1H-pyrrolo[3,2-c]pyridin-1-yl)carbonyl]-3,5-dichlorophenyl}-3-(2-hydroxyethyl)urea and cyclopropane carbonyl chloride following a similar procedure.

$^1$H NMR (400 MHz, MeOH-d$_4$): δ 8.28-8.35 (m, 2H), 7.63-7.67 (m, 2H), 7.06-7.12 (m, 1H), 6.73-6.78 (m, 1H), 3.61-3.68 (m, 2H), 3.32-3.38 (m, 2H), 1.91-2.00 (m, 1H), 0.99-1.06 (m, 2H), 0.89-0.96 (m, 2H). MS (m/z): 476.32 (M$^+$).

N-[1-(2,6-Dichloro-4-{[(2-hydroxyethyl)carbamoyl]amino}benzoyl)-1H-pyrrolo[3,2-c]pyridin-4-yl]acetamide (Compound No. 116) was prepared from 1-{4-[(4-amino-1H-pyrrolo[3,2-c]pyridin-1-yl)carbonyl]-3,5-dichlorophenyl}-3-(2-hydroxyethyl)urea and acetyl chloride following a similar procedure.

$^1$H NMR (400 MHz, MeOH-d$_4$): δ 8.32 (s, 2H), 7.66 (s, 2H), 7.09-7.13 (m, 1H), 6.79 (d, J=3.95 Hz, 1H), 3.61-3.68 (m, 2H), 3.32-3.37 (m, 2H), 2.22-2.27 (m, 3H). MS (m/z): 450.28 (M$^+$).

N-(1-{2,6-Dichloro-4-[(ethylcarbamoyl)amino]benzoyl}-1H-pyrrolo[3,2-c]pyridin-4-yl)acetamide (Compound No. 117) was prepared from 1-{4-[(4-amino-1H-pyrrolo[3,2-c]pyridin-1-yl)carbonyl]-3,5-dichlorophenyl}-3-ethylurea following a similar procedure.

N-(1-{2,6-Dichloro-4-[(propylcarbamoyl)amino]benzoyl}-1H-pyrrolo[3,2-c]pyridin-4-yl)acetamide was prepared from 1-{4-[(4-amino-1H-pyrrolo[3,2-c]pyridin-1-yl)carbonyl]-3,5-dichlorophenyl}-3-propylurea following a similar procedure.

$^1$H NMR (400 MHz, MeOH-d$_4$): δ 8.29-8.35 (m, 2H), 7.63-7.68 (m, 2H), 7.08-7.14 (m, 1H), 6.76-6.81 (m, 1H), 3.15-3.22 (m, 2H), 2.23-2.27 (m, 3H), 1.51-1.62 (m, 2H), 0.96 (s, 3H). MS: 448.31 (M$^+$).

Example 26

Synthesis of (4-amino-1H-pyrrolo[3,2-c]pyridin-1-yl)(2-chloro-6-fluorophenyl)methanone

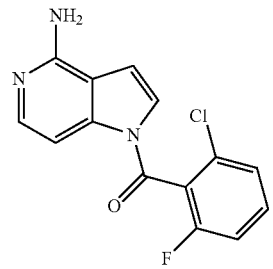 [SMILES: Nc1nccc2c1ccn2C(=O)c1c(F)cccc1Cl]

Step a: (2-chloro-6-fluorophenyl)(1H-pyrrolo[3,2-c]pyridin-1-yl)methanone

To a stirred solution of 2-chloro-6-fluorobenzoic acid (2.5 g, 14.32 mmol) in dichloromethane (20 mL), oxalyl chloride (3.029 ml, 28.64 mmol) was added at 0° C. After stirring at the same temperature for 15 min, dimethylfromamide (2-3 drops) was added, and the reaction was allowed to stir at room temperature for 1.5 hours. The reaction mixture was cooled and concentrated on rotary evaporator. The residue was taken up in dichloromethane (20 mL) and treated with 5-azaindole (1.72 g, 14.51 mmol) and triethylamine (6.1 mL, 43.52 mmol). The resulting reaction mixture was allowed to stir at room temperature for 20 hours. The reaction mixture was concentrated under vacuum, diluted with water (50 mL) and extracted with ethyl acetate (2×100 mL). The combined organic layer was washed with saturated aqueous solution of sodium bicarbonate. The organic layer was dried over anhydrous sodium sulfate, filtered and the solvent was removed under rotary evaporator. The product was isolated by silica gel column chromatography using ethyl acetate (25%) in hexanes as eluent to yield (2-chloro-6-fluorophenyl)(1H-pyrrolo[3,2-c]pyridin-1-yl)methanone (1.56 g, 39.5%).

MS (m/z): 274.68 (M+)

Step b: (2-chloro-6-fluorophenyl){4-[(2,4,4-trimethylpentan-2-yl)amino]-1H-pyrrolo[3,2-c]pyridin-1-yl}methanone To a stirred solution of (2-chloro-6-fluorophenyl)(1H-pyrrolo[3,2-c]pyridin-1-yl)methanone (1 g, 3.65 mmol) in dichloromethane (15 mL), was added 3-chloroperbenzoic acid (0.944 g, 5.47 mmol) at room temperature, followed by stirring overnight at the same temperature. The reaction mixture was concentrated on rotary evaporator, added water (50 mL) and extracted with ethyl acetate (2×100 mL). The organic layer was washed with saturated solution of sodium bicarbonate. The organic layer was dried over anhydrous sodium sulfate, filtered and the solvent was removed under vacuum to afford the N-oxide (1.08 g) that was used as such for the next step.

To a well stirred solution of (2-chloro-6-fluorophenyl)(5-oxido-1H-pyrrolo[3,2-c]pyridin-1-yl)methanone (1.07 g, 3.65 mmol) in chloroform (15 mL) tert-octylamine (2.6 mL, 16.08 mmol) was added at room temperature. Then the reaction mixture was cooled to 0° C. and p-toluenesulphonyl chloride (1.53 g, 8.04 mmol) was added portion wise at the same temperature. The reaction mixture was stirred for another 10 minutes, diluted with water (100 mL) and partitioned with dichloromethane (2×250 mL). The organic layer was washed with saturated solution of sodium bicarbonate. The organic layer was dried over anhydrous sodium sulfate, filtered and the solvent was removed under vacuum. The compound was purified by silica gel column chromatography using ethyl acetate in hexane (2%) as eluant to yield (2-chloro-6-fluorophenyl){4-[(2,4,4-trimethylpentan-2-yl)amino]-1H-pyrrolo[3,2-c]pyridin-1-yl}methanone (0.716 g, 48.78%).

$^1$H NMR (400 MHz, DMSO-$d_6$): δ 7.73 (d, J=7.65 Hz, 2H), 7.44-7.62 (m, 3H), 7.16-7.20 (m, 1H), 6.96-7.03 (m, 1H), 1.52 (s, 6H), 0.94-0.97 (m, 2H), 0.91 (s, 9H). MS (m/z): 401.9 (M$^+$).

Step c: (4-amino-1H-pyrrolo[3,2-c]pyridin-1-yl)(2-chloro-6-fluorophenyl)methanone To a stirred solution of (2-chloro-6-fluorophenyl){4-[(2,4,4-trimethylpentan-2-yl)amino]-1H-pyrrolo[3,2-c]pyridin-1-yl}methanone (716 mg, 1.78 mmol) in dichloromethane (15 mL) was added trifluoroacetic acid (1.5 ml) at room temperature. The resulting reaction mixture was stirred for 2 hours. The reaction mixture was concentrated on rotary evaporator, added aqueous ammonia solution (10 mL) and the precipitated solid was separated by filtration (0.415 g, 80.45%).

$^1$H NMR (400 MHz, DMSO-$d_6$): δ 7.70-7.78 (m, 2H), 7.48-7.63 (m, 4H), 6.91-6.99 (m, 1H), 6.54 (s, 2H). MS (m/z): 289.70 (M$^+$).

Methyl[1-(2-chloro-6-fluorobenzoyl)-1H-pyrrolo[3,2-c]pyridin-4-yl]carbamate (Compound No. 102) was prepared from (4-amino-1H-pyrrolo[3,2-c]pyridin-1-yl)(2-chloro-6-fluorophenyl)methanone and methyl chloroformate as per the procedure followed for methyl 1H-pyrrolo[3,2-c]pyridin-4-ylcarbamate.

$^1$H NMR (400 MHz, DMSO-$d_6$): δ 10.24 (s, 1H), 7.72-7.82 (m, 2H), 7.53-7.65 (m, 4H), 6.89 (br. s., 1H), 3.70 (s, 3H). MS (m/z): 347.74 (M$^+$).

Example 27

Synthesis of N-[1-(2,6-dichlorobenzoyl)-1H-pyrrolo[3,2-c]pyridin-6-yl]cyclopropanecarboxamide (Compound No. 120)

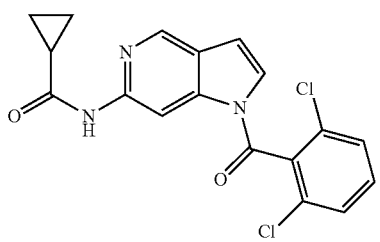 [SMILES: O=C(Nc1cc2c(ccn2C(=O)c2c(Cl)cccc2Cl)cn1)C1CC1]

Step a: Synthesis of 4-bromo-pyridine-1-oxide

A solution of 4-bromo-pyridine hydrochloride (25 g, 128 mmol) in dichloromethane (250 mL) was treated with potassium carbonate (21.25 g, 153 mmol) and the mixture was stirred for 2 hours, followed by addition of m-chloroperbezoic acid (44 g, 256 mmol). The mixture was stirred at room temperature for 16 hours, solid precipitated out, filtered and washed with ethyl acetate (2×200 mL). The filtrate was concentrated to give solid material which was washed with ether and hexane (3×30 mL, 1:1). The solid (20 g, 90%) obtained was used as such for next step.

Step b: Synthesis of 4-bromo-N-(2,4,4-trimethylpentan-2-yl)pyridin-2-amine

To a solution of 4-bromo-pyridine-1-oxide (20 g, 126 mmol) in chloroform (200 mL) tert-octylamine (71 g, 278 mmol) was added and reaction mixture was cooled to −5° C. p-Toluenesulphonyl chloride (52.91 g, 278 mmol) was added and the reaction mixture was stirred at the same temperature for 20 minutes. The reaction mixture was allowed to warm to room temperature and stirred 16 hours, diluted with dichloromethane (500 mL) and washed with saturated sodium bicarbonate solution (3×300 mL). The organic layer was separated and dried over anhydrous sodium sulphate and concentrated to give crude product as sticky material, which was purified by silica gel column chromatography using ethyl acetate and hexane as eluent to yield 8.5 gm (26.5%) of 4-bromo-N-(2,4,4-trimethylpentan-2-yl)pyridin-2-amine.

$^1$H NMR (400 MHz, MeOH-$d_4$): δ 7.78 (d, J=5.77 Hz, 1H), 6.64 (d, J=1.51 Hz, 1H), 6.56 (dd, J=5.52, 1.76 Hz, 1H), 1.91 (s, 2H), 1.43 (s, 6H), 0.95 (s, 9H). MS (m/z): 287.05 (M$^+$).

Step c: Synthesis of N$^2$-(2,4,4-trimethylpentan-2-yl)pyridine-2,4-diamine

A mixture of 4-bromo-N-(2,4,4-trimethylpentan-2-yl)pyridin-2-amine (7.5 g, 260 mmol), sodium azide (5.07 g, 780 mmol), CuI (1.4 g, 7.8 mmol), N,N-dimethylethane-1,2-diamine (1.3 g, 15 mmol) in dimethylsulfoxide (150 mL) was heated in a sealed reaction vessel at 90° C. for 16 hours. The reaction mixture was diluted with ethyl acetate (500 mL), saturated ammonium chloride (1000 mL) and stirred for 1 hour. The organic layer was separated and the aqueous layer was again extracted with ethyl acetate (3×300 mL). The combined organic layer was washed with brine, dried over anhydrous sodium sulphate and concentrated to give brown sticky mass which was purified by silica gel column chromatography using methanol and dichloromethane as eluent to yield 2 g (34%) of N$^2$-(2,4,4-trimethylpentan-2-yl)pyridine-2,4-diamine.

$^1$H NMR (400 MHz, MeOH-$d_4$): δ 7.44 (d, J=7.28 Hz, 1H), 6.17 (dd, J=7.28, 2.01 Hz, 1H), 6.03 (d, J=2.01 Hz, 1H), 1.80 (s, 2H), 1.48 (s, 6H), 1.02 (s, 9H). MS (m/z): 222.18 (M+1).

Step d: Synthesis of methyl {2-[(2,4,4-trimethylpentan-2-yl)amino]pyridin-4-yl}carbamate A solution of N$^2$-(2,4,4-trimethylpentan-2-yl)pyridine-2,4-diamine (3 g, 13.5 mmol) and triethylamine (2.7 g, 27 mmol) in dichloromethane (30 mL) was treated with methyl chloroformate (1.91 g, 20.3 mmol) under ice cooled condition followed by stirring at room temperature for 2 hours. The reaction mixture upon usual work up and silica gel column chromatography using methanol and dichloromethane as eluent yield 1.5 g (40%) of methyl {2-[(2,4,4-trimethylpentan-2-yl)amino]pyridin-4-yl}carbamate.

Step e: Synthesis of methyl {5-iodo-2-[(2,4,4-trimethylpentan-2-yl)amino]pyridin-4-yl}carbamate A solution of methyl {2-[(2,4,4-trimethylpentan-2-yl)amino]pyridin-4-yl}carbamate (1.5 g, 5.3 mmol) in acetonitrile was treated with N-iodosuccinimide (1.08 g, 4.8 mmol) in small portions while maintaining the temperature at −20° C. followed by stirring for 16 hours. Usual work up yielded 1.3 g (61%) of methyl {5-iodo-2-[(2,4,4-trimethylpentan-2-yl)amino]pyridin-4-yl}carbamate.

$^1$H NMR (400 MHz, MeOH-$d_4$): δ 8.10 (s, 1H), 7.25 (s, 1H), 3.78 (s, 3H), 1.87 (s, 2H), 1.43 (s, 6H), 0.97 (s, 9H).

Step f: Synthesis of 5-iodo-N$^2$-(2,4,4-trimethylpentan-2-yl)pyridine-2,4-diamine A mixture of methyl {5-iodo-2-[(2,4,4-trimethylpentan-2-yl)amino]pyridin-4-yl}carbamate (1.3 g, 3.2 mmol), potassium hydroxide (898 mg, 16 mmol), ethanol (10 mL) and water (10 mL) was heated at 80° C. for 2 hours. Ethanol was removed under vacuum, and the residue was stirred in water. The precipitated solid was filtered under vacuum and dried to yield 900 mg (81%) of 5-iodo-N$^2$-(2,4,4-trimethylpentan-2-yl)pyridine-2,4-diamine.

Step g: Synthesis of N$^2$-(2,4,4-trimethylpentan-2-yl)-5-[(trimethylsilyl)ethynyl]pyridine-2,4-diamine The compound was prepared following the procedure same as that of 4-amino-5-[(trimethylsilyl)ethynyl]pyridine-2-carbonitrile starting from 5-iodo-N$^2$-(2,4,4-trimethylpentan-2-yl)pyridine-2,4-diamine.

$^1$H NMR (400 MHz, MeOH-$d_4$): δ 7.48 (s, 1H), 5.65 (s, 1H), 1.57 (s, 2H), 1.20 (s, 6H), 0.77 (s, 9H), 0.22 (s, 9H).

Step h: Synthesis of N-(2,4,4-trimethylpentan-2-yl)-1H-pyrrolo[3,2-c]pyridin-6-amine The compound was prepared following the procedure same as that of 1H-pyrrolo[3,2-c]pyridine-6-carbonitrile starting from N$^2$-(2,4,4-trimethylpentan-2-yl)-5-[(trimethylsilyl)ethynyl]pyridine-2,4-diamine.

$^1$H NMR (400 MHz, MeOH-$d_4$): δ 8.24 (s, 1H), 7.05 (d, J=3.51 Hz, 1H), 6.61 (s, 1H), 6.38 (d, J=3.26 Hz, 1H), 1.80 (s, 2H), 1.45 (s, 6H), 1.02 (s, 9H).

Step i: Synthesis of N-[1-(cyclopropylcarbonyl)-1H-pyrrolo[3,2-c]pyridin-6-yl]-N-(2,4,4-trimethylpentan-2-yl)cyclopropanecarboxamide A mixture of N-(2,4,4-trimethylpentan-2-yl)-1H-pyrrolo[3,2-c]pyridin-6-amine (100 mg, 0.4 mmol) and triethylamine (103 mg, 1.02 mmol) in anhydrous dichloromethane was treated drop wise with cyclopropane carbonyl chloride (93 mg, 0.89 mmol) and stirred at room temperature for 16 hours. Usual work up and silica gel column purification using ethyl acetate and hexane afforded 80 mg (51%) of N-[1-(cyclopropylcarbonyl)-1H-pyrrolo[3,2-c]pyridin-6-yl]-N-(2,4,4-tri methyl pentan-2-yl)cyclopropanecarboxamide.

Step j: Synthesis of N-(1H-pyrrolo[3,2-c]pyridin-6-yl)-N-(2,4,4-trimethylpentan-2-yl)cyclopropane carboxamide A mixture of N-[1-(cyclopropylcarbonyl)-1H-pyrrolo[3,2-c]pyridin-6-yl]-N-(2,4,4-trimethylpentan-2-yl)cyclopropanecarboxamide (65 mg, 0.16 mmol), potassium carbonate, methanol and water was stirred at room temperature for 20 minutes. Methanol was removed under vacuum. The residue was stirred in water for 30 minutes. The precipitated solid was filtered and dried to 47 mg (90%) N-(1H-pyrrolo[3,2-c]pyridin-6-yl)-N-(2,4,4-trimethylpentan-2-yl)cyclopropane carboxamide.

$^1$H NMR (400 MHz, MeOH-$d_4$) δ: 8.74 (s, 1H), 7.36-7.55 (m, 2H), 6.70 (d, J=3.26 Hz, 1H), 2.11-2.39 (m, 2H), 1.44 (s, 3H), 1.25 (s, 3H), 1.08 (s, 9H), 0.80-0.93 (m, 2H), 0.71-0.80 (m, 1H), 0.36-0.55 (m, 2H).

Step k: Synthesis of N-[1-(2,6-dichlorobenzoyl)-1H-pyrrolo[3,2-c]pyridin-6-yl]-N-(2,4,4-trimethylpentan-2-yl)cyclopropanecarboxamide The compound was prepared from N-(1H-pyrrolo[3,2-c]pyridin-6-yl)-N-(2,4,4-trimethylpentan-2-yl)cyclopropanecarboxamide and 2,6-dichlorobenzoyl chloride following the procedure same as that of (2,6-dichlorophenyl)(1H-pyrrolo[3,2-c]pyridin-1-yl)methanone Step l: Synthesis of N-[1-(2,6-dichlorobenzoyl)-1H-pyrrolo[3,2-c]pyridin-6-yl]cyclopropanecarboxamide The compound was prepared by treating N-[1-(2,6-dichlorobenzoyl)-1H-pyrrolo[3,2-c]pyridin-6-yl]-N-(2,4,4-trimethylpentan-2-yl)cyclopropanecarboxamide with trifluoroacetic acid using the procedure described for benzyl 4-amino-1H-pyrrolo[3,2-c]pyridine-1-carboxylate.

$^1$H NMR (400 MHz, MeOH-$d_4$) δ: 9.18 (s, 1H), 8.62 (s, 1H), 7.59 (s, 3H), 6.99 (d, J=3.76 Hz, 1H), 6.76 (d, J=3.76 Hz, 1H), 1.85-2.02 (m, 1H), 0.86-1.08 (m, 4H). MS (m/z): 374.68 (M$^+$).

The following compounds were prepared following a similar procedure.

3,5-dichloro-4-({6-[(cyclopropylcarbonyl)amino]-1H-pyrrolo[3,2-c]pyridin-1-yl}carbonyl)-N-ethylbenzamide (Compound No. 130) was prepared from N-(1H-pyrrolo[3,2-c]pyridin-6-yl)-N-(2,4,4-tri methylpentan-2-yl)cyclopropane carboxamide by treating with 2,6-dichloro-4-(ethylcarbamoyl)benzoyl chloride following a procedure as per step k and l in Example 27.

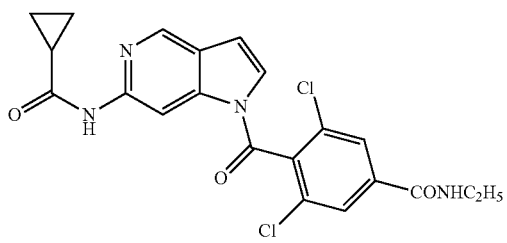

$^1$H NMR (400 MHz, DMSO-$d_6$): δ 10.97 (s, 1H), 9.19 (s, 1H), 8.85 (t, J=5.27 Hz, 1H), 8.69 (d, J=1.00 Hz, 1H), 8.12 (s, 2H), 7.26 (d, J=3.76 Hz, 1H), 6.84 (dd, J=0.75, 3.76 Hz, 1H), 2.02-2.12 (m, 1H), 1.15 (t, J=7.28 Hz, 3H), 0.79-0.90 (m, 4H). MS: 447.68 (M+).

N-[1-(2,6-dichloro-4-cyanobenzoyl)-1H-pyrrolo[3,2-c]pyridin-6-yl]cyclopropane carboxamide (Compound No. 137) was prepared from N-(1H-pyrrolo[3,2-c]pyridin-6-yl)-N-(2,4,4-trimethylpentan-2-yl)cyclopropane carboxamide by treating with 4-cyano-2,6-dichlorobenzoyl chloride following a procedure as per step k and l in Example 27.

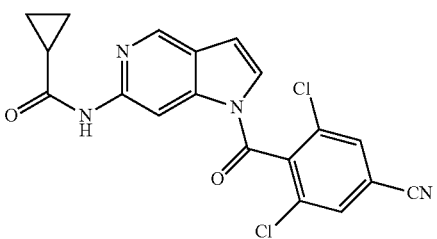 [SMILES: N#Cc1cc(Cl)c(C(=O)n2ccc3cnc(NC(=O)C4CC4)cc32)c(Cl)c1]

1H NMR (400 MHz, DMSO-d$_6$): δ 10.99 (s, 1H), 9.18 (s, 1H), 8.69 (s, 1H), 8.42 (s, 2H), 7.37 (d, J=3.76 Hz, 1H), 6.87 (d, J=3.76 Hz, 1H), 1.99-2.11 (m, 1H), 0.78-0.91 (m, 4H). MS: 399.82 (M$^+$).

Example 28

Synthesis of 3,5-dichloro-4-{[4-(cyclopropylcarbonyl)-1H-pyrrolo[3,2-c]pyridin-1-yl]carbonyl}-N-[2-(dimethylamino)ethyl]benzamide (Compound No. 122)

Step a: Synthesis of methyl 3,5-dichloro-4-({4-[(cyclopropylcarbonyl)amino]-1H-pyrrolo[3,2-c]pyridin-1-yl}carbonyl)benzoate A stirred solution of 2,6-dichloro-4-(methoxycarbonyl)benzoic acid (750 mg, 3 mmol, intermediate 32), 1-hydroxy-7-azabenzotriazole (614 mg, 4.5 mmol), dimethylaminopyridine (183 mg, 1.5 mmol), 2-(1H-7-azabenzotriazol-1-yl)-1,1,3,3-tetramethyl uronium hexafluorophosphate methanaminium (1170 mg, 4.5 mmol) in N,N-dimethylacatamide was treated with N-(1H-pyrrolo[3,2-c]pyridin-4-yl)cyclopropane carboxamide (605 mg, 3 mmol, intermediate 28) and Hunig's base (1.33 ml, 7.5 mmol). The reaction mixture was stirred at room temperature for about 1 hour and was heated at 50° C. for about 5 hours. To the reaction mixture, ice cold water was added and the precipitated solid was filtered, washed with water and dried. The solid thus obtained was purified by silica gel (100-200 mesh) column chromatography using methanol and dichloromethane gradient elution to afford methyl 3,5-dichloro-4-({4-[(cyclopropylcarbonyl)amino]-1H-pyrrolo[3,2-c]pyridin-1-yl}carbonyl)benzoate (600 mg, 47%) as an off-white solid.

$^1$H NMR (400 MHz, DMSO-d$_6$): δ 10.90 (s, 1H), 8.37 (d, J=5.56 Hz, 1H), 8.21 (d, J=5.81 Hz, 1H), 8.17 (s, 2H), 7.31 (d, J=3.79 Hz, 1H), 6.73 (d, J=3.79 Hz, 1H), 3.94 (s, 3H), 2.03-2.07 (m, 1H), 0.83-0.88 (m, 4H). MS: 432.75 (M$^+$).

Step b: Synthesis of 3,5-dichloro-4-{[4-(cyclopropylcarbonyl)amino]-1H-pyrrolo[3,2-c]pyridin-1-yl]carbonyl}benzoic acid To the stirred solution of methyl 3,5-dichloro-4-({4-[(cyclopropylcarbonyl)amino]-1H-pyrrolo[3,2-c]pyridin-1-yl}carbonyl)benzoate (500 mg, 1.1 mmol) in tetrahydrofuran and water (1:1, 5 mL) was added sodium hydroxide (46 mg, 1.1 mmol). The reaction mixture was stirred at room temperature for about 1 hour. The reaction mixture was then concentrated under vacuum and the aqueous residue was neutralized using dilute hydrochloric acid. The precipitated solid was filtered, washed with water and dried to afford 3,5-dichloro-4-{[4-(cyclopropylcarbonyl)-1H-pyrrolo[3,2-c]pyridin-1-yl]carbonyl}benzoic acid (470 m g, 97%) as an off-white solid.

$^1$H NMR (400 MHz, DMSO-d$_6$): δ 14.01 (br. s., 1H), 10.91 (s, 1H), 8.37 (d, J=5.56 Hz, 1H), 8.21 (d, J=5.56 Hz, 1H), 8.12 (s, 2H), 7.32 (d, J=4.04 Hz, 1H), 6.73 (d, J=4.04 Hz, 1H), 2.01-2.11 (m, 1H), 0.82-0.92 (m, 4H).

Step c: Synthesis of 3,5-dichloro-4-{[4-(cyclopropylcarbonyl)-1H-pyrrolo[3,2-c]pyridin-1-yl]carbonyl}-N-[2-(dimethylamino)ethyl]benzamide To a stirred solution of 3,5-dichloro-4-{[4-(cyclopropylcarbonyl)-1H-pyrrolo[3,2-c]pyridin-1-yl]carbonyl}benzoic acid (40 mg, 0.095 mmol), 1-ethyl-3-(3-dimethylaminopropyl)carbodiimide (22 mg, 0.115 mmol) and 15 mg 1-hydroxybenzotriazole (15 mg, 0.115 mmol) in dimethylformamide, was added N,N-dimethylethane-1,2-diamine (8.4 mg, 0.095 mmol). The resulting reaction mixture was stirred at room temperature for about 16 hours. The reaction mixture was poured drop wise into ie-cooled saturated aqueous sodium bicarbonate solution. The precipitated solid was filtered, washed with water and dried under vacuum. The solid thus obtained was triturated with diethyl ether, filtered and dried to get 3,5-dichloro-4-{[4-(cyclopropylcarbonyl)-1H-pyrrolo[3,2-c]pyridin-1-yl]carbonyl}-N-[2-(dimethylamino)ethyl]benzamide (11 mg, 25%).

$^1$H NMR (400 MHz, DMSO-d$_6$): δ 10.89 (s, 1H), 8.81 (t, J=5.56 Hz, 1H), 8.37 (d, J=5.81 Hz, 1H), 8.21 (d, J=5.81 Hz, 1H), 8.13 (s, 2H), 7.30 (d, J=3.79 Hz, 1H), 6.72 (d, J=3.79 Hz, 1H), 3.36-3.43 (m, 2H), 2.42 (t, J=6.69 Hz, 2H), 2.18 (s, 6H), 2.01-2.09 (m, 1H), 0.82-0.92 (m, 4H). MS: 488.79 (M$^+$).

The following compounds were prepared following analogous method using appropriate starting materials:

3,5-Dichloro-4-({4-[(cyclopropylcarbonyl)amino]-1H-pyrrolo[3,2-c]pyridin-1-yl}carbonyl)-N-(3-hydroxypropyl)benzamide (Compound No. 123)

$^1$H NMR (400 MHz, DMSO-d$_6$): δ 10.89 (s, 1H), 8.83 (t, J=5.56 Hz, 1H), 8.37 (d, J=5.56 Hz, 1H), 8.21 (d, J=5.81 Hz, 1H), 8.13 (s, 2H), 7.28 (d, J=4.04 Hz, 1H), 6.72 (d, J=3.79 Hz, 1H), 4.51 (t, J=5.18 Hz, 1H), 3.48 (q, J=6.06 Hz, 2H), 3.36-3.40 (m, 2H), 2.02-2.09 (m, 1H), 1.70 (quin, J=6.69 Hz, 2H), 0.84-0.93 (m, 4H). MS (ESI): 475.76 (M$^+$).

3,5-Dichloro-4-({4-[(cyclopropylcarbonyl)amino]-1H-pyrrolo[3,2-c]pyridin-1-yl}carbonyl)-N-[2-(2-hydroxyethoxy)ethyl]benzamide (Compound No. 124)

$^1$H NMR (400 MHz, DMSO-d$_6$): δ 10.89 (s, 1H), 8.92 (t, J=5.43 Hz, 1H), 8.37 (d, J=5.81 Hz, 1H), 8.21 (d, J=5.56 Hz, 1H), 8.08-8.16 (m, 2H), 7.30 (d, J=3.79 Hz, 1H), 6.72 (d, J=3.79 Hz, 1H), 4.61 (t, J=5.31 Hz, 1H), 3.54-3.60 (m, 2H), 3.43-3.54 (m, 6H), 1.97-2.10 (m, 1H), 0.85-0.92 (m, 4H). MS: 505.8 (M$^+$).

3,5-dichloro-4-({4-[(cyclopropylcarbonyl)amino]-1H-pyrrolo[3,2-c]pyridin-1-yl}carbonyl)-N-[2-(morpholin-4-yl)ethyl]benzamide (Compound No. 125)

$^1$H NMR (400 MHz, DMSO-d$_6$): δ 10.89 (s, 1H), 8.84 (t, J=5.81 Hz, 1H), 8.37 (d, J=5.56 Hz, 1H), 8.21 (d, J=5.31 Hz, 1H), 8.12 (s, 2H), 7.30 (d, J=3.79 Hz, 1H), 6.72 (d, J=3.79 Hz, 1H), 3.58 (t, J=4.55 Hz, 4H), 3.42 (td, J=6.66, 12.69 Hz, 2H), 2.42 (br. s., 4H), 2.00-2.10 (m, 1H), 0.85-0.97 (m, 4H). MS: 530.86 (M$^+$).

Ethyl N-[3,5-dichloro-4-({4-[(cyclopropylcarbonyl) amino]-1H-pyrrolo[3,2-c]pyridin-1-yl}carbonyl) benzoyl]-β-alaninate (Compound No. 126)

$^1$H NMR (400 MHz, DMSO-d$_6$): δ 10.89 (s, 1H), 8.96 (t, J=5.31 Hz, 1H), 8.37 (d, J=5.56 Hz, 1H), 8.20 (d, J=6.32 Hz, 1H), 8.08-8.13 (m, 2H), 7.29 (d, J=4.04 Hz, 1H), 6.72 (d, J=4.04 Hz, 1H), 4.09 (q, J=7.07 Hz, 2H), 3.49-3.58 (m, 2H), 2.62 (t, J=6.82 Hz, 2H), 2.01-2.09 (m, 1H), 1.20 (t, J=7.07 Hz, 3H), 0.82-0.89 (m, 4H). MS: 517.83 (M$^+$).

3,5-Dichloro-4-({4-[(cyclopropylcarbonyl)amino]-1H-pyrrolo[3,2-c]pyridin-1-yl}carbonyl)-N-(3-methoxypropyl)benzamide (Compound No. 131)

$^1$H NMR (400 MHz, DMSO-d$_6$): δ 10.90 (s, 1H), 8.86 (t, J=5.52 Hz, 1H), 8.37 (d, J=5.52 Hz, 1H), 8.21 (d, J=5.77 Hz, 1H), 8.12 (s, 2H), 7.29 (d, J=4.02 Hz, 1H), 6.72 (d, J=3.76 Hz, 1H), 3.36-3.42 (m, 4H), 3.25 (s, 3H), 2.01-2.08 (m, 1H), 1.78 (quin, J=6.59 Hz, 2H), 0.82-0.92 (m, 4H). MS: 489.87 (M$^+$).

3,5-Dichloro-4-({4-[(cyclopropylcarbonyl)amino]-1H-pyrrolo[3,2-c]pyridin-1-yl}carbonyl)-N-propyl-benzamide (Compound No. 133)

$^1$H NMR (400 MHz, DMSO-d$_6$): δ 10.90 (s, 1H), 8.82-8.88 (m, 1H), 8.37 (d, J=5.52 Hz, 1H), 8.21 (d, J=5.77 Hz, 1H), 8.13 (s, 2H), 7.29 (d, J=3.76 Hz, 1H), 6.72 (d, J=3.76 Hz, 1H), 3.23-3.30 (m, 2H), 2.00-2.09 (m, 1H), 1.51-1.61 (m, 2H), 0.91 (t, J=7.40 Hz, 3H), 0.82-0.92 (m, 4H). MS: 459.83 (M$^+$).

N-[3,5-Dichloro-4-({4-[(cyclopropylcarbonyl) amino]-1H-pyrrolo[3,2-c]pyridin-1-yl}carbonyl) benzoyl]-β-alanine (Compound No. 135)

$^1$H NMR (400 MHz, DMSO-d$_6$): δ 12.32 (br. s., 1H), 10.88 (s, 1H), 8.94 (br. s., 1H), 8.36 (br. s., 1H), 8.21 (d, J=5.77 Hz, 1H), 8.12 (s, 2H), 7.29 (d, J=3.76 Hz, 1H), 6.72 (d, J=3.76 Hz, 1H), 3.50 (d, J=5.02 Hz, 2H), 2.55 (br. s., 2H), 2.01-2.09 (m, 1H), 0.82-0.94 (m, 4H). MS: 488.11 (M−1).

Example 29

Synthesis of ethyl N-[3,5-dichloro-4-({4-[(cyclopropylcarbonyl)amino]-1H-pyrrolo[3,2-c]pyridin-1-yl}carbonyl)benzoyl]alaninate (Compound No. 141)

A stirred solution of 3,5-dichloro-4-({4-[(cyclopropylcarbonyl)amino]-1H-pyrrolo[3,2-c]pyridin-1-yl}carbonyl)benzoic acid (100 mg, 0.23 mmol) in anhydrous dimethylformamide (5 mL) was treated with 1-ethyl-3-(3-dimethylaminopropyl)carbodiimide (68 mg, 0.358 mmol), 1-hydroxy-7-azabenzotriazole (37 mg, 0.276 mmol), N,N-diisopropylethylamine (89 mg, 0.69 mmol). Ethyl alaninate (38 mg, 0.25 mmol) was added and the reaction mixture was stirred at room temperature for about 16 hours. The reaction mixture was poured into water (100 mL) and extracted with ethylacetate (2×30 mL). The combined organic layer was washed with brine, dried over anhydrous sodium sulphate and concentrated to give crude product which was purified by flash silica gel column chromatography using linear gradient ethyl acetate and hexane to afford ethyl N-[3,5-dichloro-4-({4-[(cyclopropylcarbonyl)amino]-1H-pyrrolo[3,2-c]pyridin-1-yl}carbonyl)benzoyl]alaninate (43 mg, 34%).

$^1$H NMR (400 MHz, DMSO-d$_6$): δ 10.96 (br. s., 1H), 8.90 (br. s., 1H), 8.37 (d, J=5.52 Hz, 1H), 8.15-8.23 (m, 3H), 7.28 (d, J=4.02 Hz, 1H), 6.72 (d, J=4.04 Hz, 1H), 4.49 (t, J=7.07 Hz, 1H), 4.13 (q, j=7.07 Hz, 2H), 2.01-2.09 (m, 1H), 1.39-1.48 (m, 1H), 1.21 (t, J=7.07 Hz, 3H), 0.83-0.89 (m, 4H). MS: 518.16 (M+1).

The following compounds were prepared from 3,5-dichloro-4-({4-[(cyclopropylcarbonyl)amino]-1H-pyrrolo[3,2-c]pyridin-1-yl}carbonyl)benzoic acid in a similar manner using appropriate amines.

3,5-Dichloro-4-({4-[(cyclopropylcarbonyl)amino]-1H-pyrrolo[3,2-c]pyridin-1-yl}carbonyl)-N-[2-(2-oxoimidazolidin-1-yl)ethyl]benzamide (Compound No. 142)

$^1$H NMR (400 MHz, DMSO-d$_6$): δ 10.89 (s, 1H), 8.86 (s, 1H), 8.37 (d, J=5.77 Hz, 1H), 8.21 (d, J=5.77 Hz, 1H), 8.12 (s, 2H), 7.28 (d, J=3.76 Hz, 1H), 6.72 (d, J=3.76 Hz, 1H), 3.58 (t, J=4.52 Hz, 4H), 2.29-2.40 (m, 6H), 2.00-2.11 (m, 1H), 1.63-1.77 (m, 2H), 0.80-0.90 (m, 4H). MS: 530.19 (M+1).

3,5-Dichloro-4-({4-[(cyclopropylcarbonyl)amino]-1H-pyrrolo[3,2-c]pyridin-1-yl}carbonyl)-N-[2-(pyridin-4-yl)ethyl]benzamide (Compound No. 145)

$^1$H NMR (400 MHz, DMSO-d$_6$): δ 10.85-10.93 (m, 1H), 8.97 (t, J=5.43 Hz, 1H), 8.53 (d, J=5.05 Hz, 1H), 8.37 (d, J=5.81 Hz, 1H), 8.21 (d, J=5.56 Hz, 1H), 8.09 (s, 2H), 7.73 (dt, J=1.89, 7.64 Hz, 1H), 7.27-7.34 (m, 2H), 7.22-7.26 (m, 1H), 6.71 (d, J=3.79 Hz, 1H), 3.59-3.73 (m, 2H), 3.03 (t, J=7.45 Hz, 2H), 2.01-2.10 (m, 1H), 0.83-0.90 (m, 4H).

3,5-dichloro-4-({4-[(cyclopropylcarbonyl)amino]-1H-pyrrolo[3,2-c]pyridin-1-yl}carbonyl)-N-(pyridin-2-ylmethyl)benzamide (Compound No. 147)

$^1$H NMR (400 MHz, DMSO-d$_6$): δ 10.90 (s, 1H), 9.52 (t, J=5.81 Hz, 1H), 8.51-8.55 (m, 2H), 8.37 (d, J=5.81 Hz, 1H), 8.16-8.24 (m, 3H), 7.35 (d, J=6.06 Hz, 2H), 7.31 (d, J=3.79 Hz, 1H), 6.73 (d, J=4.29 Hz, 1H), 4.55 (d, J=5.81 Hz, 2H), 2.01-2.07 (m, 1H), 0.90-1.12 (m, 4H). MS: 509.13 (M+1).

3,5-Dichloro-4-({4-[(cyclopropylcarbonyl)amino]-1H-pyrrolo[3,2-c]pyridin-1-yl}carbonyl)-N-[2-(pyrrolidin-1-yl)ethyl]benzamide (Compound No. 148)

$^1$H NMR (400 MHz, DMSO-d$_6$): δ 10.83 (br. s, 1H), 8.8-8.95 (m, 1H), 8.37 (d, J=5.52 Hz, 1H), 8.21 (d, J=5.52 Hz, 1H), 8.13 (s, 2H), 7.28 (d, J=4.02 Hz, 1H), 6.72 (d, J=3.76 Hz, 1H), 3.40-3.53 (m, 2H), 2.67-2.81 (m, 4H), 2.01-2.09 (m, 1H), 1.65-1.74 (m, 4H), 0.85 (d, J=6.02 Hz, 4H). MS: 515.20 (M+1).

3,5-Dichloro-4-({4-[(cyclopropylcarbonyl)amino]-1H-pyrrolo[3,2-c]pyridin-1-yl}carbonyl)-N-[3-(morpholin-4-yl)propyl]benzamide (Compound No. 149)

$^1$H NMR (400 MHz, DMSO-d$_6$): δ 10.89 (s, 1H), 8.86 (s, 1H), 8.37 (d, J=5.77 Hz, 1H), 8.21 (d, J=5.77 Hz, 1H), 8.12 (s, 2H), 7.28 (d, J=3.76 Hz, 1H), 6.72 (d, J=3.76 Hz, 1H), 3.58 (t, J=4.52 Hz, 4H), 2.29-2.40 (m, 6H), 2.00-2.11 (m, 1H), 1.63-1.77 (m, 2H), 0.80-0.90 (m, 4H). MS: 545.24 (M+1).

3,5-Dichloro-4-({4-[(cyclopropylcarbonyl)amino]-1H-pyrrolo[3,2-c]pyridin-1-yl}carbonyl)-N-[2-(piperidin-1-yl)ethyl]benzamide (Compound No. 150)

$^1$H NMR (400 MHz, DMSO-d$_6$): δ 10.89 (s, 1H), 8.86 (t, J=5.65 Hz, 1H), 8.37 (d, J=5.77 Hz, 1H), 8.21 (d, J=5.52 Hz,

1H), 8.11 (s, 2H), 7.29 (d, J=4.02 Hz, 1H), 6.72 (d, J=4.02 Hz, 1H), 3.36-3.45 (m, 2H), 2.34-2.48 (m, 6H), 2.02-2.09 (m, 1H), 1.45-1.55 (m, 4H), 1.39 (d, J=5.52 Hz, 2H), 0.80-0.90 (m, 4H). MS: 529.25 (M+1).

3,5-Dichloro-4-({4-[(cyclopropylcarbonyl)amino]-1H-pyrrolo[3,2-c]pyridin-1-yl}carbonyl)-N-(1-hydroxypropan-2-yl)benzamide (Compound No. 151)

$^1$H NMR (400 MHz, DMSO-d$_6$): δ 10.89 (s, 1H), 8.52 (d, J=7.78 Hz, 1H), 8.37 (d, J=5.52 Hz, 1H), 8.21 (d, J=5.77 Hz, 1H), 8.15 (s, 1H), 7.27 (d, J=3.76 Hz, 1H), 6.72 (d, J=3.76 Hz, 1H), 4.79 (t, J=6.02 Hz, 1H), 4.04 (td, J=6.84, 13.43 Hz, 1H), 3.47 (td, J=5.77, 11.04 Hz, 1H), 3.36-3.41 (m, 1H), 2.01-2.11 (m, 1H), 1.15 (d, J=6.78 Hz, 3H), 1.09 (t, J=7.03 Hz, 1H), 0.83-0.92 (m, 4H). MS: 476.09 (M+1).

3,5-Dichloro-4-({4-[(cyclopropylcarbonyl)amino]-1H-pyrrolo[3,2-c]pyridin-1-yl}carbonyl)-N-[2-(1H-indol-3-yl)ethyl]benzamide (Compound No. 139)

$^1$H NMR (400 MHz, DMSO-d$_6$): δ 10.88 (d, J=18.82 Hz, 2H), 9.00 (t, J=5.77 Hz, 1H), 8.38 (s, 1H), 8.21 (d, J=5.77 Hz, 1H), 8.12 (s, 2H), 7.58 (d, J=7.78 Hz, 1H), 7.35 (d, J=8.28 Hz, 1H), 7.29 (d, J=3.76 Hz, 1H), 7.21 (d, J=2.01 Hz, 1H), 7.05-7.11 (m, 1H), 6.97-7.03 (m, 1H), 6.72 (d, J=4.02 Hz, 1H), 2.98 (t, J=7.28 Hz, 2H), 1.94-2.16 (m, 1H), 1.09 (t, J=7.03 Hz, 2H), 0.85-1.02 (m, 4H). MS: 560.44 (M$^+$).

3,5-Dichloro-4-({4-[(cyclopropylcarbonyl)amino]-1H-pyrrolo[3,2-c]pyridin-1-yl}carbonyl)-N-(2,3-dihydroxypropyl)benzamide (Compound No. 143)

$^1$H NMR (400 MHz, DMSO-d$_6$): δ 10.90 (s, 1H), 8.82 (t, J=5.43 Hz, 1H), 8.37 (d, J=5.81 Hz, 1H), 8.21 (d, J=5.56 Hz, 1H), 8.15 (s, 2H), 7.28 (d, J=4.04 Hz, 1H), 6.72 (d, J=4.04 Hz, 1H), 4.87 (d, J=5.05 Hz, 1H), 4.61 (t, J=5.81 Hz, 1H), 3.17-3.26 (m, 1H), 2.02-2.08 (m, 1H), 0.85-1.02 (m, 4H). MS: 492.08 (M$^+$).

3,5-Dichloro-4-({4-[(cyclopropylcarbonyl)amino]-1H-pyrrolo[3,2-c]pyridin-1-yl}carbonyl)-N-[2-(thiophen-2-yl)ethyl]benzamide (Compound No. 144)

$^1$H NMR (400 MHz, DMSO-d$_6$): δ10.90 (s, 1H), 9.04 (t, J=5.43 Hz, 1H), 8.37 (d, J=5.56 Hz, 1H), 8.21 (d, J=5.56 Hz, 1H), 8.11 (s, 2H), 7.37 (dd, J=1.26, 5.05 Hz, 2H), 7.31 (d, J=3.79 Hz, 1H), 6.90-7.03 (m, 3H), 6.72 (s, 1H), 3.49-3.61 (m, 2H), 3.10 (t, J=6.95 Hz, 2H), 2.00-2.10 (m, 1H), 0.84-0.96 (m, 4H). MS: 528.11 (M$^+$).

3,5-Dichloro-N-cyclopropyl-4-({4-[(cyclopropylcarbonyl)amino]-1H-pyrrolo[3,2-c]pyridin-1-yl}carbonyl)benzamide (Compound No. 146)

$^1$H NMR (400 MHz, DMSO-d$_6$): δ 10.89 (s, 1H), 8.81 (d, J=4.29 Hz, 1H), 8.37 (d, J=5.56 Hz, 1H), 8.21 (d, J=5.81 Hz, 1H), 8.10 (s, 2H), 7.27 (d, J=3.79 Hz, 1H), 6.72 (d, J=3.79 Hz, 1H), 2.90 (dt, J=3.79, 7.33 Hz, 1H), 2.00-2.10 (m, 1H), 0.84-0.98 (m, 4H), 0.70-0.81 (m, 2H), 0.57-0.67 (m, 2H). MS: 458.01 (M+1).

3,5-Dichloro-4-({4-[(cyclopropylcarbonyl)amino]-1H-pyrrolo[3,2-c]pyridin-1-yl}carbonyl)-N-(2-fluoroethyl)benzamide (Compound No. 154)

$^1$H NMR (400 MHz, DMSO-d$_6$) δ: 10.89 (s, 1H), 9.11 (t, J=5.52 Hz, 1H), 8.37 (d, J=5.77 Hz, 1H), 8.19-8.25 (m, 1H), 8.16 (s, 2H), 7.30 (d, J=3.76 Hz, 1H), 6.72 (d, J=3.76 Hz, 1H), 4.63 (t, J=4.89 Hz, 1H), 4.51 (t, J=4.89 Hz, 1H), 3.66 (q, J=5.10 Hz, 1H), 3.59 (q, J=5.27 Hz, 1H), 1.99-2.10 (m, 1H), 0.83-0.89 (m, 4H). MS: 464.00 (M+1).

3,5-Dichloro-4-({4-[(cyclopropylcarbonyl)amino]-1H-pyrrolo[3,2-c]pyridin-1-yl}carbonyl)-N-(2,2,2-trifluoroethyl)benzamide (Compound No. 155)

$^1$H NMR (400 MHz, DMSO-d$_6$): δ 10.89 (s, 1H), 9.50 (t, J=6.15 Hz, 1H), 8.37 (d, J=5.52 Hz, 1H), 8.21 (d, J=5.77 Hz, 1H), 8.19 (s, 2H), 7.33 (d, J=4.02 Hz, 1H), 6.72 (d, J=3.76 Hz, 1H), 4.18 (dd, J=6.27, 9.54 Hz, 2H), 1.88-2.18 (m, 1H), 0.70-1.00 (m, 4H). MS: 500.02 (M+1).

3,5-Dichloro-4-({4-[(cyclopropylcarbonyl)amino]-1H-pyrrolo[3,2-c]pyridin-1-yl}carbonyl)-N-(3-ethoxypropyl)benzamide (Compound No. 156)

$^1$H NMR (400 MHz, DMSO-d$_6$): δ 10.89 (s, 1H), 8.85 (t, J=5.40 Hz, 1H), 8.37 (d, J=5.77 Hz, 1H), 8.21 (d, J=5.77 Hz, 1H), 8.12 (s, 2H), 7.28 (d, J=3.76 Hz, 1H), 6.72 (d, J=3.76 Hz, 1H), 3.37-3.48 (m, 6H), 1.98-2.10 (m, 1H), 1.72-1.83 (m, 2H), 1.12 (t, J=7.03 Hz, 3H), 0.80-0.90 (m, 4H). MS: 504.12 (M+1).

3,5-Dichloro-4-({4-[(cyclopropylcarbonyl)amino]-1H-pyrrolo[3,2-c]pyridin-1-yl}carbonyl)-N-[(2R)-1-methoxypropan-2-yl]benzamide (Compound No. 159)

$^1$H NMR (400 MHz, DMSO-d$_6$): δ10.89 (s, 1H), 8.65 (d, J=8.03 Hz, 1H), 8.37 (d, J=5.77 Hz, 1H), 8.21 (d, J=5.52 Hz, 1H), 8.15 (d, J=1.76 Hz, 2H), 7.29 (d, J=3.76 Hz, 1H), 6.72 (d, J=3.76 Hz, 1H), 4.23 (td, J=6.71, 13.68 Hz, 1H), 3.38-3.47 (m, 1H), 3.25-3.31 (s, 3H), 2.00-2.10 (m, 1H), 1.13-1.20 (m, 3H), 0.82-0.89 (m, 4H). MS: 490.2 (M+1).

3,5-Dichloro-4-({4-[(cyclopropylcarbonyl)amino]-1H-pyrrolo[3,2-c]pyridin-1-yl}carbonyl)-N-[2-(1H-pyrrol-1-yl)ethyl]benzamide (Compound No. 168)

$^1$H NMR (400 MHz, DMSO-d$_6$): δ 10.90 (s, 1H), 8.98 (br. s., 1H), 8.37 (d, J=5.52 Hz, 1H), 8.21 (d, J=5.77 Hz, 1H), 8.08 (s, 1H), 7.30 (d, J=3.76 Hz, 1H), 6.78 (s, 2H), 6.72 (d, J=3.76 Hz, 1H), 6.00 (br. s., 2H), 4.10 (t, J=6.02 Hz, 2H), 3.59 (d, J=5.27 Hz, 2H), 2.01-2.08 (m, 1H), 0.82-0.89 (m, 4H). MS: 510.37 (M$^+$).

3,5-Dichloro-4-({4-[(cyclopropylcarbonyl)amino]-1H-pyrrolo[3,2-c]pyridin-1-yl}carbonyl)-N-[2-(pyridin-3-yl)ethyl]benzamide (Compound No. 169)

$^1$H NMR (400 MHz, DMSO-d$_6$): δ 10.90 (s., 1H), 8.98 (s., 1H), 8.46 (d, J=19.32 Hz, 2H), 8.37 (s., 1H), 8.20 (s., 1H), 8.08 (s., 2H), 7.69 (s., 1H), 7.32 (d, J=13.55 Hz, 2H), 6.72 (s, 1H), 3.57-3.68 (m., 2H), 2.86-2.91 (m 2H), 2.05 (m., 1H), 0.84-0.92 (m, 4H). MS: 522.38 (M$^+$).

3,5-Dichloro-4-({4-[(cyclopropylcarbonyl)amino]-1H-pyrrolo[3,2-c]pyridin-1-yl}carbonyl)-N-(cyclopropylmethyl)benzamide (Compound No. 170)

$^1$H NMR (400 MHz, DMSO-d$_6$): δ 10.89 (s, 1H), 8.97 (t, J=5.52 Hz, 1H), 8.37 (d, J=5.77 Hz, 1H), 8.21 (d, J=5.77 Hz, 1H), 8.15 (s, 2H), 7.30 (d, J=4.02 Hz, 1H), 6.72 (d, J=3.76 Hz, 1H), 3.19 (t, J=6.15 Hz, 2H), 2.01-2.10 (m, 1H), 1.06 (d, 3,5-Dichloro-4-({4-[(cyclopropylcarbonyl)amino]-1H-pyrrolo[3,2-c]pyridin-1-yl}carbonyl)-N-[(3R)-piperidin-3-ylmethyl]benzamide (Compound No. 171)

¹H NMR (400 MHz,): δ 10.89 (br. s., 1H), 8.15 (d, J=5.87 Hz, 1H), 8.06 (s, 3H), 7.66 (d, J=5.91 Hz, 1H), 6.93 (d, J=3.71 Hz, 1H), 6.55 (d, J=3.71 Hz, 1H), 3.28-3.39 (m, 1H), 3.17-3.28 (m, 1H), 2.80-2.91 (m, 3H), 2.58-2.73 (m, 3H), 1.90 (tt, J=4.90, 8.14 Hz, 1H), 1.63-1.72 (m, 2H), 1.38-1.58 (m, 2H), 1.02-1.18 (m, 2H), 0.90-0.98 (m, 2H). MS: 514.40 (M⁺).

3,5-Dichloro-N-cyclobutyl-4-({4-[(cyclopropylcarbonyl)amino]-1H-pyrrolo[3,2-c]pyridin-1-yl}carbonyl)benzamide (Compound No. 132)

¹H NMR (400 MHz, DMSO-d₆): δ 10.90 (s, 1H), 9.00 (d, J=7.28 Hz, 1H), 8.37 (d, J=5.52 Hz, 1H), 8.21 (d, J=5.27 Hz, 1H), 8.14 (s, 2H), 7.27 (d, J=4.02 Hz, 1H), 6.72 (d, J=3.76 Hz, 1H), 4.38-4.48 (m, 1H), 2.20-2.30 (m, 2H), 2.00-2.15 (m, 3H), 1.63-1.78 (m, 2H), 0.82-0.89 (m, 4H). MS: 471.86 (M⁺).

Example 30

Synthesis of 4-{[4-(acetylamino)-1H-pyrrolo[3,2-c]pyridin-1-yl]carbonyl}-3,5-dichloro-N-[3-(morpholin-4-yl)propyl]benzamide (Compound No. 162)

This compound was prepared following an analogous procedure as in Example 28.

Step a: Methyl 4-{[4-(acetylamino)-1H-pyrrolo[3,2-c]pyridin-1-yl]carbonyl}-3,5-dichlorobenzoate This was prepared using 2,6-dichloro-4-(methoxycarbonyl)benzoic acid and N-(1H-pyrrolo[3,2-c]pyridin-4-yl)acetamide (Intermediate 29) in an analogous manner.

¹H NMR (400 MHz, DMSO-d₆): δ 10.61 (s, 1H), 8.36 (d, J=5.81 Hz, 1H), 8.20 (d, J=5.56 Hz, 1H), 8.15-8.18 (m, 2H), 7.33 (d, J=3.79 Hz, 1H), 6.79 (d, J=3.79 Hz, 1H), 3.95 (s, 3H), 2.16 (s, 3H).

Step b: 4-[(4-acetyl-1H-pyrrolo[3,2-c]pyridin-1-yl)carbonyl]-3,5-dichlorobenzoic acid ¹H NMR (400 MHz, DMSO-d6): δ 13.80-14.24 (m, 1H), 10.62 (br. s., 1H), 8.37 (br. s., 1H), 8.21 (br. s., 1H), 8.12 (br. s., 2H), 7.34 (br. s., 1H), 6.79 (br. s., 1H), 2.17 (br. s., 3H).

Step c: 4-{[4-(acetylamino)-1H-pyrrolo[3,2-c]pyridin-1-yl]carbonyl}-3,5-dichloro-N-[3-(morpholin-4-yl)propyl]benzamide This was prepared analogously from 4-[(4-acetyl-1H-pyrrolo[3,2-c]pyridin-1-yl)carbonyl]-3,5-dichlorobenzoic acid and 3-(morpholin-4-yl)propylamine.

¹H NMR (400 MHz, DMSO-d₆): δ 10.61 (s, 1H), 8.86 (t, J=5.27 Hz, 1H), 8.36 (d, J=5.77 Hz, 1H), 8.20 (d, J=5.52 Hz, 1H), 8.12 (s, 2H), 7.31 (d, J=3.76 Hz, 1H), 6.78 (d, J=3.76 Hz, 1H), 3.58 (t, J=4.52 Hz, 4H), 2.29-2.40 (m, 6H), 2.16 (s, 3H), 1.71 (quin, J=7.03 Hz, 2H). MS: 519.17 (M+1).

The following compounds were prepared following analogous procedure using appropriate starting materials.

4-{[4-(Acetylamino)-1H-pyrrolo[3,2-c]pyridin-1-yl]carbonyl}-3,5-dichloro-N-[2-(dimethylamino)ethyl]benzamide (Compound No. 128)

¹H NMR (400 MHz, DMSO-d6): δ 10.60 (s, 1H), 8.72-8.87 (m, 1H), 8.36 (d, J=5.31 Hz, 1H), 8.20 (d, J=5.31 Hz, 1H), 8.13 (s, 2H), 7.32 (d, J=3.79 Hz, 1H), 6.78 (br. s., 1H), 3.37-3.44 (m, 2H), 2.38-2.46 (m, 2H), 2.11-2.24 (m, 9H). MS: 462.33 (M⁺).

Ethyl N-(4-{[4-(acetylamino)-1H-pyrrolo[3,2-c]pyridin-1-yl]carbonyl}-3,5-dichlorobenzoyl)-b-alaninate (Compound No. 129)

¹H NMR (400 MHz, DMSO-d₆): δ 10.60 (s, 1H), 8.96 (t, J=5.08 Hz, 1H), 8.36 (d, J=5.62 Hz, 1H), 8.20 (d, J=5.68 Hz, 1H), 8.11 (s, 2H), 7.31 (d, J=3.98 Hz, 1H), 6.78 (d, J=3.79 Hz, 1H), 4.09 (q, J=7.12 Hz, 2H), 3.50-3.56 (m, 2H), 2.62 (t, J=6.82 Hz, 2H), 2.16 (s, 3H), 1.20 (t, J=7.17 Hz, 3H). MS: 491.33 (M⁺).

4-{[4-(Acetylamino)-1H-pyrrolo[3,2-c]pyridin-1-yl]carbonyl}-3,5-dichloro-N-(3-methoxypropyl)benzamide (Compound No. 134)

¹H NMR (400 MHz, DMSO-d₆): δ 10.61 (s, 1H), 8.86 (t, J=5.52 Hz, 1H), 8.36 (d, J=5.77 Hz, 1H), 8.20 (d, J=5.52 Hz, 1H), 8.13 (s, 2H), 7.31 (d, J=3.76 Hz, 1H), 6.78 (d, J=4.02 Hz, 1H), 3.37-3.42 (m, 3H), 3.24-3.27 (m, 3H), 2.16 (s, 3H), 1.78 (quin, J=6.59 Hz, 2H). MS: 463.86 (M⁺).

4-{[4-(Acetylamino)-1H-pyrrolo[3,2-c]pyridin-1-yl]carbonyl}-3,5-dichloro-N-(2-fluoroethyl)benzamide (Compound No. 157)

¹H NMR (400 MHz, DMSO-d₆): δ 10.61 (s, 1H), 9.12 (t, J=5.40 Hz, 1H), 8.36 (d, J=5.77 Hz, 1H), 8.18-8.25 (m, 1H), 8.16 (s, 2H), 7.32 (d, J=3.76 Hz, 1H), 6.78 (d, J=3.76 Hz, 1H), 4.63 (t, J=4.89 Hz, 1H), 4.52 (t, J=5.02 Hz, 1H), 3.66 (q, J=5.02 Hz, 1H), 3.59 (q, J=5.27 Hz, 1H), 2.16 (s, 3H). MS: 437.92 (M⁺).

4-{[4-(Acetylamino)-1H-pyrrolo[3,2-c]pyridin-1-yl]carbonyl}-3,5-dichloro-N-(pyridin-2-ylmethyl)benzamide (Compound No. 160)

¹H NMR (400 MHz, DMSO-d₆): δ 10.61 (s, 1H), 9.52 (t, J=6.02 Hz, 1H), 8.54 (d, J=4.27 Hz, 1H), 8.36 (d, J=5.77 Hz, 1H), 8.19-8.23 (m, 3H), 7.75-7.83 (m, 1H), 7.39 (d, J=7.78 Hz, 1H), 7.34 (d, J=4.02 Hz, 1H), 7.27-7.32 (m, 1H), 6.78 (d, J=3.76 Hz, 1H), 4.62 (d, J=5.77 Hz, 2H), 2.16 (s, 3H). MS: 482.31 (M⁺).

4-{[4-(Acetylamino)-1H-pyrrolo[3,2-c]pyridin-1-yl]carbonyl}-3,5-dichloro-N-[2-(1H-indol-3-yl)ethyl]benzamide (Compound No. 158)

¹H NMR (400 MHz, DMSO-d₆): δ 10.86 (br. s., 1H), 10.61 (br. s., 1H), 9.01 (br. s., 1H), 8.36 (d, J=5.27 Hz, 1H), 8.21 (d, J=5.27 Hz, 1H), 8.12 (s, 2H), 7.59 (d, J=7.53 Hz, 1H), 7.29-7.39 (m, 2H), 7.22 (br. s., 1H), 7.07 (d, J=7.53 Hz, 1H), 7.01 (d, J=8.03 Hz, 1H), 6.79 (br. s., 1H), 5.76 (s, 1H), 3.60 (t., 2H), 2.98 (t, 2H), 2.16 (. s., 3H). MS: 534.39 (M⁺).

4-{[4-(Acetylamino)-1H-pyrrolo[3,2-c]pyridin-1-yl]carbonyl}-3,5-dichloro-N-[2-(pyridin-2-yl)ethyl]benzamide (Compound No. 161)

¹H NMR (400 MHz, DMSO-d₆): δ 10.60 (s, 1H), 8.97 (t, J=5.27 Hz, 1H), 8.52 (d, J=4.02 Hz, 1H), 8.36 (d, J=5.77 Hz,

1H), 8.20 (d, J=6.27 Hz, 1H), 8.10 (s, 2H), 7.73 (dt, J=2.01, 7.65 Hz, 1H), 7.29-7.33 (m, 2H), 7.24 (dd, J=4.77, 7.53 Hz, 1H), 6.78 (d, J=3.76 Hz, 1H), 3.64-3.71 (m, 2H), 3.03 (t, J=7.40 Hz, 2H), 2.16 (s, 3H). MS: 497.06 (M+1).

4-{[4-(Acetylamino)-1H-pyrrolo[3,2-c]pyridin-1-yl]carbonyl}-3,5-dichloro-N-(2,3-dihydroxypropyl)benzamide $^1$H NMR (400 MHz, DMSO-d$_6$): δ 10.61 (s, 1H), 8.81 (t, J=5.65 Hz, 1H), 8.36 (d, J=5.77 Hz, 1H), 8.20 (d, J=5.52 Hz, 1H), 8.15 (s, 2H), 7.30 (d, J=4.02 Hz, 1H), 6.78 (d, J=3.76 Hz, 1H), 4.87 (d, J=5.02 Hz, 1H), 4.61 (t, J=5.77 Hz, 1H), 3.63-3.71 (m, 1H), 2.16 (s, 3H). MS: 466.01 (M+1).

Example 31

Synthesis of 3,5-dichloro-N-ethyl-4-{[4-(propanoylamino)-1H-pyrrolo[3,2-c]pyridin-1-yl]carbonyl}benzamide (Compound No. 138)

Step a: Synthesis of N-(1H-pyrrolo[3,2-c]pyridin-4-yl)propanamide

This was prepared by treating benzyl 4-amino-1H-pyrrolo[3,2-c]pyridine-1-carboxylate with propionyl chloride following a procedure similar to the one described herein. for intermediate 28.
MS: 379.06 (M$^+$)

Step b: Synthesis of methyl 3,5-dichloro-4-{[4-(propanoylamino)-1H-pyrrolo[3,2-c]pyridin-1-yl]carbonyl}benzoate A stirred solution of 2,6-dichloro-4-(methoxycarbonyl)benzoic acid (600 mg, 2.3 mmol), in dimethylacetamide (10 mL) was treated with 2-(1H-7-azabenzotriazol-1-yl)-1,1,3,3-tetramethyl uronium hexafluorophosphate methanaminium (1300 mg, 3.45 mmol), 1-hydroxy-7-azabenzotriazole (469 mg, 3.45 mmol), N,N-diisopropylethylamine (1.05 mL, 5.75 mmol) and dimethylaminopyridine (140 mg, 1.15 mmol) were added and the mixture was stirred at room temperature for about 1 hour. This was followed by addition of N-(1H-pyrrolo[3,2-c]pyridin-4-yl)propanamide (450 mg, 2.3 mmol) and stirring at room temperature for about 16 hours. The reaction mixture was poured into water (150 mL) and extracted with ethyl acetate (2×50 mL). The combined organic layer was washed with brine (100 mL) and organic layer was separated and dried over anhydrous sodium sulphate to give crude product which was purified by silica gel (100-200 mesh size) column chromatography using ethylacetate and hexane as eluting system to give pure methyl 3,5-dichloro-4-{[4-(propanoylamino)-1H-pyrrolo[3,2-c]pyridin-1-yl]carbonyl}benzoate. (250 mg, 25%)

Step c: Synthesis of 3,5-dichloro-4-{[4-(propanoylamino)-1H-pyrrolo[3,2-c]pyridin-1-yl]carbonyl}benzoic acid A mixture of methyl 3,5-dichloro-4-{[4-(propanoylamino)-1H-pyrrolo[3,2-c]pyridin-1-yl]carbonyl}benzoate (250 mg, 0.59 mmol) and sodium hydroxide (23 mg, 0.59 mmol) in tetrahydrofuran and water (1:1) was stirred at room temperature for about 1 hour. Tetrahydrofuran was removed in vaccuo and aqueous layer was diluted with water (5 mL) and acidified with hydrochloric acid (2N, up to pH 2). The solid thus obtained was filtered and dried to afford 3,5-dichloro-4-{[4-(propanoylamino)-1H-pyrrolo[3,2-c]pyridin-1-yl]carbonyl}benzoic acid (170 mg, 70%). The material was taken as such for the next step.

Step d: Synthesis of 3,5-dichloro-N-methyl-4-{[4-(propanoylamino)-1H-pyrrolo[3,2-c]pyridin-1-yl]carbonyl}benzamide A solution of 3,5-dichloro-4-{[4-(propanoylamino)-1H-pyrrolo[3,2-c]pyridin-1-yl]carbonyl}benzoic acid (50 mg, 0.123 mmol) in anhydrous dimethylformamide (5 mL) was treated with 1-ethyl-3-(3-dimethylaminopropyl)carbodiimide (36 mg, 0.184 moles), Hunig's base (24 mg, 0.185 mmol), 47 mg (0.369 mmol) and ethylamine (0.05 mL, 2N tetrahydrofuran solution, 0.123 mmol) of methylamine. The resulting mixture was stirred at room temperature for about 16 hours. The reaction mixture was poured in water (25 mL) and extracted with ethyl acetate (3×20 mL). The combined organic layer was washed with brine (30 mL), dried over anhydrous sodium sulphate and concentrated to give crude product which was purified using column chromatography with ethyl acetate hexane as eluent (13 mg, 21%). 1H NMR (400 MHz, DMSO-d$_6$): δ 10.55 (s, 1H), 8.86 (t, J=5.40 Hz, 1H), 8.36 (d, J=5.52 Hz, 1H), 8.17-8.24 (m, 1H), 8.13 (s, 2H), 7.25-7.34 (m, 1H), 6.75 (d, J=4.02 Hz, 1H), 3.36-3.42 (m, 2H), 2.42-2.48 (m, 2H), 1.05-1.19 (m, 6H). MS: 433.89 (M$^+$).

The following compound was prepared in an analogous fashion using methylamine.

3,5-Dichloro-N-methyl-4-{[4-(propanoylamino)-1H-pyrrolo[3,2-c]pyridin-1-yl]carbonyl}benzamide (Compound No. 140)

$^1$H NMR (400 MHz, DMSO-d$_6$): δ 10.54 (s, 1H), 8.84 (d, J=4.77 Hz, 1H), 8.36 (d, J=5.52 Hz, 1H), 8.16-8.23 (m, 1H), 8.11 (s, 2H), 7.29 (d, J=3.76 Hz, 1H), 6.76 (d, J=3.76 Hz, 1H), 2.84 (d, J=4.52 Hz, 3H), 1.04-1.17 (m, 3H). MS: 419.91 (M$^+$).

Example 32

Synthesis of N-(2-aminoethyl)-3,5-dichloro-4-({4-[(cyclopropylcarbonyl)amino]-1H-pyrrolo[3,2-c]pyridin-1-yl}carbonyl)benzamide (Compound No. 127)

Step a: Synthesis of tert-butyl {2-[(3,5-dichloro-4-{[4-(cyclopropylcarbonyl)-1H-pyrrolo[3,2-c]pyridin-1-yl]carbonyl}benzoyl)amino]ethyl}carbamate To the stirred mixture of 3,5-dichloro-4-{[4-(cyclopropylcarbonyl)-1H-pyrrolo[3,2-c]pyridin-1-yl]carbonyl}benzoic acid (50 mg, 0.119 mmol), 1-ethyl-3-(3-dimethylaminopropyl)carbodiimide (26.8 mg, 0.14 mmol) and 1-hydroxybenzotriazole (19 mg, 0.14 mmol) in N,N-dimethylformamide, was added tert-butyl(2-aminoethyl)carbamate (19 mg, 0.119 mmol). The reaction mixture was stirred at room temperature for about 16 hours. The reaction mixture was poured drop wise into cold saturated solution of sodium bicarbonate. The precipitated solid was filtered, washed with water and dried. Purification by preparative thin layer chromatography (2% methanol and dichloromethane as eluent) afforded tert-butyl {2-[(3,5-dichloro-4-{[4-(cyclopropylcarbonyl)-1H-pyrrolo[3,2-c]pyridin-1-yl]carbonyl}benzoyl)amino]ethyl}carbamate (23 mg, 35%).
$^1$H NMR (400 MHz, DMSO-d$_6$): δ 10.89 (s, 1H), 8.86 (s, 1H), 8.37 (d, J=5.56 Hz, 1H), 8.21 (d, J=6.06 Hz, 1H), 8.10 (s, 2H), 7.25 (d, J=4.04 Hz, 1H), 6.97 (s, 1H), 6.73 (d, J=3.79 Hz, 1H), 3.13 (d, J=6.06 Hz, 2H), 2.05 (s, 1H), 1.38 (s, 9H), 0.84-0.88 (m, 4H).

Step b: Synthesis of N-(2-aminoethyl)-3,5-dichloro-4-({4-[(cyclopropylcarbonyl)amino]-1H-pyrrolo[3,2-c]pyridin-1-yl}carbonyl)benzamide A solution of tert-butyl {2-[(3,5-dichloro-4-{[4-(cyclopropylcarbonyl)-1H-pyrrolo[3,2-c]pyridin-1-yl]carbonyl}benzoyl)amino]ethyl}carbamate (20 mg, 0.035 mmol) in dichloromethane (5 mL) was treated dropwise with trifluoroacetic acid (0.1 mL). The resulting reaction mixture was stirred at room temperature for about 1 hour, concentrated under vacuum and residue was neutralized using saturated sodium bicarbonate solution. Precipitated solid was filtered, washed with water and dried to get N-(2-aminoethyl)-3,5-dichloro-4-({4-[(cyclopropylcarbonyl)amino]-1H-pyrrolo[3,2-c]pyridin-1-yl}carbonyl)benzamide (11 mg, 73%).

$^1$H NMR (400 MHz, DMSO-d$_6$): δ 10.83-10.92 (m, 1H), 8.79 (br. s., 1H), 8.37 (d, J=5.56 Hz, 2H), 8.21 (d, J=5.56 Hz, 3H), 8.12-8.15 (m, 2H), 7.27 (d, J=4.04 Hz, 1H), 6.72 (d, J=4.04 Hz, 1H), 3.12 (br. s., 1H), 2.65-2.73 (m, 2H), 2.01-2.09 (m, 1H), 0.82-0.88 (m, 4H). MS 460.31 (M$^+$).

Example 33

Synthesis of N-[3,5-dichloro-4-({4-[(cyclopropylcarbonyl)amino]-1H-pyrrolo[3,2-c]pyridin-1-yl}carbonyl)benzoyl]alanine (Compound No. 152)

A mixture of ethyl N-[3,5-dichloro-4-({4-[(cyclopropylcarbonyl)amino]-1H-pyrrolo[3,2-c]pyridin-1-yl}carbonyl)benzoyl]alaninate (20 mg, 0.038 mmol) in tetrahydrofuran and water (1:1, 1 mL) was treated with sodium hydroxide (1.5 mg) and stirred at room temperature for about 1 hour. Tetrahydrofuran was removed under vaccuo and the residue was acidified with hydrochloric acid solution (1N, up to pH 2). The solid was filtered and dried to get pure N-[3,5-dichloro-4-({4-[(cyclopropylcarbonyl)amino]-1H-pyrrolo[3,2-c]pyridin-1-yl}carbonyl)benzoyl]alanine (12 mg, 66%).

1H NMR (400 MHz, DMSO-d6): δ 12.57-12.88 (m, 1H), 10.80-11.10 (m, 1H), 9.09 (d, J=6.78 Hz, 1H), 8.37 (d, J=5.77 Hz, 1H), 8.14-8.28 (m, 3H), 7.34 (d, J=3.76 Hz, 1H), 6.75 (br. s., 1H), 4.46 (s, 1H), 2.06 (s, 1H), 1.43 (d, J=7.28 Hz, 3H), 0.82-0.88 (m, 4H). MS: 490.07 (M+1).

Example 34

Synthesis of N-(1-{2,6-dichloro-4-[(methylamino)methyl]benzoyl}-1H-pyrrolo[3,2-c]pyridin-4-yl)cyclopropanecarboxamide (Compound No. 163)

Step a: Synthesis of N-{1-[4-(bromomethyl)-2,6-dichlorobenzoyl]-1H-pyrrolo[3,2-c]pyridin-4-yl}cyclopropanecarboxamide A solution of N-{1-[2,6-dichloro-4-(hydroxymethyl)benzoyl]-1H-pyrrolo[3,2-c]pyridin-4-yl}cyclopropanecarboxamide (0.37 mmol) in dichloromethane was cooled to 0° C. and was treated dropwise with phosphorous tribromide (0.74 mmol). The reaction mixture was then stirred at room temperature for about 2 hours, diluted with dichloromethane and washed with saturated sodium bicarbonate solution. The organic layer was separated, dried over anhydrous sodium sulfate and concentrated to get N-{1-[4-(bromomethyl)-2,6-dichlorobenzoyl]-1H-pyrrolo[3,2-c]pyridin-4-yl}cyclopropanecarboxamide as white solid.

$^1$H NMR (400 MHz, DMSO-d$_6$): δ 10.89 (s, 1H), 8.36 (d, J=5.77 Hz, 1H), 8.20 (d, J=6.27 Hz, 1H), 7.84-7.88 (m, 2H), 7.22 (d, J=4.02 Hz, 1H), 6.72 (d, J=4.02 Hz, 1H), 4.78 (s, 2H), 2.05 (quin, J=5.90 Hz, 1H), 0.82-0.88 (m, 4H). MS: 467.15 (M$^+$).

Step b: Synthesis of N-{1-(2,6-dichloro-4-[(methylamino)methyl]benzoyl}-1H-pyrrolo[3,2-c]pyridin-4-yl)cyclopropanecarboxamide A solution of N-{1-[4-(bromomethyl)-2,6-dichlorobenzoyl]-1H-pyrrolo[3,2-c]pyridin-4-yl}cyclopropanecarboxamide (50 mg, 0.107 mmol) in acetonitrile was treated with cesium carbonate (69.74 mg, 0.2140 mmol) and stirred for about 15 minutes. The mixture was cooled to 0° C. followed by the portion wise addition of methyl amine (10.68 mg, 0.16 mmol). The reaction mixture was then stirred at room temperature for about 20 minutes and concentrated under vacuum, followed by addition of ice cold water to give N-(1-{2,6-dichloro-4-[(methylamino)methyl]benzoyl}-1H-pyrrolo[3,2-c]pyridin-4-yl)cyclopropanecarboxamide (27.5 mg) as white solid.

$^1$H NMR (400 MHz, DMSO-d$_6$): δ 10.88 (s, 1H), 8.36 (d, J=5.77 Hz, 1H), 8.20 (d, J=5.52 Hz, 1H), 7.67 (s, 2H), 7.15 (d, J=4.02 Hz, 1H), 6.72 (d, J=3.76 Hz, 1H), 3.75 (s, 2H), 2.24-2.35 (m, 3H), 1.98-2.10 (m, 1H), 0.82-0.88 (m, 4H). MS: 417.28 (M$^+$).

The following compounds were prepared in an analogous manner using appropriate amine starting materials.

N-(1-{2,6-Dichloro-4-[(ethylamino)methyl]benzoyl}-1H-pyrrolo[3,2-c]pyridin-4-yl)cyclopropanecarboxamide (Compound No. 164)

$^1$H NMR (400 MHz, DMSO-d$_6$): δ 10.88 (s, 1H), 8.35 (d, J=5.52 Hz, 1H), 8.20 (d, J=5.77 Hz, 1H), 7.67 (s, 2H), 7.15 (d, J=3.76 Hz, 1H), 6.72 (d, J=3.76 Hz, 1H), 3.79 (s, 2H), 2.3-2.75 (m, 2H), 1.99-2.11 (m, 1H), 1.00-1.09 (m, 3H), 0.82-0.88 (m, 4H). MS: 431.31 (M$^+$).

N-{1-[2,6-Dichloro-4-({[2-(2-oxoimidazolidin-1-yl)ethyl]amino}methyl)benzoyl]-1H-pyrrolo[3,2-c]pyridin-4-yl}cyclopropanecarboxamide (Compound No. 165)

$^1$H NMR (400 MHz, DMSO-d$_6$): δ 10.88 (s, 1H), 8.35 (d, J=5.77 Hz, 1H), 8.20 (d, J=5.52 Hz, 1H), 7.67 (s, 1H), 7.16 (d, J=3.76 Hz, 1H), 6.71 (d, J=3.76 Hz, 1H), 6.27 (s, 1H), 3.81 (s, 1H), 3.18-3.27 (m, 2H), 3.14 (t, J=6.40 Hz, 2H), 3.14 (t, J=6.40 Hz, 2H), 3.14 (t, J=6.40 Hz, 2H), 2.57-2.68 (m, 2H), 1.99-2.10 (m, 1H), 0.82-0.88 (m, 4H). MS: 516.08 (M$^+$).

N-{1-[2,6-Dichloro-4-({[3-(morpholin-4-yl)propyl]amino}methyl)benzoyl]-1H-pyrrolo[3,2-c]pyridin-4-yl}cyclopropanecarboxamide (Compound No. 166)

$^1$H NMR (400 MHz, DMSO-d$_6$): δ10.88 (br. s., 1H), 8.36 (d, J=5.52 Hz, 1H), 8.20 (d, J=5.77 Hz, 1H), 7.67 (s, 2H), 7.14 (d, J=3.76 Hz, 1H), 6.72 (d, J=3.51 Hz, 1H), 3.79 (s, 2H), 3.56 (t, J=4.27 Hz, 5H), 2.28-2.38 (m, 7H), 1.99-2.10 (m, 1H), 1.53-1.65 (m, 2H), 0.82-0.88 (m, 4H). MS: 530.44 (M$^+$).

N-[1-(2,6-Dichloro-4-{[(3-hydroxypropyl)amino]methyl}benzoyl)-1H-pyrrolo[3,2-c]pyridin-4-yl]cyclopropanecarboxamide (Compound No. 167)

$^1$H NMR (400 MHz, DMSO-d$_6$): δ 10.88 (s, 1H), 8.35 (d, J=5.52 Hz, 1H), 8.20 (d, J=5.77 Hz, 1H), 7.67 (s, 2H), 7.14 (d, J=4.02 Hz, 1H), 6.72 (d, J=3.76 Hz, 1H), 4.44 (br. s., 1H), 3.79 (s, 2H), 3.48 (t, J=6.15 Hz, 2H), 2.56 (t, J=6.78 Hz, 2H), 2.01-2.08 (m, 1H), 1.55-1.65 (m, 2H), 0.82-0.94 (m, 4H). MS: 461.34 (M$^+$).

Example 35

Synthesis of 3,5-dichloro-4-({3-chloro-4-[(cyclopropylcarbonyl)amino]-1H-pyrrolo[3,2-c]pyridin-1-yl}carbonyl)-N-methylbenzamide (Compound No. 153)

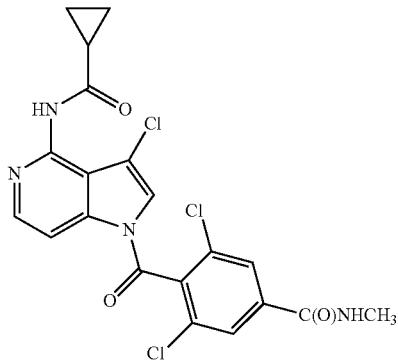

A well stirred mixture of 2,6-dichloro-4-(methylcarbamoyl)benzoic acid (60 mg, 0.25 mmol), 1-hydroxy-7-azabenzotriazole (51.86 mg, 0.38 mmol), N,N-dimethyl aminopyridine (15.50 mg, 0.127 mmol), and 2-(1H-7-azabenzotriazol-1-yl)-1,1,3,3-tetramethyl uronium hexafluorophosphate methanaminium (145 mg, 0.38 mmol) in dimethylamine was treated with N-(1H-pyrrolo[3,2-c]pyridin-4-yl)cyclopropanecarboxamide (63 mg, 0.25 mmol) and N, N-diisopropylethyl amine (0.06 mL, 0.38 mmol). The reaction mixture was stirred overnight at room temperature. The contents were diluted with water and extracted with ethyl acetate. The combined organic portion was washed with brine, dried over sodium sulfate, filtered and concentrated. The crude product was purified by silica gel column chromatography and eluted with 3% methanol and dichlorometane to afford 3,5-dichloro-4-({3-chloro-4-[(cyclopropylcarbonyl)amino]-1H-pyrrolo[3,2-c]pyridin-1-yl}carbonyl)-N-methylbenzamide (28.4 mg, 24.13%) as an off white solid.

$^1$H NMR (400 MHz, DMSO-d$_6$): δ 10.61 (s, 1H), 8.81 (d, J=4.02 Hz, 1H), 8.48 (d, J=5.77 Hz, 1H), 8.31 (d, J=5.77 Hz, 1H), 8.09 (s, 2H), 7.80 (s, 1H), 2.84 (d, J=4.27 Hz, 3H), 1.90-2.05 (m, 1H), 0.72-0.90 (m, 4H). MS: 465.73 (M$^+$).

3,5-Dichloro-4-({3-chloro-4-[(cyclopropylcarbonyl)amino]-1H-pyrrolo[3,2-c]pyridin-1-yl}carbonyl)-N-ethylbenzamide (Compound No. 136) was prepared from 1H-pyrrolo[3,2-c]pyridine and 2,6-dichloro-4-(ethylcarbamoyl)benzoic acid using analogous procedure.

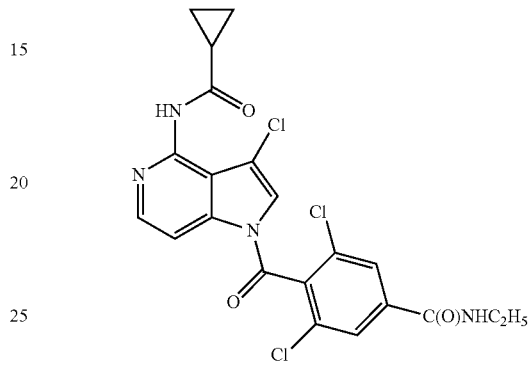

$^1$H NMR (400 MHz, DMSO-d$_6$): δ 10.65 (s, 1H), 8.85 (t, J=5.40 Hz, 1H), 8.48 (d, J=5.77 Hz, 1H), 8.32 (d, J=5.52 Hz, 1H), 8.07-8.15 (m, 2H), 7.82 (s, 1H), 1.86-1.93 (m, 1H), 1.16 (t, J=7.28 Hz, 3H), 0.72-0.90 (m, 4H). MS: 479.75 (M$^+$).

Janus Kinase inhibitors of formula (I) as exemplified herein are shown in Table 1 and 2.

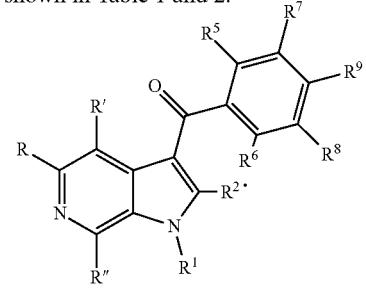

TABLE 1

| | | | | |
|---|---|---|---|---|
| R = R' = R$^1$ = R$^7$ = R$^8$ = H | | | | |
| Compound No. | R" | R$^5$ | R$^6$ | R$^9$ |
| 1 | H | F | Cl | H |
| 2 | H | Cl | Cl | —C(O)NHC$_2$H$_5$ |
| 3 | H | Cl | Cl | NH$_2$ |
| 4 | H | Cl | Cl | 2-methoxypyrimidin-5-yl |
| 5 | —NHC(O)-cyclopropyl | Cl | Cl | H |
| 6 | H | Cl | Cl | CN |
| 7 | —NHC(O)CH$_3$ | Cl | Cl | —C(O)NHCH$_3$ |
| 8 | —NHC(O)CH$_3$ | Cl | F | H |
| 9 | —NHC(O)CH$_3$ | Cl | Cl | —C(O)NHC$_2$H$_5$ |
| 10 | H | Cl | Cl | Br |
| 11 | —NHC(O)-cyclopropyl | Cl | F | H |
| 12 | —NHC(O)-cyclopropyl | Cl | Cl | —C(O)NHCH$_3$ |
| 13 | —NHC(O)-cyclopropyl | Cl | Cl | —C(O)NHC$_2$H$_5$ |
| 14 | H | Cl | Cl | —CONH(CH$_2$)$_2$OCH$_3$ |
| 15 | —NHC(O)CH$_3$ | Cl | Cl | —C(O)NHC$_3$H$_7$ |
| 16 | —NHC(O)-cyclopropyl | Cl | Cl | —C(O)NH(CH$_2$)$_2$OCH$_3$ |
| 17 | —NHC(O)CH$_3$ | Cl | Cl | —C(O)NH(CH$_2$)$_2$OCH$_3$ |
| 21 | —NHC(O)CH$_3$ | Cl | Cl | CN |
| 22 | —NHC(O)-cyclopropyl | Cl | Cl | Br |

TABLE 1-continued

| Compound No. | R″ | $R^5$ | $R^6$ | $R^9$ |
|---|---|---|---|---|
| 23 | —NHC(O)-cyclopropyl | Cl | Cl | 3,5-dimethyl-1,2-oxazol-4-yl |
| 24 | —NHC(O)$CH_3$ | Cl | Cl | Br |
| 25 | —NHC(O)-cyclopropyl | Cl | Cl | —C(O)O$CH_3$ |
| 26 | —NHC(O)-cyclopropyl | Cl | Cl | —$NH_2$ |
| 27 | —NHC(O)-cyclopropyl | Cl | Cl | —NHC(O)$CH_3$ |
| 28 | —NHC(O)$C_2H_5$ | Cl | F | H |
| 29 | —NHC(O)-cyclopropyl | Cl | Cl | —C(O)NH($CH_2$)$_2$O($CH_2$)$_2$OH |
| 30 | —NHC(O)-cyclopropyl | Cl | Cl | —C(O)NH($CH_2$)$_3$OH |
| 31 | —NHC(O)-cyclopropyl | Cl | Cl | —C(O)NH($CH_2$)$_3$(morpholin-4-yl) |
| 32 | —NHC(O)-cyclopropyl | Cl | Cl | —C(O)NH$CH_2$C(OH)$CH_2$OH |
| 33 | —NHC(O)-cyclopropyl | Cl | Cl | —C(O)NH($CH_2$)$_2$N($CH_3$)$_2$ |
| 34 | —NHC(O)-cyclopropyl | Cl | Cl | —C(O)NH($CH_2$)$_2$(piperidin-1-yl) |
| 35 | —NHC(O)-cyclopropyl | Cl | Cl | —C(O)NH$CH_2$C(O)O$CH_3$ |
| 36 | —NHC(O)-cyclopropyl | Cl | Cl | —C(O)NH$CH_2$C(O)OH |
| 38 | —NHC(O)$C_2H_5$ | Cl | Cl | —C(O)NH$CH_3$ |
| 39 | —NHCO-cyclopropyl | Cl | Cl | CN |
| 40 | —NHC(O)$CH_3$ | Cl | Cl | —C(O)NH($CH_2$)$_2$N($CH_3$)$_2$ |
| 41 | —NHC(O)$CH_3$ | Cl | Cl | —C(O)NH($CH_2$)$_2$O($CH_2$)$_2$OH |
| 42 | —NHC(O)$CH_3$ | Cl | Cl | —C(O)NH($CH_2$)$_2$(piperidin-1-yl) |
| 43 | —NHC(O)$CH_3$ | Cl | Cl | —C(O)NH($CH_2$)$_2$(morpholin-4-yl) |
| 44 | —NHC(O)$CH_3$ | Cl | Cl | —C(O)NH($CH_2$)$_2$(pyrrolidin-1-yl) |
| 45 | —NHC(O)-cyclopropyl | Cl | Cl | Cl |
| 46 | —NHC(O)-cyclopropyl | Cl | Cl | 3,5-dimethyl-1H-pyrazol-4yl |
| 47 | —NHC(O)-cyclopropyl | Cl | Cl | Pyrimidin-5-yl |
| 48 | —NHC(O)-cyclopropyl | Cl | Cl | 6-methoxypyridin-3-yl |
| 49 | —NHC(O)-cyclopropyl | Cl | Cl | 6-fluoropyridin-3-yl |
| 50 | —NHC(O)-cyclopropyl | Cl | Cl | 1-methyl-1H-pyrazol-4-yl |
| 51 | —NHC(O)-cyclopropyl | F | F | CN |
| 52 | —NHC(O)-cyclopropyl | F | F | —C(O)O$CH_3$ |
| 53 | —NHC(O)$CH_3$ | F | F | CN |
| 54 | —NHC(O)-cyclopropyl | Cl | Cl | —C(O)NH-cyclopropyl |
| 55 | —NHC(O)-cyclopropyl | Cl | Cl | —C(O)NH$CH_2$-cyclopropyl |
| 56 | —NHC(O)-cyclopropyl | Cl | Cl | —C(O)NH($CH_2$)$_3$O$C_2H_5$ |
| 57 | —NHC(O)-cyclopropyl | Cl | Cl | —C(O)NH($CH_2$)$_3$$CH_3$ |
| 58 | —NHC(O)-cyclopropyl | Cl | Cl | —$CH_2$OH |
| 59 | —NHC(O)-cyclopropyl | F | F | —C(O)NH($CH_2$)$_2$F |
| 60 | —NHC(O)-cyclopropyl | F | F | —C(O)NH$C_2H_5$ |
| 61 | —NHC(O)-cyclopropyl | F | F | —C(O)NH$CH_3$ |
| 62 | —NHC(O)-cyclopropyl | F | F | —C(O)NH($CH_2$)$_3$OH |
| 63 | —NHC(O)-cyclopropyl | F | F | —CONH($CH_2$)$_2$N($CH_3$)$_2$ |
| 64 | —NHC(O)-cyclopropyl | F | F | —C(O)NH($CH_2$)$_3$O$C_2H_5$ |
| 65 | —NHC(O)-cyclopropyl | F | F | 3,5-dimethyl-1,2-oxazol-4-yl |
| 66 | —NHC(O)-cyclopropyl | Cl | Cl | —$CH_2$NH$CH_3$ |
| 67 | —NHC(O)-cyclopropyl | Cl | Cl | —$CH_2$NH$C_2H_5$ |
| 69 | —NHC(O)-cyclopropyl | F | F | Br |

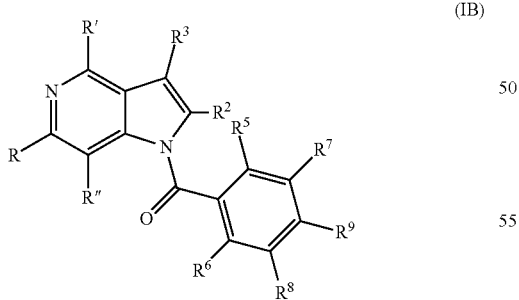

(IB)

TABLE 2

| Compound No. | R′ | $R^5$ | $R^6$ | $R^9$ |
|---|---|---|---|---|
| 72 | H | Cl | Cl | —C(O)NH$CH_3$ |
| 73 | H | Cl | Cl | —C(O)NH$C_2H_5$ |

TABLE 2-continued

R = R'' = R³ = R⁷ = R⁸ = H

| Compound No. | R' | R⁵ | R⁶ | R⁹ |
|---|---|---|---|---|
| 74 | —NHC(O)OCH₃ | Cl | Cl | H |
| 75 | H | Cl | Cl | —C(O)NH(CH₂)₂OH |
| 76 | H | Cl | Cl | —CONHCH₂CN |
| 77 | —NHC(O)-cyclopropyl | Cl | Cl | H |
| 78 | H | Cl | Cl | —NHC(O)NHC₂H₅ |
| 79 | H | Cl | Cl | —NHC(O)OCH₃ |
| 80 | H | Cl | Cl | —NHC(O)NH(CH₂)₂OH |
| 81 | H | Cl | Cl | —NHC(O)N(CH₃)₂ |
| 82 | H | Cl | Cl | —NHC(O)CH₂CN |
| 83 | H | Cl | Cl | —(CH=CH)C(O)NH₂ |
| 84 | H | Cl | Cl | —(CH=CH)CN |
| 85 | —N(C(O)-cyclopropyl)₂ | Cl | Cl | CN |
| 86 | —NHC(O)-cyclopropyl | Cl | Cl | CN |
| 87 | —NHC(O)-cyclopropyl | Cl | Cl | 3,5-dimethyl-1,2-oxazol-4-yl |
| 88 | —NHC(O)-cyclopropyl | Cl | Cl | 3,5-dimethyl-1H-pyrazol-4-yl |
| 89 | —NHC(O)-cyclopropyl | Cl | Cl | Pyrimidin-5-yl |
| 90 | H | Cl | Cl | —CH₂OH |
| 91 | —NHC(O)-cyclopropyl | Cl | Cl | —C(O)NH(CH₂)₂OH |
| 92 | —NHC(O)CH₃ | Cl | Cl | —C(O)NHC₂H₅ |
| 93 | —NHC(O)-cyclopropyl | Cl | Cl | —C(O)NHC₂H₅ |
| 94 | H | Cl | Cl | —NHC(O)CH₂F |
| 95 | H | Cl | Cl | CN |
| 96 | —NHC(O)-cyclopropyl | Cl | Cl | —CH₂OH |
| 97 | —NHC(O)CH₃ | Cl | Cl | —CH₂OH |
| 98 | —NHC(O)-cyclopropyl | Cl | Cl | —C(O)NH(CH₂)₂OCH₃ |
| 99 | —NHC(O)CH₃ | Cl | Cl | CN |
| 100 | —NHC(O)-cyclopropyl | Cl | Cl | —C(O)NH₂ |
| 101 | —NHC(O)CH₃ | Cl | Cl | —C(O)NH(CH₂)₂OCH₃ |
| 102 | —NHC(O)OCH₃ | Cl | F | H |
| 103 | —NHC(O)-cyclopropyl | Cl | Cl | —NHC(O)NHC₂H₅ |
| 104 | H | Cl | Cl | —NHC(O)NH(CH₂)₂OCH₃ |
| 105 | —NHC(O)CH₃ | Cl | Cl | —C(O)NHCH₃ |
| 106 | —NHC(O)-cyclopropyl | Cl | Cl | —C(O)NHCH₃ |
| 107 | —NHC(O)-cyclopropyl | Cl | Cl | —C(O)NHCH(CH₃)₂ |
| 108 | —NHC(O)OCH₃ | Cl | Cl | —C(O)NHC₂H₅ |
| 109 | —NHC(O)-cyclopropyl | Cl | Cl | —NHC(O)-cyclopropyl |
| 110 | —NHC(O)-cyclopropyl | Cl | Cl | —NHC(O)CH₃ |
| 111 | —NHC(O)-cyclopropyl | Cl | Cl | —NHC(O)NH(CH₂)₂OCH₃ |
| 112 | —NHC(O)-cyclopropyl | Cl | Cl | —NHC(O)N(CH₃)(CH₂)₂OH |
| 113 | —NHC(O)-cyclopropyl | Cl | Cl | —NHC(O)NH-cyclopropyl |
| 114 | —NHC(O)CH₃ | Cl | Cl | —NHC(O)NH-cyclopropyl |
| 115 | —NHC(O)CH₃ | Cl | Cl | —NHC(O)NH(CH₂)₂OH |
| 116 | —NHC(O)CH₃ | Cl | Cl | —NHC(O)NH(CH₂)₂OH |
| 117 | —NHC(O)CH₃ | Cl | Cl | —NHC(O)NHC₂H₅ |
| 121 | —NHC(O)-cyclopropyl | Cl | Cl | —C(O)OCH₃ |
| 122 | —NHC(O)-cyclopropyl | Cl | Cl | —C(O)NH(CH₂)₂N(CH₃)₂ |
| 123 | —NHC(O)-cyclopropyl | Cl | Cl | —C(O)NH(CH₂)₃OH |
| 124 | —NHC(O)-cyclopropyl | Cl | Cl | —C(O)NH(CH₂)₂O(CH₂)₂OH |
| 125 | —NHC(O)-cyclopropyl | Cl | Cl | —C(O)NH(CH₂)₂(morpholin-4-yl) |
| 126 | —NHC(O)-cyclopropyl | Cl | Cl | —C(O)NH(CH₂)₂C(O)OC₂H₅ |
| 127 | —NHC(O)-cyclopropyl | Cl | Cl | —C(O)NH(CH₂)₂NH₂ |
| 128 | —NHC(O)CH₃ | Cl | Cl | —C(O)NH(CH₂)₂N(CH₃)₂ |
| 129 | —NHC(O)CH₃ | Cl | Cl | —C(O)NH(CH₂)₂C(O)OC₂H₅ |
| 131 | —NHC(O)-cyclopropyl | Cl | Cl | —C(O)NH(CH₂)₃OCH₃ |
| 132 | —NHC(O)-cyclopropyl | Cl | Cl | —C(O)NH-cyclobutyl |
| 133 | —NHC(O)-cyclopropyl | Cl | Cl | —C(O)NH(CH₂)₂CH₃ |
| 134 | —NHC(O)CH₃ | Cl | Cl | —C(O)NH(CH₂)₃OCH₃ |
| 135 | —NHC(O)-cyclopropyl | Cl | Cl | —C(O)NH(CH₂)₂COOH |
| 138 | —NHC(O)C₂H₅ | Cl | Cl | —C(O)NHC₂H₅ |
| 139 | —NHC(O)-cyclopropyl | Cl | Cl | —C(O)NH(CH₂)₂-(IH-indol-3-yl) |
| 140 | —NHC(O)C₂H₅ | Cl | Cl | —C(O)NHCH₃ |
| 141 | —NHC(O)-cyclopropyl | Cl | Cl | —C(O)NHCH(CH₃)C(O)OC₂H₅ |
| 142 | —NHC(O)-cyclopropyl | Cl | Cl | —C(O)NH(CH₂)₂(2-oxoimidazolidin-1-yl) |
| 143 | —NHC(O)-cyclopropyl | Cl | Cl | —C(O)NHCH₂CH(OH)CH₂OH |
| 144 | —NHC(O)-cyclopropyl | Cl | Cl | —C(O)NH(CH₂)₂-(thiophen-2-yl) |
| 145 | —NHC(O)-cyclopropyl | Cl | Cl | —C(O)NH(CH₂)₂-(pyridin-4-yl) |
| 146 | —NHC(O)-cyclopropyl | Cl | Cl | —C(O)NH-cyclopropyl |
| 147 | —NHC(O)-cyclopropyl | Cl | Cl | —C(O)NHCH₂-(pyridin-2-yl) |
| 148 | —NHC(O)-cyclopropyl | Cl | Cl | —C(O)NH(CH₂)₂-(pyrrolidin-1-yl) |
| 149 | —NHC(O)-cyclopropyl | Cl | Cl | —C(O)NH(CH₂)₃-(morpholin-4-yl) |
| 150 | —NHC(O)-cyclopropyl | Cl | Cl | —C(O)NH(CH₂)₂-(piperidin-1-yl) |
| 151 | —NHC(O)-cyclopropyl | Cl | Cl | —C(O)NHCH(CH₃)CH₂OH |
| 152 | —NHC(O)-cyclopropyl | Cl | Cl | —C(O)NHCH(CH₃)COOH |
| 154 | —NHC(O)-cyclopropyl | Cl | Cl | —C(O)NH(CH₂)₂F |
| 155 | —NHC(O)-cyclopropyl | Cl | Cl | —C(O)NHCH₂CF₃ |

TABLE 2-continued

R = R" = R$^3$ = R$^7$ = R$^8$ = H

| Compound No. | R' | R$^5$ | R$^6$ | R$^9$ |
|---|---|---|---|---|
| 156 | —NHC(O)-cyclopropyl | Cl | Cl | —C(O)NH(CH$_2$)$_3$OC$_2$H$_5$ |
| 157 | —NHC(O)CH$_3$ | Cl | Cl | —C(O)NH(CH$_2$)$_2$F |
| 158 | —NHC(O)CH$_3$ | Cl | Cl | —C(O)NH(CH$_2$)$_2$-(IH-indol-3-yl) |
| 159 | —NHC(O)-cyclopropyl | Cl | Cl | —C(O)NHCH(CH$_3$)CH$_2$OCH$_3$ |
| 160 | —NHC(O)CH$_3$ | Cl | Cl | —C(O)NHCH$_2$-(pyridin-2-yl) |
| 161 | —NHC(O)CH$_3$ | Cl | Cl | —C(O)NH(CH$_2$)$_2$-(pyridin-2-yl) |
| 162 | —NHC(O)CH$_3$ | Cl | Cl | —C(O)NH(CH$_2$)$_3$-(morpholin-4-yl) |
| 163 | —NHC(O)-cyclopropyl | Cl | Cl | —CH$_2$NHCH$_3$ |
| 164 | —NHC(O)-cyclopropyl | Cl | Cl | —CH$_2$NHC$_2$H$_5$ |
| 165 | —NHC(O)-cyclopropyl | Cl | Cl | —CH$_2$NH(CH$_2$)$_2$(2-oxoimidazolidin-1-yl) |
| 166 | —NHC(O)-cyclopropyl | Cl | Cl | —CH$_2$NH(CH$_2$)$_3$(morpholin-4-yl) |
| 167 | —NHC(O)-cyclopropyl | Cl | Cl | —CH$_2$NH(CH$_2$)$_3$OH |
| 168 | —NHC(O)-cyclopropyl | Cl | Cl | —C(O)NH(CH$_2$)$_2$(pyrrol-1-yl) |
| 169 | —NHC(O)-cyclopropyl | Cl | Cl | —C(O)NH(CH$_2$)$_2$(pyridin-3-yl) |
| 170 | —NHC(O)-cyclopropyl | Cl | Cl | —C(O)NHCH$_2$-cyclopropyl |
| 171 | —NHC(O)-cyclopropyl | Cl | Cl | —C(O)NHCH$_2$-(piperidin-3-yl) |

KINASE ACTIVITY ASSAY

A number of different assays for kinase activity, preferably Janus kinase activity can be utilized. In addition to the assay mentioned in the in vitro enzyme assay below, one of ordinary skill in the art will know of other assays that can be utilized and can modify an assay for a particular application. Such assays and modification thereon are within the sprit and scope of the present invention. The compounds of the present invention are tested for their capacity to inhibit Janus kinase activity, wherein the compounds show IC$_{50}$ of less than 1000 nM, preferably less than 500 nM, more preferably less than 100 nM, even more preferably less than 50 nM.

In Vitro Enzyme Assay:

Reagent Preparation:

Kinase buffer [50 mM HEPES (pH 7.5), 1 mM EGTA, 10 mM MgCl$_2$, 2 mM DTT and 0.01% Tween-20) was prepared and dilutions of a compound of formula (I) and other reagents were subsequently made in it. Two times concentrated compound of formula (I) solution: A compound of formula (I) was diluted to 100-fold final concentration in DMSO, followed by 50-fold dilution with Kinase buffer (1% DMSO final concentration). Four times concentrated Substrate/ATP mix solution: Biotin-SRCtide and ATP were diluted to 4-fold final concentration in Kinase buffer. Biotin-SRCtide solution (purchased from Anaspec) was mixed with ATP solution (1:1). Four times concentrated Enzyme solution: JAK1 or JAK2 or JAK3 or TYK2 enzyme [Human baculo virus expressed JAK1, JAK2, JAK3 and TYK2 were purchased from Carna Bioscience, Inc. All enzymes only contain the catalytic domain. JAK1 (aa 850-1154) and TYK2 (aa 871-1187) are expressed with an N-terminally fused GST-tag, and JAK2 and JAK3 with an N-terminally fused His-tag] was diluted to 4-fold final concentration in Kinase buffer and always kept on ice. Detection buffer: LANCE detection buffer (10 times concentrated) was diluted 10-fold in H$_2$O. Four times concentrated stop solution: EDTA was diluted to a concentration of 40 mM in detection buffer. Four times concentrated ULight/Eu-antibody (from Perkin Elmer) mix solution: ULight-Streptavidin was diluted to a concentration of 100 nM (25 ng/mL final concentrations) and Eu-anti-phospho-Tyrosine (PT66) (from Perkin Elmer) was diluted to a concentration of 8 nM (2 ng/mL final concentration) in detection buffer.

Protocol:

Cell-free in vitro kinase assay was performed in 384 well plates. Two times concentrated compound solution (5 μL) was pipetted into a HTS 384SV Small Volume Plate. Four times concentrated Substrate/ATP mix (2.5 μL) solution was added along with 4 times concentrated Enzyme solution (2.5 μL). Plate was covered with TopSeal-A and incubated at room temperature for indicated time (Table 3). Four times concentrated Stop solution (5 μL, 10 mM final concentration) was added and incubated for 5 minutes at room temperature. Four times concentrated ULight/Eu-antibody mix solution (5 μL) was added and again plate was covered with TopSeal and incubated overnight at 4° C. TopSeal was removed and HTRF signal was measured at 615 nm and 655 nm (excitation at 320 or 340 nm) on Tecan M1000 Multi mode plate reader. Ratio (665 nm/615 nm)×10$^4$ was calculated and IC$_{50}$ values were deduced from Graph-pad prism 4.2.

ABBREVIATION

HEPES: 4-(2-Hydroxyethyl)-1-piperazineethanesulfonic acid

EGTA: Ethylene glycol tetraacetic acid

DTT: Dithiothreitol

Tween-20: Polysorbate 20

DMSO: Dimethylsulfoxide

MgCl$_2$: Magnesium chloride

EDTA: Ethylenediaminetetraacetic acid

HTRF: Homogeneous Time Resolved Fluorescence

H$_2$O: Water

TABLE 3

Assay condition of kinase assay

| Final concentration | JAK3 | JAK2 | JAK1 | TYK2 |
|---|---|---|---|---|
| Enzyme (ng/mL) | 100 | 50 | 250 | 250 |
| SRCtide (nM) | 100 | 25 | 400 | 200 |
| ATP (μM) | 3 | 10 | 60 | 16 |
| Reaction (min) | 30 | 30 | 120 | 45 |

In the Table 4 below, IC$_{50}$ of JAK assay is provided as follows: A=<50 nM, B=<100 nM, C=<500 nM and D=<1000 nM. The IC$_{50}$ value of TYK2 ranges from less than 50 nM to about 100 nM.

TABLE 4

IC$_{50}$ for the representative compounds of formula (I)

| Compound No. | JAK1 | JAK2 | JAK3 | Compound No. | JAK1 | JAK2 | JAK3 |
|---|---|---|---|---|---|---|---|
| 3 | D | C | D | 5 | C | C | C |
| 6 | C | C | C | 11 | C | B | B |
| 12 | C | C | B | 13 | D | C | C |
| 16 | D | C | C | 18 | D | B | D |
| 19 | C | A | C | 22 | C | D | C |
| 23 | D | C | C | 26 | C | C | B |
| 27 | D | C | B | 29 | D | D | C |
| 30 | C | C | C | 31 | C | D | C |
| 32 | C | C | A | 33 | B | B | B |
| 34 | C | C | C | 35 | C | C | C |
| 36 | C | B | A | 39 | C | A | A |
| 42 | D | D | D | 44 | D | D | D |
| 47 | D | B | B | 51 | C | B | A |
| 54 | C | C | C | 55 | C | C | C |
| 56 | C | C | C | 58 | D | D | D |
| 59 | C | C | C | 60 | C | D | C |
| 61 | D | C | C | 62 | D | C | C |
| 63 | C | C | C | 64 | C | D | D |
| 66 | B | B | A | 67 | B | C | B |
| 77 | D | C | C | 86 | D | C | C |
| 87 | C | B | D | 89 | D | A | C |
| 93 | C | D | D | 95 | D | C | C |
| 96 | D | C | C | 103 | D | C | C |
| 107 | C | C | C | 111 | D | C | C |
| 112 | D | C | C | 113 | D | C | C |
| 115 | D | C | C | 120 | B | A | A |
| 122 | D | C | B | 127 | C | B | A |
| 130 | C | A | B | 137 | C | A | C |
| 141 | D | D | D | 143 | D | C | A |
| 147 | C | C | C | 148 | C | C | B |
| 149 | C | D | C | 150 | C | C | C |
| 151 | D | C | C | 154 | D | C | C |
| 163 | C | C | B | 164 | C | C | C |
| 165 | D | C | C | 166 | C | D | C |
| 167 | C | C | C | 168 | D | D | C |
| 169 | D | C | D | 170 | C | D | D |
| 171 | C | B | B | — | — | — | — |

We claim:

1. A method for inhibiting JAK1, JAK2, JAK3, or TYK2 in a subject, comprising administering to a subject in need thereof a therapeutically effective amount of a compound having the structure of formula (I), formula (I)

a pharmaceutically acceptable salt thereof, a prodrug thereof, or a hydrate thereof, wherein:

A represents CR and B represents N;

R and R' independently represent H, (C$_1$-C$_6$) alkyl, halogen, —CN, —NR$^a$R$^b$, —NR$^a$COR$^b$ or —CONR$^a$R$^b$;

R" represents H, halogen or —NR$^a$COR$^b$;

R$^1$ represents H or (C$_1$-C$_3$) alkyl;

R$^2$ represents H, (C$_1$-C$_3$) alkyl, halo or —CN;

R$^3$ represents —COR$^4$;

R$^4$ represents

R$^7$, R$^8$, and R$^9$ independently represent H, alkyl, alkenyl, alkynyl, cycloalkyl, aryl, aralkyl, heteroaryl, heteroarylalkyl, heterocyclyl, heterocyclylalkyl, alkoxy, halo, —NO$_2$, —(CH$_2$)$_q$C(O)NR$^c$R$^d$, —(CH$_2$)$_q$NR$^c$COR$^d$, —(CH$_2$)$_q$NR$^c$CONR$^c$R$^d$, —(CH$_2$)$_q$NR$^c$C(O)OR$^d$, —(CH$_2$)$_q$NR$^c$R$^d$, —(CH=CH)—(CH$_2$)$_s$C(O)OR$^e$, —(CH=CH)—(CH$_2$)$_s$CONR$^c$R$^d$, —(CH=CH)—(CH$_2$)$_s$CN, —(CH=CH)—(CH$_2$)$_s$R$^e$, —(CH$_2$)$_s$C(O)OR$^e$, —(CH)$_r$CN, —(CH$_2$)$_r$OR$^e$, —(CH$_2$)$_r$R$^e$, —(CH$_2$)$_r$C(O)OR$^e$, —(CH)$_r$halo, —S(O)$_p$R$^e$, —S(O)$_p$NR$^c$R$^d$, —NR$^c$S(O)$_p$R$^d$, and wherein alkyl, alkenyl, alkynyl, cycloalkyl, aryl, heteroaryl heterocyclyl are optionally substituted;

R$^c$ and R$^d$ independently represent H, (C$_1$-C$_8$) alkyl, (C$_3$-C$_8$) cycloalkyl, aryl, aralkyl, heteroaryl, heteroarylalkyl, —(CH$_2$)$_r$OR$^e$, —(CH$_2$)$_r$SR$^e$, —(CH$_2$)$_r$CN, —(CH$_2$)$_r$halo, —(CH$_2$)$_r$C(O)OR$^e$, —(CH$_2$)$_r$NR$^c$R$^d$, —COR$^e$, —S(O)$_p$R$^e$, or —(CH$_2$)$_r$R$^e$, wherein alkyl, cycloalkyl, aryl and heteroaryl are optionally substituted; or R$^c$ and R$^d$ are taken together with the N atom to which they are attached to form 3-8 membered heterocyclyl, optionally containing additional heteroatom(s) selected from N, O, or S, wherein heterocyclyl is optionally substituted;

R$^e$ represents H, (C$_1$-C$_6$) alkyl, —CF$_3$, (C$_3$-C$_8$) cycloalkyl, heterocyclyl, aryl or heteroaryl; wherein alkyl, cycloalkyl, heterocyclyl, aryl and heteroaryl are optionally substituted;

p represents an integer of 1 or 2;

q represents an integer of 0, 1, 2 or 3;

r represents an integer of 0, 1, 2, 3 or 4; and s represents an integer of 0, 1 or 2;

R$^a$ and R$^b$ independently represent H, (C$_1$-C$_8$) alkyl, (C$_3$-C$_8$) cycloalkyl or OR'''; or R$^a$ and R$^b$ are taken together with the N atom to which they are attached to form 3-8 membered heterocyclyl, optionally containing additional heteroatom(s) selected from N, O or S, wherein heterocyclyl is optionally substituted; and R''' represents H or (C$_1$-C$_3$) alkyl.

2. The method of claim 1, wherein R" represents H or —NR$^a$COR$^b$.

3. The method of claim 1, wherein R" represents —NR$^a$COR$^b$.

4. The method of claim 1, wherein R$^1$ represents H or (C$_1$-C$_3$) alkyl.

5. The method of claim 1, wherein R represents H or —NR$^a$COR$^b$.

6. The method of claim 1, wherein R$^a$ represents H or (C$_1$-C$_3$) alkyl and R$^b$ represents H, (C$_1$-C$_3$) alkyl, (C$_1$-C$_3$) alkoxy or (C$_3$-C$_5$) cycloalkyl.

7. The method of claim 1, wherein the compound is selected from the group consisting of:
(2-Chloro-6-fluorophenyl)(1H-pyrrolo[2,3-c]pyridine-3-yl)methanone,
3,5-Dichloro-N-ethyl-4-(1H-pyrrolo[2,3-c]pyridin-3-ylcarbonyl)benzamide,
(4-Amino-2,6-dichlorophenyl)(1H-pyrrolo[2,3-c]pyridin-3-yl)methanone,
[2,6-Dichloro-4-(2-methoxypyrimidin-5-yl)phenyl](1H-pyrrolo[2,3-c]pyridin-3-yl)methanone,
N-[3-(2,6-Dichlorobenzoyl)-1H-pyrrolo[2,3-c]pyridin-7-yl]cyclopropanecarboxamide,
3,5-Dichloro-4-(1H-pyrrolo[2,3-c]pyridin-3-ylcarbonyl)benzonitrile,
4-{[7-(Acetylamino)-1H-pyrrolo[2,3-c]pyridin-3-yl]carbonyl}-3,5-dichloro-N-methylbenzamide,
N-[3-(2-Chloro-6-fluorobenzoyl)-1H-pyrrolo[2,3-c]pyridin-7-yl]acetamide,
4-{[7-(Acetylamino)-1H-pyrrolo[2,3-c]pyridin-3-yl]carbonyl}-3,5-dichloro-N-ethylbenzamide,
(4-Bromo-2,6-dichlorophenyl)(1H-pyrrolo[2,3-c]pyridin-3-yl)methanone,
N-[3-(2-Chloro-6-fluorobenzoyl)-1H-pyrrolo[2,3-c]pyridin-7-yl]cyclopropanecarboxamide,
3,5-Dichloro-4-({7-[(cyclopropylcarbonyl)amino]-1H-pyrrolo[2,3-c]pyridin-3-yl}carbonyl)-N-methylbenzamide,
3,5-Dichloro-4-({7-[(cyclopropylcarbonyl)amino]-1H-pyrrolo[2,3-c]pyridin-3-yl}carbonyl)-N-ethylbenzamide,
3,5-Dichloro-N-(2-methoxyethyl)-4-(1H-pyrrolo[2,3-c]pyridin-3-ylcarbonyl)benzamide,
4-{[7-(Acetylamino)-1H-pyrrolo[2,3-c]pyridin-3-yl]carbonyl}-3,5-dichloro-N-propylbenzamide,
3,5-Dichloro-4-({7-[(cyclopropylcarbonyl)amino]-1H-pyrrolo[2,3-c]pyridin-3-yl}carbonyl)-N-(2-methoxyethyl)benzamide,
4-{[7-(Acetylamino)-1H-pyrrolo[2,3-c]pyridin-3-yl]carbonyl}-3,5-dichloro-N-(2-methoxyethyl)benzamide,
N-[3-(2,6-Dichlorobenzoyl)-1H-pyrrolo[2,3-c]pyridin-5-yl]cyclopropanecarboxamide,
N-[3-(2-Chloro-6-fluorobenzoyl)-1H-pyrrolo[2,3-c]pyridin-5-yl]cyclopropanecarboxamide,
3,5-Dichloro-4-{(5-[(cyclopropylcarbonyl)amino]-1H-pyrrolo[2,3-c]pyridin-3-yl}carbonyl)-N-methylbenzamide,
N-[3-(2,6-Dichloro-4-cyanobenzoyl)-1H-pyrrolo[2,3-c]pyridin-7-yl]acetamide,
N-[3-(4-Bromo-2,6-dichlorobenzoyl)-1H-pyrrolo[2,3-c]pyridin-7-yl]cyclopropanecarboxamide,
N-{3-[2,6-Dichloro-4-(3,5-dimethyl-1,2-oxazol-4-yl)benzoyl]-1H-pyrrolo[2,3-c]pyridin-7-yl}cyclopropanecarboxamide,
N-[3-(4-Bromo-2,6-dichlorobenzoyl)-1H-pyrrolo[2,3-c]pyridin-7-yl]acetamide,
Methyl 3,5-dichloro-4-({7-[(cyclopropylcarbonyl)amino]-1H-pyrrolo[2,3-c]pyridin-3-yl}carbonyl)benzoate,
N-[3-(4-Amino-2,6-dichlorobenzoyl)-1H-pyrrolo[2,3-c]pyridin-7-yl]cyclopropanecarboxamide,
N-{3-[4-(Acetylamino)-2,6-dichlorobenzoyl]-1H-pyrrolo[2,3-c]pyridin-7-yl}cyclopropanecarboxamide,
N-[3-(2-Chloro-6-fluorobenzoyl)-1H-pyrrolo[2,3-c]pyridin-7-yl]propanamide,
3,5-Dichloro-4-({7-[(cyclopropylcarbonyl)amino]-1H-pyrrolo[2,3-c]pyridin-3-yl}carbonyl)-N-[2-(2-hydroxyethoxy)ethyl]benzamide,
3,5-Dichloro-4-({7-[(cyclopropylcarbonyl)amino]-1H-pyrrolo[2,3-c]pyridin-3-yl}carbonyl)-N-(3-hydroxypropyl)benzamide,
3,5-Dichloro-4-({7-[(cyclopropylcarbonyl)amino]-1H-pyrrolo[2,3-c]pyridin-3-yl}carbonyl)-N-[3-(morpholin-4-yl)propyl]benzamide,
3,5-Dichloro-4-({7-[(cyclopropylcarbonyl)amino]-1H-pyrrolo[2,3-c]pyridin-3-yl}carbonyl)-N-(2,3-dihydroxypropyl)benzamide,
3,5-Dichloro-4-({7-[(cyclopropylcarbonyl)amino]-1H-pyrrolo[2,3-c]pyridin-3-yl}carbonyl)-N-[2-(dimethylamino)ethyl]benzamide,
3,5-Dichloro-4-({7-[(cyclopropylcarbonyl)amino]-1H-pyrrolo[2,3-c]pyridin-3-yl}carbonyl)-N-[2-(piperidin-1-yl)ethyl]benzamide,
Methyl N-[3,5-dichloro-4-({7-[(cyclopropylcarbonyl)amino]-1H-pyrrolo[2,3-c]pyridin-3-yl}carbonyl)benzoyl]glycinate,
N-[3,5-Dichloro-4-({7-[(cyclopropylcarbonyl)amino]-1H-pyrrolo[2,3-c]pyridin-3-yl}carbonyl)benzoyl]glycine,
N-[3-(2-Chloro-3,6-difluorobenzoyl)-1H-pyrrolo[2,3-c]pyridin-7-yl]cyclopropanecarboxamide,
3,5-Dichloro-N-methyl-4-{[7-(propanoylamino)-1H-pyrrolo[2,3-c]pyridin-3-yl]carbonyl}benzamide,
N-[3-(2,6-Dichloro-4-cyanobenzoyl)-1H-pyrrolo[2,3-c]pyridin-7-yl]cyclopropanecarboxamide,
4-{[7-(Acetylamino)-1H-pyrrolo[2,3-c]pyridin-3-yl]carbonyl}-3,5-dichloro-N-[2-(dimethylamino)ethyl]benzamide,
4-{[7-(Acetylamino)-1H-pyrrolo[2,3-c]pyridin-3-yl]carbonyl}-3,5-dichloro-N-[2-(2-hydroxyethoxy)ethyl]benzamide,
4-{[7-(Acetylamino)-1H-pyrrolo[2,3-c]pyridin-3-yl]carbonyl}-3,5-dichloro-N-[2-(piperidin-1-yl)ethyl]benzamide,
4-{[7-(Acetylamino)-1H-pyrrolo[2,3-c]pyridin-3-yl]carbonyl}-3,5-dichloro-N-[2-(morpholin-4-yl)ethyl]benzamide,
4-{[7-(Acetylamino)-1H-pyrrolo[2,3-c]pyridin-3-yl]carbonyl}-3,5-dichloro-N-[2-(pyrrolidin-1-yl)ethyl]benzamide,
N-[3-(2,4,6-Trichlorobenzoyl)-1H-pyrrolo[2,3-c]pyridin-7-yl]cyclopropanecarboxamide,
N-{3-[2,6-Dichloro-4-(3,5-dimethyl-1H-pyrazol-4-yl)benzoyl]-1H-pyrrolo[2,3-c]pyridin-7-yl}cyclopropanecarboxamide,
N-{3-[2,6-Dichloro-4-(pyrimidin-5-yl)benzoyl]-1H-pyrrolo[2,3-c]pyridin-7-yl}cyclopropanecarboxamide,
N-{3-[2,6-Dichloro-4-(6-methoxypyridin-3-yl)benzoyl]-1H-pyrrolo[2,3-c]pyridin-7-yl}cyclopropanecarboxamide,
N-{3-[2,6-Dichloro-4-(6-fluoropyridin-3-yl)benzoyl]-1H-pyrrolo[2,3-c]pyridin-7-yl}cyclopropanecarboxamide,
N-{3-[2,6-Dichloro-4-(1-methyl-1H-pyrazol-4-yl)benzoyl]-1H-pyrrolo[2,3-c]pyridin-7-yl}cyclopropanecarboxamide,
N-[3-(4-Cyano-2,6-difluorobenzoyl)-1H-pyrrolo[2,3-c]pyridin-7-yl]cyclopropanecarboxamide,
Methyl 4-({7-[(cyclopropylcarbonyl)amino]-1H-pyrrolo[2,3-c]pyridin-3-yl}carbonyl)-3,5-difluorobenzoate,
N-[3-(4-Cyano-2,6-difluorobenzoyl)-1H-pyrrolo[2,3-c]pyridin-7-yl]acetamide,
3,5-Dichloro-N-cyclopropyl-4-({7-[(cyclopropylcarbonyl)amino]-1H-pyrrolo[2,3-c]pyridin-3-yl}carbonyl)benzamide, 3,5-Dichloro-4-({7-[(cyclopropylcarbonyl)amino]-1H-pyrrolo[2,3-c]pyridin-3-yl}carbonyl)-N-(cyclopropylmethyl)benzamide, 3,5-Dichloro-4-({7-[(cyclopropylcarbonyl)amino]-1H-pyrrolo[2,3-c]pyridin-3-yl}carbonyl)-N-(3-ethoxypropyl)benzamide, N-Butyl-3,5-Dichloro-4-({7-[(cyclopropylcarbonyl)amino]-1H-pyrrolo[2,3-c]pyridin-3-yl}carbonyl)benzamide, N-{3-[2,6-Dichloro-4-(hydroxymethyl)benzoyl]-1H-pyrrolo[2,3-c]pyridin-7-yl}cyclopropanecarboxamide, 4-({7-[(Cyclopropylcarbonyl)amino]-1H-pyrrolo[2,3-c]pyridin-3-yl}carbonyl)-3,5-difluoro-N-(2-fluoroethyl)benzamide, 4-({7-[(Cyclopropylcarbonyl)amino]-1H-pyrrolo[2,3-c]pyridin-3-yl}carbonyl)-N-ethyl-3,5-difluorobenzamide, 4-({7-[(Cyclopropylcarbonyl)amino]-1H-pyrrolo[2,3-c]pyridin-3-yl}carbonyl)-3,5-difluoro-N-methylbenzamide, 4-({7-[(Cyclopropylcarbonyl)amino]-1H-pyrrolo[2,3-c]pyridin-3-yl}carbonyl)-3,5-difluoro-N-(3-hydroxypropyl)benzamide, 4-({7-[(Cyclopropylcarbonyl)amino]-1H-pyrrolo[2,3-c]pyridin-3-yl}carbonyl)-N-[2-(dimethylamino)ethyl]-3,5-difluorobenzamide, 4-({7-[(Cyclopropylcarbonyl)amino]-1H-pyrrolo[2,3-c]pyridin-3-yl}carbonyl)-N-(3-ethoxypropyl)-3,5-difluorobenzamide, N-{3-[4-(3,5-Dimethyl-1,2-oxazol-4-yl)-2,6-difluorobenzoyl]-1H-pyrrolo[2,3-c]pyridin-7-yl}cyclopropanecarboxamide, N-(3-{2,6-Dichloro-4-[(methylamino)methyl]benzoyl}-1H-pyrrolo[2,3-c]pyridin-7-yl)cyclopropanecarboxamide, N-(3-{2,6-Dichloro-4-[(ethylamino)methyl]benzoyl}-1H-pyrrolo[2,3-c]pyridin-7-yl)cyclopropanecarboxamide, N-[3-(2,6-Dichlorobenzoyl)-2-methyl-1H-pyrrolo[2,3-c]pyridin-7-yl]cyclopropanecarboxamide, N-[3-(4-Bromo-2,6-difluorobenzoyl)-1H-pyrrolo[2,3-c]pyridin-7-yl]cyclopropanecarboxamide, N-[3-(2,6-Difluorobenzoyl)-2-methyl-1H-pyrrolo[2,3-c]pyridin-7-yl]cyclopropanecarboxamide, and 3,5-Dichloro-4-({7-[(cyclopropylcarbonyl)amino]-2-methyl-1H-pyrrolo[2,3-c]pyridin-3-yl}carbonyl)-N-methylbenzamide, a pharmaceutically acceptable salt thereof, a prodrug thereof, or a hydrate thereof.

\* \* \* \* \*